US011629162B2

(12) United States Patent
Tan et al.

(10) Patent No.: US 11,629,162 B2
(45) Date of Patent: Apr. 18, 2023

(54) TRITERPENE SAPONIN VARIANTS, METHODS OF SYNTHESIS AND USE THEREOF

(71) Applicant: MEMORIAL SLOAN-KETTERING CANCER CENTER, New York, NY (US)

(72) Inventors: Derek S. Tan, New York, NY (US); David Y. Gin, New York, NY (US); William E. Walkowicz, New York, NY (US); Alberto Fernandez-Tejada, New York, NY (US); Govindaswami Ragupathi, New York, NY (US)

(73) Assignee: Memorial Sloan-Kettering Cancer Center, New York, NY (US)

( * ) Notice: Subject to any disclaimer, the term of this patent is extended or adjusted under 35 U.S.C. 154(b) by 0 days.

(21) Appl. No.: 16/063,608

(22) PCT Filed: Dec. 19, 2016

(86) PCT No.: PCT/US2016/067530
§ 371 (c)(1),
(2) Date: Jun. 18, 2018

(87) PCT Pub. No.: WO2017/106836
PCT Pub. Date: Jun. 22, 2017

(65) Prior Publication Data
US 2019/0010181 A1  Jan. 10, 2019

Related U.S. Application Data

(60) Provisional application No. 62/268,837, filed on Dec. 17, 2015.

(51) Int. Cl.
| | |
|---|---|
| *C07H 15/256* | (2006.01) |
| *C07H 13/06* | (2006.01) |
| *C07J 63/00* | (2006.01) |
| *C07H 15/18* | (2006.01) |
| *A61K 39/39* | (2006.01) |
| *A61K 39/00* | (2006.01) |

(52) U.S. Cl.
CPC ........... *C07H 15/256* (2013.01); *C07H 13/06* (2013.01); *C07H 15/18* (2013.01); *C07J 63/008* (2013.01); *A61K 39/39* (2013.01); *A61K 2039/55577* (2013.01)

(58) Field of Classification Search
CPC ...... C07H 15/256; C07H 13/06; C07H 15/18; A61K 39/39
USPC .......................................................... 514/33
See application file for complete search history.

(56) References Cited

U.S. PATENT DOCUMENTS

| | | |
|---|---|---|
| 7,645,454 B2 | 1/2010 | Danishefsky et al. |
| 2005/0026982 A1 | 2/2005 | Johannsen et al. |

FOREIGN PATENT DOCUMENTS

| | | |
|---|---|---|
| AU | 2015203675 A1 | 7/2015 |
| WO | WO 2015/184451 | 12/2015 |

OTHER PUBLICATIONS

Berge, Stephen M. et al., "Pharmaceutical Salts," Journal of Pharmaceutical Sciences, vol. 66, No. 1, pp. 1-19, Jan. 1977.
Lide, David R. "CRC Handbook of Chemistry and Physics, 1913-1995," 75th Edition CRC Press, pp. 1-35, 1994.
Smith, Michael B. et al., "March's Advance Organic Chemistry, Reactions, Mechanisms, and Structure" Fifth Edition, A Wiley-Interscience Publication, John Wiley & Sons, Inc., pp. 1-1054, 2001.
Sorrell, Thomas N. "Organic Chemistry," University Science Books, pp. 1-222, 1999.
Extended European Search Report dated Sep. 5, 2019 for European National phase application No. 16876910.7.
Chea, Eric K. et al., "Synthesis and Preclinical Evaluation of QS-21 Variants Leading to Simplified Vaccine Adjuvants and Mechanistic Probes," J. Am. Chem., vol. 134, No. 32, pp. 13448-13457, 2012.
Fernandez-Tejada, Alberto et al., "Design, synthesis, and immunologic evaluation of vaccine adjuvant conjugates based on QS-21 and tucaresol," Bioorganic & Medicinal Chemistry, vol. 22, No. 21, pp. 5917-5923, 2014.
Walkowicz, William E. et al., "Quillaja Saponin Variants with Central Glycosidin linkage Modifications exhibit distinct Conformations and adjuvant activities," Chemical Science, vol. 7, No. 3, pp. 2371-2380, 2016.
Fernandez-Tejada, Alberto et al., "Development of Improved Vaccine Adjuvants Based on the Saponin Natural Product QS-21 through Chemical Synthesis," Acc. Chem. Res., vol. 49, pp. 1741-1756, 2016.
International Search Report for International Application No. PCT/US16/067530 dated Feb. 24, 2017.
International Written Opinion for International Application No. PCT/US16/067530 dated Feb. 24, 2017.
C. Diaz et al. "Rosacea: A Cutaneous Marker of Helicobracter pylori infection? Resultsof a Pilot Study," Acta Dermatology Venereology, vol. 83, pp. 282-286 (2003).
A. Fernandez-Tejada et al. "Development of a minimal saponin vaccine aduvant based on QS-21," Nature Chemistry, vol. 6, No. 7, pp. 635-643 (Jul. 7, 2014).
European Communication Pursuant to Article 94(3) EPC dated Apr. 8, 2021 for European Patent Application No. 16876910.7.

*Primary Examiner* — Shaojia A Jiang
*Assistant Examiner* — Michael C Henry
(74) *Attorney, Agent, or Firm* — Hunton Andrews Kurth LLP

(57) ABSTRACT

A number of triterpene saponin variants with different modifications on their central glycosyl ester linkage are described. Also described are methods of making and method of using such triterpene saponin variants.

13 Claims, 7 Drawing Sheets

TRITERPENE SAPONIN VARIANTS, METHODS OF SYNTHESIS AND USE THEREOF

CROSS REFERENCE TO RELATED APPLICATION(S)

The present application relates to and claims priority from International Patent Application No. PCT/US2016/067530, filed on Dec. 19, 2016 and from U.S. Provisional Patent Application No. 62/268,837, filed on Dec. 17, 2015, the entire disclosures of which are incorporated herein by reference.

STATEMENT REGARDING FEDERALLY SPONSORED RESEARCH

This invention was made with government support under GM058833, AI085622 and CA008748 awarded by National Institutes of Health. The government has certain rights in the invention.

FIELD

The present invention generally relates to triterpene glycoside saponin-derived adjuvants, syntheses thereof, and intermediates thereto. More specifically, the invention relates to saponin variants with central glycosidic linkage modifications that exhibit distinct conformations and adjuvant activities.

BACKGROUND

Most of the immunological adjuvants are emulsions that stimulate an immune response, which have shown valuable potentials in the development of vaccines against toxins and viruses such as diphtheria-tetanus-pertussis, hepatitis B, hepatitis A, human papilloma virus and influenza viruses. However, they have very limited functions in the development of therapeutic and prophylactic vaccines for other diseases, such as cancer, HIV infection, malaria, herpes, tuberculosis because of poor antigen immunogenicity and insufficient cell-mediated Th1-type immune responses. On the other hand, certain immunological adjuvants, such as the saponin natural product QS-21, are isolated from the bark of *Quillaja saponaria* Molina tree, to stimulate both the Th1 and Th2 immune responses against exogenous antigens, which make them ideal for use in the development of vaccines against infectious diseases, neurodegenerative disorders, and cancer. As a purified plant extract containing water soluble triterpene glucoside compounds, QS-21 is currently under clinical evaluation as an adjuvant for various trial vaccines, including those for HIV, malaria and cancer.

Nevertheless, QS-21 suffers from several liabilities including chemical instability at room temperature, which hinders vaccine deployment in the developing world, dose-limiting toxicity involving local erythema and inflammation as well as systematic flu-like symptoms, and low-yielding (0.001%) purification from the natural source. In order to address the aforementioned concerns, one key approach would be make various modifications on various substructures or domains of QS-21 and other saponin compounds, as well as the linkages between these domains to investigate the specific structures that play critical roles in their stabilities, purification, functions or applications, and provide potential variant candidates that may exhibit advantageous characteristics in some of the foregoing aspects thereof.

In the structure of QS-21 and other related compounds, the potential role the central glycosyl ester linkage plays in their stabilities, functions and applications remain elusive, and the modifications on the central glycosyl ester linkage has not yet been studied. In the present invention, the design, synthesis, immunologic evaluation, and molecular dynamics analysis of a series of novel QS-21 variants with different linker lengths, stereochemistry, and flexibility have been developed or investigated to explore their specific conformations and in vivo adjuvant activities.

SUMMARY

One aspect of the present application relates to a compound of formula (I) or a pharmaceutically acceptable salt thereof,

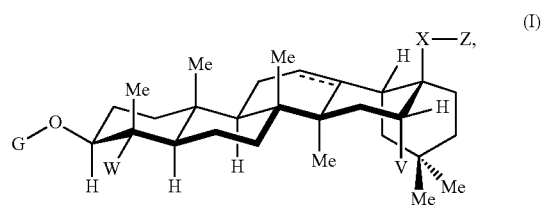

wherein G is hydrogen, a branched trisaccharide of formula XII or a stereoisomer of formula V

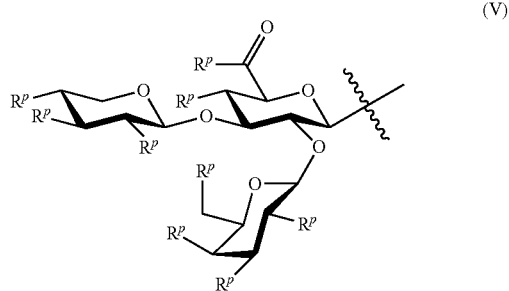

wherein W is Me, CHO, $CH_2OR^x$, $C(O)R^y$ or

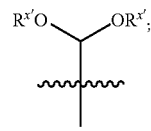

wherein each occurrence of $R^p$ is independently hydrogen or $OR^x$; wherein each occurrence of $R^x$ is independently hydrogen or an optionally substituted group selected from 6-10-membered aryl, benzyl, $C_{1-6}$ aliphatic, or $C_{1-6}$ heteroaliphatic having 1-2 heteroatoms independently selected from the group consisting of nitrogen, oxygen, and sulfur; or two $R^x$ are taken together to form a 5-7-membered heterocyclic ring having 1-2 heteroatoms independently selected from the group consisting of nitrogen, oxygen, and sulfur; wherein each occurrence of $R^{x'}$ is independently an optionally substituted group selected from 6-10-membered aryl, benzyl, $C_{1-6}$ aliphatic, or $C_{1-6}$ heteroaliphatic having 1-2 heteroatoms independently selected from the group consisting of nitrogen, oxygen, and sulfur; or two $R^{x'}$ are taken together to form a 5-7-membered heterocyclic ring having 1-2 heteroatoms independently selected from the group consisting of nitrogen, oxygen, and sulfur; wherein each occurrence of $R^y$ is OH or $OR^x$; wherein ═ is a single or double band; wherein V is hydrogen or $OR^x$; wherein X has the structure of ─(A-B-D-E)─, wherein each of A, B, D and E is C(O), NH, S, O, $C_{1-5}$ aliphatic or is absent, with the proviso that at least one of A, B, D and E is present at any time and that X is not a β-ester with a structure of ─C(O)O─; wherein Z comprises a carbohydrate domain having the structure:

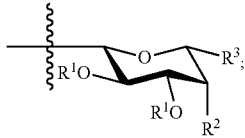

(IX)

wherein each occurrence of $R^1$ is $R^x$ or a carbohydrate domain having the structure:

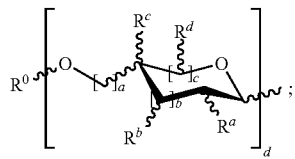

wherein each occurrence of a, b, and c is independently 0, 1, or 2; wherein d is an integer from 1-5, wherein each d bracketed structure may be the same or different; with the proviso that the d bracketed structure represents a furanose or pyranose moiety, and the sum of b and c is 1 or 2; wherein $R^0$ is hydrogen or an optionally substituted moiety selected from the group consisting of acyl, $C_{1-10}$ aliphatic, $C_{1-6}$ heteroaliphatic, 6-10-membered aryl, arylalkyl, 5-10-membered heteroaryl having 1-4 heteroatoms independently selected from nitrogen, oxygen, and sulfur, 4-7-membered heterocyclyl having 1-2 heteroatoms independently selected from the group consisting of nitrogen, oxygen, and sulfur; wherein each occurrence of $R^a$, $R^b$, $R^c$, and $R^d$ is independently hydrogen, halogen, OH, OR, $OR^x$, $NR_2$, NHCOR, or an optionally substituted group selected from acyl, $C_{1-10}$ aliphatic, $C_{1-6}$ heteroaliphatic, 6-10-membered aryl, arylalkyl, 5-10-membered heteroaryl having 1-4 heteroatoms independently selected from nitrogen, oxygen, and sulfur; 4-7-membered heterocyclyl having 1-2 heteroatoms independently selected from the group consisting of nitrogen, oxygen, and sulfur; wherein each occurrence of R is independently hydrogen, an optionally substituted group selected from acyl, arylalkyl, 6-10-membered aryl, $C_{1-12}$ aliphatic, or $C_{1-12}$ heteroaliphatic having 1-2 heteroatoms independently selected from the group consisting of nitrogen, oxygen, and sulfur; or two R on the same nitrogen atom are taken with the nitrogen to form a 4-7-membered heterocyclic ring having 1-2 heteroatoms independently selected from the group consisting of nitrogen, oxygen, and sulfur; wherein $R^2$ is $NHC(O)R^4$, $OC(O)R^4$, $OC(O)OR^4$, $OC(O)NHR^4$, $OC(O)SR^4$, $NHC(O)OR^4$, $NHC(O)NHR^4$, $NHC(O)N(R^4)_2$, $NHR^4$ or $N(R^4)_2$; wherein $R^3$ is hydrogen, halogen, $CH_2OR^1$, or an optionally substituted group selected from the group consisting of acyl, $C_{1-10}$ aliphatic, $C_{1-6}$ heteroaliphatic, 6-10-membered aryl, arylalkyl, 5-10-membered heteroaryl having 1-4 heteroatoms independently selected from the group consisting of nitrogen, oxygen, and sulfur, and 4-7-membered heterocyclyl having 1-2 heteroatoms independently selected from the group consisting of nitrogen, oxygen, and sulfur; wherein $R^4$ is $T-R^z$, wherein T is a covalent bond or a bivalent $C_{1-12}$ saturated or unsaturated, straight or branched, aliphatic or heteroaliphatic chain, wherein $R^z$ is hydrogen, halogen, $C(O)OR^q$, $NC(O)OR^q$, $OR^q$, $NHC(O) R^q$, $OR^1$, $SR^q$, $NHC(S) R^q$, $OC(O)R^q$, $OC(O) OR^q$, $OC(O)NHR^q$, $OC(O)SR^q$, $NHC(O)OR^q$, $NHC(O) NHR^q$, $NHC(O)N(R^q)_2$, $NHR^q$ or $N(R^q)_2$, or an optionally substituted group selected from acyl, arylalkyl, heteroarylalkyl, $C_{1-6}$ aliphatic, 6-10-membered aryl, 5-10-membered heteroaryl having 1-4 heteroatoms independently selected from nitrogen, oxygen, and sulfur, 4-7-membered heterocyclyl having 1-2 heteroatoms independently selected from the group consisting of nitrogen, oxygen and sulfur; or two $R^q$ on the same nitrogen atom are taken with the nitrogen to form a 4-7-membered heterocyclic ring having 1-2 heteroatoms independently selected from the group consisting of nitrogen, oxygen, and sulfur, and wherein $R^q$ is hydrogen, a detectable label, a protecting group, an optionally substituted group selected from acyl, arylalkyl, 6-10-membered aryl, $C_{11-12}$ aliphatic, and $C_{1-12}$ heteroaliphatic having 1-2 heteroatoms independently selected from the group consisting of nitrogen, oxygen, and sulfur, or an optionally substituted group selected from acyl, arylalkyl, 6-10-membered aryl, $C_{1-12}$ aliphatic, and $C_{1-12}$ heteroaliphatic having 1-2 heteroatoms independently selected from the group consisting of nitrogen, oxygen, and sulfur, wherein the optionally substituted group further comprises a detectable label.

Another aspect of the present application relates to a pharmaceutical composition. The pharmaceutical composition comprises the compound or a pharmaceutically acceptable salt thereof of the present application, an immunologically effective amount of an antigen, and a pharmaceutically acceptable excipient.

Another aspect of the present application relates to a method for immunizing a subject. The method comprises administering to the subject an effective amount of the pharmaceutical composition of the present application.

Another aspect of the present application relates to a method for treating a disorder in a subject. The method comprises administering to the subject an effective amount of the pharmaceutical composition of the present invention, wherein the disorder is cancer, an infectious disease or a neurodegenerative disease.

BRIEF DESCRIPTION OF THE DRAWINGS

The above and other objects and advantages of the application will be apparent upon consideration of the following detailed description, taken in conjunction with the accompanying figures and paragraphs. The following are brief descriptions of the drawings herein, which illustrate certain aspects and embodiments of the present application, but are not considered limiting in any way.

DETAILED DESCRIPTION

Figure 1:
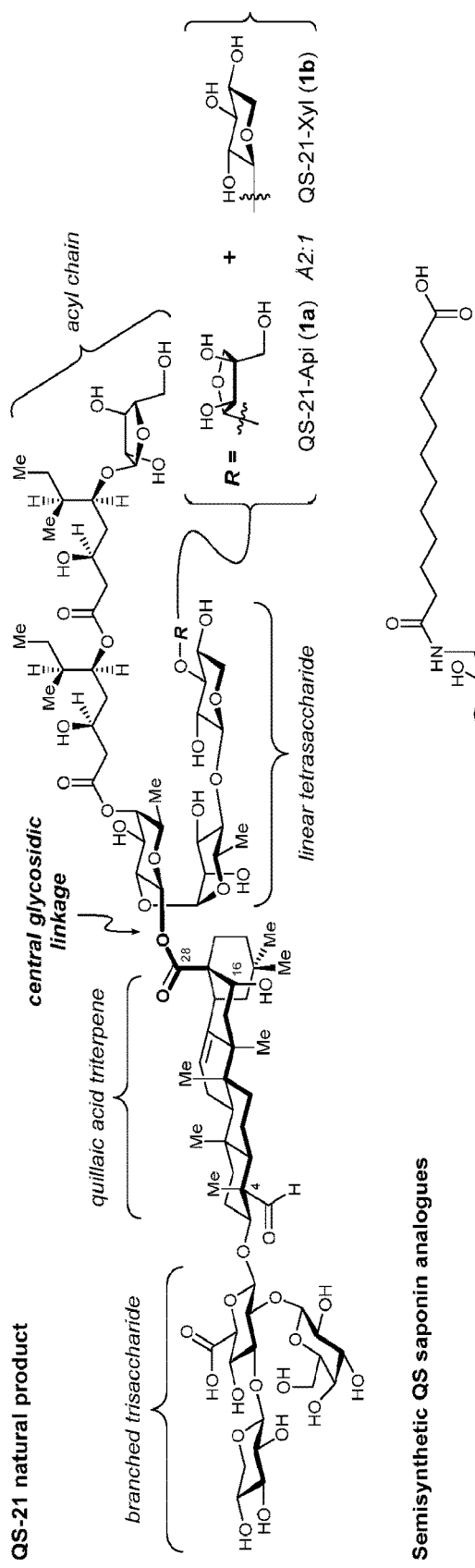
FIG. 1 shows the structures of QS-21 natural product and semisynthetic QS saponin analogues. Panel a: Structure of the saponin natural product immunoadjuvant QS-21 (≈2:1 mixture of 1a/1b). Panel b: Structures of a simplified semisynthetic lead compound 2 and corresponding glycosidic linkage variants 3-9 designed to probe the effects of linker length, stereochemistry, and conformational flexibility upon adjuvant activity. Four-number SQS (synthetic QS) codes designate structural variants in each of the four corresponding structural domains of QS-21, left to right, with 0 assigned to the natural product structure.
Figure 1:
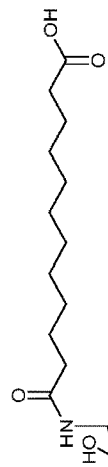
Figure 1:
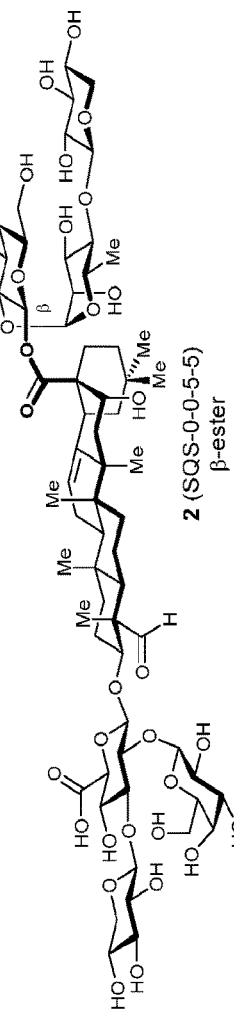
Figure 1:
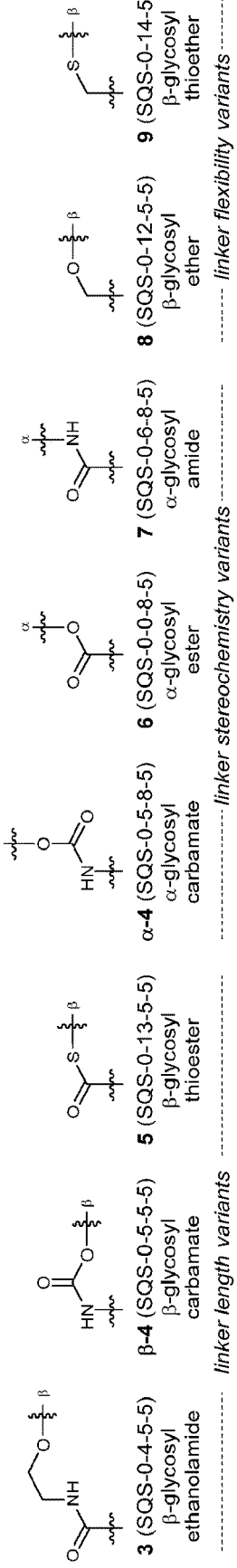

Some modes for carrying out the present invention are presented in terms of its aspects, herein discussed below. However, the present invention is not limited to the described embodiment and a person skilled in the art will appreciate that many other embodiments of the present invention are possible without deviating from the basic concept of the present invention, and that any such work around will also fall under scope of this application. It is envisioned that other styles and configurations of the present invention can be easily incorporated into the teachings of the present invention, and only one particular configuration shall be shown and described for purposes of clarity and disclosure and not by way of limitation of scope.

Headings used herein are for organizational purposes only and are not meant to be used to limit the scope of the description or the enclosed paragraphs. As used throughout this application, the word "may" is used in a permissive sense (i.e., meaning having the potential to), rather than the mandatory sense (i.e., meaning must). The terms "a" and "an" herein do not denote a limitation of quantity, but rather denote the presence of at least one of the referenced items.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about", it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed.

Definition

As used herein, the following definitions shall apply to the present application unless otherwise indicated.

The term "aliphatic" or "aliphatic group" means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-12 aliphatic carbon atoms. In some embodiments, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," means that a moiety has one or more units of unsaturation.

The term "bivalent $C_{1-12}$ (or $C_{1-26}$, $C_{1-16}$, $C_{1-8}$) or saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —$(CH_2)_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "alkynylene" refers to a bivalent alkynyl group. A substituted alkynylene chain is a polymethylene group containing at least one double bond in which one or more hydrogen atoms are replaced with a substituent. Suitable substituents include those described below for a substituted aliphatic group.

The term "acyl" used alone or a part of a larger moiety, refers to groups formed by removing a hydroxy group from a carboxylic acid.

The term "halogen" means F, Cl, Br, or I.

The terms "aralkyl" and "arylalkyl" are used interchangeably and refer to alkyl groups in which a hydrogen atom has been replaced with an aryl group. Such groups include, without limitation, benzyl, cinnamyl, and dihyrocinnamyl.

The term "aryl" used alone or as part of a larger moiety as in "aralkyl", "aralkoxy", or "aryloxyalkyl" refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl", as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-" used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl.

The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring", "heteroaryl group" or "heteroaromatic" any of which terms include rings that are optionally substituted. The terms "heteroaralkyl" and "heteroarylalkyl" refer to an alkyl group substituted by a heteroaryl moiety, wherein the alkyl and heteroaryl portions independently are optionally substituted.

The term "heteroaliphatic" means aliphatic groups wherein one or two carbon atoms are independently replaced by one or more of oxygen, sulfur, nitrogen, or phosphorus. Heteroaliphatic groups may be substituted or unsubstituted, branched or unbranched, cyclic or acyclic, and include "heterocycle", "heterocyclyl", "heterocycloaliphatic" or "heterocyclic" groups.

The terms "heterocycle", "heterocyclyl", "heterocyclic radical" and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+NR$ (as in N-substituted pyrrolidinyl). A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl.

The terms "heterocycle", "heterocyclyl", "heterocyclyl ring", "heterocyclic group", "heterocyclic moiety" and "heterocyclic radical" are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic.

The term "heterocyclylalkyl" refers to an alkyl group substituted by a heterocyclyl, wherein the alkyl and heterocyclyl portions independently are optionally substituted.

The term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group refers to the original group and groups that may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. For example, the term "optionally substituted methyl group" includes, but is not limited to, $CH_3$, $CH_2Cl$, $CHCl_2$ and $CCl_3$.

The term "stable" as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $-(CH_2)_{0-4}R^\circ$; $-(CH_2)_{0-4}R^\circ$; $-O(CH_2)_{0-4}R^\circ$, $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-(CH_2)_{0-4}O(CH_2)_{0-1}$-pyridyl which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ_3$; $-(CH_2)_{0-4}OC(O)R^\circ$; $-OC(O)(CH_2)_{0-4}SR^\circ$, $SC(S)SR^\circ$; $-(CH_2)_{0-4}SC(O)R^\circ$; $-(CH_2)_{0-4}C(O)NR^\circ_2$; $-C(S)NR^\circ_2$; $-C(S)SR^\circ$; $-SC(S)SR^\circ$, $-(CH_2)_{0-4}OC(O)NR^\circ_2$; $-C(O)N(OR)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2R^\circ$; $-(CH_2)_{0-4}OS(O)_2R^\circ$; $-S(O)_2NR^\circ_2$; $-(CH_2)_{0-4}S(O)R^\circ$; $-N(R^\circ)S(O)_2NR^\circ_2$; $-N(R^\circ)S(O)_2R^\circ$; $-N(OR)R^\circ$; $-C(NH)NR^\circ_2$; $-P(O)_2R^\circ$; $-P(O)R^\circ_2$; $-OP(O)R^\circ_2$; $-OP(O)(OR^\circ)_2$; $SiR^\circ_3$; $-(C_{1-4}$ straight or branched)alkylene)$O-N(R^\circ)_2$; or $-(C_{1-4}$ straight or branched)alkylene)$C(O)O-N(R^\circ)_2$, wherein each $R^\circ$ may be substituted as defined below and is independently hydrogen, $C_{1-6}$ aliphatic, $-CH_2Ph$, $-O(CH_2)_{0-1}Ph$, $-CH_2$-(5-6-membered heteroaryl ring), or a 5-6-membered saturated, partially unsaturated, or aryl ring having 0-4 heteroatoms independently selected from nitrogen, oxygen, and sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, and sulfur, which may be substituted as defined below.

Suitable monovalent substituents on $R^\circ$ (or the ring formed by taking two independent occurrences of $R^\circ$ together with their intervening atoms), are independently halogen, $-(CH_2)_{0-2}R$, -(haloR), $-(CH_2)_{0-2}OH$, $-(CH_2)_{0-2}OR$, $-(CH_2)_{0-2}CH(OR)_2$; $-O(haloR)$, $-CN$, $-N_3$, $-(CH_2)_{0-2}C(O)R$, $-(CH_2)_{0-2}C(O)OH$, $-(CH_2)_{0-2}C(O)OR$, $-(CH_2)_{0-2}SR$, $-(CH_2)_{0-2}SH$, $-(CH_2)_{0-2}NH_2$, $-(CH_2)_{0-2}NHR$, $-(CH_2)_{0-2}NR_2$, $-NO_2$, $-SiR_3$, $-OSiR_3$, $-C(O)SR$, $-(C_{1-4}$ straight or branched alkylene)$C(O)OR$, or $-SSR$, wherein each R is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, and sulfur. Suitable divalent substituents on a saturated carbon atom of $R^\circ$ include $=O$ and $=S$.

Suitable divalent substituents on a saturated carbon atom of an "optionally substituted" group include the following: $=O$, $=S$, $=NNR^*_2$, $=NNHC(O)R^*$, $=NNHC(O)OR^*$, $=NNHS(O)_2R^*$, $=NR^*$, $=NOR^*$, $-O(C(R^*_2))_{2-3}O-$, or $-S(C(R^*_2))_{2-3}S-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur. Suitable divalent substituents that are bound to vicinal substitutable carbons of an "optionally substituted" group include: $-O(CR^*_2)_{2-3}O-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur.

Suitable substituents on the aliphatic group of $R^*$ include halogen, $-R$, -(haloR), $-OH$, $-OR$, $-O(haloR)$, $-CN$, $-C(O)OH$, $-C(O)OR$, $-NH_2$, $-NHR$, $-NR_2$, or $-NO_2$, wherein each R, is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, and sulfur.

Suitable substituents on a substitutable nitrogen of an "optionally substituted" group include $-R^\dagger$, $-NR^\dagger_2$, $-C(O)R^\dagger$, $-C(O)OR^\dagger$, $-C(O)C(O)R^\dagger$, $-C(O)CH_2C(O)R^\dagger$, $-S(O)_2R^\dagger$, $-S(O)_2NR^\dagger_2$, $-C(S)NR^\dagger_2$, $-C(NH)NR^\dagger_2$, or $-N(R^\dagger)S(O)_2R^\dagger$; wherein each $R^\dagger$ is independently hydrogen, $C_{1-6}$ aliphatic which may be substituted as defined below, unsubstituted $-OPh$, or an unsubstituted 5-6-membered saturated, partially unsaturated, or aryl ring having 0-4 heteroatoms independently selected from nitrogen, oxygen, and sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, and sulfur. Suitable substituents on the aliphatic group of $R^\dagger$ are independently halogen, $-R$, -(haloR), $-OH$, $-OR$, $-O(haloR)$, $-CN$, $-C(O)OH$, $-C(O)OR$, $-NH_2$, $-NHR$, $-NR_2$, or $-NO_2$, wherein each R is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, and sulfur.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration", "administered systemically", "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

The term "enriched" as used herein refers to a mixture having an increased proportion of one or more species. In some embodiments, the mixture is "enriched" following a process that increases the proportion of one or more desired species in the mixture. In some embodiments, the desired species comprise(s) greater than 10% of the mixture. In some embodiments, the desired species comprise(s) greater than 25% of the mixture. In some embodiments, the desired species comprise(s) greater than 40% of the mixture. In some embodiments, the desired species comprise(s) greater than 60% of the mixture. In some embodiments, the desired species comprise(s) greater than 75% of the mixture. In some embodiments, the desired species comprise(s) greater than 85% of the mixture. In some embodiments, the desired species comprise(s) greater than 90% of the mixture. In some embodiments, the desired species comprise(s) greater than 95% of the mixture. Such proportions can be measured any number of ways, for example, as a molar ratio, volume to volume, or weight to weight.

The term "pure" refers to compounds that are substantially free of compounds of related non-target structure or chemical precursors (when chemically synthesized). This quality may be measured or expressed as "purity". In some embodiments, a target compound has less than about 30%, 20%, 10%, 5%, 2%, 1%, 0.5%, and 0.1% of non-target structures or chemical precursors. In certain embodiments, a pure compound of present invention is only one prosapogenin compound (i.e., separation of target prosapogenin from other prosapogenins).

The term "carbohydrate" refers to a sugar or polymer of sugars. The terms "saccharide", "polysaccharide", "carbohydrate", and "oligosaccharide", may be used interchangeably. Most carbohydrates are aldehydes or ketones with many hydroxyl groups, usually one on each carbon atom of the molecule. Carbohydrates generally have the molecular formula $C_nH_{2n}O_n$. A carbohydrate may be a monosaccharide, a disaccharide, trisaccharide, oligosaccharide, or polysaccharide. The most basic carbohydrate is a monosaccharide, such as glucose, sucrose, galactose, mannose, ribose, arabinose, xylose, and fructose. Disaccharides are two joined monosaccharides. Exemplary disaccharides include sucrose, maltose, cellobiose, and lactose. Typically, an oligosaccharide includes between three and six monosaccharide units (e.g., raffinose, stachyose), and polysaccharides include six or more monosaccharide units. Exemplary polysaccharides include starch, glycogen, and cellulose. Carbohydrates may contain modified saccharide units such as 2'-deoxyribose wherein a hydroxyl group is removed, 2'-fluororibose wherein a hydroxyl group is replace with a fluorine, or N-acetylglucosamine, a nitrogen-containing form of glucose. (e.g., 2'-fluororibose, deoxyribose, and hexose). Carbohydrates may exist in many different forms, for example, conformers, cyclic forms, acyclic forms, stereoisomers, tautomers, anomers, and isomers.

The term "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in *J. Pharmaceutical Sciences,* 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

The compounds of the present disclosure may contain one or more acidic functional groups and, thus, are capable of forming pharmaceutically-acceptable salts with pharmaceutically acceptable bases. The term "pharmaceutically acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary, tertiary, or quaternary amine. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate. Representative organic amines useful for the formation of base addition salts include ethylamine, diethylamine, ethylenediamine, ethanolamine, diethanolamine, piperazine and the like.

Unless otherwise stated, structures depicted herein are also meant to include all isomeric (e.g., enantiomeric, diastereomeric, and geometric (or conformational)) forms of the structure; for example, the R and S configurations for each stereocenter, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

Provided compounds may comprise one or more saccharide moieties. Unless otherwise specified, both D- and L-configurations, and mixtures thereof, are within the scope of the invention. Unless otherwise specified, both α- and β-linked embodiments, and mixtures thereof, are contemplated by the present invention.

If, for instance, a particular enantiomer of a compound of the present disclosure is desired, it may be prepared by asymmetric synthesis, chiral chromatography, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention.

One of ordinary skill in the art will appreciate that the synthetic methods, as described herein, utilize a variety of protecting groups.

The term "protecting group" refers to a functional group that masks or blocks a particular functional moiety (e.g., O, S, or N), thus permitting, if desired, a reaction to be carried out selectively at another reactive site in a multifunctional compound. In preferred embodiments, a protecting group reacts selectively in good yield to give a protected substrate that is stable to the projected reactions; the protecting group is preferably selectively removable by readily available, preferably non-toxic reagents that do not attack the other functional groups; the protecting group forms a separable derivative (more preferably without the generation of new stereogenic centers); and the protecting group will preferably have a minimum of additional functionality to avoid further sites of reaction. As detailed herein, oxygen, sulfur, nitrogen, and carbon protecting groups may be utilized.

By way of non-limiting example, oxygen proteinting groups (which include hydroxyl protecting groups and carboxyl protecting groups) include methyl, methoxymethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, a-naphthyldiphenylmethyl, p-methoxyphenyldiphenylmethyl, di(p-methoxyphenyl)phenylmethyl, tri (p-methoxyphenyl)methyl, 4-(4'-bromophenacyloxyphenyl) diphenylmethyl, 4,4',4"-tris(4,5-dichlorophthalimidophenyl)methyl, 4,4',4"-tris (levulinoyloxyphenyl)methyl, 4,4',4"-tris (benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-naphthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, a-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

For protecting 1,2- or 1,3-diols, the protecting groups include methylene acetal, ethylidene acetal, 1-t-butylethylidene ketal, 1-phenylethylidene ketal, (4-methoxyphenyl) ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

Amino-protecting groups include methyl carbamate, ethyl carbamante, 9-fluorenylmethyl carbamate (Fmoc), 9-(2-sulfo)fluorenylmethyl carbamate, 9-(2,7-dibromo)fluorenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido) propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl) ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxycarbonylamino) acetamide, 3-(p-hydroxyphenyl)propanamide, 3-(o-nitrophenyl)propanamide, 2-methyl-2-(o-nitrophenoxy) propanamide, 2-methyl-2-(o-phenylazophenoxy) propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)-amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyl-eneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N',N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide. Exemplary protecting groups are detailed herein, however, it will be appreciated that the present invention is not intended to be limited to these protecting groups; rather, a variety of additional equivalent protecting groups can be readily identified using the above criteria and utilized in the method of the present invention.

Triterpene Saponin Variants

The structure of saponin compounds, for example QS-21 (compound 1), contain four various domains: a branched trisaccharide, a quillaic acid triterpene, a bridging linear oligosaccharide, and a pseudo-dimeric acyl chain (see FIG. 1, Panel a). The primary constituents of natural QS-21 extracts are a ≈2:1 mixture of xylose (1a) and apiose (1b) isomers at the terminus of the linear oligosaccharide domain. In the present invention, a number of saponin variants have been obtained by way of modifying the central glycosyl ester linkage that connects the triterpene and the linear oligosaccharide domains. The central glycosyl ester linkage is a unique structural feature of the *Quillaja saponaria* (QS) saponins that has never been unexplored before.

One aspect of the present disclosure relates to a triterpene saponin variant having the structure of formula I or a pharmaceutically acceptable salt thereof,

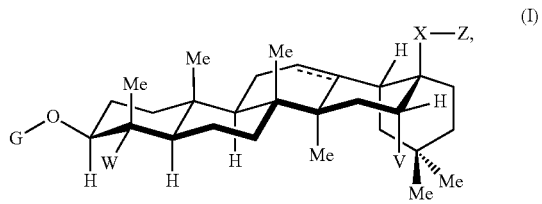

(I)

wherein G is hydrogen, a monosaccharide, a disaccharide or an oligosaccharide wherein W is Me, —CHO, —CH$_2$OR$^x$, —C(O)R$^y$ or

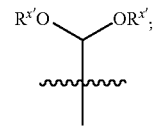

wherein each occurrence of R$^x$ is independently hydrogen or an oxygen protecting group, optionally selected from the group consisting of alkyl ethers, benzyl ethers, silyl ethers, acetals, ketals, esters, carbamates, and carbonates;

wherein each occurrence of R$^{x'}$ is independently an optionally substituted group selected from 6-10-membered aryl, benzyl, C$_{1-6}$ aliphatic, or C$_{1-6}$ heteroaliphatic having 1-2 heteroatoms independently selected from the group consisting of nitrogen, oxygen, and sulfur; or two R$^{x'}$ are taken together to form a 5-7-membered heterocyclic ring having 1-2 heteroatoms independently selected from the group consisting of nitrogen, oxygen, and sulfur;

wherein each occurrence of R$^y$ is —OH, or a carboxyl protecting group selected from the group consisting of esters, amides, and hydrazides; In some embodiments, R$^y$ is —OH or —OR$^x$.

wherein $=$ is a single or double bond;

wherein V is hydrogen or —OR$^x$;

wherein X has the structure of $-(A-B-D-E)-$, wherein each of A, B, D and E is —C(O)—, —NH—, —S—, —O—, C$_{1-5}$ aliphatic or is absent with the proviso that at least one of A, B, D and E is present at any time and that X is not a β-ester with a structure of —C(O)O—. As used herein, the term "β" refers to the stereochemical configuration at the anomeric carbon in Z that is directly attached to the X moiety in formula I.

wherein Z is hydrogen, a cyclic or acyclic, optionally substituted moiety selected from the group consisting of acyl, aliphatic, heteroaliphatic, aryl, arylalkyl, and heteroaryl; or a carbohydrate domain having the structure:

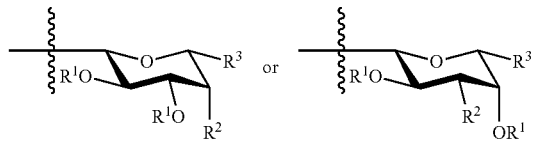

wherein each occurrence of R$^1$ is R$^x$ or a carbohydrate domain having the structure:

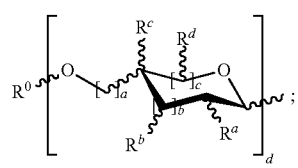

wherein each occurrence of a, b, and c is independently 0, 1, or 2; wherein d is an integer from 1-5, wherein each d bracketed structure may be the same or different; with the proviso that the d bracketed structure represents a furanose or pyranose moiety, and the sum of b and c is 1 or 2; wherein $R^O$ is hydrogen, an oxygen protecting group selected from the group consisting of alkyl ethers, benzyl ethers, silyl ethers, acetals, ketals, esters, carbamates, and carbonates; or an optionally substituted moiety selected from the group consisting of acyl, $C_{1-10}$ aliphatic, $C_{1-6}$ heteroaliphatic, 6-10-membered aryl, arylalkyl, 5-10-membered heteroaryl having 1-4 heteroatoms independently selected from nitrogen, oxygen, and sulfur, 4-7-membered heterocyclyl having 1-2 heteroatoms independently selected from the group consisting of nitrogen, oxygen, and sulfur; wherein each occurrence of $R^a$, $R^b$, $R^c$, and $R^d$ is independently hydrogen, halogen, OH, OR, $OR^x$, $NR_2$, NHCOR, or an optionally substituted group selected from acyl, $C_{1-10}$ aliphatic, $C_{1-6}$ heteroaliphatic, 6-10-membered aryl, arylalkyl, 5-10-membered heteroaryl having 1-4 heteroatoms independently selected from nitrogen, oxygen, and sulfur; 4-7-membered heterocyclyl having 1-2 heteroatoms independently selected from the group consisting of nitrogen, oxygen, and sulfur; wherein $R^2$ is hydrogen, halogen, OH, OR, OR, $OC(O)R^4$, $OC(O)OR^4$, $OC(O)NHR^4$, $OC(O)NRR^4$, $OC(O)SR^4$, $NHC(O)R^4$, $NRC(O)R^4$, $NHC(O)OR^4$, $NHC(O)NHR^4$, $NHC(O)NRR^4$, $N(R^4)_2$, $NHR^4$, $NRR^4$, $N_3$, or an optionally substituted group selected from $C_{1-10}$ aliphatic, $C_{1-6}$ heteroaliphatic, 6-10-membered aryl, arylalkyl, 5-10-membered heteroaryl having 1-4 heteroatoms independently selected from the group consisting of nitrogen, oxygen, and sulfur, 4-7-membered heterocyclyl having 1-2 heteroatoms independently selected from the group consisting of nitrogen, oxygen, and sulfur; wherein $R^3$ is hydrogen, halogen, $CH_2OR^1$, or an optionally substituted group selected from the group consisting of acyl, $C_{1-10}$ aliphatic, $C_{1-6}$ heteroaliphatic, 6-10-membered aryl, arylalkyl, 5-10-membered heteroaryl having 1-4 heteroatoms independently selected from the group consisting of nitrogen, oxygen, and sulfur; 4-7-membered heterocyclyl having 1-2 heteroatoms independently selected from the group consisting of nitrogen, oxygen, and sulfur; wherein $R^4$ is

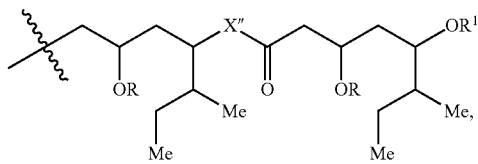

wherein X" is —O—, —NR—; or wherein $R^4$ is $T-R^z$, wherein T is a covalent bond or a bivalent $C_{1-26}$ saturated or unsaturated, straight or branched, aliphatic or heteroaliphatic chain; and $R^z$ is hydrogen, halogen, —OR, $—OR^x$, $—OR^1$, —SR, $—NR^2$, —NC(O)OR, —C(O)OH or an optionally substituted group selected from acyl, arylalkyl, heteroarylalkyl, $C_{1-6}$ aliphatic, 6-10-membered aryl, 5-10-membered heteroaryl having 1-4 heteroatoms independently selected from nitrogen, oxygen, and sulfur, 4-7-membered heterocyclyl having 1-2 heteroatoms independently selected from the group consisting of nitrogen, oxygen and sulfur; or two $R^4$ on the same nitrogen atom are taken with the nitrogen to form a 4-7-membered heterocyclic ring having 1-2 heteroatoms independently selected from the group consisting of nitrogen, oxygen, and sulfur; and wherein each occurrence of R is independently hydrogen, an optionally substituted group selected from acyl, arylalkyl, 6-10-membered aryl, $C_{1-12}$ aliphatic, or $C_{1-12}$ heteroaliphatic having 1-2 heteroatoms independently selected from the group consisting of nitrogen, oxygen, and sulfur; or two R on the same nitrogen atom are taken with the nitrogen to form a 4-7-membered heterocyclic ring having 1-2 heteroatoms independently selected from the group consisting of nitrogen, oxygen, and sulfur.

In some embodiments, X is selected from the group consisting of α- and β-glycosyl ethanolamide, α- and β-glycosyl carbamate, α- and β-glycosyl thioester, α-glycosyl ester, α- and β-glycosyl amide, α- and β-glycosyl ether and α- and β-glycosyl thioether. As used herein, the term "α" or "β" refers to the stereochemical configuration at the anomeric carbon in Z that is directly attached to the X moiety in formula I.

In some embodiments, X is selected from the group consisting of β-glycosyl ethanolmide, α-glycosyl carbamate, β-glycosyl carbamate, β-glycosyl thioester, α-glycosyl ester, α-glycosyl amide, β-glycosyl ether and β-glycosyl thioether. In some embodiments, X is β-glycosyl thioester, α-glycosyl amide, β-glycosyl ether or β-glycosyl thioether. In some embodiments, X is β-glycosyl thioester.

In some embodiments, G is a monosaccharide of formula II, or a stereoisomer of formula II,

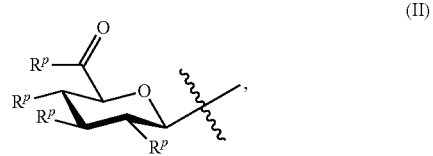

wherein each occurrence of $R^p$ is independently hydrogen or $OR^x$.

In some embodiments, G is a disaccharide of formula III, or a stereoisomer of formula III,

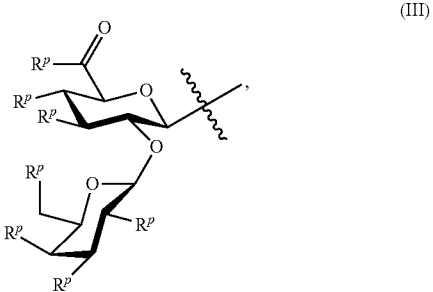

wherein each occurrence of $R^p$ is independently hydrogen or $OR^x$.

In some embodiments, G is an oligosaccharide of formula IV, or a stereoisomer of formula IV,

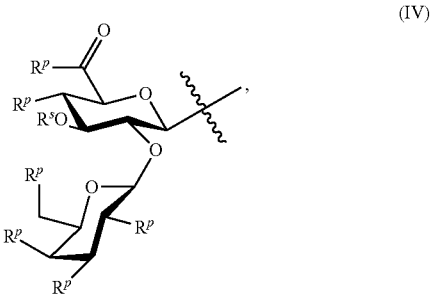

wherein each occurrence of $R^p$ is independently hydrogen or $OR^x$, and wherein $R^s$ is

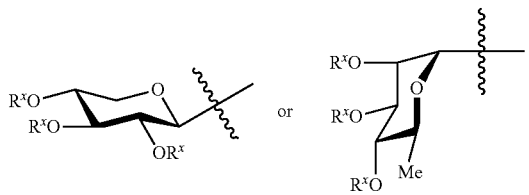

or a stereoisomer thereof.

In some embodiments, G is

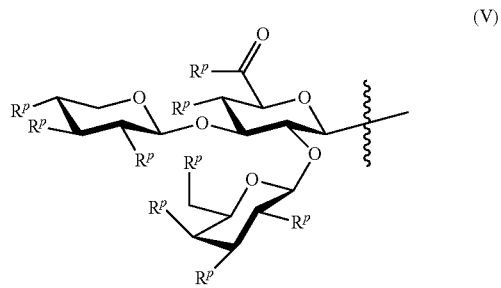

(V)

In some embodiments, G is

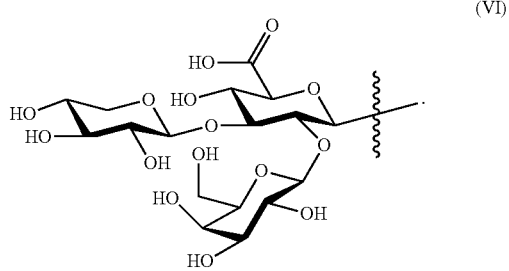

(VI)

In some embodiments, Z is

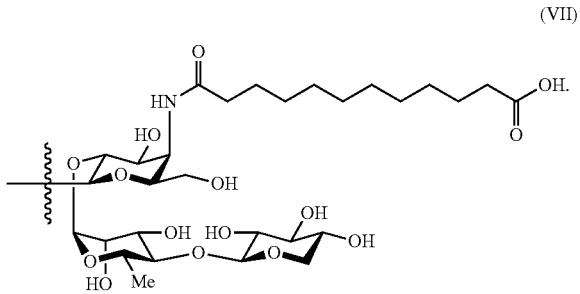

(VII)

In some embodiments, G is formula V, Z is formula VI and X is selected from the group consisting of β-glycosyl ethanolmide, β-glycosyl carbamate, β-glycosyl thioester, α-glycosyl carbamate, α-glycosyl ester, α-glycosyl amide, β-glycosyl ether and β-glycosyl thioether.

In some embodiments, G is formula V, Z is formula VI, and X is β-glycosyl thioester, α-glycosyl amide, β-glycosyl ether or (β-glycosyl thioether.

In some embodiments, G is formula V, Z is formula VI, and X is a β-glycosyl thioester.

Compounds of this disclosure include those described generally above, and are further illustrated by the classes, subclasses, and species disclosed herein. In some embodiments, provided compounds are variants or analogs of naturally occurring triterpene glycoside saponins and intermediates thereto. For purposes of this invention, the chemical elements are identified in accordance with the Periodic Table of the Elements, CAS version, *Handbook of Chemistry and Physics*, 75$^{th}$ Ed. Additionally, general principles of organic chemistry are described in *Organic Chemistry*, Thomas Sorrell, University Science Books, Sausalito: 1999, and *March's Advanced Organic Chemistry*, 5$^{th}$ Ed., Ed.: Smith, M. B. and March, J., John Wiley & Sons, New York: 2001, the entire contents of which are hereby incorporated by reference.

In some embodiments, W is methyl. In some embodiments, W is —CHO. In some embodiments, W is —CH$_2$OR$^x$. In some embodiments, W is —C(O)OR. In some embodiments, W is —CH$_2$OH. In some embodiments, W is —CH$_2$OBn. In some embodiments, W is —CH$_2$OSiEt$_3$. In some embodiments, W is —C(O)OH. In some embodiments, W is —C(O)OBn.

In some embodiments, V is —OR$^x$. In some embodiments, V is —OH. In some embodiments, V is hydrogen.

In the description provided above, ⚌ represents a single or double bond. It will be appreciated that compounds of formula I can be subjected to hydrogenation conditions (infra) that reduce the double bond to a single bond.

In some embodiments, the linker group is an optionally substituted, straight or branched C$_{1-12}$ aliphatic or heteroaliphatic group. In some examples, the linker group is —(CH$_2$)$_k$—, wherein k is an integer between 1 and 10, inclusive. In some embodiments, Z is an optionally substituted aliphatic group. In some embodiments, Z is an optionally substituted C$_{1-30}$ aliphatic group. In some embodiments, Z is an optionally substituted C$_{1-20}$ aliphatic group. In some embodiments, Z is an optionally substituted C$_{1-16}$ aliphatic group. In some examples, Z is an optionally substituted C$_{1-12}$ aliphatic group. In some embodiments, Z is an optionally substituted C$_{1-10}$ aliphatic group. In some embodiments, Z is an optionally substituted C$_{1-6}$ aliphatic group. In some examples, Z is an optionally substituted C$_{2-12}$ aliphatic group.

In some embodiments, Z is an optionally substituted heteroaliphatic group. In some embodiments, Z is an optionally substituted C$_{1-30}$ heteroaliphatic group. In some embodiments, Z is an optionally substituted C$_{1-20}$ heteroaliphatic group. In some embodiments, Z is an optionally substituted C$_{1-16}$ heteroaliphatic group. In some embodiments, Z is an optionally substituted C$_{1-12}$ heteroaliphatic group. In some embodiments, Z is an optionally substituted C$_{1-10}$ heteroaliphatic group. In some embodiments, Z is an optionally substituted C$_{1-6}$ heteroaliphatic group. In some embodiments, Z is an optionally substituted C$_{2-12}$ heteroaliphatic group.

In certain embodiments, Z is an optionally substituted heteroaryl group having 1-4 heteroatoms independently selected from nitrogen, oxygen, and sulfur. In certain embodiments, Z is an optionally substituted 5-12-membered heteroaryl group. In certain embodiments, Z is an optionally substituted 5-10-membered heteroaryl group. In certain embodiments, Z is an optionally substituted 6-8-membered heteroaryl group.

In certain embodiments, Z is an optionally substituted aryl group. In certain embodiments, Z is an optionally substituted 6-12-membered aryl group. In certain embodiments, Z is an optionally substituted 6-10-membered aryl group. In certain embodiments, Z is an optionally substituted 6-8-membered aryl group.

In some embodiments, Z is an optionally substituted heterocyclyl group. In certain embodiments, Z is an optionally substituted 4-7-membered heterocyclyl group having 1-2 heteroatoms independently selected from the group consisting of nitrogen, oxygen, and sulfur.

In some embodiments, Z is an optionally substituted arylalkyl group. In some embodiments, Z is an optionally substituted $C_{7-12}$ arylalkyl group. In some examples, Z is an optionally substituted $C_{7-10}$ arylalkyl group. In some examples, Z is an optionally substituted $C_{7-8}$ arylalkyl group.

In some embodiments, Z is a monosaccharide. In some examples, Z is an oligosaccharide. In certain embodiments, Z is a carbohydrate domain having the structure:

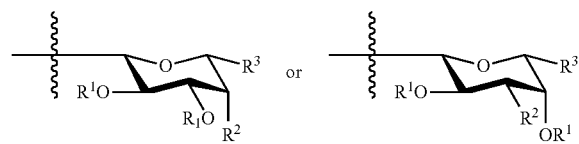

wherein each of $R^1$, $R^2$, and $R^3$ is defined as described in classes and subclasses above and herein.

In certain embodiments, Z has the structure:

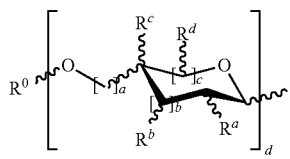

wherein each of $R^0$, $R^a$, $R^b$, $R^c$, $R^d$, a, b, c, and d is defined as described in classes and subclasses above and herein.

As described above, the Z moiety is linked to the triterpene core via X. In some examples, Z is a monosaccharide and is D-fucosyl. In some examples, Z is a monosaccharide and is L-fucosyl. In some examples, Z is a monosaccharide and is not fucosyl. In some examples, Z is a monosaccharide and is not β-D-fucosyl.

In some examples, Z is an oligosaccharide, and the carbohydrate domain directly attached to X is fucosyl. In some examples, Z is an oligosaccharide, and the carbohydrate domain directly attached to X is not D-fucosyl. In some examples, Z is an oligosaccharide, and the carbohydrate domain directly attached to X is not β-D-fucosyl. In some examples, Z is an oligosaccharide, and the carbohydrate domain directly attached to X is not α-D-fucosyl. In some examples, Z is an oligosaccharide, and the carbohydrate domain directly attached to X is not fucosyl.

In some examples, Z is an optionally substituted monosaccharide and is D-fucosyl. In some examples, Z is an optionally substituted monosaccharide and is L-fucosyl. In some examples, Z is an optionally substituted monosaccharide and is not β-D-fucosyl. In some examples, when a carbohydrate domain of Z is directly attached to X, the carbohydrate domain directly attached to X is not fucosyl. In certain examples, when Z is H, Me, or allyl, at least seven $R^x$ groups are silyl ethers. In some examples, Z and $R^x$ are not all simultaneously hydrogen or methyl. In some examples, Z is not Me. In some examples, Z is not H. In some examples, Z is not allyl. In some examples, Z is not H or Me if all $R^x$ groups are simultaneously hydrogen or if at least four $R^x$ groups are simultaneously methyl In some embodiments, $R^y$ is not a lipophilic group. In some examples, when a carbohydrate moiety of Z is non-acylated and all $R^x$ are simulataneously hydrogen, the 3-O-glucuronic acid residue of the triterpene is not covalently attached, directly or indirectly, to a compound having a lipophilic domain, wherein the lipophilic domain is attached via the carboxylic acid carbon atom present on the 3-O-glucuronic acid residue.

In certain embodiments, each occurrence of $R^y$ is independently —OH. In certain examples, each occurrence of $R^y$ is independently —OR. In certain examples, each occurrence of $R^y$ is independently a carboxyl protecting group. Suitable carboxyl protecting groups are well known in the art and include those described in detail in *Protecting Groups in Organic Synthesis*, T. W. Greene and P. G. M. Wuts, $3^{rd}$ edition, John Wiley & Sons, 1999, the entirety of which is incorporated herein by reference.

In some embodiments, each occurrence of $R^y$, when taken with its attached carbonyl group, independently comprises an ester. In some examples, each occurrence of $R^y$, when taken with its attached carbonyl group, independently comprises an amide. In some examples; each occurrence of $R^y$, when taken with its attached carbonyl group, independently comprises a hydrazide.

In some embodiments, each occurrence of $R^y$ is independently —OBn. In other embodiments, each occurrence of $R^y$ is independently —OEt.

In certain embodiments, each occurrence of $R^x$ is independently hydrogen. In certain examples, each occurrence of $R^x$ is independently a suitable hydroxyl protecting group. Suitable hydroxyl protecting groups are well known in the art. In some examples, no more than four $R^x$ groups are simultaneously methyl.

In some embodiments, $R^s$ is

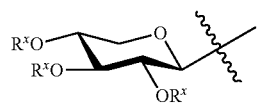

or a stereoisomer thereof.

In some embodiments, $R^s$ is

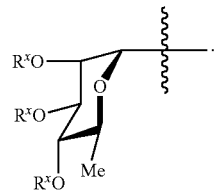

In some embodiments, $R^s$ is

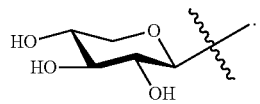

In some embodiments, $R^s$ is

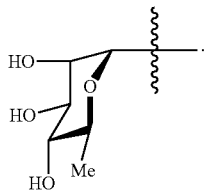

In some embodiments, each occurrence of $R^x$, when taken with its attached oxygen atom, independently comprises a methyl ether, ethyl ether, benzyl ether, silyl ether, ester, acetal, ketal, or carbonate. In some embodiments, $R^x$ comprises a methyl ether. In some embodiments, $R^x$ comprises a ethyl ether. In some embodiments, $R^x$ comprises a benzyl ether. In some examples, $R^x$ comprises a silyl ether. In some examples, $R^x$ comprises an ester. In some examples, $R^x$ comprises an acetal. In some embodiments, $R^x$ comprises a ketal. In some embodiments, $R^x$ comprises a carbonate.

In certain embodiments, $R^x$ is methyl. In certain embodiments, $R^x$ is ethyl. In certain embodiments, $R^x$ is benzyl. In certain embodiments, $R^x$ is $SiR_3$. In certain embodiments, $R^x$ is $SiMe_3$. In certain embodiments, $R^x$ is TBS.

In certain embodiments, $R^x$ is

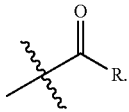

In certain embodiments, $R^x$ is

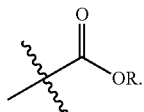

In certain embodiments, $R^x$ is

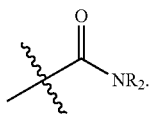

In some embodiments, two —$OR^x$ attached to adjacent carbon atoms on a saccharide ring are taken together to form a 5-7-membered heterocyclic ring having 1-2 heteroatoms independently selected from the group consisting of nitrogen, oxygen, and sulfur. In some embodiments, two —$OR^x$ attached to adjacent carbon atoms on a saccharide ring are taken together to form a cyclic acetal protecting group. In some embodiments, two —$OR^x$ attached to adjacent carbon atoms on a saccharide ring are taken together to form a cyclic ketal protecting group.

In certain embodiments, each $R^{x'}$ is independently hydrogen. In certain embodiments, each $R^{x'}$ is independently an optionally substituted 6-10-membered aryl group. In certain embodiments, each $R^{x'}$ is independently an optionally substituted $C_{1-6}$ aliphatic group. In certain embodiments, each $R^{x'}$ is independently an optionally substituted $C_{1-6}$ heteroaliphatic group having 1-2 heteroatoms independently selected from the group consisting of nitrogen, oxygen, and sulfur. In some embodiments, two $R^{x'}$ are taken together to form a 5-7-membered heterocyclic ring having 1-2 heteroatoms independently selected from the group consisting of nitrogen, oxygen, and sulfur.

In some embodiments, all $R^x$ are hydrogen.

In certain embodiments, $R^1$ is a carbohydrate domain having the structure:

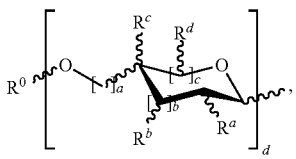

wherein each of $R^0$, $R^a$, $R^b$, $R^c$, $R^d$, a, b, c, and d is defined as described in classes and subclasses above and herein. In some embodiments, a is 0. In some embodiments, a is 1.

In some embodiments, b is 0. In some embodiments, b is 1. In some embodiments, b is 2.

In some embodiments, c is 0. In some embodiments, c is 1. In some embodiments, c is 2.

In certain embodiments, the sum of b and c is 1. In certain embodiments, the sum of b and c is 2.

In certain embodiments, d is an integer from 1-7. In some embodiments, d is an integer from 1-5. In some embodiments, d is an integer from 1-4. In some embodiments, d is an integer from 1-2. In certain embodiments, each d-bracketed structure is the same. In certain embodiments, each d-bracketed structure is different. In certain embodiments, two or more d-bracketed structures are the same. In some embodiments, one or more d-bracketed structures is a furanose moiety. In some embodiments, one or more d-bracketed structure is a pyranose moiety.

In some embodiments, $R^0$ is hydrogen. In some embodiments, $R^0$ is an oxygen protecting group selected from the group consisting of alkyl ethers, benzyl ethers, silyl ethers, acetals, ketals, esters, carbamates, and carbonates. In other embodiments, $R^0$ is an optionally substituted moiety selected from the group consisting of acyl and $C_{1-10}$ aliphatic.

In some embodiments, each occurrence of $R^a$, $R^b$, $R^c$, and $R^d$ is hydrogen. In some embodiments, each occurrence of $R^a$, $R^b$, $R^c$, and $R^d$ is —OH. In some embodiments, each occurrence of $R^a$, $R^b$, $R^c$, and $R^d$ is independently —OR. In some embodiments, each occurrence of $R^a$, $R^b$, $R^c$, and $R^d$ is independently —$OR^x$. In some embodiments, each occurrence of $R^a$, $R^b$, $R^c$, and $R^d$ is independently an optionally substituted $C_{1-10}$ aliphatic group. In some embodiments, each occurrence of $R^a$, $R^b$, $R^c$, and $R^d$ is independently an optionally substituted $C_{1-6}$ heteroaliphatic group. In some embodiments, each occurrence of $R^a$, $R^b$, $R^c$, and $R^d$ is —$CH_2OH$. In some embodiments, each occurrence of $R^a$, $R^b$, $R^c$, and $R^d$ is methyl.

As generally described above, in certain embodiments, $R^1$ is a carbohydrate domain. In some embodiments, $R^1$ is a monosaccharide. In some embodiments, $R^1$ is an oligosaccharide. In certain embodiments, each occurrence of $R^1$ is independently selected from the group consisting of:

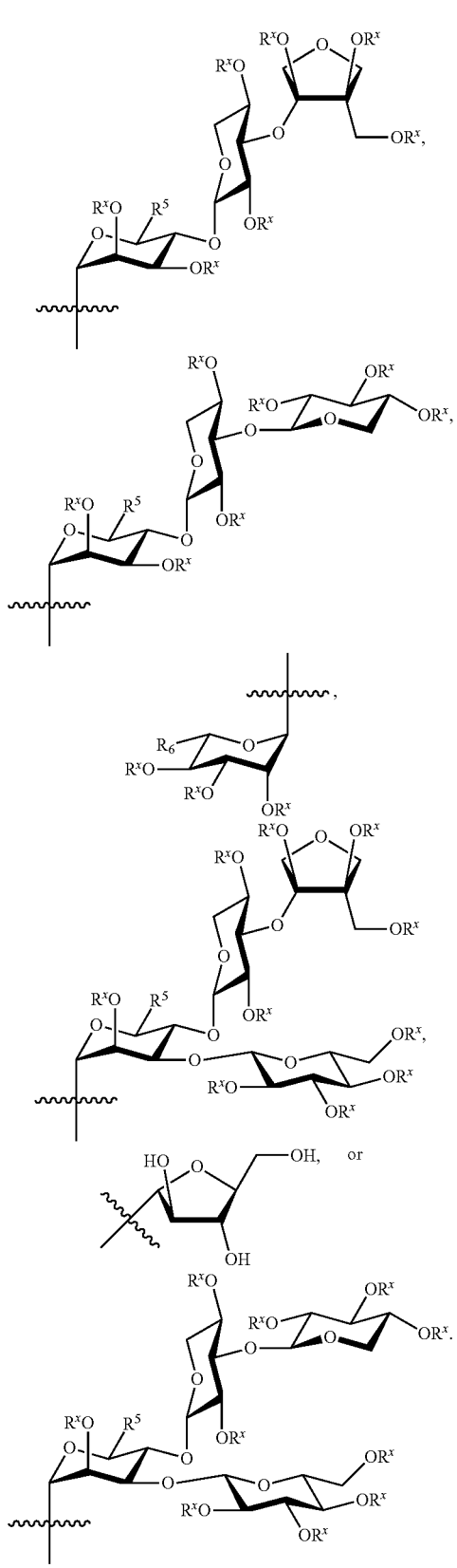

In certain embodiments, R² is hydrogen. In certain embodiments, R² is halogen. In certain embodiments, R² is —OH. In certain embodiments, R² is OR. In certain embodiments, R² is —OC(O)R⁴. In certain embodiments, R² is —OC(O)OR⁴. In certain embodiments, R² is —OC(O)NHR⁴. In certain embodiments, R² is —OC(O)NRR⁴. In certain embodiments, R² is —OC(O)SR⁴. In certain embodiments, R² is —NHC(O)R⁴. In certain embodiments, R² is —NRC(O)R⁴. In certain embodiments, R² is —NHC(O)OR⁴. In certain embodiments, R² is —NHC(O)NHR⁴. In certain embodiments, R² is —NHC(O)NRR⁴. In certain embodiments, R² is —N(R⁴)₂. In certain embodiments, R² is —NHR⁴. In certain embodiments, R² is NRR⁴. In some embodiments, R² is N₃.

In some embodiments, R² is an optionally substituted group selected from $C_{1-30}$ aliphatic. In some embodiments, R² is an optionally substituted group selected from $C_{1-20}$ aliphatic. In some embodiments, R² is an optionally substituted group selected from $C_{1-10}$ aliphatic.

In some embodiments R² is an optionally substituted group selected from $C_{1-30}$ heteroaliphatic. In some embodiments, R² is an optionally substituted group selected from $C_{1-20}$ heteroaliphatic. In some embodiments, R² is an optionally substituted group selected from $C_{1-10}$ heteroaliphatic. In some embodiments, R² is an optionally substituted group selected from $C_{1-6}$ heteroaliphatic.

In some embodiments, R³ is hydrogen. In some embodiments, R³ is halogen. In some embodiments, R³ is —OH. In some embodiments, R³ is —OR. In some embodiments, R³ is —OR^x. In some embodiments, R³ is an optionally substituted $C_{1-10}$ aliphatic group. In some embodiments, R³ is an optionally substituted $C_{1-6}$ heteroaliphatic group. In some embodiments, R³ is not hydrogen. In some embodiments, R³ is not —OH. In some embodiments, R³ is —CH₂OR. In some embodiments, R³ is —CH₂OH. In some embodiments, R³ is methyl. In some embodiments, R³ is not methyl. In some embodiments, R³ is CH₂OR¹.

In some embodiments, R⁴ is

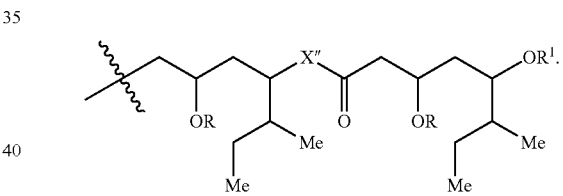

In some embodiments, X" is —O—. In some embodiments, X" is —NR—.

In some embodiments, R⁴ is

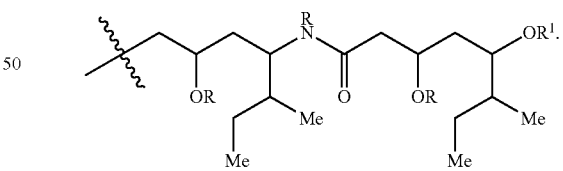

In some embodiments, R⁴ is

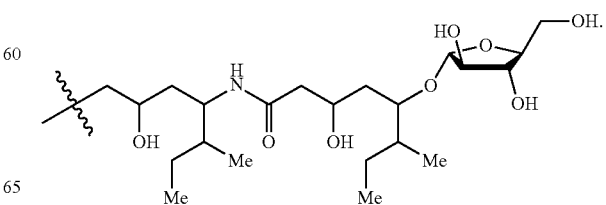

In some embodiments, $R^4$ is

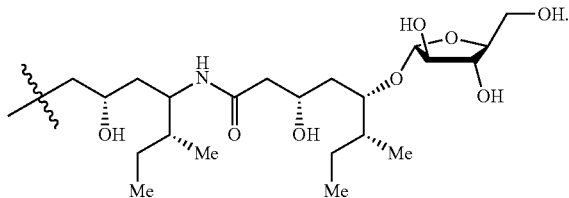

In certain embodiments, $R^2$ is —NHC(O)$R^4$; and $R^4$ is

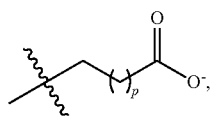

wherein p is an integer from 0 to 12, inclusive. In certain embodiments, $R^2$ is —NHC(O)$R^4$; and $R^4$ is

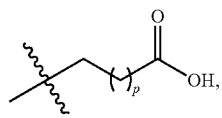

wherein p is an integer from 0 to 12, inclusive. In certain embodiments, $R^2$ is —NHC(O)$R^4$; and $R^4$ is

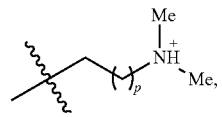

wherein p is an integer from 0 to 12, inclusive. In certain embodiments, $R^2$ is —NHC(O)$R^4$; and $R^4$ is

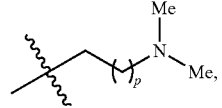

wherein p is an integer from 0 to 12, inclusive. In certain embodiments, $R^2$ is —NHC(O)$R^4$; and $R^4$ is

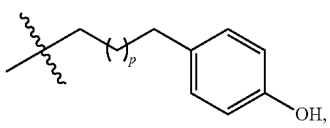

wherein p is an integer from 0 to 12, inclusive. In certain embodiments, $R^2$ is —NHC(O)$R^4$; and $R^4$ is

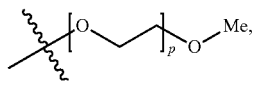

wherein p is an integer from 1 to 12, inclusive. In certain embodiments, $R^2$ is —NHC(O)$R^4$; and $R^4$ is

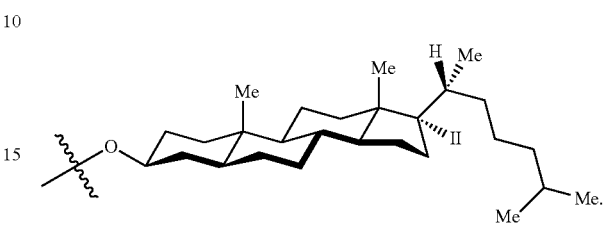

In certain embodiments, two $R^4$ on the same nitrogen atom are taken with the nitrogen to form a 4-7-membered heterocyclic ring having 1-2 heteroatoms independently selected from the group consisting of nitrogen, oxygen, and sulfur.

As described above, in certain embodiments, $R^4$ is T-$R^z$. In some embodiments, T is a covalent bond or a bivalent $C_{1-26}$ saturated or unsaturated, straight or branched, hydrocarbon chain, wherein one or two methylene units of T are optionally and independently replaced by O, —S—, —N(R)—, —C(O)—, —C(O)O—, —OC(O)—, —N(R)C(O)—, —C(O)N(R)—, —S(O), —S(O)$_2$—, —N(R)SO$_2$—, or —SO$_2$N(R)—. In certain embodiments, T is a covalent bond or a bivalent $C_{1-16}$ saturated or unsaturated, straight or branched, aliphatic or heteroaliphatic chain. In certain embodiments, T is a covalent bond or a bivalent $C_{1-12}$ saturated or unsaturated, straight or branched, aliphatic or heteroaliphatic chain. In certain embodiments s, T is a covalent bond or a bivalent $C_{1-8}$ saturated or unsaturated, straight or branched, aliphatic or heteroaliphatic chain. In certain embodiments, -T- is selected from the group consisting of

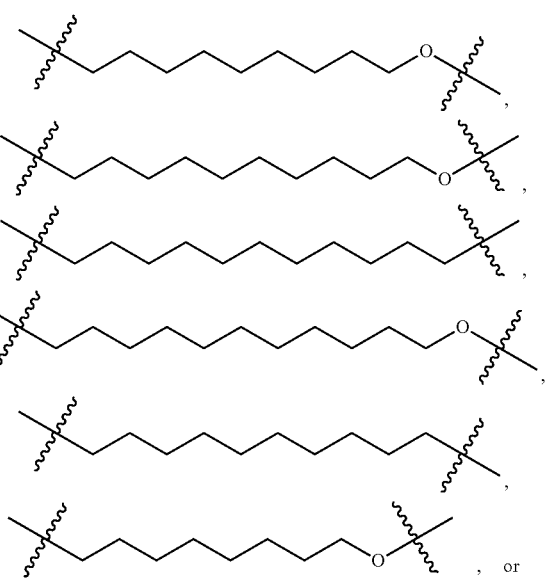

, or

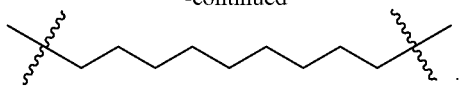

In some embodiments, $R^z$ is hydrogen. In some embodiments, $R^z$ is halogen. In certain embodiments, $R^z$ is —NC(O)OR. In some embodiments, $R^z$ is —OR. In some embodiments, $R^z$ is —OR$^1$. In some embodiments s, $R^z$ is —OR. In some embodiments, $R^z$ is —NR$^2$. In certain embodiments, $R^z$ is an optionally substituted acyl group. In certain embodiments, $R^z$ is —C(O)OH. In certain embodiments, $R^Z$ is an optionally substituted arylalkyl group. In certain embodiments, $R^z$ is an optionally substituted heteroarylalkyl group. In certain embodiments, $R^z$ is an optionally substituted $C_{1-6}$ aliphatic group. In certain embodiments, $R^z$ is an optionally substituted 6-10-membered aryl group. In certain embodiments, $R^z$ is an optionally substituted 5-10-membered heteroaryl having 1-4 heteroatoms independently selected from nitrogen, oxygen, and sulfur group. In certain embodiments, $R^z$ is an optionally substituted 4-7-membered heterocyclyl having 1-2 heteroatoms independently selected from the group consisting of nitrogen, oxygen and sulfur. In certain embodiments, $R^z$ is a monosaccharide. In certain embodiments, $R^z$ is an oligosaccharide. In certain embodiments, $R^z$ is methyl. In certain embodiments, $R^z$ is

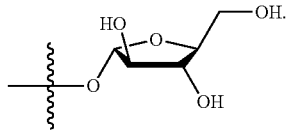

In some embodiments, each occurrence of R is independently hydrogen. In some embodiments, each occurrence of R is independently an optionally substituted acyl group. In some embodiments each occurrence of R is independently an optionally substituted arylalkyl group. In some embodiments, each occurrence of R is independently an optionally substituted $C_{7-12}$ arylalkyl group. In some embodiments, each occurrence of R is independently an optionally substituted 6-10-membered aryl group. In some examples, each occurrence of R is independently an optionally substituted $C_{1-12}$ aliphatic group. In some embodiments, each occurrence of R is independently an optionally substituted $C_{1-6}$ aliphatic group. In some embodiments, each occurrence of R is independently an optionally substituted $C_{1-6}$ heteroaliphatic group having 1-2 heteroatoms independently selected from the group consisting of nitrogen, oxygen, and sulfur. In some examples, two R on the same nitrogen atom are taken with the nitrogen to form a 4-7-membered heterocyclic ring having 1-2 heteroatoms independently selected from the group consisting of nitrogen, oxygen, and sulfur.

In certain embodiments, $R^5$ and $R^6$ are independently hydrogen, an optionally substituted group selected from the group consisting of acyl, $C_{1-10}$ aliphatic, $C_{1-6}$ heteroaliphatic, 6-10-membered aryl, arylalkyl, 5-10-membered heteroaryl having 1-4 heteroatoms independently selected from the group consisting of nitrogen, oxygen, and sulfur; 4-7-membered heterocyclyl having 1-2 heteroatoms independently selected from the group consisting of nitrogen, oxygen, and sulfur. In certain embodiments, $R^5$ and $R^6$ are independently hydrogen. In some embodiments, $R^5$ and $R^6$ are independently —OH. In some embodiments s, $R^5$ and $R^6$ are independently —OR. In some embodiments, $R^5$ and $R^6$ are independently —OR$^x$. In some embodiments, $R^5$ and $R^6$ are independently an optionally substituted $C_{1-10}$ aliphatic group. In some embodiments, $R^5$ and $R^6$ are independently an optionally substituted $C_{1-6}$ heteroaliphatic group. In some embodiments, $R^5$ and $R^6$ are independently —CH$_2$OR. In some embodiments, $R^5$ and $R^6$ are independently CH$_2$OH. In some embodiments, $R^5$ and $R^6$ are independently methyl.

In some embodiments, each of $R^3$, $R^5$, and $R^6$ is independently an optionally substituted $C_{1-10}$ aliphatic group. In some embodiments, each of $R^3$, $R^5$, and $R^6$ is independently methyl. In some embodiments, each of $R^3$, $R^5$, and $R^6$ is independently —CH$_2$OR. In some embodiments, one or more of $R^3$, $R^5$, and $R^6$ is —CH$_2$OH. In some embodiments, each of $R^3$, $R^5$, and $R^6$ is —CH$_2$OH.

As described in further detail below, some materials used in the synthesis of compounds of formula I may be commerically available extracts derived from natural sources as mixtures of saponins. Such extracts may contain saccharide moieties attached to the C3-position of the triterpene that differ from those depicted in formula I. Examples of saponins and prosapogenins that may be used according to the present invention include those derived from Glycyrrhizic acid, Hederasaponin C, β-Aescin, Helianthoside 2, Ginsenoside Rd, and Saponinum album, to name but a few. All naturally-derived glycosylation variants of the C3 position of the triterpene core are contemplated by the present invention.

In some embodiments, G of formula I is hydrogen, thereby providing a compound shown below

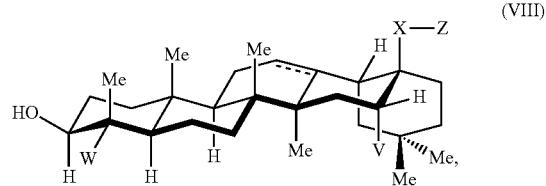

wherein each of W, V, X and Z is defined as described in classes and subclasses above and herein.

In some embodiments, the compound of formula (I) or a pharmaceutically acceptable salt thereof has the following structure:

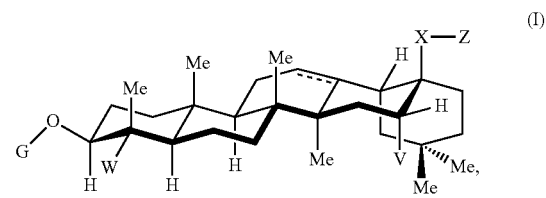

wherein G is hydrogen, a branched trisaccharide of formula V or a stereoisomer of formula V

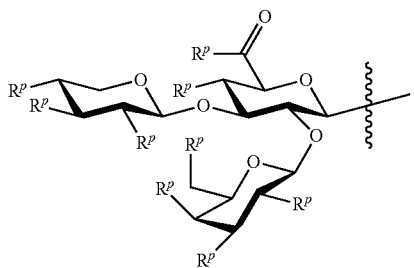

wherein W is Me, CHO, CH$_2$OR$^x$, C(O)R$^y$ or

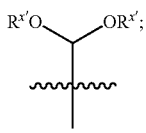

wherein each occurrence of R$^p$ is independently hydrogen or OR$^x$; wherein each occurrence of R$^x$ is independently hydrogen or independently an optionally substituted group selected from 6-10-membered aryl, benzyl, C$_{1-6}$ aliphatic, or C$_{1-6}$ heteroaliphatic having 1-2 heteroatoms independently selected from the group consisting of nitrogen, oxygen, and sulfur; or two R$^x$ are taken together to form a 5-7-membered heterocyclic ring having 1-2 heteroatoms independently selected from the group consisting of nitrogen, oxygen, and sulfur; wherein each occurrence of R$^{x'}$ is independently an optionally substituted group selected from 6-10-membered aryl, benzyl, C$_{1-6}$ aliphatic, or C$_{1-6}$ heteroaliphatic having 1-2 heteroatoms independently selected from the group consisting of nitrogen, oxygen, and sulfur; or two R$^{x'}$ are taken together to form a 5-7-membered heterocyclic ring having 1-2 heteroatoms independently selected from the group consisting of nitrogen, oxygen, and sulfur; wherein each occurrence of R$^y$ is OH or OR$^x$; wherein $=$ is a single or double bond; wherein V is hydrogen or OR$^x$; wherein X has the structure of $-(A-B-D-E)-$, wherein each of A, B, D and E is $-C(O)-$, $-NH-$, $-S-$, $-O-$, C$_{1-s}$ aliphatic or is absent, with the proviso that at least one of A, B, D and E is present at any time and that X is not a β-ester with a structure of $-C(O)O-$; wherein Z comprises a carbohydrate domain having the structure:

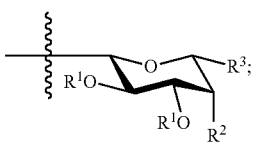

wherein each occurrence of R$^1$ is R$^x$ or a carbohydrate domain having the structure:

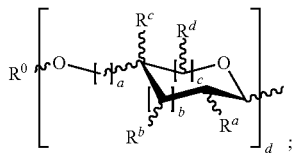

wherein each occurrence of a, b, and c is independently 0, 1, or 2; wherein d is an integer from 1-5, wherein each d bracketed structure may be the same or different; with the proviso that the d bracketed structure represents a furanose or pyranose moiety, and the sum of b and c is 1 or 2; wherein R$^0$ is hydrogen or an optionally substituted moiety selected from the group consisting of acyl, C$_{1-10}$ aliphatic, C$_{1-6}$ heteroaliphatic, 6-10-membered aryl, arylalkyl, 5-10-membered heteroaryl having 1-4 heteroatoms independently selected from nitrogen, oxygen, and sulfur, 4-7-membered heterocyclyl having 1-2 heteroatoms independently selected from the group consisting of nitrogen, oxygen, and sulfur; wherein each occurrence of R$^a$, R$^b$, R$^c$, and R$^d$ is independently hydrogen, halogen, OH, OR, OR$^x$, NR$_2$, NHCOR, or an optionally substituted group selected from acyl, C$_{1-10}$ aliphatic, C$_{1-6}$ heteroaliphatic, 6-10-membered aryl, arylalkyl, 5-10-membered heteroaryl having 1-4 heteroatoms independently selected from nitrogen, oxygen, and sulfur; 4-7-membered heterocyclyl having 1-2 heteroatoms independently selected from the group consisting of nitrogen, oxygen, and sulfur; wherein each occurrence of R is independently hydrogen, an optionally substituted group selected from acyl, arylalkyl, 6-10-membered aryl, C1-12 aliphatic, or C1-12 heteroaliphatic having 1-2 heteroatoms independently selected from the group consisting of nitrogen, oxygen, and sulfur; or two R on the same nitrogen atom are taken with the nitrogen to form a 4-7-membered heterocyclic ring having 1-2 heteroatoms independently selected from the group consisting of nitrogen, oxygen, and sulfur; wherein R$^2$ is NHC(O)R$^4$, OC(O)R$^4$, OC(O)OR$^4$, OC(O)NHR$^4$, OC(O)SR$^4$, NHC(O)OR$^4$, NHC(O)NHR$^4$, NHC(O)N(R$^4$)$_2$, NHR$^4$ or N(R$^4$)$_2$; wherein R$^3$ is hydrogen, halogen, CH$_2$OR, or an optionally substituted group selected from the group consisting of acyl, C$_{1-10}$ aliphatic, C$_{1-6}$ heteroaliphatic, 6-10-membered aryl, arylalkyl, 5-10-membered heteroaryl having 1-4 heteroatoms independently selected from the group consisting of nitrogen, oxygen, and sulfur, and 4-7-membered heterocyclyl having 1-2 heteroatoms independently selected from the group consisting of nitrogen, oxygen, and sulfur; wherein R$^4$ is T-R$^z$, wherein T is a covalent bond or a bivalent C$_{1-12}$ saturated or unsaturated, straight or branched, aliphatic or heteroaliphatic chain, wherein R$^z$ is hydrogen, halogen, C(O)OR$^q$, NC(O)OR$^q$, OR$^q$, NHC(O) R$^q$, OR$^1$, SR$^q$, NHC(S) R$^q$, OC(O)R$^q$, OC(O) OR$^q$, OC(O)NHR$^q$, OC(O)SR$^q$, NHC(O)OR$^q$, NHC(O) NHR$^q$, NHC(O)N(R$^q$)$_2$, NHR$^q$ or N(R$^q$)$_2$, or an optionally substituted group selected from acyl, arylalkyl, heteroarylalkyl, C$_{1-6}$ aliphatic, 6-10-membered aryl, 5-10-membered heteroaryl having 1-4 heteroatoms independently selected from nitrogen, oxygen, and sulfur, 4-7-membered heterocyclyl having 1-2 heteroatoms independently selected from the group consisting of nitrogen, oxygen and sulfur; or two R$^q$ on the same nitrogen atom are taken with the nitrogen to form a 4-7-membered heterocyclic ring having 1-2 heteroatoms independently selected from the group consisting of nitrogen, oxygen, and sulfur, and wherein R$^q$ is hydrogen, a detectable label, a protecting group, an optionally substituted group selected from acyl, arylalkyl, 6-10-membered aryl, C$_{1-12}$ aliphatic, and C$_{1-12}$ heteroaliphatic having 1-2 heteroatoms independently selected from the group consisting of nitrogen, oxygen, and sulfur, or an optionally substituted group selected from acyl, arylalkyl, 6-10-membered aryl, C$_{1-12}$ aliphatic, and C$_{1-12}$ heteroaliphatic having 1-2 heteroatoms independently selected from the group consisting of nitrogen, oxygen, and sulfur, wherein the optionally substituted group further comprises a detectable label.

In some further embodiments, the detectable label can be a fluorescent molecule, an isotope, a luminescent marker or biomarker, a nucleotide chromophore, an enzyme substrate, a nucleic acid, an antibody, an enzyme, calorimetric labels, a magnetic particle, an echogenic gas, a paramagnetic metal ion, X-ray absorbers, affinity tags, organometallic groups or any combination thereof.

Examples of fluorescent molecules include, but are not limited to, hydroxycoumarin, aminocoumarin, methoxycoumarin, cascade blue, pacific blue, pacific orange, lucifer yellow, nitrobenzoxadiazole (NBD), R-phycoerythrin, PE-Cy5 conjugates, PE-Cy7 conjugates, Red 613, PerCP, Tru-Red, FluorX, fluorescein, BODIPY, Cy2, Cy3, Cy3B, Cy3.5, Cy5, Cy5.5, Cy7, SeTau-647, TRITC, rhodamine, Texas Red, allophycocyanin (APC), APC-Cy7 conjugates, and derivatives thereof.

Examples of isotope label include, but are not limited to, $^{11}C$, $^{13}N$, $^{15}O$, $^{13}O$, $^{18}F$, $^{66}Ga$, $^{68}Ga$, $^{44}Sc$, $^{72}As$, $^{60}Cu$, $^{61}Cu$, $^{62}Cu$, $^{64}Cu$, $^{198}Pb$, $^{197}Hg$, $^{97}Ru$, $^{52}Fe$, $^{55}Co$, $^{82}Rb$, $^{82}Sr$, $^{68}Ge$, $^{89}Zr$, $^{86}Y$, $^{99m}Tc$, $^{111}In$, $^{123}I$, $^{124}I$, $^{125}I$, $^{131}I$, $^{44}Ti$, $^{203}Pb$, $^{201}Tl$, $^{67}Cu$ and $^{67}Ga$. Such isotopes are particularly useful for PET (positron emission tomography) or SPECT (single photon emission computed tomography). Other non-limiting examples of radioisotopes include yttrium ($^{90}Y$), lutetium ($^{177}Lu$), actinium ($^{225}Ac$), praseodymium, astatine ($^{211}At$), rhenium ($^{186}Re$), bismuth ($^{212}Bi$ or $^{213}Bi$), holmium ($^{166}Ho$), samarium ($^{153}Sm$), iridium ($^{192}Ir$), rhodium $^{105}Rh$), iodine ($^{131}I$ or $^{125}I$), indium ($^{111}In$), technetium ($^{99}Tc$), phosphorus ($^{32}P$), sulfur ($^{35}S$), carbon ($^{14}C$), tritium ($^{3}H$), chromium ($^{51}Cr$), chlorine ($^{31}Cl$), cobalt ($^{57}Co$ or $^{58}Co$), iron ($^{59}Fe$), selenium ($^{75}Se$) and gallium ($^{67}Ga$).

Suitable radioisotopes for direct conjugation include, without limitation, $^{18}F$, $^{124}I$, $^{125}I$, $^{131}I$, and mixtures thereof. Suitable radioisotopes for use with a chelating agent include, without limitation, $^{47}Sc$, $^{64}Cu$, $^{67}Cu$, $^{89}Sr$, $^{86}Y$, $^{87}Y$, $^{90}Y$, $^{105}Rh$, $^{111}Ag$, $^{111}In$, $^{117m}Sn$, $^{149}Pm$, $^{153}Sm$, $^{166}Ho$, $^{177}Lu$, $^{186}Re$, $^{188}Re$, $^{211}At$, $^{212}Bi$, and mixtures thereof.

Examples of luminescent markers and biomarkers include, but are not limited to, luciferase (e.g., bacterial, firefly, click beetle and the like), luciferin, aequorin, enzymes (e.g., galactosidases, glucorinidases, phosphatases such as alkaline phosphatase, peroxidases such as horseradish peroxidase, and cholinesterases) and antibodies.

Examples of calorimetric labels include, but are not limited to, colloidal gold or colored glass or plastic (e.g., polystyrene, polypropylene, and latex) beads.

Examples of echogenic gases include, but are not limited to, a sulfur hexafluoride or perfluorocarbon gas, such as perfluoromethane, perfluoroethane, perfluoropropane, perfluorobutane, perfluorocyclobutane, perfluoropentane, or perfluorohexane.

Examples of paramagnetic metal ions include, but are not limited to, Gd(III), Dy(III), Fe(III), and Mn(II).

Examples of X-ray absorbers include, but are not limited to, Re, Sm, Ho, Lu, Pm, Y, Bi, Pd, Gd, La, Au, Au, Yb, Dy, Cu, Rh, Ag, and Ir.

Example of organometallic group includes, but are not limited to, $SnMe_3$.

Means of detecting the labels described above are well known to those of skill in the art. Thus, for example, radiolabels can be detected using photographic film or scintillation counters, fluorescent markers can be detected using a photo-detector to detect emitted light. Enzymatic labels are typically detected by providing the enzyme with an enzyme substrate and detecting the reaction product produced by the action of the enzyme on the enzyme substrate, and calorimetric labels can be detected by visualizing the colored label. Exemplary methods for in vivo detection or imaging of detectable labels include, but are not limited to, radiography, magnetic resonance imaging (MRI), positron emission tomography (PET), single-photon emission computed tomography (SPECT, or less commonly, SPET), scintigraphy, ultrasound, CAT scan, photoacoustic imaging, thermography, linear tomography, poly tomography, zonography, orthopantomography (OPT or OPG), and computed tomography (CT) or computed axial tomography (CAT scan).

Affinity tags can include molecules, peptides, polypeptides, particles, and/or other substances capable of being captured by a capture moiety or enrichment device. Examples of affinity tags include biotin, desthiobiotin, histidine, poly-histidine, glutathione S transferase (GST), myc, hemagglutinin (HA), FLAG, fluorescence tag, tandem affinity purification (TAP) tags, or derivatives thereof. The TAP tag may comprise calmodulin-binding protein, TEV, and protein A or G subunit. In some embodiments, the affinity tag comprises a magnetic particle. In other embodiments, the affinity tag is a molecule or particle other than a magnetic particle. In some instances, an affinity tag does not comprise an antibody.

An affinity tag label may comprise one affinity tag, or, for example, may comprise at least 2, 5, 10, 20, 30, 40, 50, 60, 70, 80, 90, 100, or more affinity tags.

In some embodiments, the detectable label is $^{123}I$, $^{124}I$, $^{125}I$, $^{131}I$, $^{18}F$, F or $SnMe_3$.

In some further embodiments, X is selected from the group consisting of α- and β-glycosyl ethanolmide, α- and β-glycosyl carbamate, α- and β-glycosyl thioester, α-glycosyl ester, α- and β-glycosyl amide, α- and β-glycosyl ether, and α- and β-glycosyl thioether, wherein α or β refers to the stereochemical configuration at the anomeric carbon in the Z moiety that is directly attached to the X moiety in formula I.

In some further embodiments, the —X—Z moiety is selected from the group consisting of

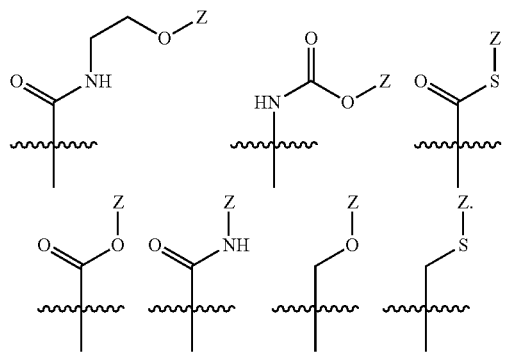

In some further embodiments, the —X—Z moiety is selected from the group consisting of

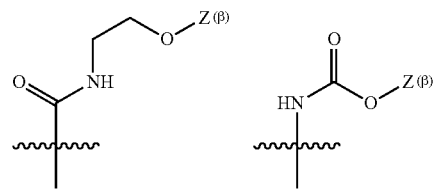

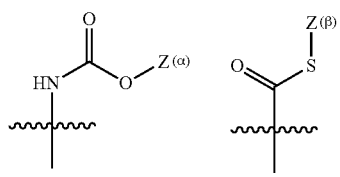 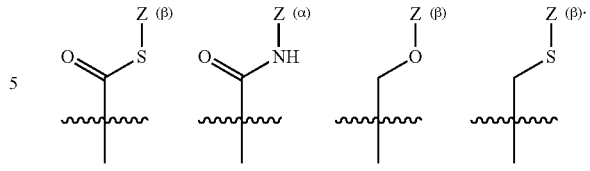

In some further embodiments, the —X—Z moiety is

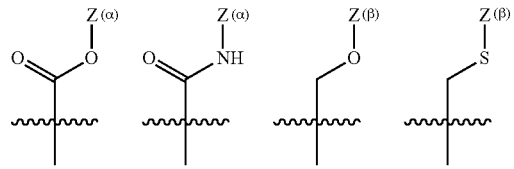 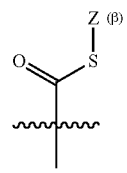

wherein α or β refers to the stereochemical configuration at the anomeric carbon in formula IX that is directly attached to the X moiety in formula I.

In some further embodiments, the —X—Z moiety is selected from the group consisting of In some further embodiments, G is hydrogen.

In some further embodiments, G is formula VI and Z is formula VII.

In some further embodiments, the compound is selected from the group consisting of (3)

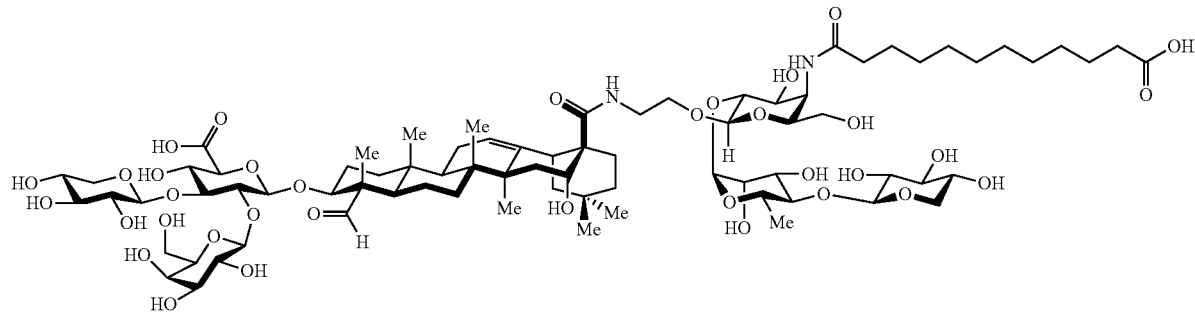

(4α)

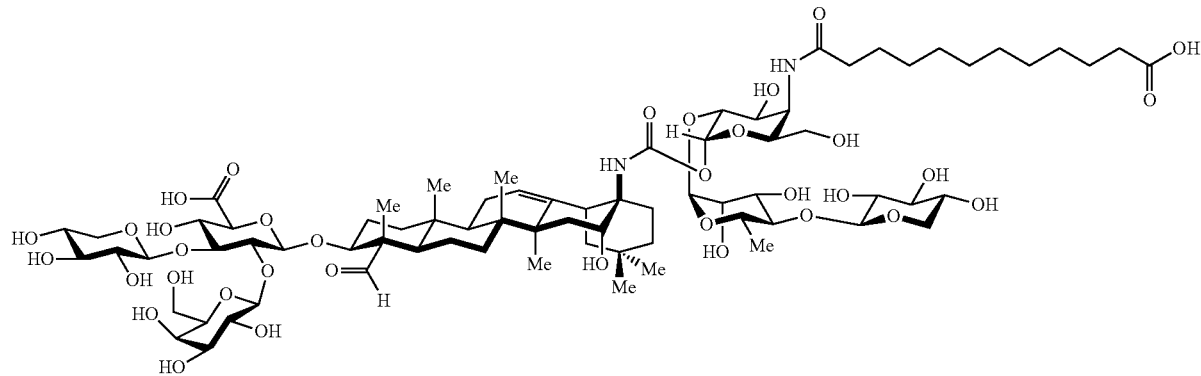

(4β)
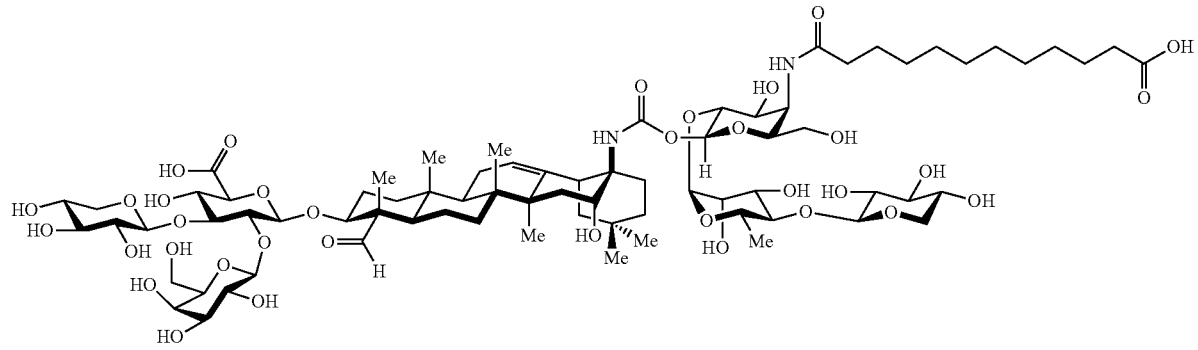
(5)
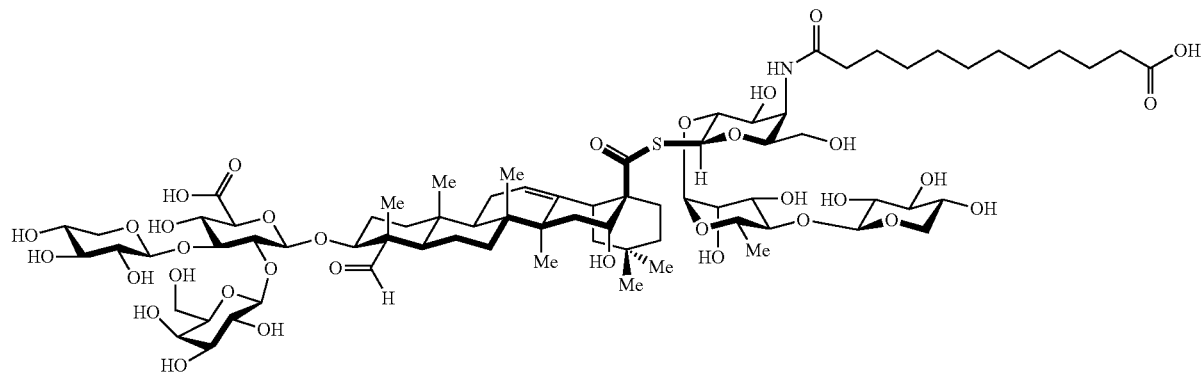
(6)
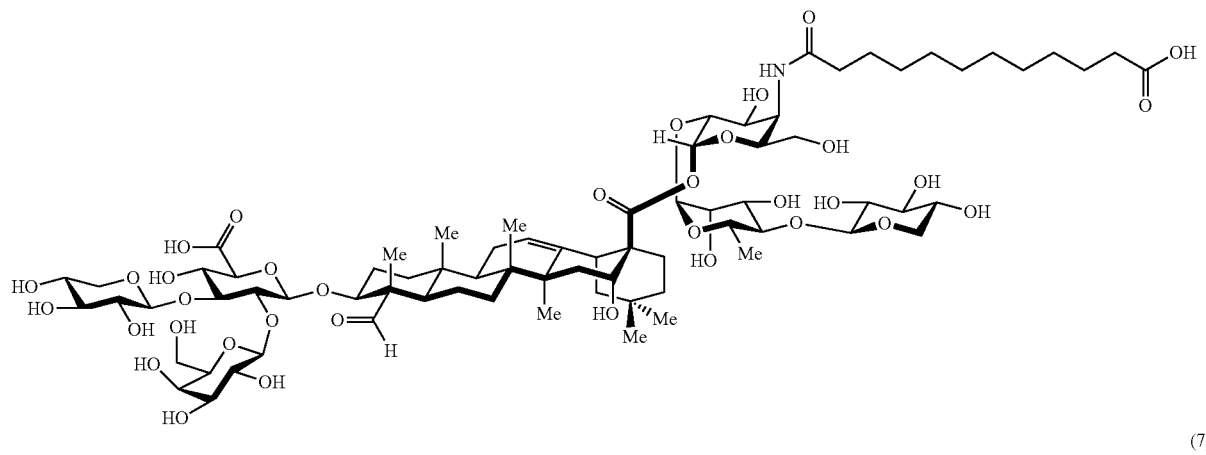
(7)
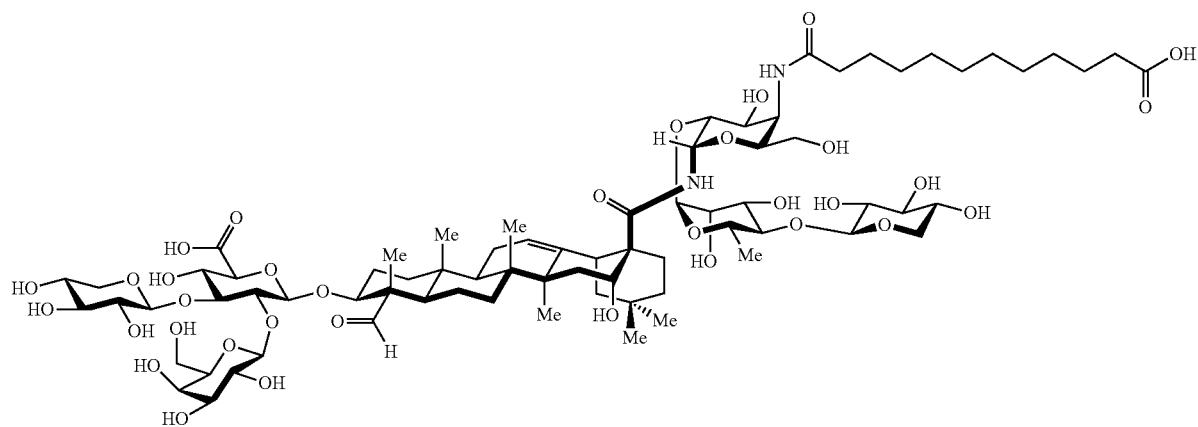

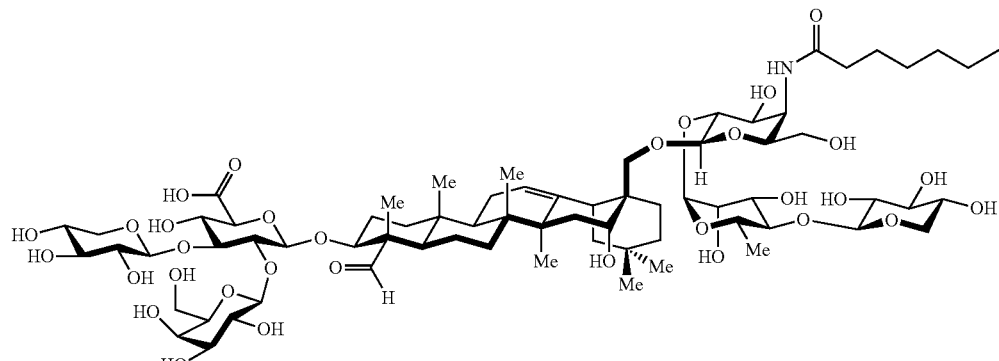
(8)
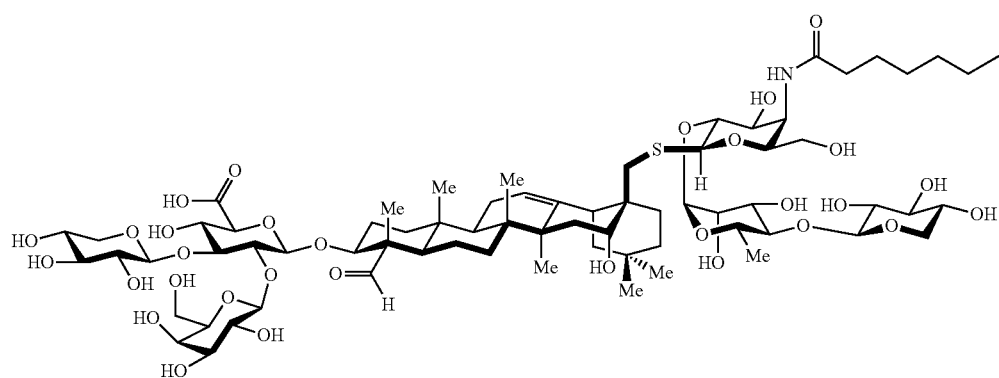
(9)
In some embodiments, G is formula VI and Z is selected from the group consisting of formula C1-C11 and mixtures thereof:
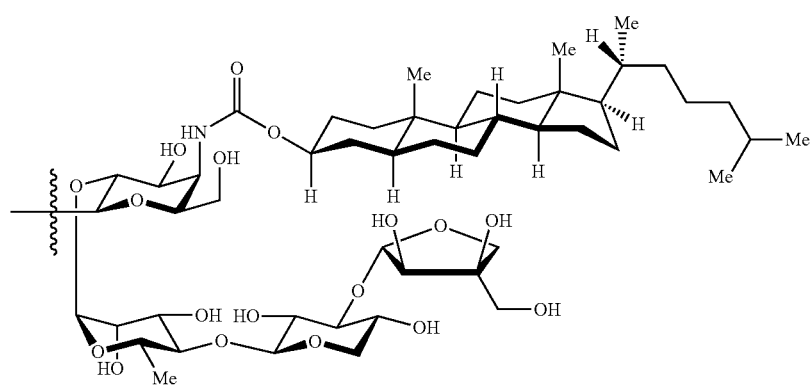
(C1)
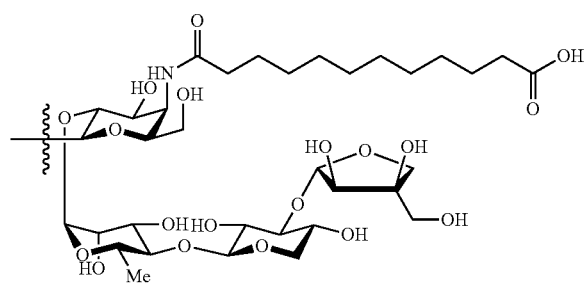
(C2)
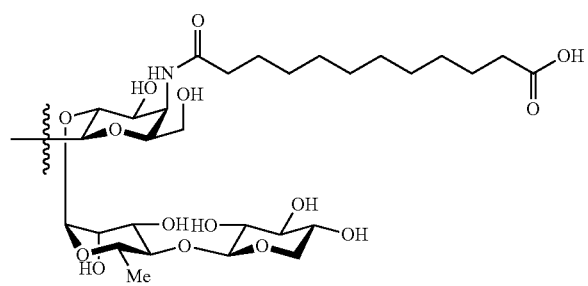
(C3)

(C4)
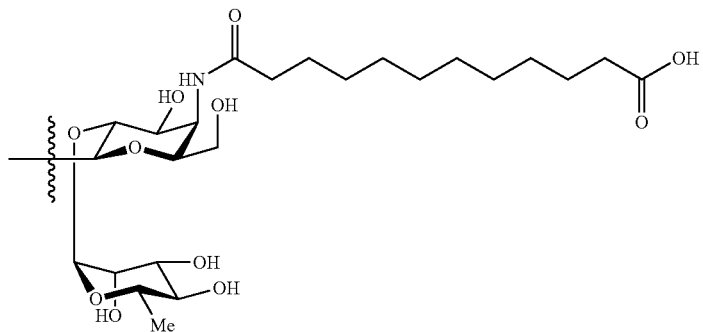
(C5)
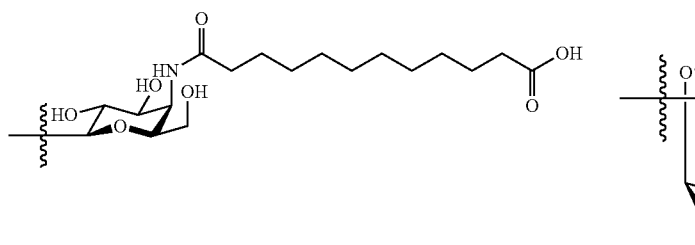
(C6)
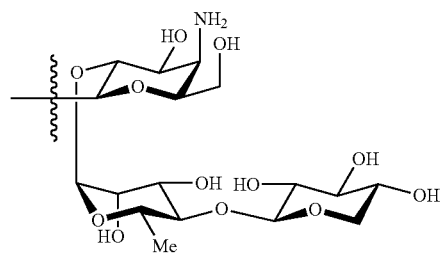
(C7)
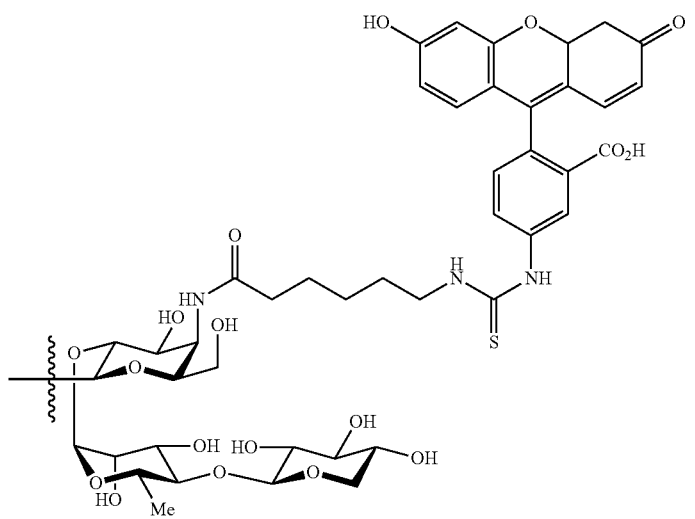
(C8)
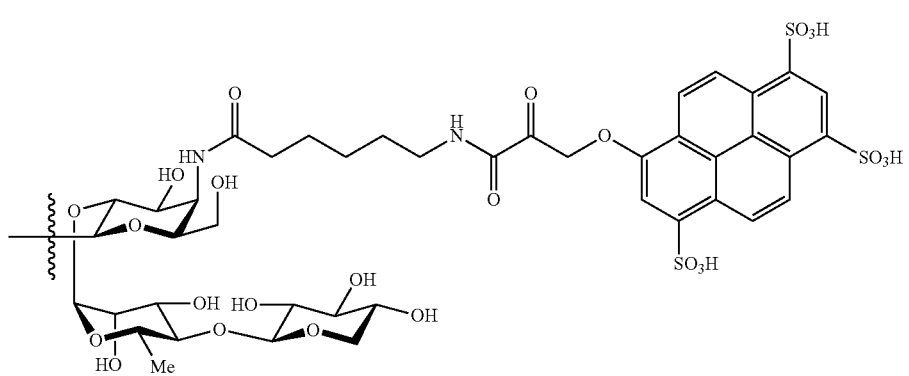

-continued
(C9)
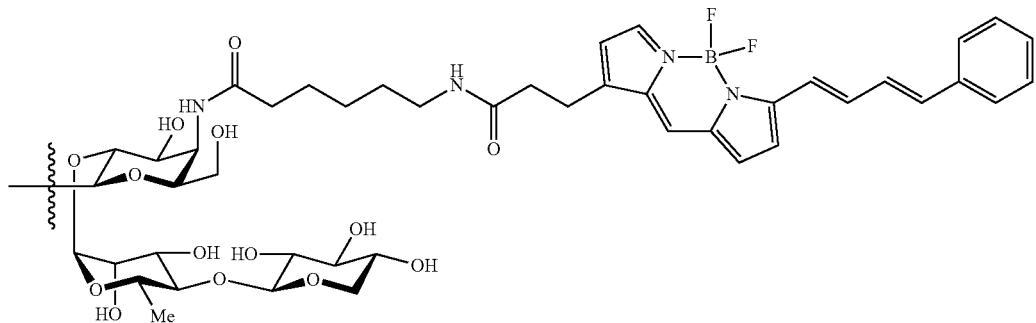
(C10)
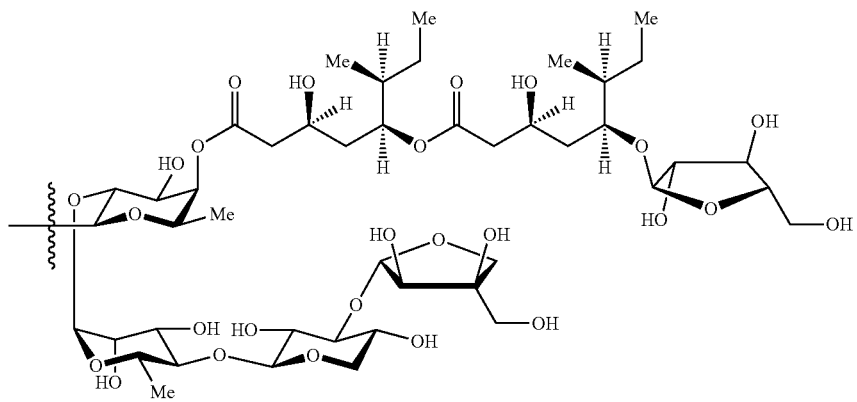
(C11)
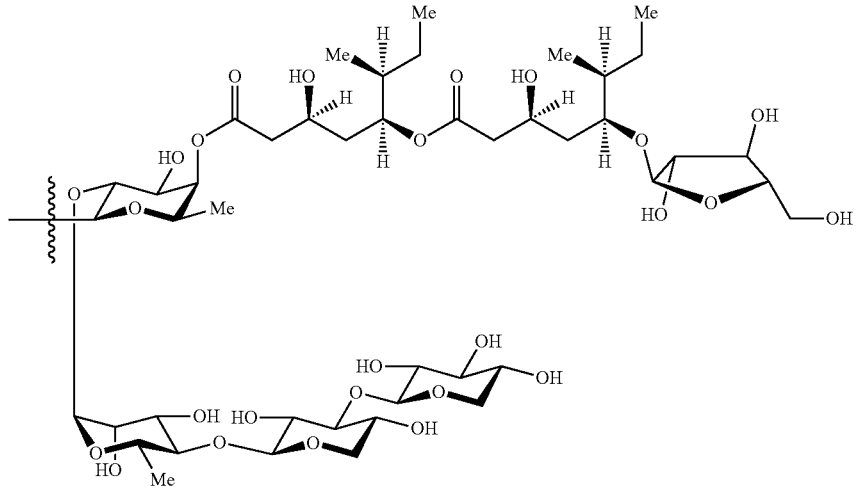
In some embodiments, G is formula VI and Z is
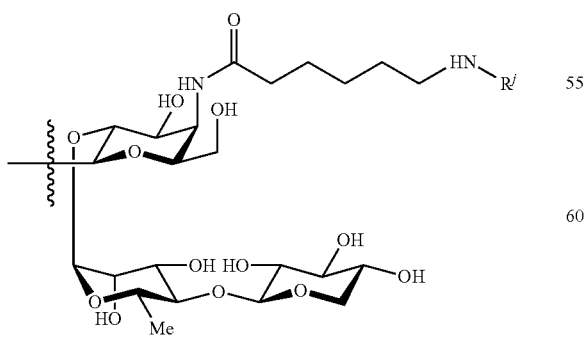
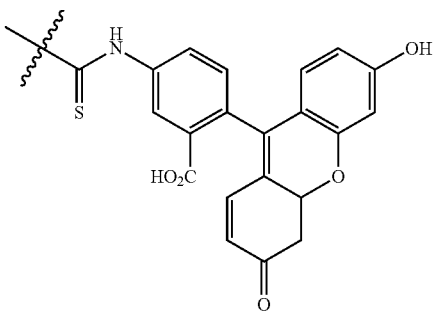
wherein $R^j$ is hydrogen,

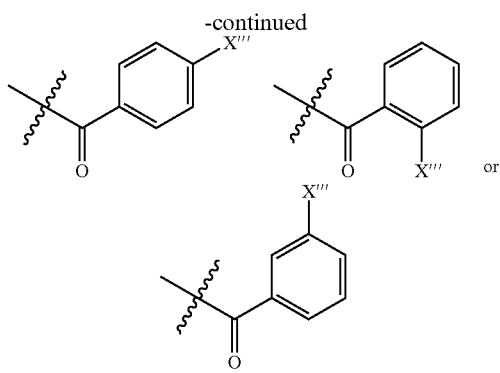

wherein X''' is I, $^{123}$I, $^{124}$I, $^{125}$I, $^{131}$I, F, $^{18}$F or SnMe$_3$.

In some embodiments, G is hydrogen and Z is

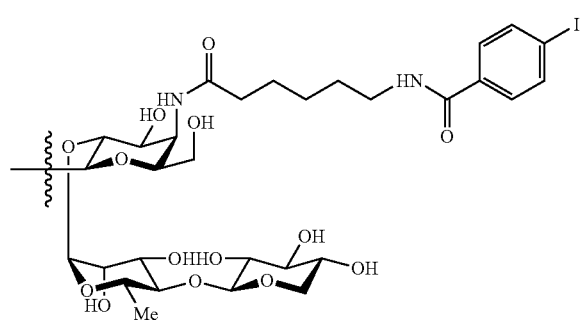

wherein W and V of formula I are selected from the group consisting of (1) W is CH$_2$OH and V is OH, (2) W is Me and V is OH, (3) W is CHO and V is hydrogen, (4) W is CH$_2$OH and V is hydrogen, and (5) W is Me and V is hydrogen.

Pharmaceutical Compositions

Another aspect of the present application provides "pharmaceutically acceptable" compositions, which comprise a therapeutically effective amount of one or more of the compounds described herein, an effective amount of an antigen, and one or more pharmaceutically acceptable carriers (additives) and/or diluents.

As described in detail, the pharmaceutical compositions of the present application may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream or foam; sublingually; ocularly; transdermally; or nasally, pulmonary and to other mucosal surfaces.

Method of Use

The triterpene saponin variants of the present application (e.g., compounds of formulae I and VIII) may be used as adjuvants or to enhance the cellular uptake of toxins. The inventive compounds may be particularly useful in the treatment or prevention of neoplasms or other proliferative diseases in vivo. However, inventive compounds described above may also be used in vitro for research or clinical purposes.

Adjuvants

Most protein and glycoprotein antigens are poorly immunogenic or non-immunogenic when administered alone. Strong adaptive immune responses to such antigens often requires the use of adjuvants. Immune adjuvants are substances that, when administered to a subject, increase the immune response to an antigen or enhance certain activities of cells from the immune system. An adjuvant may also allow the use of a lower dose of antigen to achieve a useful immune response in a subject.

Common adjuvants include alum, Freund's adjuvant (an oil-in-water emulsion with dead mycobacteria), Freund's adjuvant with MDP (an oil-in-water emulsion with muramyldipeptide, MDP, a constituent of mycobacteria), alum plus *Bordetella pertussis* (aluminum hydroxide gel with killed *B. pertussis*). Such adjuvants are thought to act by delaying the release of antigens and enhancing uptake by macrophages. Immune stimulatory complexes (ISCOMs) such as Quil-A (a *Quillaja* saponin extract) are open cage-like complexes typically with a diameter of about 40 nm that are built up by cholesterol, lipid, immunogen, and saponin. ISCOMs deliver antigen to the cytosol, and have been demonstrated to promote antibody response and induction of T helper cell as well as cytotoxic T lymphocyte responses in a variety of experimental animal models.

Enhanced Uptake of Toxins

Triterpene saponins have been shown to exhibit cell membrane-permeabilizing properties, and have been investigated for their therapeutic potential. In some cases, saponins have virtually no effect alone, but when used in combination with another drug will significantly amplify the effects of the other drug. In certain embodiments, the triterpene saponin variants of the present application are used to enhance the uptake of other cytotoxic agents.

Vaccines

Compositions of the present application are useful as vaccines to induce active immunity towards antigens in subjects. Any animal that may experience the beneficial effects of the compositions of the present application within the scope of subjects that may be treated. In some embodiments, the subjects are mammals. In some embodiments, the subjects are humans.

The vaccines of the present application may be used to confer resistance to infection or cancer by either passive or active immunization. When the vaccines of the present application are used to confer resistance through active immunization, a vaccine of the present application is administered to an animal to elicit a protective immune response which either prevents or attenuates a proliferative or infectious disease. When the vaccines of the present application are used to confer resistance to infection through passive immunization, the vaccine is provided to a host animal (e.g., human, dog, or mouse), and the antisera elicited by this vaccine is recovered and directly provided to a recipient suspected of having an infection or disease or exposed to a causative organism.

The present application thus concerns and provides a means for preventing or attenuating a proliferative disease resulting from organisms or tumor cells which have antigens that are recognized and bound by antisera produced in response to the immunogenic polypeptides included in vaccines of the present invention. As used herein, a vaccine is said to prevent or attenuate a disease if its administration to an animal results either in the total or partial attenuation (i.e., suppression) of a symptom or condition of the disease, or in the total or partial immunity of the animal to the disease.

The administration of the vaccine (or the antisera which it elicits) may be for either a "prophylactic" or "therapeutic" purpose. When provided prophylactically, the vaccine(s) are provided in advance of any symptoms of proliferative disease. The prophylactic administration of the vaccine(s) serves to prevent or attenuate any subsequent presentation of the disease. When provided therapeutically, the vaccine(s) is provided upon or after the detection of symptoms which indicate that an animal may be infected with a pathogen or have a certain cancer. The therapeutic administration of the vaccine(s) serves to attenuate any actual disease presentation. Thus, the vaccines may be provided either prior to the onset of disease proliferation (so as to prevent or attenuate an anticipated infection or cancer) or after the initiation of an actual proliferation.

Thus, in one aspect the present application provides vaccines comprising one or more bacterial, viral, protozoal, or tumor-related antigens in combination with one or more inventive compounds. In some embodiments, the vaccine comprises a single bacterial, viral, protozoal, or tumor-related antigen in combination with one inventive compound. In some embodiments, the vaccine comprises two or more bacterial, viral, protozoal, or tumor-related antigens in combination with a single inventive compound. In some embodiments, the vaccine comprises a two or more bacterial, viral, protozoal, or tumor-related antigens in combination with two or more inventive compounds. In some embodiments, the vaccine comprises a single bacterial, viral, protozoal, or tumor-related antigens in combination with two or more inventive compounds.

In some embodiments, one or more antigens of provided vaccines are bacterial antigens.

In certain embodiments, one or more antigens of provided vaccines are viral-associated antigens.

In certain embodiments, one or more antigens of provided vaccines are tumor-associated antigens.

In certain embodiments, an antigen is covalently bound to a compound of formula I or VIII. In some embodiments, an antigen is not covalently bound to a compound of formula I or VIII.

One of ordinary skill in the art will appreciate that vaccines may optionally include a pharmaceutically acceptable excipient or carrier. Thus, according to another aspect, provided vaccines comprise one or more antigens that are optionally conjugated to a pharmaceutically acceptable excipient or carrier. In some embodiments, said one or more antigens are conjugated covalently to a pharmaceutically acceptable excipient. In other embodiments, said one or more antigens are non-covalently associated with a pharmaceutically acceptable excipient.

As described above, adjuvants may be used to increase the immune response to an antigen. The vaccines of the present application may be used invoke an immune response when administered to a subject. In certain embodiments, an immune response to an antigen may be potentiated by administering to a subject a provided vaccine in an effect amount to potentiate the immune response of said subject to said antigen.

As described above, the compounds of the present application may be used in cancer vaccines as adjuvants in combination with tumor-associated antigens. In certain embodiments, said vaccines may be used in the treatment or prevention of neoplasms. In certain embodiments, the neoplasm is a benign neoplasm. In other embodiments, the neoplasm is a malignant neoplasm. Any cancer may be treated using compounds of the invention with an antigen.

In certain embodiments, the malignancy is a hematological malignancy.

Other cancers besides hematological malignancies may also be treated using compounds of formulae I and VIII. In certain embodiments, the cancer is a solid tumor.

In certain embodiments, compounds and pharmaceutical compositions of the present application can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (e.g., an inventive compound may be administered concurrently with another antiproliferative agent), or they may achieve different effects (e.g., control of any adverse effects).

For example, other therapies or anticancer agents that may be used in combination with the inventive anticancer agents of the present application include surgery, radiotherapy (γ-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), to name a few. Additionally, the present invention also encompasses the use of certain cytotoxic or anticancer agents currently in clinical trials and which may ultimately be approved by the FDA (including, but not limited to, epothilones and analogues thereof and geldanamycins and analogues thereof). For a more comprehensive discussion of updated cancer therapies see, www.nci.nih.gov, a list of the FDA approved oncology drugs at www.fda.gov/cder/cancer/druglistframe.htm, and The Merck Manual, Seventeenth Ed. 1999, the entire contents of which are hereby incorporated by reference.

In another aspect, the present application provides a method of treating infectious disease in a subject comprising administering to the subject a therapeutically effective amount of a compound of formula I or VIII. In some embodiments, the infection is bacterial. In some embodiments, the infection is viral. In some embodiments, the infection is protozoal. In some embodiments, the subject is human.

In another aspect, the present application provides a method of treating neurodegenerative disorders in a subject comprising administering to the subject a therapeutically effective amount of a compound of formula I or VIII. In some embodiments, the present application can be used in the treatment of neurodegenerative diseases.

Formulations

The triterpene saponin variants of the present application may be combined with a pharmaceutically acceptable excipient to form a pharmaceutical composition. In certain embodiments, the pharmaceutical composition includes a pharmaceutically acceptable amount of an inventive compound. The amount of active ingredient which can be combined with a carrier material to produce a single dosage form will vary depending upon the host being treated, and the particular mode of administration. The amount of active ingredient that can be combined with a carrier material to produce a single dosage form will generally be that amount of the compound which produces a therapeutic effect. Generally, this amount will range from about 1% to about 99% of active ingredient, preferably from about 5% to about 70%, most preferably from about 10% to about 30%. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present application include those suitable for oral, nasal, topical (including buccal and sublingual), rectal, vaginal and/or parenteral administration. The formulations may conveniently be presented in unit dosage form and may be prepared by any methods well known in the art of pharmacy. In certain embodiments, a formulation of the present application comprises an excipient selected from the group consisting of cyclodextrins, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present application.

Methods of preparing these formulations or compositions include the step of bringing into association a compound of the present application with the carrier and, optionally, one or more accessory ingredients. In general, the formulations are prepared by uniformly and intimately bringing into association a compound of the present application with liquid carriers, or finely divided solid carriers, or both, and then, if necessary, shaping the product.

Formulations of the present application suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present application as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol, glycerol monostearate, and non-ionic surfactants; absorbents, such as kaolin and bentonite clay; lubricants, such as talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made in a suitable machine in which a mixture of the powdered compound is moistened with an inert liquid diluent.

The tablets, and other solid dosage forms of the pharmaceutical compositions of the present application, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the present application include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the present application for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present application which are suitable for vaginal administration also include pessaries, tampons, creams, gels, pastes, foams or spray formulations containing such carriers as are known in the art to be appropriate.

Dosage forms for the topical or transdermal administration of a compound of this invention-include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of the present application, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of the present application, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present application to the body. Dissolving or dispersing the compound in the proper medium can make such dosage forms. Absorption enhancers can also be used to increase the flux of the compound across the skin. Either providing a rate controlling membrane or dispersing the compound in a polymer matrix or gel can control the rate of such flux.

Ophthalmic formulations, eye ointments, powders, solutions and the like, are also contemplated as being within the scope of the present application.

Pharmaceutical compositions of the present application suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

In certain embodiments, a compound or pharmaceutical preparation is administered orally. In other embodiments, the compound or pharmaceutical preparation is administered intravenously. Alternative routs of administration include sublingual, intramuscular, and transdermal administrations.

When the compounds of the present invention are administered as pharmaceuticals, to humans and animals, they can be given per se or as a pharmaceutical composition containing, for example, 0.1% to 99.5% (more preferably, 0.5% to 90%) of active ingredient in combination with a pharmaceutically acceptable carrier.

The preparations of the present application may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present application, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of the present application may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required to achieve the desired therapeutic effect and then gradually increasing the dosage until the desired effect is achieved.

In some embodiments, a compound or pharmaceutical composition of the present application is provided to a subject chronically. Chronic treatments include any form of repeated administration for an extended period of time, such as repeated administrations for one or more months, between a month and a year, one or more years, or longer. In many embodiments, a chronic treatment involves administering a compound or pharmaceutical composition of the present application repeatedly over the life of the subject. Preferred chronic treatments involve regular administrations, for example one or more times a day, one or more times a week, or one or more times a month. In general, a suitable dose such as a daily dose of a compound of the present application will be that amount of the compound that is the lowest dose effective to produce a therapeutic effect. Such an effective dose will generally depend upon the factors described above. Generally doses of the compounds of present application for a patient, when used for the indicated effects, will range from about 0.0001 to about 100 mg per kg of body weight per day. Preferably the daily dosage will range from 0.001 to 50 mg of compound per kg of body weight, and even more preferably from 0.01 to 10 mg of compound per kg of body weight. However, lower or higher doses can be used. In some embodiments, the dose administered to a subject may be modified as the physiology of the subject changes due to age, disease progression, weight, or other factors.

In some embodiments, provided adjuvant compounds are administered as pharmaceutical compositions or vaccines. In certain embodiments, the amount of adjuvant compound administered is 1-2000 µg. In certain embodiments, the amount of adjuvant compound administered is 1-1000 µg. In certain embodiments, the amount of adjuvant compound administered is 1-500 µg. In certain embodiments, the amount of adjuvant compound administered is 1-250 µg. In certain embodiments, the amount of adjuvant compound administered is 100-1000 µg. In certain embodiments, the amount of adjuvant compound administered is 100-500 µg. In certain embodiments, the amount of adjuvant compound administered is 100-200 µg. In certain embodiments, the amount of adjuvant compound administered is 250-500 µg. In certain embodiments, the amount of adjuvant compound administered is 10-1000 µg. In certain embodiments, the amount of adjuvant compound administered is 500-1000 µg. In certain embodiments, the amount of adjuvant compound administered is 50-250 µg. In certain embodiments, the amount of adjuvant compound administered is 50-500 µg.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, in certain embodiments the compound is administered as a pharmaceutical formulation (composition) as described above.

The compounds according to the present application may be formulated for administration in any convenient way for use in human or veterinary medicine, by analogy with other pharmaceuticals.

The present application also provides kits comprising pharmaceutical compositions of a compound of the present application. In certain embodiments, such kits including the combination of a compound of formula I or VIII and an antigen. The agents may be packaged separately or together. The kit optionally includes instructions for prescribing the medication. In certain embodiments, the kit includes multiple doses of each agent. The kit may include sufficient quantities of each component to treat a subject for a week, two weeks, three weeks, four weeks, or multiple months. The kit may include a full cycle of immunotherapy. In some embodiments, the kit includes a vaccine comprising one or more bacterial, viral, protozoal, or tumor-associated antigens, and one or more provided compounds.

The entire contents of all references cited above and herein are hereby incorporated by reference. The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

EXAMPLES

Example 1: Triterpene Saponin Variants with Modified Central Glycosal Linkage

As shown FIG. 1, Panel b, a number of triterpene saponin variants with modified central glycosal linkage (structures 3-9) is created based on a lead structure 2 (SQS-0-0-5-5) of saponin. Specifically, the central glycosal linkage in structure 2 was modified in structures 3-9 to modulate the distance and orientation of the two domains of the triterpene and the linear oligosaccharide. Construction of these variants in the context of the complex saponin structure proved challenging, requiring formation of sterically-encumbered glycosidic bonds without the aid of neighboring group participation. As a result, several of the linkages were formed using unconventional glycosylation promoters. In addition, molecular dynamics simulations of these synthetic variants and the major natural product isomer QS-21-Api (FIG. 1, Panel a) revealed distinctive conformational preferences that correlate with observed adjuvant activities. Furthermore, in a preclinical mouse vaccination model, these linkage variants exhibited a remarkable range of adjuvant activities and toxicities, providing new insights into the structural requirements for adjuvant activity in the QS saponin class.

As described in more details below, 8 different triterpene saponin variants with central glycosidic linkage modifications have been synthesized. Each of the newly synthesized triterpene saponin variants has a unique chemical structure. It is noted that each of 8 triterpene saponin variants is not a single chemical compounds, rather each of them represents a groups of *Quillaja* saponin compounds that share the same or similar central glycosyl ester linkage or modification of the central glycosyl ester linkage. In this regard, the examples provide not only 8 unique triterpene saponin variant compounds, but also 8 groups of triterpene saponin variant compounds with each group covers a wide variety of different compounds sharing certain structure feature(s).

These triterpene saponin variants are specifically designed to possess various distances, stereochemistries, and conformations, which may influence their adjuvant activities, due to the different modifications on their central glycosyl ester linkage. These 8 triterpene saponin variant compounds, on the basis of their specific modified central glycosyl ester linkages, are β-glycosyl ethanolamide 3, β-glycosyl carbamate β-4, and β-glycosyl thioester 5, α-glycosyl ester 6, α-glycosyl amide 7, and α-glycosyl carbamate α-4, β-glycosyl ether 8 and β-glycosyl thioether 9 (see FIG. 1, Panel b). Among them, the β-glycosyl ethanolamide 3, β-glycosyl carbamate β-4, and β-glycosyl thioester 5 were designed to increase the distance between the triterpene and trisaccharide domains. Meanwhile, the α-glycosyl ester 6, α-glycosyl amide 7, and α-glycosyl carbamate α-4 were designed to probe the importance of stereochemistry at this glycosidic linkage. Finally, the β-glycosyl ether 8 and β-glycosyl thioether 9 were designed to probe the effect of increasing conformational flexibility between the two domains. Notably, these linkages would need to be assembled in the context of the complex saponin framework, which features sterically congested aldehyde and carboxylic acid functionalities, as well as numerous, previously established protecting groups that are incompatible with strongly acidic or basic conditions, limiting the range of potential functional group manipulations and glycosylation conditions that could be used.

Example 2: Method of Synthesis

General Synthetic Procedures

Reactions were performed in flame-dried sealed-tubes or modified Schlenk (Kjeldahl shape) flasks fitted with a glass stopper under a positive pressure of argon, unless otherwise noted. Air- and moisture-sensitive liquids and solutions were transferred via syringe. The appropriate carbohydrate and sulfoxide reagents were dried via azeotropic removal of water with toluene. Molecular sieves were activated at 350° C. and were crushed immediately prior to use, then flame-dried under vacuum. Organic solutions were concentrated by rotary evaporation below 30° C. Flash column chromatography was performed employing 230-400 mesh silica gel. Thin-layer chromatography was performed using glass plates precoated to a depth of 0.25 mm with 230-400 mesh silica gel impregnated with a fluorescent indicator (254 nm).

Materials

Dichloromethane, tetrahydrofuran, diethyl ether, and toluene were purified by passage through two packed columns of neutral alumina under an argon atmosphere. 1 Methanol was distilled from magnesium at 760 Torr. Trifluoromethanesulfonic anhydride was distilled from phosphorus pentoxide at 760 Torr. Boron trifluoride diethyl etherate was distilled from calcium hydride at 760 Torr. All other chemicals were obtained from commercial vendors and were used without further purification unless noted otherwise.

Instrumentation

Infrared (IR) spectra were obtained using a Perkin Elmer Spectrum BX spectrophotometer or a Bruker Tensor 27. Data are presented as the frequency of absorption ($cm^{-1}$). Proton and carbon-13 nuclear magnetic resonance ($^1H$ NMR and $^{13}C$ NMR) spectra were recorded on a Bruker Avance III instrument; chemical shifts are expressed in parts per million (δ scale) downfield from tetramethylsilane and are referenced to residual proton in the NMR solvent (d-chloroform: δ 7.26 for 1H NMR, δ 77.16 for $^{13}C$ NMR; d6-benzene: δ 7.16 for $^1H$ NMR, δ 128.06 for $^{13}C$ NMR; d4-methanol: δ 3.31 for $^1H$ NMR, δ 49.00 for $^{13}C$ NMR; d3-acetonitrile: δ 1.94 for $^1H$ NMR, δ 1.32 for $^{13}C$ NMR; deuterium oxide: δ 4.79 for $^1H$ NMR).

Data are presented as follows: chemical shift, multiplicity (s=singlet, bs=broad singlet, d=doublet, t=triplet, q=quartet, m=multiplet and/or multiple resonances), coupling constant in Hertz (Hz), integration, assignment. RP-HPLC purification and analyses were carried out on a Waters 2545 binary gradient HPLC system equipped with a Waters 2996 photodiode array detector, and absorbances were monitored at wavelengths of 210-600 nm.

Briefly, the syntheses of these variants began with functionalization of the protected prosapogenin 10, abbreviated herein as PPS, to provide the corresponding glycosyl acceptors. The general key steps for the synthesis of these variant compounds are described below, while the specific details for synthesizing each of the variant compounds are already described above.

Figure 2:
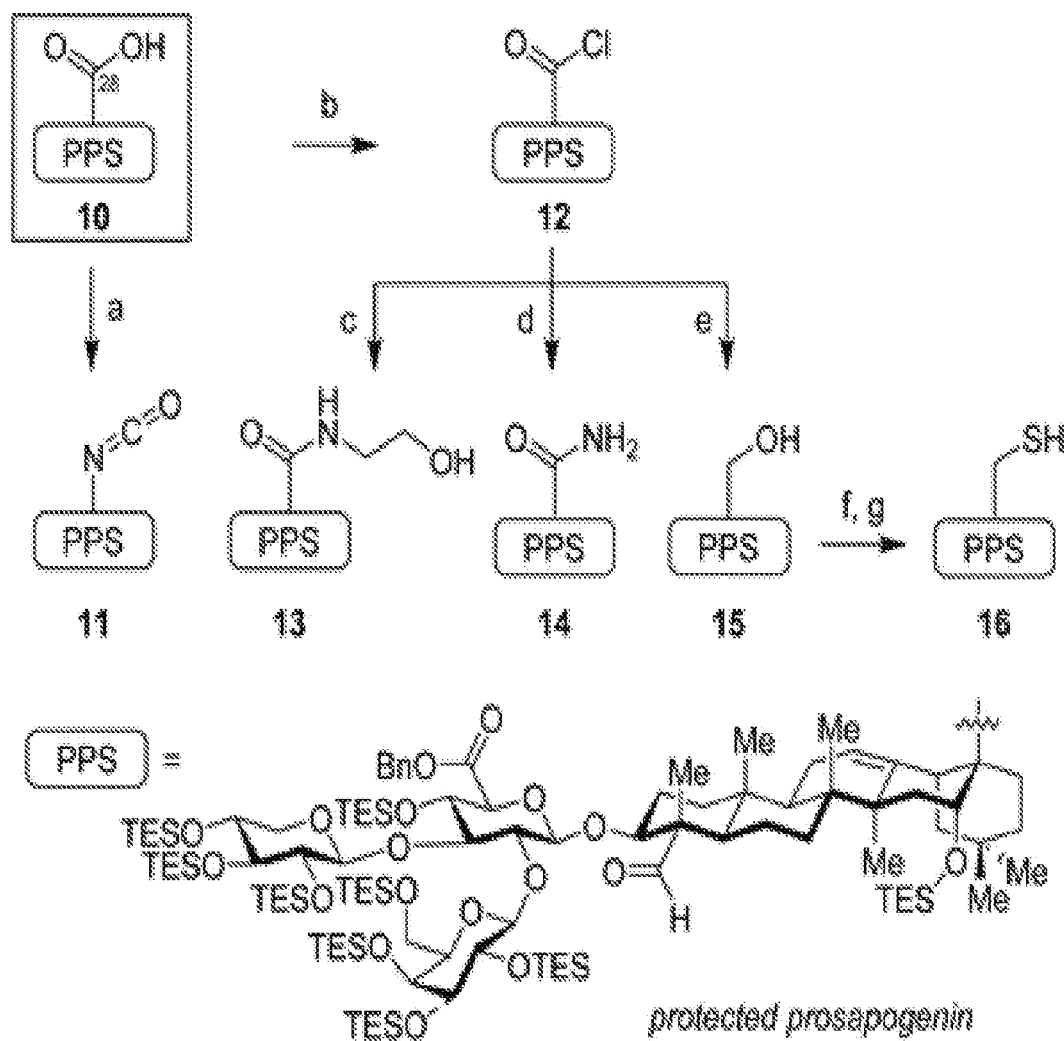
FIG. 2 depicts Scheme 1: synthesis of glycosyl acceptors from protected prosapogenin (PPS) 10. Reagents and conditions: (a) (PhO)$_2$P(O)N$_3$, Et$_3$N, PhH, 80° C., 79%; (b) SOCl$_2$, pyr, CH$_2$Cl$_2$, 0° C., 99%; (c) HO(CH$_2$)$_2$NH$_2$, CH$_2$Cl$_2$, 0° C., 88%; (d) NH$_3$, CH$_2$Cl$_2$, 0° C., 92%; (e) Bu$_4$NBH$_4$, CH$_2$Cl$_2$, 0° C., 87%; (f) Tf$_2$O, pyr, CH$_2$Cl$_2$, 0° C.; AcSK, 18-crown-6, 1:1 THF/DMF, 0° C., 92%; (g) H$_2$NNH$_2$, DTT, 1:1 THF/DMF, 90%. DTT=dithiothreitol; PPS=protected prosapogenin.

(1) Synthesis of Glycosyl Acceptors from the C28 Carboxylic Acid of a Protected Prosapogenin In reference to the Scheme 1 (see FIG. 2), the C28-carboxylic acid was treated with diphenylphosphoryl azide to give an acyl azide intermediate, which, upon continued heating, underwent Curtius rearrangement to isocyanate 11. Alternatively, activation of the C28-carboxylic acid in 10 with thionyl chloride proceeded in quantitative yield to afford the bench-stable acyl chloride 12, which was readily functionalized with a variety of nucleophiles, including ethanolamine to form ethanolamide 13, and ammonia to provide primary amide 14. While addition of nucleophiles such as NaSH and 9-fluorenylmethylthiol furnished the corresponding thioacid and thioester products in poor yields, these proved recalcitrant to purification and were not advanced further. Access to neopentyl alcohol 15 required careful chemoselective reduction of acyl chloride 12 with tetrabutylammonium borohydride. Extended reaction times and other hydride reductants (DIBAL-H, Red-Al, $NaBH_4$, super-hydride) led to overreduced and desilylated byproducts.

Conversion of this sterically encumbered alcohol 15 to the corresponding thiol 16 also proved challenging. Tosylation or mesylation was sluggish and the resulting sulfonate derivatives were completely unreactive to thiol nucleophiles. Ultimately, it has been resorted to conversion of alcohol 15 to the corresponding triflate, which proved to be a competent electrophile for substitution with potassium thioacetate in the presence of 18-crown-6 ether. Treatment of the resulting thioacetate with hydrazine under reducing conditions (DTT) furnished the desired prosapogenin thiol 16 in excellent yield (83% over two steps).

Figure 3:
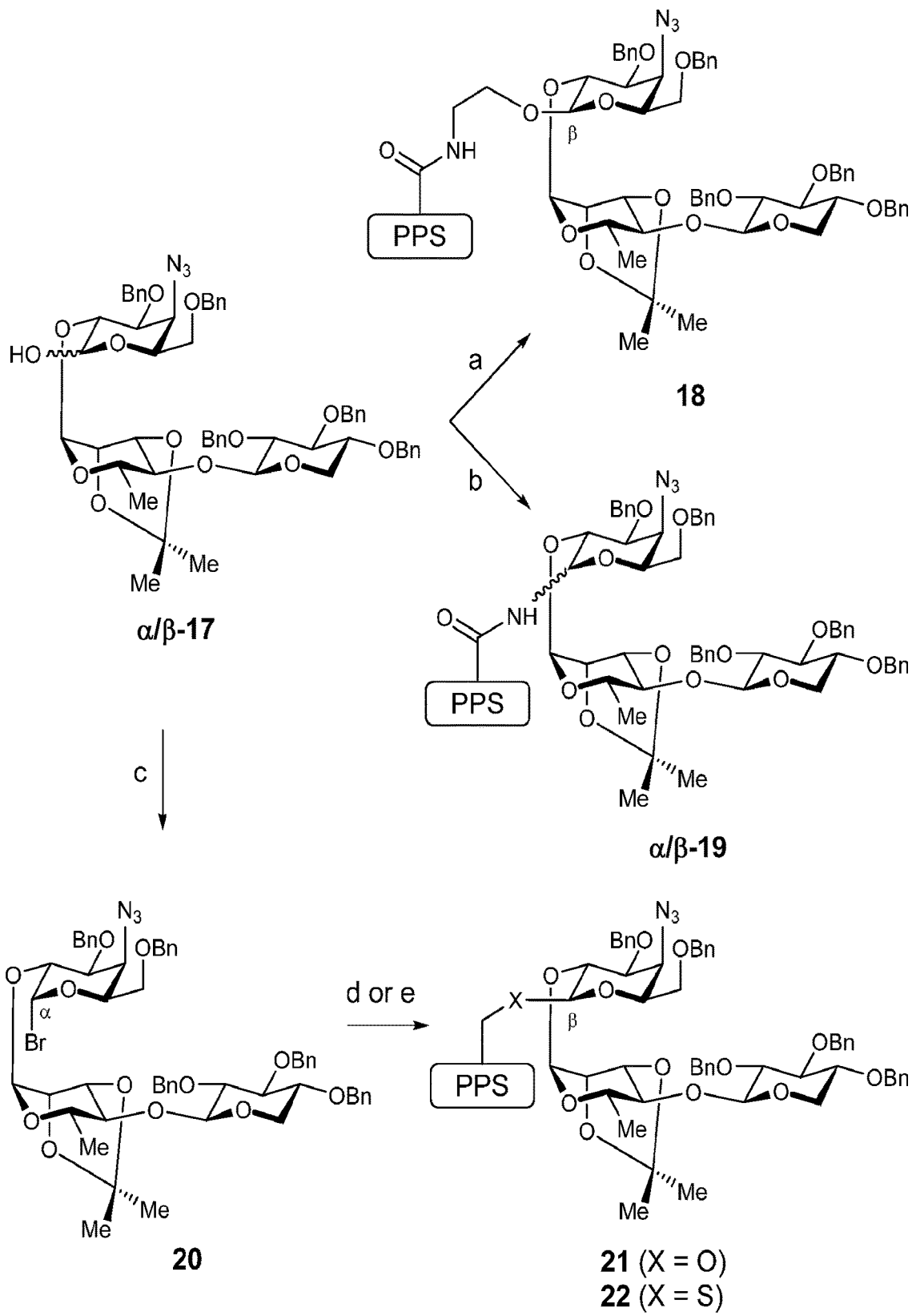
FIG. 3 depicts Scheme 2: synthesis of glycosidic linkage variants via traditional glycosylations using the glycosyl donor as an electrophile. Reagents and conditions: (a) Ph$_2$SO, Tf$_2$O, TBP, CH$_2$Cl$_2$, −45° C., then add 13, 87% (β only); (b) Ph$_2$SO, Tf$_2$O, TBP, CH$_2$Cl$_2$, −45° C., then add 14, 60-78% combined yield of separable anomers (2 equiv. 14→2:1 to 4:1 β/α-19; 2 equiv. 17→1:6 β/α-19); (c) (COBr)$_2$, DMF, TBP, CH$_2$Cl$_2$, 0° C., 74%; (d) X=O:15, AgOTf, TBP, CH$_2$Cl$_2$, −40° C., 69% isolated yield of 3-anomer (>20:1 β/α ratio in crude product); (e) X=S: 16, NaH, 2.5:1 THF/DMF, 0° C., 69%. TBP=2,4,6-tri-tert-butylpyridine.

(2) Construction of Glycosidic Linkages Using the Linear Trisaccharide Glycosyl Donor as an Electrophile In reference to Scheme 2 (FIG. 3), although glycosylation reactions to form all of the linkage chemotypes targeted herein are well-documented in the literature, synthesis of glycosyl linkages with this level of complexity and in sterically demanding environments are limited in many cases (amide 23, thioether 24), and apparently without precedent in another (thioester). Our initial efforts began with the previously described trisaccharide hemiacetal 17, 21 which successfully underwent dehydrative glycosylation ($Ph_2SO/Tf_2O$) with prosapogenin ethanolamide 13 to give the ethanolamide-linked intermediate 18 in excellent yield (87%) and with complete β-selectivity.

In contrast, glycosylation of prosapogenin primary amide 14 required extensive optimization of reaction conditions to achieve anomeric selectivity. Ultimately, it has been found that use of a two-fold excess of the glycoside acceptor 14 favored formation of β-19 (2:1 to 4:1 β/α, 60-78% combined yield of separable anomers). Notably, the anomeric preference could be reversed to favor α-19 when a two-fold excess of the donor 17 was used (6:1 α/β, 71% combined yield). Unfortunately, while these anomers were separable, the β-glycosyl amide linkage in 0-19 proved surprisingly acid-sensitive, and was cleaved under even mildly acidic conditions (e.g., SiO2, HF.pyr, AcOH). Despite considerable efforts, global deprotection could not be achieved due to competing cleavage of the glycosidic C—N bond under the reaction conditions (3:1 TFA/H2O) to reform the primary amide 14 and hemiacetal 17. In contrast, a corresponding (β-glycosyl pivalamide model system 25 was significantly more stable (SiO2), highlighting the complexities of working with the complete saponin scaffold. Unlike its β-anomer, the axially-disposed glycosyl amide in α-19 showed no observable acid lability, illustrating the significant changes in reactivity that may arise from minor structural perturbations of the central glycosidic linkage.

Next sought to prepare the glycosyl ether linkage in 21. To our surprise, repeated attempts at glycosylation of prosapogenin neopentyl alcohol 15 with the same trisaccharide hemiacetal donor 17 under dehydrative or Schmidt conditions gave no isolable glycosylation products. However, it has been found that the glycosylation could be effected smoothly with trisaccharide bromide donor 20 (prepared from hemiacetal 17 with oxalyl bromide, DMF) under the silver triflate-promoted Koenigs-Knorr reaction at low temperature to give the ether-linked intermediate 21 with >20:1 β/α selectivity.

The analogous reaction with neopentyl thiol 16 was precluded by the thiophilicity of silver. However, it has been found that the corresponding thiolate (NaH) rapidly displaced the bromide in trisaccharide donor 20 to give glycosyl thioether 22 with complete β-selectivity.

Figure 4:
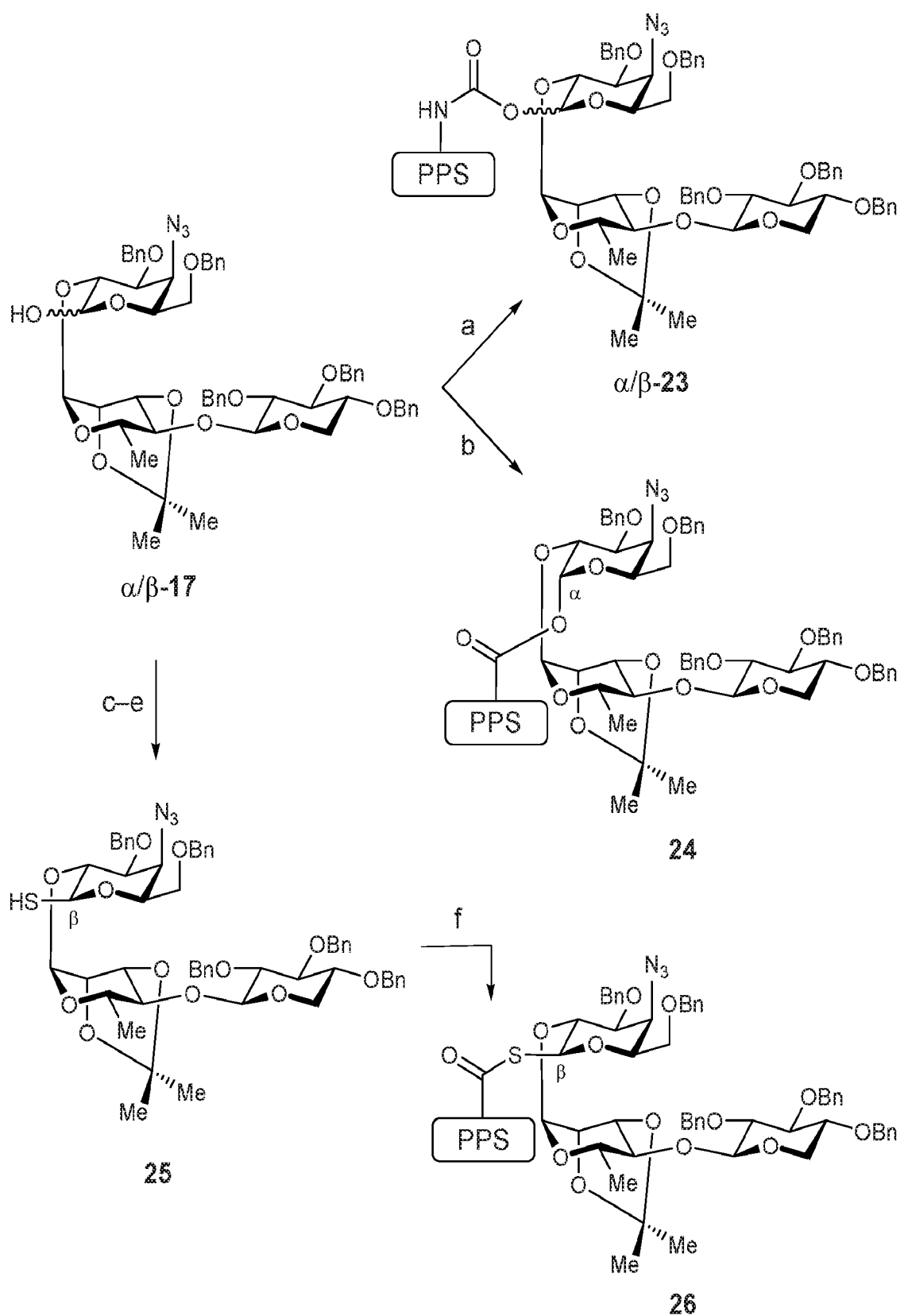
FIG. 4 depicts Scheme 3: synthesis of glycosidic linkage variants using the glycosyl donor as a nucleophile. Reagents and conditions: (a) NaH, then add 11, THF, 79% combined yield of separable anomers (2:1 β/α: 53% β-23, 26% α-23); (b) NaH, then add 12, 1:1 THF/DMF, −20° C., 70% (6:1 α/β: 60% α-24, 10% 3-24); (c) (COBr)$_2$, DMF, TBP, CH$_2$Cl$_2$, 0° C., 80%; (d) Cs$_2$CO$_3$, AcSH, 1:1 THF/DMF, 87% (β only); (e) H$_2$NNH$_2$, DTT, 1:1 MeOH/THF, 94%; (f) 12, NaH, THF, 0° C., 87% (β only). DTT=dithiothreitol.

(3) Construction of Glycosidic Linkages Using the Linear Trisaccharide Glycosyl Donor as a Nucleophile In reference to Scheme 3 (FIG. 4), the natural β-glycosyl ester linkage in the lead compound 2 (SQS-0-0-5-5) can be accessed by Schmidt glycosylation of the C28-carboxylic acid in PPS 10 with the corresponding trisaccharide trichloroacetimidate donor, yet 21 analogous efforts to synthesize thioester and α-ester linkages using a variety of traditional glycosylation methods (Lewis acid-catalyzed displacement of glycosyl donors, dehydrative glycosylations, displacement of glycosyl bromides under phase transfer conditions) led to complex mixtures of anomers and other unidentified impurities. Thus, to access these QS-21 analogues, as well as the corresponding carbamates, we used a conceptual reverse of polarity, with the glycoside acting as a nucleophile. First, treatment of trisaccharide hemiacetal donor 17 with NaH followed by addition of prosapogenin isocyanate 11 afforded carbamate-linked intermediates β-23 and α-23 as an easily separable mixture of anomers (2:1 β/α, 79% combined yield). In contrast, acylation of hemiacetal donor 17 with prosapogenin acid chloride 12 could be achieved with preferential formation of the α-glycosyl ester intermediate 24 (6:1 α/β, 70% combined yield of separable anomers). Conversely, addition of NaH to a solution of prosapogenin acid chloride 12 and trisaccharide thiohemiacetal 25 (generated by displacement of bromide in 20 with thioacetate, followed by deacetylation) furnished β-glycosyl thioester intermediate 26 in 87% yield with complete anomeric selectivity. Although all three of these linkages were formed under similar reaction conditions (NaH; acylation), the diverse anomeric selectivities can be attributed to the anomeric ratio of the corresponding hemi(thio)acetal substrates and solvent effects.

Figure 5:
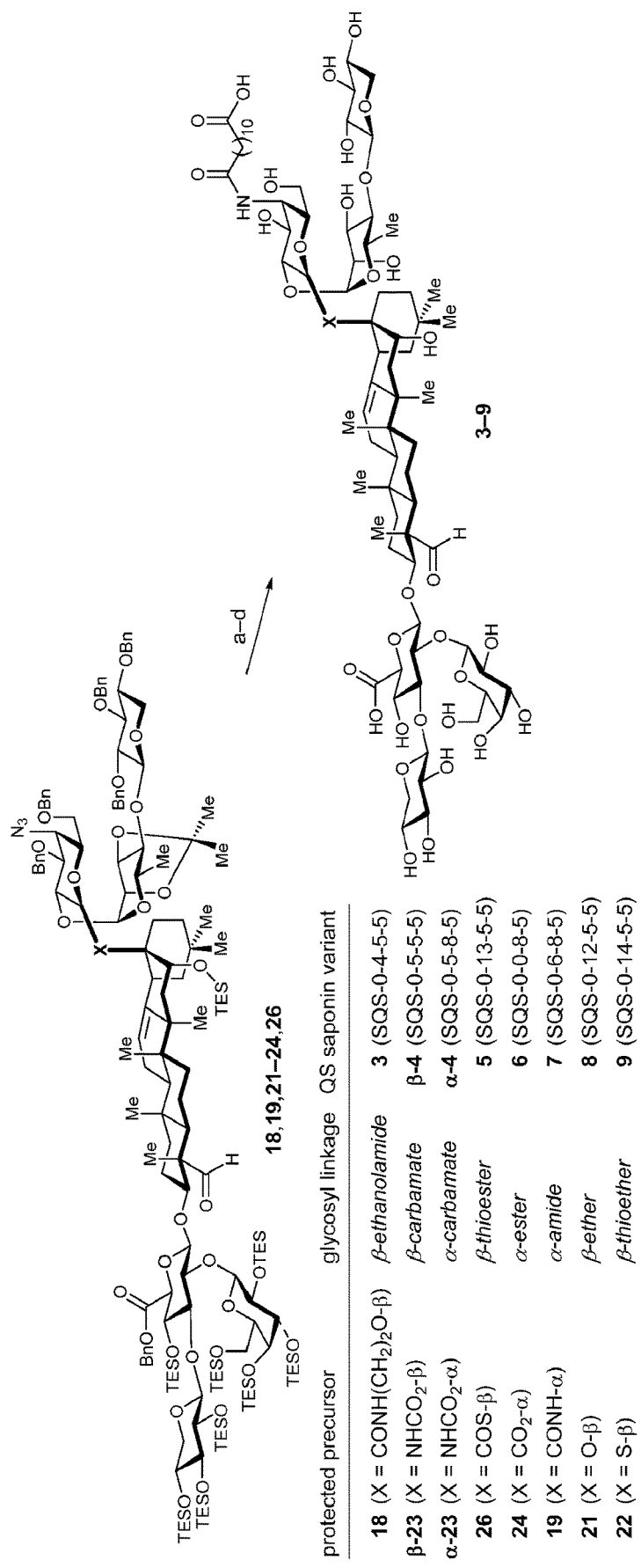
FIG. 5 depicts Scheme 4: installation of acyl chains and global deprotection of QS saponin linkage variants. Reagents and conditions (a) H$_2$S, pyr, Et3N, 78-94%; (b) dodecanedioic acid monobenzyl ester, i-BuOCOCl, Et3N, THF, 0° C., 4 h, then add appropriate amine from step a, 57-93%; (c) H$_2$, Pd/C, 1:1 THF/EtOH, 4-16 h; (d) 3:1 TFA/H$_2$O, 0° C., 1 h, 33-82% yield (two steps).

(4) Installation of Acyl Chains and Global Deprotection of QS Saponin Linkage Variants In reference to Scheme 4 (FIG. 5) with all of the desired glycosylated intermediates (18, 19, 21-24, 26) in hand, each was advanced to the corresponding QS saponin central linkage variant (3-9) in a three-step sequence involving: (1) azide reduction ($H_2S$, $Et_3N$), (2) acylation of the resulting amine with dodecanedioic acid monobenzyl ester, and (3) global deprotection via hydrogenolysis ($H_2$, Pd/C) and acid hydrolysis (TFA/$H_2O$), followed by HPLC purification.

Figure 6:
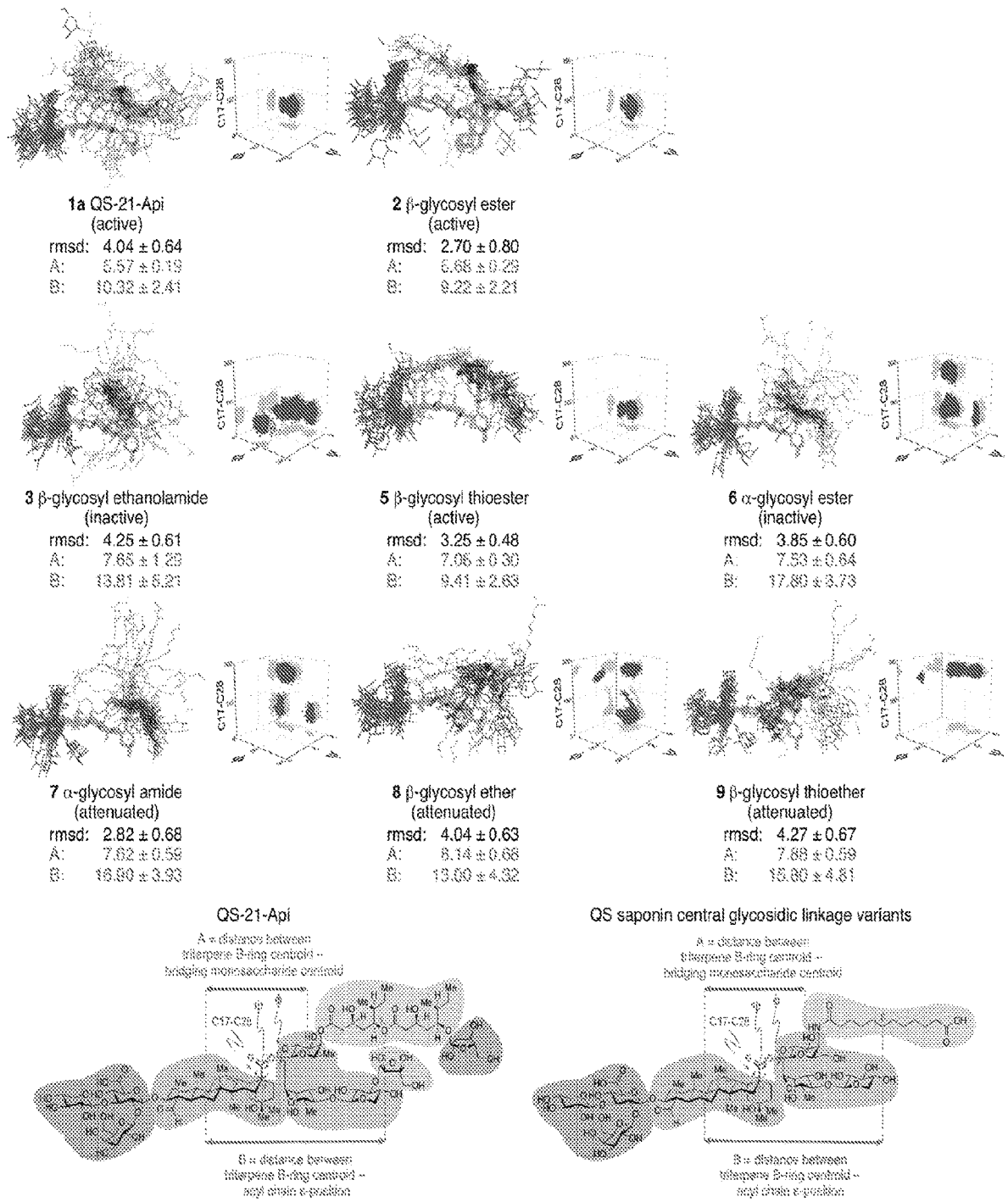
FIG. 6 shows ensembles obtained from unrestrained 200 ns molecular dynamics simulations of QS-21-Api (1a) and saponin variants 2, 3, and 5-9. The rmsd (Å) for heavy atoms relative to average structure, key distance constraints (Å), and three-dimensional plots of torsional angle distributions (C17-C28, ψ, φ, arbitrary scale) about the central glycosidic linker are shown. QS saponin structural domains are color-coded: branched trisaccharide (magenta), triterpene (green), linear trisaccharide (orange), acyl chain (gray), terminal sugars (QS-21 only: cyan, red). In the three-dimensional plots, torsional angle distributions are shown in blue and projections onto each plane are shown in gray. Active adjuvants exhibit distinctive and tightly-clustered torsional angle distributions about the central glycosidic linkage and comparatively shorter distances between the centroid of the triterpene B-ring and the centroid of the bridging monosaccharide (A, blue) as well as between the centroid of the triterpene B-ring and the acyl chain ε-position (B, red).

In the final step described above, the modified central glycosyl ester linkages (including the eight different samples described above) have been incorporated into the finally obtained triterpene saponin variant compounds. FIG. 6 shows ensembles obtained from unrestrained 200 ns molecular dynamics simulations of QS-21-Api (1a) and saponin variants 2, 3 and 5-9.

Example 3: Synthesis of β-Ethanolamide Variant 3
(Sqs-0-4-5-5)

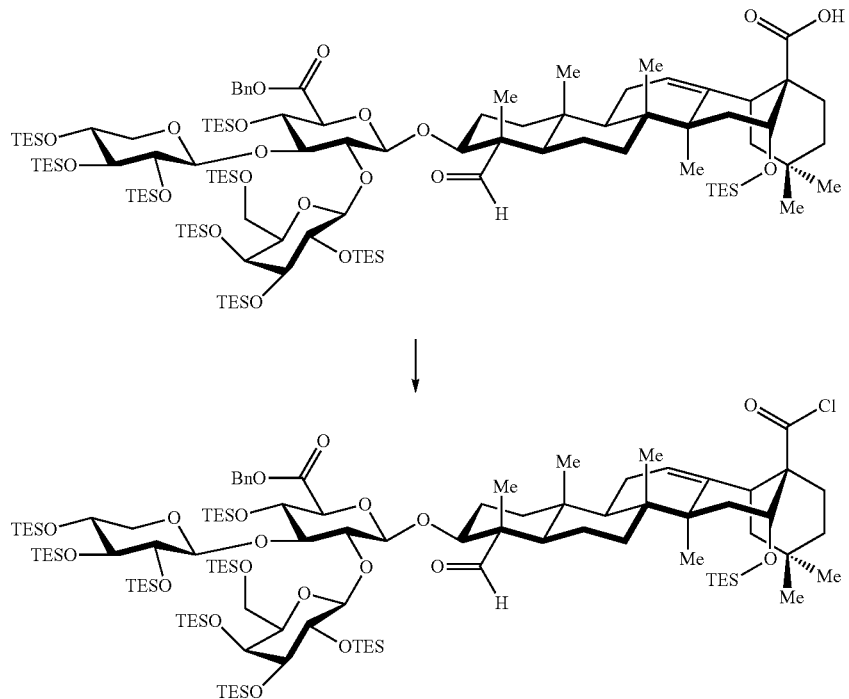

Production of Protected Prosapogenin Acid Chloride 12

Thionyl chloride (31 μl, 0.425 mmol, 2 equiv) was added, drop-wise, to an ice-cooled solution of protected prosapogenin 10 and pyridine (170 μl, 2.13 mmol, 10 equiv) in dichloromethane (6 ml). After two hours, a majority of the volatiles were removed under a stream of nitrogen, then high-vacuum. Residual solids were suspended in anhydrous benzene and filtered through celite. Solvent removal in vacuo furnished 12 (441 mg, 99% yield) as a white foam.

TLC $R_f$ 0.36 (20:1 hexanes/ethyl acetate); FTIR (NaCl, film):) 2953, 2911, 2877, 1792 (O-CClst), 1756, 1725, 14.58, 1414, 1378, 1240, 1171, 1102, 1007, 739 cm$^{-1}$; $^1$H-NMR (600 MHz, C6D6) δ 9.75 (s, 1H), 7.20-7.17 (m, 2H), 7.10-6.97 (m, 3H), 5.42 (t, J=3.5 Hz, 1H), 5.18 (d, J=12.4 Hz, 1H), 4.99 (dd, J=22.3, 9.9 Hz, 2H), 4.79-4.71 (m, 2H), 4.59 (d, J=7.0 Hz, 1H), 4.47 (t, J=8.7 Hz, 1H), 4.37 (t, J=9.1 Hz, 1H), 4.25-4.18 (m, 2H), 4.15 (d, J=9.4 Hz, 1H), 4.13-4.08 (m, 1H), 4.05 (dd, J=11.2, 5.0 Hz, 1H), 4.00 (dd, J=9.3, 7.4 Hz, 1H), 3.95 (dd, J=9.5, 5.5 Hz, 1H), 3.84-3.76 (m, 2H), 3.73-3.66 (m, 3H), 3.65-3.61 (m, 1H), 3.49 (t, J=10.8 Hz, 1H), 3.16 (dd, J=14.1, 4.1 Hz, 1H), 2.39 (t, J=13.6 Hz, 1H), 1.97-1.67 (m, 8H), 1.58 (dd, J=10.2, 7.4 Hz, 1H), 1.46 (m, 139H), 0.81-0.70 (m, 18H), 0.62 (dd, J=8.0, 3.0 Hz, 7H). $^{13}$C-NMR (151 MHz, C6D6) δ 209.67, 177.78, 168.61, 141.76, 135.75, 128.54, 128.38, 128.24, 128.19, 123.96, 102.72, 101.57, 101.40, 83.84, 79.58, 79.26, 77.85, 77.00, 76.78, 76.32, 75.76, 75.32, 73.16, 73.01, 72.28, 71.69, 66.90, 65.97, 61.41, 59.13, 54.48, 49.01, 46.61, 46.53, 42.64, 41.61, 39.92, 37.92, 35.97, 35.25, 34.90, 32.58, 32.34, 30.61, 30.40, 26.59, 25.40, 24.13, 23.46, 20.43, 16.88, 15.66, 11.87, 7.82, 7.64, 7.51, 7.48, 7.45, 7.38, 7.37, 7.35, 7.27, 7.19, 7.07, 7.06, 6.29, 6.15, 6.08, 6.00, 5.95, 5.86, 5.81, 5.76, 5.68, 5.62, 5.48, 5.42, 5.33, 5.14, 4.96, 4.94, 4.77, 4.57; HRMS m/z (ESI): For methyl ester derivative, calcd for $C_{102}H_{210}O_{25}NaSi_9$ [M+Na]$^+$ 2110.2982, found 2110.2986.

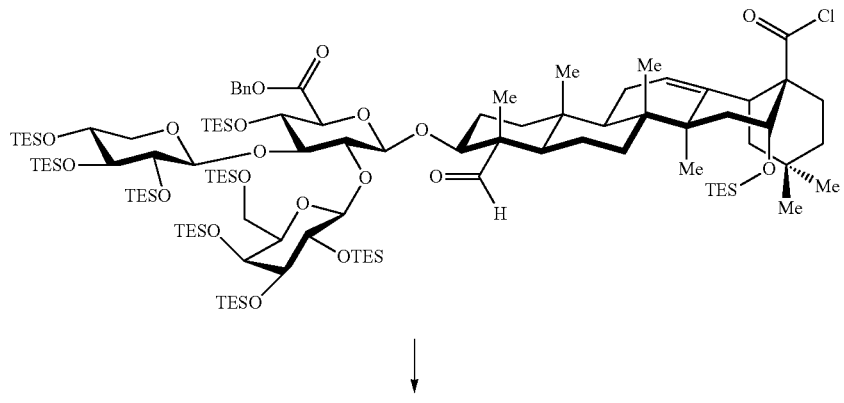

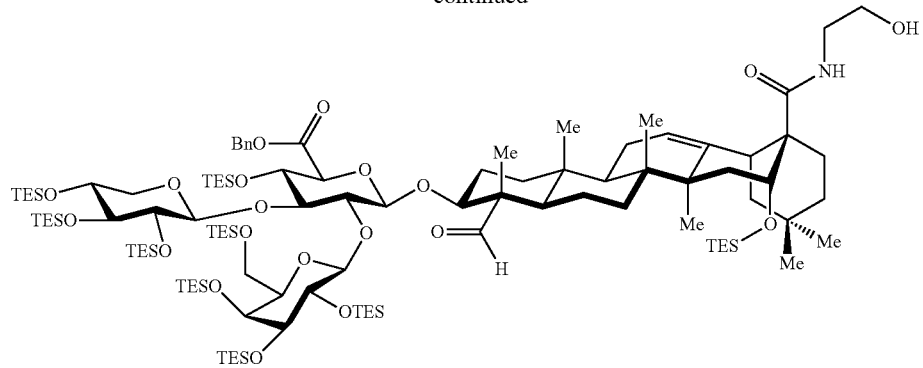

Protected Prosapogenin Ethanolamide 13

Ethanolamine (29 μL, 0.478 mmol, 10 equiv) was added to an ice-cooled solution of acyl chloride 12 (100 mg, 0.0478 mmol), 1 equiv) in dichloromethane (2 mL). After 10 minutes, reaction was warmed to room temperature, concentrated, and purified by silica gel chromatography (hexanes:ethyl acetate, 4:1 to 2:1) to give ethanolamide 13 (89 mg, 88% yield).

TLC $R_f$ 0.32 (2:1 hexanes/ethyl acetate); FTIR (NaCl, film) 3407 (br), 2953, 2911, 2877, 1754, 1725, 1656, 1632, 1518, 1459, 1414, 1378, 1239, 1171, 1103, 1005, 971, 899, 864, 825, 799, 738, 695, 668 cm$^{-1}$; $^1$H-NMR (600 MHz, CDCl$_3$) δ 9.72 (s, 1H), 7.40-7.29 (m, 5H), 6.54 (t, J=5.5 Hz, 1H), 5.51-5.46 (m, 1H), 5.28 (d, J=12.4 Hz, 1H), 5.10 (d, J=12.4 Hz, 1H), 4.56 (d, J=7.4 Hz, 1H), 4.53-4.50 (m, 1H), 4.43 (d, J=7.3 Hz, 1H), 4.17 (d, J=7.4 Hz, 1H), 3.95-3.89 (m, 2H), 3.88-3.77 (m, 4H), 3.75 (t, J=9.3 Hz, 1H), 3.70-3.65 (m, 2H), 3.62-3.53 (m, 3H), 3.50-3.32 (m, 5H), 3.27-3.18 (m, 2H), 3.13 (t, J=10.9 Hz, 1H), 3.03 (t, J=4.9 Hz, 1H), 2.56 (dd, J=13.5, 4.1 Hz, 1H), 2.37 (t, J=13.0 Hz, 1H), 2.11-2.03 (m, 1H), 1.92 (dd, J=8.9, 3.6 Hz, 2H), 1.88-1.76 (m, 2H), 1.74-1.66 (m, 2H), 1.66-1.49 (m, 5H), 1.46-1.36 (m, 6H), 1.31 (s, 3H), 1.29-1.24 (m, 2H), 1.17-1.07 (m, 5H), 1.07-0.88 (m, 97H), 0.81-0.54 (m, 61H); $^{13}$C-NMR (151 MHz, CDCl$_3$) δ 212.72, 179.86, 168.37, 144.93, 135.26, 128.45, 128.25, 128.12, 122.65, 103.68, 101.39, 100.83, 86.42, 78.79, 78.71, 76.44, 75.93, 75.89, 75.82, 75.80, 75.07, 72.60, 72.52, 71.37, 71.09, 66.84, 65.33, 62.93, 60.23, 53.79, 49.33, 49.08, 47.30, 45.95, 43.01, 41.88, 41.84, 39.65, 37.93, 36.02, 35.38, 34.07, 32.53, 31.81, 31.40, 30.53, 26.31, 25.36, 24.25, 23.42, 20.16, 16.72, 15.84, 12.26, 7.56, 7.47, 7.25, 7.16, 7.15, 7.13, 6.98, 6.85, 6.78, 5.92, 5.65, 5.44, 5.37, 5.34, 5.26, 5.23, 5.01, 4.42; HRMS (ESI) m/z: Calcd for C$_{110}$H$_{209}$NO$_{20}$NaSi$_9$ (M+Na)$^+$ 2139.3189, found 2139.3206.

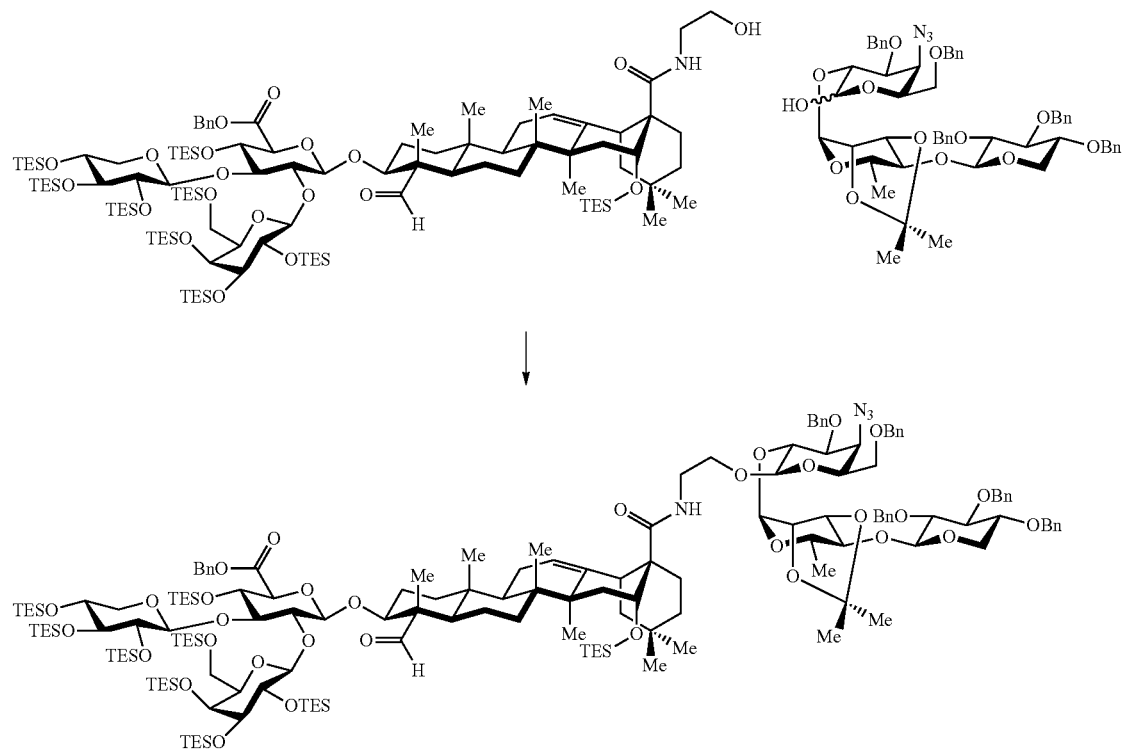

Production of Protected Prosapogenin Ethanolamide Trisaccharide Azide 18

Trifluoromethanesulfonic anhydride (5.2 µL, 0.041, 1.5 equiv) was added to a solution of trisaccharide 17 (20 mg, 0.021 mmol, 1.00 equiv), phenyl sulfoxide (12.5 mg, 0.061 mmol, 3.0 equiv) and 2,4,6-tritertbutylpyridine (18 mg, 0.074 mmol, 3.6 equiv) in dichloromethane (1 mL) at −78° C. The reaction stirred in a cold bath at −78° C. for 5 min and then was transferred to a bath between −40° C. for 60 min. A solution of ethanolamide 13 (84 mg, 0.040 mmol, 1.95 equiv) was added in dichloromethane (1.0 ml) via syringe. After 30 min, flask was transferred to an ice-bath and stirred for 15 min. Triethylamine was added, concentrated and purified via silica gel chromatography (hexanes:ethyl acetate, 10:1 to 2:1) furnishing β-glycoside 18 (55 mg, 87% yield) as a colorless film.

TLC $R_f$ 0.67 (5:1 benzene/ethyl acetate); FTIR (NaCl, film) 3430, 2953, 2911, 2877, 2105, 1751, 1724, 1653, 1497, 1457, 1414, 1379, 1240, 1172, 1098, 1006, 910, 864, 826, 799, 737, 697, 666 cm$^{-1}$; $^1$H-NMR (600 MHz, CDCl$_3$) δ 9.71 (s, 1H), 7.39-7.22 (m, 30H), 6.36 (t, J=5.5 Hz, 1H), 5.43 (t, J=3.8 Hz, 1H), 5.38 (s, 1H), 5.27 (d, J=12.3 Hz, 1H), 5.10 (d, J=12.4 Hz, 1H), 4.91-4.87 (m, 2H), 4.87-4.80 (m, 2H), 4.76-4.69 (m, 2H), 4.68 (d, J=11.1 Hz, 1H), 4.61 (d, J=11.7 Hz, 1H), 4.58-4.52 (m, 4H), 4.51 (d, J=3.0 Hz, 1H), 4.43 (d, J=7.2 Hz, 1H), 4.20 (d, J=7.5 Hz, 2H), 4.15 (dd, J=7.4, 5.5 Hz, 1H), 4.07 (d, J=3.5 Hz, 1H), 4.04 (d, J=5.6 Hz, 1H), 3.96-3.91 (m, 3H), 3.89-3.79 (m, 6H), 3.77 (t, J=9.2 Hz, 1H), 3.69 (ddd, J=10.8, 6.8, 4.7 Hz, 1H), 3.65-3.53 (m, 11H), 3.49 (ddd, J=10.4, 8.4, 5.1 Hz, 1H), 3.40 (dd, J=9.4, 2.5 Hz, 1H), 3.38-3.17 (m, 7H), 3.14 (t, J=11.0 Hz, 1H), 2.52 (dd, J=13.7, 4.5 Hz, 1H), 2.34 (t, J=13.0 Hz, 1H), 2.02-1.51 (m, 12H), 1.42-1.38 (m, 1H), 1.37 (s, 3H), 1.34 (s, 3H), 1.31 (s, 3H), 1.22 (d, J=6.0 Hz, 3H), 1.13-1.03 (m, 4H), 1.03-0.90 (m, 82H), 0.89 (s, 3H), 0.87 (s, 3H), 0.81-0.56 (m, 56H); $^{13}$C-NMR (151 MHz, CDCl$_3$) δ 212.60, 177.85, 168.36, 144.49, 138.81, 138.73, 138.23, 137.41, 136.89, 135.20, 128.58, 128.55, 128.47, 128.41, 128.32, 128.26, 128.24, 128.21, 128.18, 128.16, 128.07, 127.95, 127.88, 127.82, 127.77, 127.48, 122.56, 109.12, 103.64, 102.86, 102.06, 101.38, 100.82, 98.24, 86.43, 83.87, 81.87, 81.39, 78.81, 78.71, 78.25, 78.12, 77.95, 76.45, 75.99, 75.97, 75.92, 75.81, 75.49, 75.07, 74.87, 74.62, 73.71, 73.21, 72.61, 72.51, 71.83, 71.38, 71.09, 68.76, 68.44, 66.87, 65.33, 64.56, 63.81, 60.24, 58.36, 53.82, 49.25, 49.12, 47.22, 46.06, 41.85, 41.73, 39.94, 39.57, 37.97, 36.06, 35.95, 35.39, 34.66, 34.53, 34.07, 32.59, 31.98, 31.59, 31.42, 30.48, 29.06, 27.80, 26.91, 26.49, 26.30, 25.35, 25.27, 24.38, 23.35, 22.66, 20.70, 20.21, 18.77, 17.62, 16.94, 15.75, 14.14, 12.23, 11.45, 7.56, 7.46, 7.25, 7.17, 7.16, 13, 7.09, 6.99, 6.89, 6.85, 6.78, 5.92, 5.64, 5.44, 5.37, 5.34, 5.26, 5.23, 5.20, 5.18, 5.14, 5.06, 0.01, 4.41; HRMS (ESI) m/z: Calcd for C$_{165}$H$_{270}$N$_4$O$_{32}$NaSi$_9$ (M+Na)$^+$ 3094.7445, found 3094.7344.

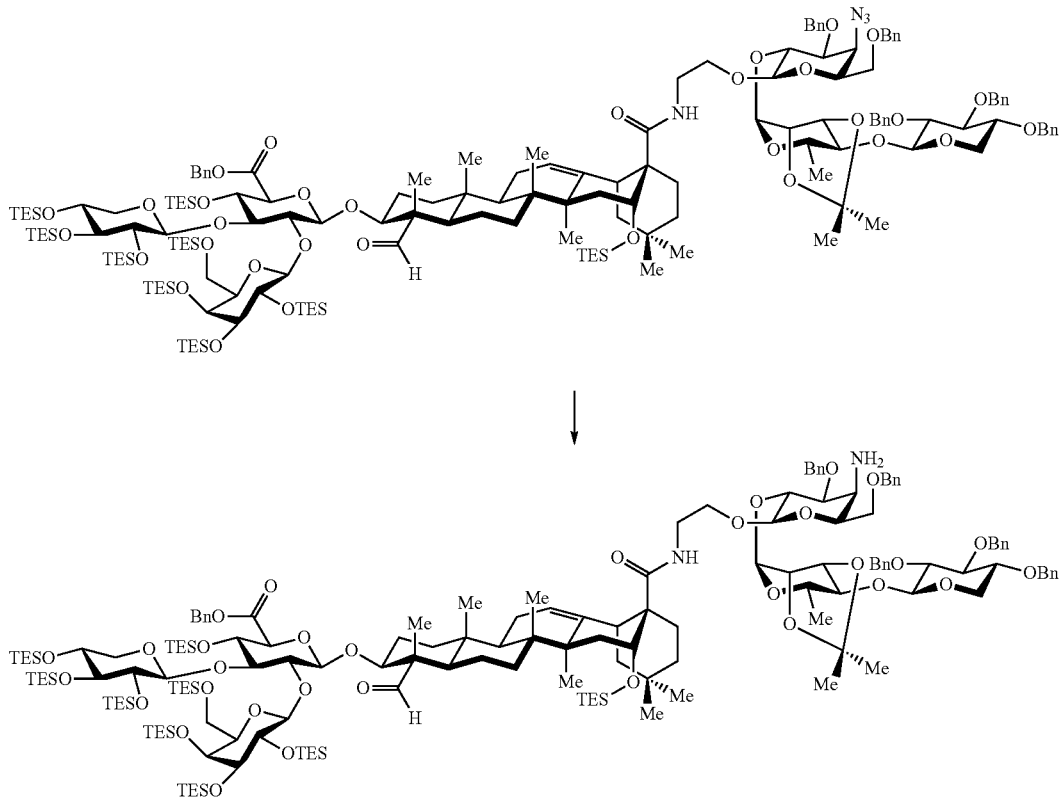

Production of Protected Prosapogenin Ethanolamide Trisaccharide Amine S1

An excess of hydrogen sulfide as bubbled through an ice-cooled solution of azide 18 (35 mg, 0.011, 1 equiv) in pyridine and triethylamine (3:1, 2 mL) for two min via steel needle, then needle removed from septum. After stirring for 2 min, ice-bath was removed and warmed to ambient temperature. After 4.5 h, the dark green solution was purged of excess hydrogen sulfide, then volatiles removed with a stream of nitrogen. The resulting light-orange solid was purified by silica gel chromatography (hexanes:ethyl acetate+0.5% triethylamine, 8:1 to 1:1) to give amine S1 (27 mg, 78% yield). TLC $R_f$ 0.44 (3% methanol/dichloromethane); FTIR (NaCl film) 3422, 3031, 2953, 2910, 2876, 1751, 1734, 1719, 1653, 1648, 1507, 1496, 1465, 1457, 1454, 1419, 1413, 1379, 1240, 1097, 1008, 908, 863, 825, 734, 697, 668 cm$^{-1}$; $^1$H-NMR (600 MHz, CDCl$_3$) δ 9.70 (s, 1H), 39.89, 39.56, 37.94, 35.95, 35.35, 34.03, 32.58, 31.91, 31.49, 30.49, 27.82, 26.50, 26.29, 25.34, 24.34, 23.44, 20.18, 17.53, 16.81, 15.92, 12.23, 7.55, 7.46, 7.25, 7.17, 7.16, 7.13, 6.98, 6.85, 6.79, 5.92, 5.63, 5.44, 5.37, 5.33, 5.25, 5.22, 5.01, 4.41; HRMS (ESI) m/z: Calcd for C$_{165}$H$_{273}$N$_2$O$_{32}$Si$_9$ (M+H) 3046.7720, found 3046.7788.

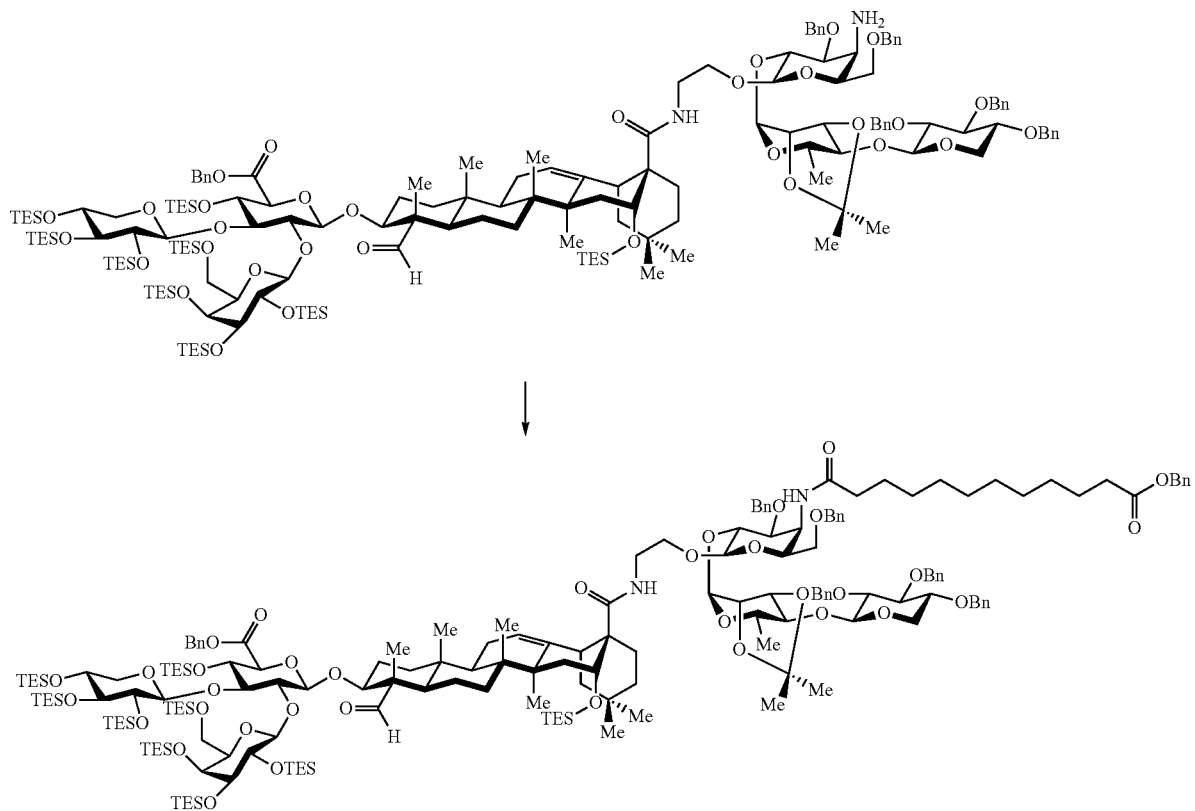

7.39-7.22 (m, 30H), 6.31 (t, J=5.5 Hz, 1H), 5.42-5.36 (m, 2H), 5.27 (d, J=12.4 Hz, 1H), 5.09 (d, J=12.4 Hz, 1H), 4.91-4.87 (m, 2H), 4.83 (q, J=11.1 Hz, 2H), 4.73-4.64 (m, 3H), 4.61 (d, J=11.7 Hz, 1H), 4.58-4.54 (m, 3H), 4.54-4.51 (m, 1H), 4.49 (d, J=11.6 Hz, 1H), 4.42 (d, J=7.2 Hz, 1H), 4.23 (d, J=7.7 Hz, 1H), 4.20-4.14 (m, 2H), 4.07 (d, J=5.6 Hz, 1H), 3.96-3.90 (m, 3H), 3.88-3.78 (m, 5H), 3.78-3.67 (m, 4H), 3.67-3.63 (m, 1H), 3.63-3.53 (m, 8H), 3.51-3.43 (m, 2H), 3.43-3.29 (m, 6H), 3.28-3.23 (m, 2H), 3.22-3.17 (m, 1H), 3.13 (t, J=10.9 Hz, 1H), 2.52 (dd, J=13.3, 2.9 Hz, 1H), 2.33 (t, J=13.0 Hz, 1H), 2.02-1.94 (m, 1H), 1.89-1.76 (m, 4H), 1.72-1.54 (m, 3H), 1.48-1.38 (m, 2H), 1.38-1.32 (m, 8H), 1.29 (s, 3H), 1.21 (d, J=6.0 Hz, 3H), 1.10-1.02 (m, 4H), 1.02-0.90 (m, 83H), 0.89-0.86 (m, 9H), 0.81-0.55 (m, 58H); $^{13}$C-NMR (151 MHz, CDCl$_3$) δ 212.57, 177.70, 168.37, 144.75, 138.81, 138.70, 138.23, 137.78, 137.34, 135.20, 131.04, 129.31, 128.53, 128.48, 128.46, 128.41, 128.34, 128.30, 128.26, 128.25, 128.18, 128.15, 128.13, 128.05, 128.03, 128.00, 127.97, 127.94, 127.88, 127.86, 127.84, 127.81, 127.76, 127.70, 127.51, 127.48, 124.77, 122.23, 109.10, 103.65, 103.09, 102.06, 101.37, 100.82, 98.07, 86.39, 83.86, 82.07, 81.86, 78.78, 78.70, 78.25, 78.07, 77.96, 76.44, 76.09, 75.93, 75.88, 75.82, 75.80, 75.49, 75.06, 74.65, 74.58, 73:59, 73.35, 73.21, 72.60, 72.51, 71.36, 71.10, 71.01, 69.35, 68.65, 66.88, 65.32, 64.51, 63.80, 60.23, 53.79, 49.27, 49.00, 48.74, 47.18, 45.97,

Production of Protected Ethanolamide Variant S3

Isobutyl chloroformate (6.1 µL, 0.047 mmol, 3.0 equiv) was added to an ice-cooled solution of 12-(benzyloxy)-12-oxododecanoic acid S2 (30 mg, 0.094 mmol, 6 equiv) and triethylamine (22 µL, 0.156 mmol, 10 equiv) in tetrahydrofuran (3.0 mL) and stirred for 4 hours, then transferred via cannula to an ice-cooled solution of amine S1 (42 mg, 0.013 mmol, 1 equiv) in tetrahydrofuran (2.0 mL). After 24 h, suspension was diluted with saturated sodium bicarbonate and then extracted with ethyl acetate (3×25 ml). Combined organics were washed with brine, dried over sodium sulfate, concentrated, and purified with silica gel chromatography (hexanes:ethyl acetate+0.5% triethylamine, 10:1 to 1:1) to give fully protected ethanolamide analogue S2 (44 mg, 84% yield) as a colorless film.

TLC $R_f$ 0.37 (3:1 hexanes/ethyl acetate); FTIR (NaCl film) 3582, 3417, 3090, 3063, 3030, 2952, 2911, 2876, 1738, 1727, 1657, 1547, 1512, 1498, 1454, 1413, 1379, 1240, 1166, 1094, 1069, 1007, 910, 863, 823, 799, 731, 696 cm$^{-1}$; $^1$H-NMR (600 MHz, CDCl$_3$) δ 9.70 (s, 1H), 7.39-7.24 (m, 35H), 6.16 (t, J=5.6 Hz, 1H), 5.45 (d, J=10.0 Hz, 1H), 5.40 (s, 1H), 5.31 (t, J=3.7 Hz, 1H), 5.25 (d, J=12.4 Hz, 1H), 5.14-5.07 (m, 3H), 4.91-4.79 (m, 5H), 4.74 (d, J=11.4 Hz, 1H), 4.71 (d, J=11.7 Hz, 1H), 4.67 (d, J=11.0 Hz, 1H), 4.61 (d, J=11.7 Hz, 1H), 4.56 (d, J=7.4 Hz, 1H), 4.54-4.46 (m, 3H), 4.45-4.39 (m, 2H), 4.25 (d, J=7.5 Hz, 1H), 4.20-4.14

(m, 2H), 4.07 (d, J=5.6 Hz, 1H), 3.95-3.89 (m, 3H), 3.88-3.78 (m, 5H), 3.75 (t, J=9.3 Hz, 1H), 3.72-3.44 (m, 15H), 3.43-3.28 (m, 5H), 3.25 (t, J=8.0 Hz, 1H), 3.23-3.16 (m, 2H), 3.13 (t, J=10.9 Hz, 1H), 2.49 (dd, J=13.1, 4.6 Hz, 1H), 2.37-2.29 (m, 3H), 2.17 (tt, J=11.2, 5.7 Hz, 2H), 1.95 (dt, J=14.5, 3.5 Hz, 1H), 1.85-1.75 (m, 4H), 1.69-1.52 (m, 8H), 1.48-1.42 (m, 3H), 1.38-1.30 (m, 8H), 1.29 (s, 3H), 1.28-1.23 (m, 6H), 1.21 (d, J=6.2 Hz, 7H), 1.19-1.15 (m, 2H), 1.10-1.01 (m, 4H), 1.01-0.89 (m, 85H), 0.89-0.84 (m, 9H), 0.81-0.54 (m, 60H); $^{13}$C-NMR (151 MHz, CDCl$_3$) δ 212.60, 177.74, 173.67, 173.33, 168.38, 144.94, 138.80, 138.65, 138.21, 137.58, 137.40, 136.12, 135.19, 128.52, 128.48, 128.43, 128.41, 128.31, 128.27, 128.25, 128.15, 128.13, 128.10, 128.03, 127.87, 127.84, 127.81, 127.77, 127.76, 127.73, 127.56, 127.48, 122.05, 109.09, 103.63, 102.64, 102.07, 101.37, 100.82, 98.08, 86.37, 83.85, 81.85, 79.51, 78.78, 78.70, 78.17, 78.04, 77.97, 76.43, 75.94, 75.92, 75.85, 75.80, 75.50, 75.06, 74.83, 74.67, 73.66, 73.21, 72.97, 72.59, 72.50, 71.36, 71.12, 70.85, 68.98, 68.15, 66.88, 66.04, 65.32, 64.56, 63.82, 60.22, 53.76, 49.25, 48.93, 47.13, 46.13, 45.94, 41.83, 41.76, 39.53, 39.49, 37.91, 36.96, 36.62, 35.96, 35.26, 34.33, 34.04, 32.56, 31.83, 31.49, 30.49, 29.44, 29.40, 29.36, 29.23, 29.14, 27.79, 26.48, 26.31, 25.92, 25.32, 24.96, 24.68, 24.41, 23.39, 23.35, 20.15, 17.42, 16.75, 15.85, 12.22, 7.56, 7.46, 7.24, 7.16, 7.16, 7.13, 6.98, 6.85, 6.79, 5.91, 5.63, 5.43, 5.37, 5.33, 5.25, 5.22, 5.01, 4.41; HRMS (ESI) m/z: Calcd for $C_{184}H_{298}N_2O_{35}Si_9Na$ [M+23] 3379.9421, found 3370.9590.

Production of Ethanolamide Variant 3 (SQS-0-4-5-5)

A solution of fully protected β-ethanolamide analogue (S2) (25.0 mg, 0.008 mmol, 1.0 equiv) in tetrahydrofuran (5 mL) and ethanol (5 mL) in a 25 mL round bottom flask was charged with 10% (dry basis) palladium on carbon, wet, Degussa type E101 NE/W (17 mg, 0.016 mmol, 2.2 equiv). Reaction mixture was stirred under hydrogen pressure (50 psi) overnight, then filtered through a 0.45 m polyvinylidene fluoride filter disk, washed with methanol (5 mL), and concentrated. To the hydrogenation product was added a precooled (0° C.) solution of trifluoroacetic acid (5.0 mL, TFA/H20 3:1). After vigorous stirring for 60 min, the solution was concentrated in vacuo at 0° C. to give white solid residue. This crude product was partially dissolved in a solution of aqueous acetonitrile (5:1 water:acetonitrile) and purified by RP-HPLC on an XBridge Prep BEH300 C18 column (5 m, 10×250 mm) using a linear gradient of 10→49% acetonitrile (0.05% TFA) in water (0.05% TFA) over 18 min at a flow rate of 5 mL/min. The fraction containing the major peak (tR=16.42 min) was collected and lyophilized to dryness to afford SQS-0-4-5-5 (3) (5.5 mg, 45% yield) as a white solid. $^1$H-NMR (600 MHz, D2O/CD3CN) δ 9.30 (s, 1H), 6.98 (d, J=9.6 Hz, 1H), 6.80 (t, J=5.2 Hz, 1H), 5.41 (t, J=3.8 Hz, 1H), 4.86 (d, J=1.8 Hz, 1H), 4.60 (d, J=7.8 Hz, 1H), 4.47 (d, J=7.8 Hz, 1H), 4.44 (d, J=7.8 Hz, 1H), 4.35 (d, J=7.8 Hz, 1H), 4.26 (d, J=7.8 Hz, 1H), 3.86-3.67 (m, 10OH), 3.65 (dd, J=11.1, 7.8 Hz, 2H), 3.61-3.50 (m, 4H), 3.50-3.37 (m, 8H), 3.34-3.18 (m, 5H),

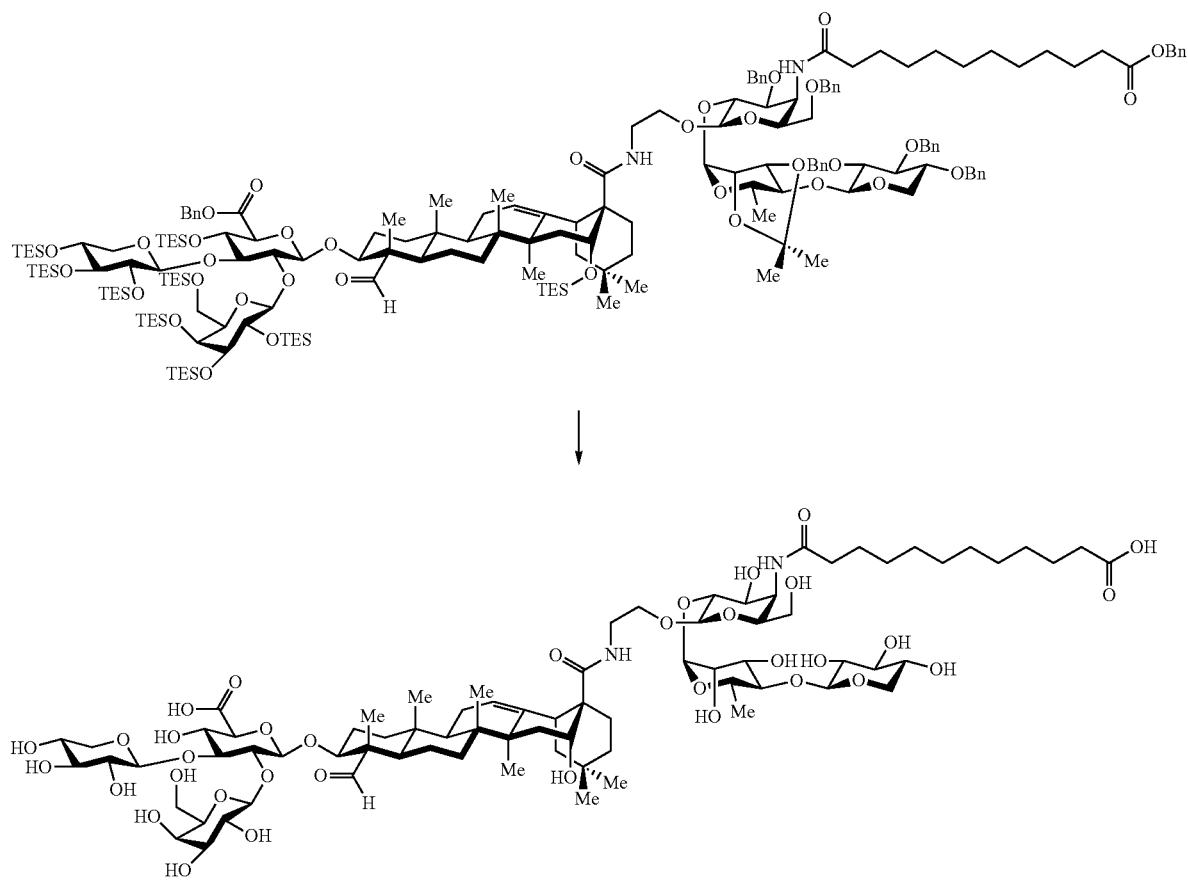

3.18-3.07 (m, 5H), 2.69 (dd, J=13.1, 2.6 Hz, 1H), 2.29-2.12 (m, 5H), 1.86-1.74 (m, 4H), 1.72-1.56 (m, 4H), 1.53-1.35 (m, 9H), 1.24 (s, 4H), 1.12 (d, J=6.2 Hz, 3H), 1.03 (s, 3H), 0.87 (s, 3H), 0.86 (s, 3H), 0.80 (s, 3H), 0.65 (s, 3H); HRMS (ESI) m/z: Calcd for $C_{78}H_{126}N_2O_{35}Si_9Na$ [M+23] 1673.8039, found 1673.8019.

Example 4: Synthesis of α/β-Carbamate Variants α/β-4

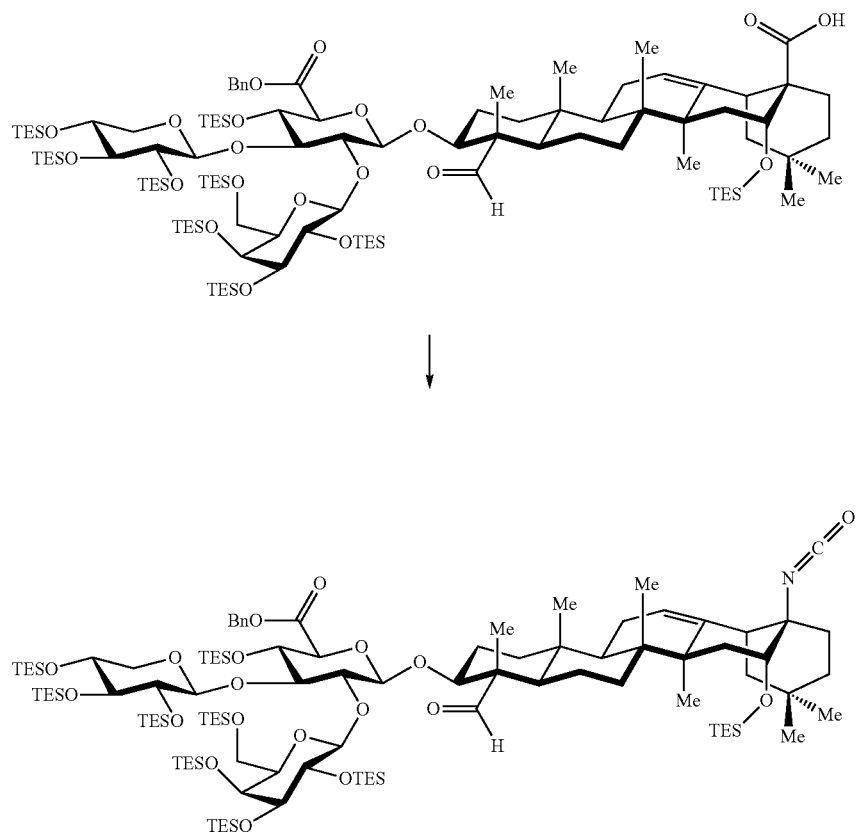

Production of Protected Prosapogenin Isocyanate 11

Diphenylphosphoryl azide (24 μl, 0.116 mmol, 1.5 eq) was added to a solution of 10 (161 mg, 0.0776 mmol, 1 equiv) and triethylamine (19 μl, 0.136 mmol, 1.75 eq) in benzene (8 ml) in a vessel fitted with a water-cooled condenser, then submerged in an oil bath at 90° C. After 30 min, additional portions of triethylamine (86 μl, 0.62 mmol, 8 equiv) and diphenylphosphoryl azide (80 μl, 0.387 mmol, 5 equiv) were added sequentially. After 20 min, reaction was cooled to room temperature, concentrated, and purified by silica gel chromatography (hexanes/ethyl acetate, 40:1 to 10:1) to give isocyanate 11 (127 mg, 79% yield).

TLC $R_f$ 0.41 (20:1 hexanes/ethyl acetate); FTIR (NaCl, film) 2953, 2912, 2876, 2248 (NCO st), 1754, 1724, 1458, 1413, 1377, 1239, 1171, 1101, 1006, 971, 908, 864, 825, 801, 736, 695 cm$^{-1}$; $^1$H-NMR (500 MHz, CDCl$_3$) δ 9.71 (s, 1H), 7.38-7.28 (m, 5H), 5.37 (s, 1H), 5.28 (d, J=12.4 Hz, 1H), 5.10 (d, J=12.4 Hz, 1H), 4.55 (d, J=7.4 Hz, 1H), 4.42 (d, J=7.3 Hz, 1H), 4.18 (d, J=7.3 Hz, 1H), 3.96-3.72 (m, 8H), 3.63-3.54 (m, 3H), 3.51-3.45 (m, 1H), 3.42-3.31 (m, 3H), 3.28-3.22 (m, 1H), 3.13 (t, J=10.9 Hz, 1H), 2.51-2.43 (m, 1H), 2.22 (t, J=13.6 Hz, 1H), 2.07 (m, 1H), 1.99-1.55 (m, 9H), 1.53 (s, 2H), 1.52-1.35 (m, 3H), 1.33 (s, 3H), 1.32 (s, 3H), 1.23 (m, 6H), 0.93 (m, 103H), 0.81-0.54 (m, 60H); $^{13}$C-NMR (151 MHz, CDCl$_3$) δ 212.92, 168.33, 142.29, 135.26, 128.52, 128.49, 128.46, 128.34, 128.28, 128.25, 128.23, 128.21, 128.19, 128.19, 128.13, 123.76, 122.06, 103.68, 101.40, 100.83, 86.53, 78.81, 78.71, 77.45, 76.44, 75.91, 75.81, 75.08, 72.61, 72.52, 71.38, 71.08, 66.87, 66.84, 65.33, 62.11, 62.08, 60.22, 53.84, 49.44, 48.29, 47.09, 46.16, 41.34, 41.32, 39.77, 39.63, 37.91, 37.18, 37.14, 36.38, 36.11, 33.70, 32.45, 32.40, 32.38, 32.36, 30.63, 30.61, 26.51, 26.44, 25.37, 24.30, 24.27, 23.42, 20.26, 17.04, 17.01, 15.78, 12.30, 7.57, 7.47, 7.38, 7.28, 7.25, 7.23, 7.22, 7.16, 7.14, 7.11, 7.08, 7.05, 7.04, 7.03, 6.99, 6.95, 6.94, 6.91, 6.85, 6.83, 6.81, 6.79, 6.77, 5.93, 5.65, 5.48, 5.44, 5.41, 5.37, 5.35, 5.30, 5.28, 5.26, 5.23, 5.19, 4.94, 4.88, 4.86, 4.42, 4.38; HRMS (ESI) m/z: Calcd for $C_{108}H_{203}NO_{19}NaSi_9$ (M+Na)$^+$ 2093.2771, found 2093.2708.

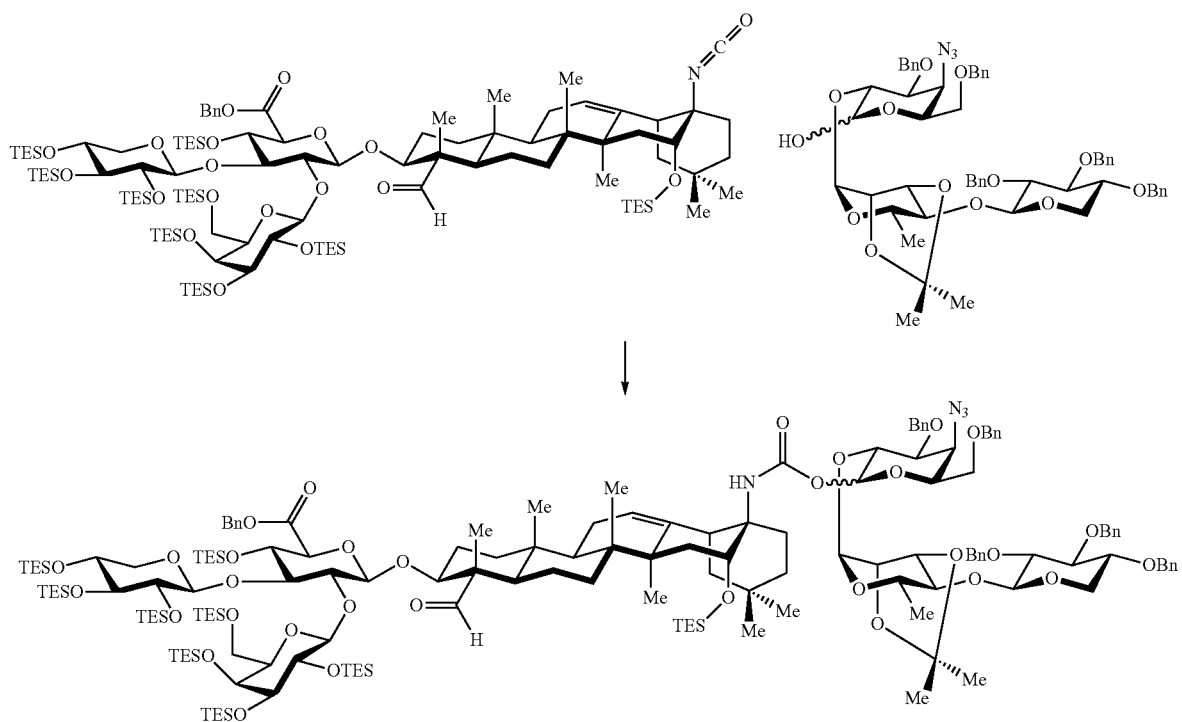

Production of Protected Prosapogenin Carbamate Azides α/β-23

Sodium hydride (60% dispersion in mineral oil, 4.3 mg, 0.108 mmol, 3 equiv) was added to a solution of hemiacetal (35 mg, 0.036 mmol, 1 equiv) in tetrahydrofuran (0.5 mL). After 80 min, isocyanate was added in 0.5 mL tetrahydrofuran. After three hours, suspension was diluted with concentrated ammonium chloride, and extracted with ethyl acetate (3×25 mL). Combined organics were washed with brine and dried over sodium sulfate, decanted, concentrated, and purified via silica gel chromatography (hexanes/ethyl acetate, 20:1 to 4:1) to give easily separable glycosyl carbamates (57 mg β-23 and 29 mg α-23, total yield 79%).

β-23: TLC $R_f$ 0.42 (4:1 hexanes/ethyl acetate); FTIR (NaCl, film) 3422, 2953, 2877, 2107, 1745, 1497, 1456, 1378, 1240, 1096, 1007, 909, 863, 825, 730, 697, 666 cm$^{-1}$; $^1$H-NMR (500 MHz, CDCl$_3$) δ 9.70 (s, 1H), 7.40-7.27 (m, 30H), 5.35 (s, 1H), 5.34-5.32 (m, 1H), 5.29 (d, J=2.0 Hz, 1H), 5.27 (d, J=6.3 Hz, 1H), 5.10 (d, J=12.4 Hz, 1H), 4.90-4.81 (m, 4H), 4.77-4.69 (m, 3H), 4.65-4.60 (m, 3H), 4.57-4.48 (m, 4H), 4.42 (d, J=7.2 Hz, 1H), 4.18 (d, J=7.3 Hz, 1H), 4.11-4.06 (m, 2H), 4.04 (d, J=5.7 Hz, 1H), 3.96-3.72 (m, 9H), 3.71-3.52 (m, 11H), 3.52-3.43 (m, 1H), 3.42-3.31 (m, 3H), 3.26 (q, J=7.6 Hz, 2H), 3.22-3.16 (m, 1H), 3.13 (t, J=11.0 Hz, 1H), 2.52-2.45 (m, 1H), 2.33 (t, J=13.7 Hz, 1H), 2.02 (d, J=14.2 Hz, 1H), 1.93-1.73 (m, 4H), 1.74-1.65 (m, 2H), 1.64-1.56 (m, 1H), 1.52-1.51 (m, 1H), 1.49 (s, 3H), 1.47-1.33 (m, 3H), 1.31 (d, J=2.5 Hz, 6H), 1.28-1.23 (m, 4H), 1.10 (d, J=13.8 Hz, 2H), 1.05-0.87 (m, 89H), 0.85 (s, 3H), 0.79 (s, 3H), 0.76-0.52 (m, 53H); $^{13}$C NMR (151 MHz, CDCl$_3$) δ 212.76, 168.32, 151.95, 141.94, 138.80, 138.58, 138.23, 137.62, 136.81, 135.24, 128.55, 128.49, 128.45, 128.42, 128.29, 128.26, 128.19, 128.13, 127.98, 127.96, 127.93, 127.91, 127.77, 127.74, 127.53, 127.49, 124.99, 109.02, 103.65, 102.34, 101.39, 100.82, 98.50, 93.20, 86.46, 83.96, 82.45, 81.63, 78.80, 78.71, 78.14, 78.12, 78.00, 76.43, 75.99, 75.90, 75.80, 75.63, 75.06, 74.93, 74.09, 73.72, 73.21, 72.60, 72.50, 72.05, 71.92, 71.89, 71.37, 71.07, 68.10, 66.83, 65.32, 64.44, 63.83, 60.21, 58.27, 55.96, 53.83, 49.33, 47.32, 46.59, 46.06, 41.20, 39.63, 37.91, 36.12, 36.01, 33.17, 32.48, 32.24, 32.08, 30.54, 29.70, 27.79, 26.45, 26.41, 25.34, 24.56, 23.50, 20.20, 17.97, 16.90, 15.80, 12.26, 7.56, 7.46, 7.24, 7.16, 7.13, 7.06, 6.98, 6.85, 6.79, 5.92, 5.64, 5.43, 5.36, 5.33, 5.25, 5.22, 4.92, 4.87, 4.41; HRMS (ESI) m/z: Calcd for $C_{163}H_{266}N_4O_{32}NaSi_9$ [M+Na] 3066.7132, found 3066.7073.

α-23: TLC $R_f$ 0.60 (4:1 hexanes/ethyl acetate); FTIR (NaCl, film) 2953, 2877, 2108, 1745, 1456, 1379, 1240, 1096, 1008, 733, 665 cm$^{-1}$; $^1$H-NMR (600 MHz, CDCl$_3$) δ 9.69 (s, 1H), 7.41-7.26 (m, 31H), 5.97 (d, J=3.8 Hz, 1H), 5.37 (t, J=3.6 Hz, 1H), 5.31-5.26 (m, 2H), 5.10 (d, J=12.4 Hz, 1H), 4.88 (d, J=11.0 Hz, 1H), 4.85-4.76 (m, 3H), 4.74-4.67 (m, 2H), 4.66-4.58 (m, 3H), 4.43 (d, J=7.2 Hz, 1H), 4.36 (s, 1H), 4.28-4.24 (m, 1H), 4.21-4.15 (m, 2H), 4.15-4.09 (m, 2H), 4.07 (d, J=5.8 Hz, 1H), 3.99-3.89 (m, 4H), 3.89-3.73 (m, 6H), 3.65-3.51 (m, 9H), 3.50-3.44 (m, 1H), 3.40 (dd, J=9.4, 2.5 Hz, 1H), 3.38-3.33 (m, 2H), 3.30 (t, J=7.9 Hz, 1H), 3.25 (dd, J=8.6, 7.4 Hz, 1H), 3.19 (dd, J=11.7, 8.9 Hz, 1H), 3.13 (t, J=10.9 Hz, 1H), 2.53 (dd, J=14.4, 4.4 Hz, 1H), 2.28 (t, J=13.4 Hz, 1H), 2.21-2.14 (m, 1H), 1.94-1.48 (m, 13H), 1.39-1.19 (m, 15H), 1.15-0.82 (m, 101H), 0.82-0.51 (m, 61H); $^{13}$C-NMR (151 MHz, CDCl$_3$) δ 212.17, 168.37, 151.39, 142.42, 138.80, 138.46, 138.23, 137.57, 137.47, 135.23, 128.48, 128.45, 128.42, 128.40, 128.35, 128.29, 128.26, 128.25, 128.23, 128.19, 128.15, 128.12, 128.09, 128.01, 128.00, 127.91, 127.89, 127.86, 127.74, 127.61, 127.59, 127.53, 127.49, 127.46, 124.22, 109.09, 103.52, 102.47, 101.36, 100.82, 99.01, 91.59, 86.14, 83.76, 81.63, 78.77, 78.71, 78.33, 78.22, 77.92, 77.61, 76.44, 76.33, 75.91, 75.82, 75.79, 75.48, 75.05, 74.52, 73.92, 73.83, 73.10, 72.59, 72.48, 72.18, 71.39, 71.10, 68.85, 68.29, 66.85, 65.62, 65.33, 63.63, 60.28, 60.14, 56.04, 53.74, 49.08, 46.67, 45.96, 44.57, 41.06, 39.67, 37.76, 36.31, 35.94, 33.26, 32.49, 32.14, 31.93, 31.92, 30.65, 29.70, 27.66, 26.56, 26.15, 25.28, 24.40, 23.38, 20.16, 17.45, 16.76, 15.72, 12.04, 7.56, 7.46, 7.25, 7.19, 7.16, 7.13, 7.10, 7.07, 6.98, 6.85, 6.79, 5.92, 5.63, 5.44, 5.42, 5.36, 5.33, 5.30, 5.28, 5.25, 5.22, 4.88, 4.41; HRMS (ESI) m/z: Calcd for C163H266N4O32NaSi9 [M+Na] 3066.7132, found 3066.6929.

4H), 4.77 (s, 1H), 4.72 (d, J=11.7 Hz, 1H), 4.68-4.59 (m, 5H), 4.59-4.46 (m, 4H), 4.43 (d, J=7.2 Hz, 1H), 4.18 (d, J=7.3 Hz, 1H), 4.13-4.06 (m, 2H), 3.97-3.87 (m, 4H), 3.87-3.45 (m, 20H), 3.42-3.31 (m, 4H), 3.26 (dt, J=11.1, 8.0 Hz, 2H), 3.22-3.16 (m, 1H), 3.13 (t, J=10.9 Hz, 1H), 2.54-2.46 (m, 1H), 2.33 (dd, J=15.2, 11.4 Hz, 1H), 2.02 (dd, J=13.6, 2.4 Hz, 1H), 1.94-1.75 (m, 4H), 1.75-1.53 (m, 5H), 1.48-1.34 (m, 6H), 1.28-1.24 (m, 4H), 1.12-0.86 (m, 104H), 0.85 (s, 4H), 0.79 (s, 4H), 0.78-0.53 (m, 60H); $^{13}$C-NMR

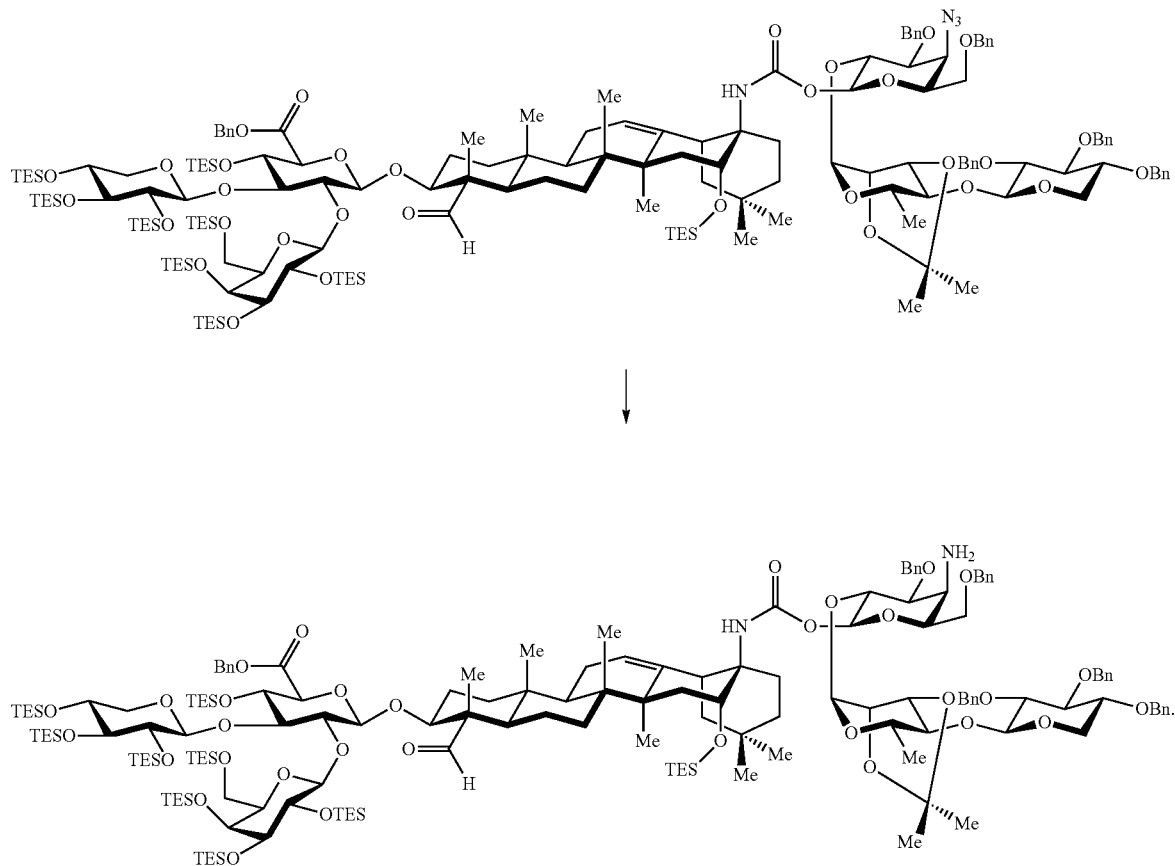

Production of Protected Prosapogenin β-Carbamate Amine β-S4

An excess of hydrogen sulfide was bubbled through an ice-cooled solution of azide β-23 (17 mg, 0.006 mmol, 1 eq) in pyridine and triethylamine (3.5:1, 4.5 mL) for two min via steel needle, then needle removed from septum. After stirring for 2 min, ice-bath was removed and warmed to ambient temperature. After 7 h, the dark green solution was purged of excess hydrogen sulfide, then volatiles removed with a stream of nitrogen. The resulting light-orange solid was purified by silica gel chromatography (hexanes:ethyl acetate+0.5% triethylamine, 8:1 to 1:1) to give amine β-S4 (14 mg, 83% yield).

TLC R$_f$ 0.42 (hexanes:ethyl acetate, 2:1+0.5% triethylamine); FTIR (NaCl, film) 3425, 3066, 3033, 2955, 2913, 2878, 1741, 1498, 1458, 1415, 1382, 1314, 1242, 1098, 904, 865, 827, 735, 699, 667 cm$^{-1}$; $^1$H-NMR (500 MHz, CDCl$_3$) δ 9.70 (s, 1H), 7.41-7.27 (m, 30H), 5.39-5.30 (m, 3H), 5.28 (d, J=12.4 Hz, 1H), 5.10 (d, J=12.4 Hz, 1H), 4.92-4.80 (m, (151 MHz, CDCl$_3$) δ 212.78, 168.32, 152.02, 142.07, 138.80, 138.55, 138.24, 138.01, 137.35, 135.24, 128.49, 128.45, 128.42, 128.41, 128.30, 128.27, 128.12, 128.02, 127.98, 127.94, 127.93, 127.82, 127.76, 127.74, 127.53, 127.50, 124.90, 109.00, 103.66, 102.31, 101.38, 100.81, 98.37, 93.52, 86.48, 83.96, 82.45, 82.37, 78.80, 78.70, 78.11, 77.99, 76.43, 76.07, 75.89, 75.79, 75.63, 75.06, 74.95, 74.15, 73.99, 73.69, 73.21, 72.59, 72.50, 72.02, 71.37, 71.07, 71.03, 68.82, 66.83, 65.31, 64.37, 63.83, 60.21, 55.86, 53.81, 49.33, 48.50, 47.33, 46.58, 46.03, 41.19, 39.81, 39.62, 37.89, 36.11, 36.00, 33.16, 32.66, 32.48, 32.27, 32.02, 31.93, 30.90, 30.55, 29.70, 29.37, 27.82, 26.64, 26.46, 26.41, 25.34, 24.54, 24.45, 23.50, 22.70, 20.18, 17.97, 17.01, 16.88, 15.78, 14.14, 12.25, 7.56, 7.46, 7.24, 7.16, 7.13, 7.05, 6.98, 6.85, 6.79, 5.91, 5.63, 5.43, 5.36, 5.33, 5.25, 5.22, 4.95, 4.86, 4.40; HRMS (ESI) m/z: Calcd for C$_{163}$H$_{269}$N$_2$O$_{32}$Si$_9$ [M+H]$^+$ 3018.7407, found 3018.7476.

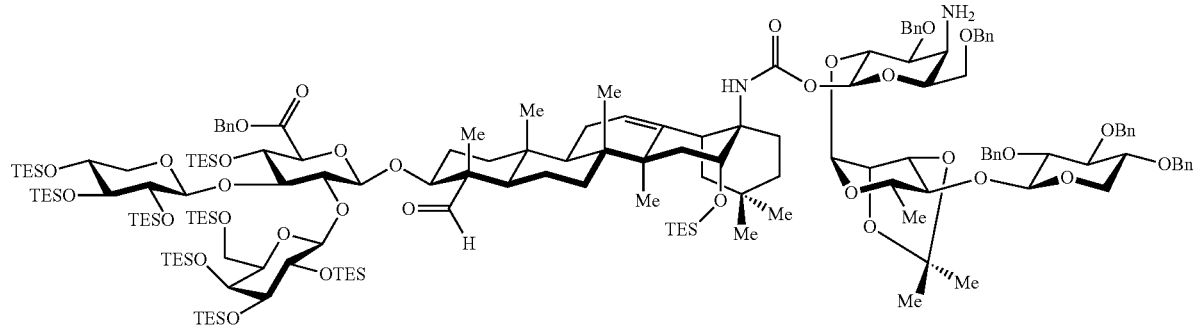

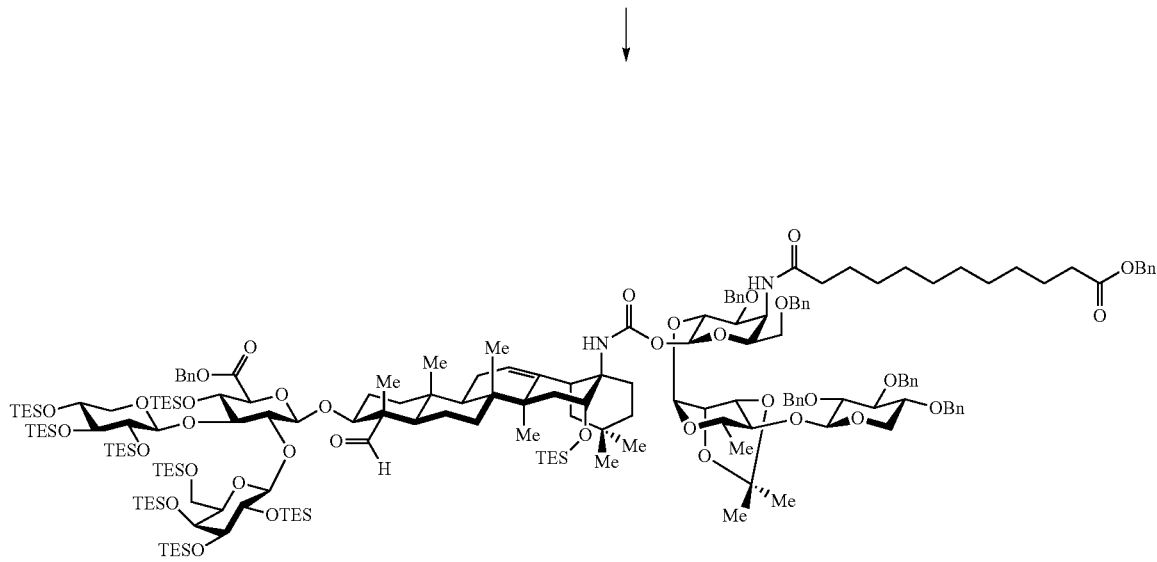

Production of Protected Prosapogenin α-Carbamate Amine α-S6

An excess of hydrogen sulfide was bubbled through an ice-cooled solution of azide α-23 (29 mg, 0.010 mmol, 1 eq) in pyridine and triethylamine (3.5:1, 4.5 mL) for two min via steel needle, then needle removed from septum. After stirring for 2 min, ice-bath was removed and warmed to ambient temperature. After 6 h, the dark green solution was purged of excess hydrogen sulfide, then volatiles removed with a stream of nitrogen. The resulting light-orange solid was purified by silica gel chromatography (hexanes:ethyl acetate+0.5% triethylamine, 8:1 to 1:1) to give amine (α-S6) (22.5 mg, 78% yield).

TLC $R_f$ 0.11 (hexanes:ethyl acetate, 2:1+0.5% triethylamine); FTIR (NaCl, film) 3426, 3066, 3033, 2955, 2913, 2878, 1741, 1498, 1458, 1415, 1382, 1314, 1242, 1098, 1009, 904, 865, 827, 735, 699, 667 cm$^{-1}$; $^1$H-NMR (600 MHz, CDCl$_3$) δ 9.68 (s, 1H), 7.40-7.27 (m, 33H), 6.00 (d, J=3.6 Hz, 1H), 5.37 (s, 1H), 5.33-5.25 (m, 2H), 5.09 (d, J=12.4 Hz, 1H), 4.89 (d, J=11.1 Hz, 1H), 4.85 (d, J=11.0 Hz, 1H), 4.82 (d, J=7.3 Hz, 1H), 4.79 (d, J=11.0 Hz, 1H), 4.70 (d, J=11.7 Hz, 1H), 4.68-4.49 (m, 7H), 4.42 (d, J=7.3 Hz, 1H), 4.40 (s, 1H), 4.34 (s, 1H), 4:19-4.07 (m, 4H), 4.02 (t, J=6.2 Hz, 1H), 3.95-3.89 (m, 3H), 3.88-3.77 (m, 4H), 3.75 (t, J=9.2 Hz, 1H), 3.71 (dd, J=10.0, 3.6 Hz, 1H), 3.67-3.51 (m, 9H), 3.50-3.44 (m, 2H), 3.42-3.38 (m, 1H), 3.35 (t, J=8.5 Hz, 2H), 3.31 (t, J=7.7 Hz, 1H), 3.27-3.23 (m, 1H), 3.19 (dd, J=11.5, 9.1 Hz, 1H), 3.13 (t, J=10.9 Hz, 1H), 2.48 (dd, J=13.4, 2.7 Hz, OH), 2.32-2.20 (m, 2H), 1.94-1.76 (m, 5H), 1.75-1.67 (m, 1H), 1.68-1.57 (m, 2H), 1.53-1.47 (m, 3H), 1.35-1.32 (m, 2H), 1.31 (s, 3H), 1.30 (s, 3H), 1.25 (s, 3H), 1.22 (d, J=6.0 Hz, 3H), 1.13-1.07 (m, 2H), 1.03-0.88 (m, 105H), 0.86 (s, 4H), 0.85 (s, 4H), 0.80 (s, 3H), 0.79-0.53 (m, 66H); $^{13}$C-NMR (151 MHz, CDCl$_3$) δ 212.18, 168.37, 151.64, 142.45, 138.81, 138.46, 138.24, 138.00, 137.81, 135.24, 128.45, 128.44, 128.39, 128.26, 128.25, 128.18, 128.12, 127.90, 127.88, 127.83, 127.74, 127.58, 127.46, 127.36, 124.25, 109.02, 103.49, 102.43, 101.35, 100.82, 98.69, 91.74, 83.75, 81.55, 78.71, 78.21, 77.91, 76.44, 75.81, 75.47, 75.05, 74.49, 73.77, 73.70, 73.10, 72.59, 72.48, 71.39, 71.20, 71.10, 70.42, 68.82, 66.85, 65.40, 65.32, 63.61, 60.29, 55.89, 53.75, 49.28, 49.10, 46.71, 45.98, 44.92, 41.08, 39.67, 37.77, 36.31, 35.94, 33.27, 32.51, 32.16, 31.99, 30.65, 29.70, 27.70, 26.57, 26.22, 25.28, 24.42, 23.40, 20.17, 17.45, 16.74, 15.70, 12.04, 7.56, 7.46, 7.25, 7.18, 7.13, 7.12, 6.98, 6.85, 6.79, 5.92, 5.63, 5.44, 5.36, 5.33, 5.25, 5.22, 4.89, 4.41.

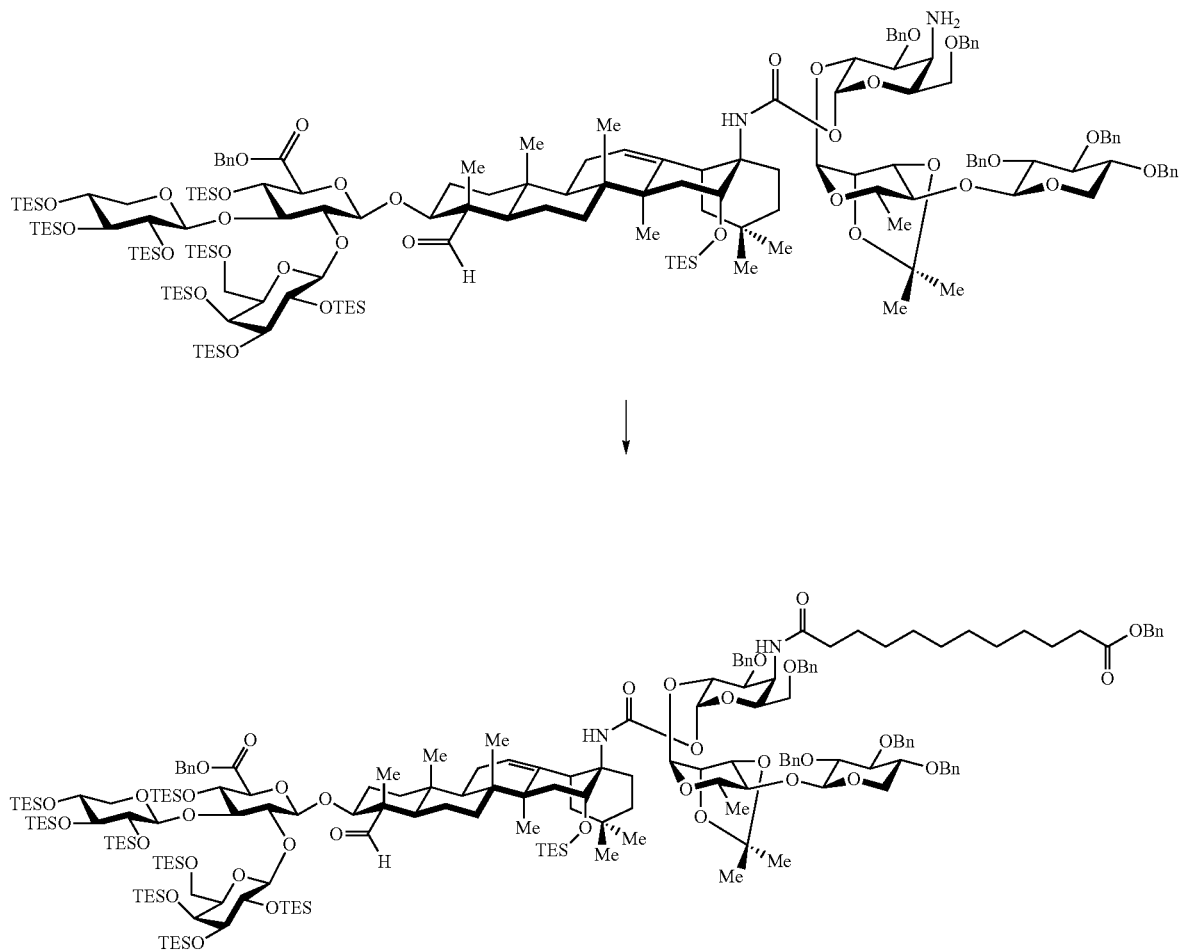

Production of Protected α-Carbamate Variant α-S7

Isobutyl chloroformate (4.5 μL, 0.037 mmol, 5 equiv) was added to an ice-cooled solution of carboxylic acid S2 (14 mg, 0.045 mmol, 6 equiv) and triethylamine (8.3 μL, 0.060 mmol, 8 equiv) in tetrahydrofuran (2 mL) and stirred for β hours, then transferred via cannula to an ice-cooled solution of amine α-S6 (22.5 mg, 0.008 mmol, 1 equiv) in tetrahydrofuran (0.6 mL). After 2.5 h, suspension was diluted with saturated sodium bicarbonate and then extracted with ethyl acetate (3×25 ml). Combined organics were washed with brine, dried over sodium sulfate, concentrated, and purified with silica gel chromatography (hexanes:ethyl acetate+0.5% triethylamine, 10:1 to 1:1) to give amide α-S7 (23 mg, 93% yield) as a colorless film.

TLC $R_f$ 0.73 (hexanes:ethyl acetate, 2:1+0.5% triethylamine); FTIR (NaCl, film) 3421, 3089, 3064, 3031, 2953, 2913, 2876, 1740, 1678, 1655, 1607, 1587, 1456, 1413, 1380, 1312, 1240, 1165, 1097, 1008, 908, 863, 825, 735, 697, 666 cm$^{-1}$; $^1$H-NMR (600 MHz, CDCl$_3$) δ 9.69 (s, 1H), 7.38-7.27 (m, 35H), 5.99 (d, J=3.6 Hz, 1H), 5.50 (d, J=10.1 Hz, 1H), 5.36 (s, 1H), 5.31 (s, 1H), 5.28 (d, J=12.4 Hz, 1H), 5.10 (d, J=14.9 Hz, 3H), 4.91-4.87 (m, 2H), 4.86-4.77 (m, 4H), 4.70 (d, J=11.7 Hz, 1H), 4.63 (d, J=11.1 Hz, 1H), 4.61 (d, J=11.7 Hz, 1H), 4.56 (d, J=7.4 Hz, 1H), 4.51 (d, J=11.6 Hz, 1H), 4.46-4.40 (m, 4H), 4.33 (s, 1H), 4.18 (d, J=7.3 Hz, 1H), 4.15-4.09 (m, 3H), 3.95-3.89 (m, 3H), 3.88-3.73 (m, 7H), 3.65-3.52 (m, 8H), 3.51-3.45 (m, 3H), 3.40 (d, J=9.4 Hz, 1H), 3.37-3.33 (m, 2H), 3.30 (t, J=7.6 Hz, 1H), 3.25 (t, J=8.0 Hz, 1H), 3.19 (dd, J=13.6, 6.8 Hz, 1H), 3.13 (t, J=10.9 Hz, 1H), 2.47 (dd, J=13.6, 2.4 Hz, 1H), 2.34 (t, J=7.6 Hz, 2H), 2.30-2.15 (m, 4H), 1.90-1.57 (m, 13H), 1.52-1.47 (m, 2H), 1.46 (s, 3H), 1.33 (s, 4H), 1.30-1.20 (m, 24H), 1.13-1.02 (m, 6H), 1.02-0.90 (m, 95H), 0.89 (s, 3H), 0.87 (s, 3H), 0.85 (s, 6H), 0.80-0.51 (m, 66H); $^{13}$C-NMR (151 MHz, CDCl$_3$) 212.23, 173.69, 173.41, 168.36, 151.40, 142.24, 138.78, 138.40, 138.24, 138.05, 137.56, 136.11, 135.24, 128.52, 128.45, 128.42, 128.39, 128.25, 128.19, 128.15, 128.14, 128.12, 128.00, 127.90, 127.80, 127.73, 127.63, 127.47, 124.43, 109.00, 103.51, 102.53, 101.36, 100.82, 98.90, 91.22, 86.13, 83.77, 81.49, 78.78, 78.71, 78.14, 77.90, 76.44, 76.26, 76.10, 75.92, 75.82, 75.50, 75.06, 74.48, 73.83, 73.75, 73.09, 72.59, 72.48, 71.68, 71.40, 71.10, 70.85, 69.88, 68.76, 66.84, 66.05, 65.40, 65.32, 63.62, 60.29, 56.00, 53.76, 49.12, 46.88, 46.68, 45.97, 44.85, 41.05, 39.64, 37.78, 36.96, 36.28, 35.93, 34.33, 33.25, 32.49, 32.14, 31.97, 30.63, 29.70, 29.40, 29.37, 29.31, 29.19, 29.12, 27.69, 26.57, 26.20, 25.87, 25.29, 24.94, 24.40, 23.38, 22.70, 20.15, 17.48, 16.63, 15.74, 14.14, 12.05, 7.56, 7.46, 7.25, 7.19, 7.13, 7.11, 6.98, 6.85, 6.79, 5.92, 5.63, 5.44, 5.36, 5.33, 5.25, 5.22, 4.89, 4.41; HRMS (ESI) m/z: Calcd for $C_{182}H_{294}N_2O_{35}NaSi_9$ [M+Na] 3342.9108, found 3342.9001.

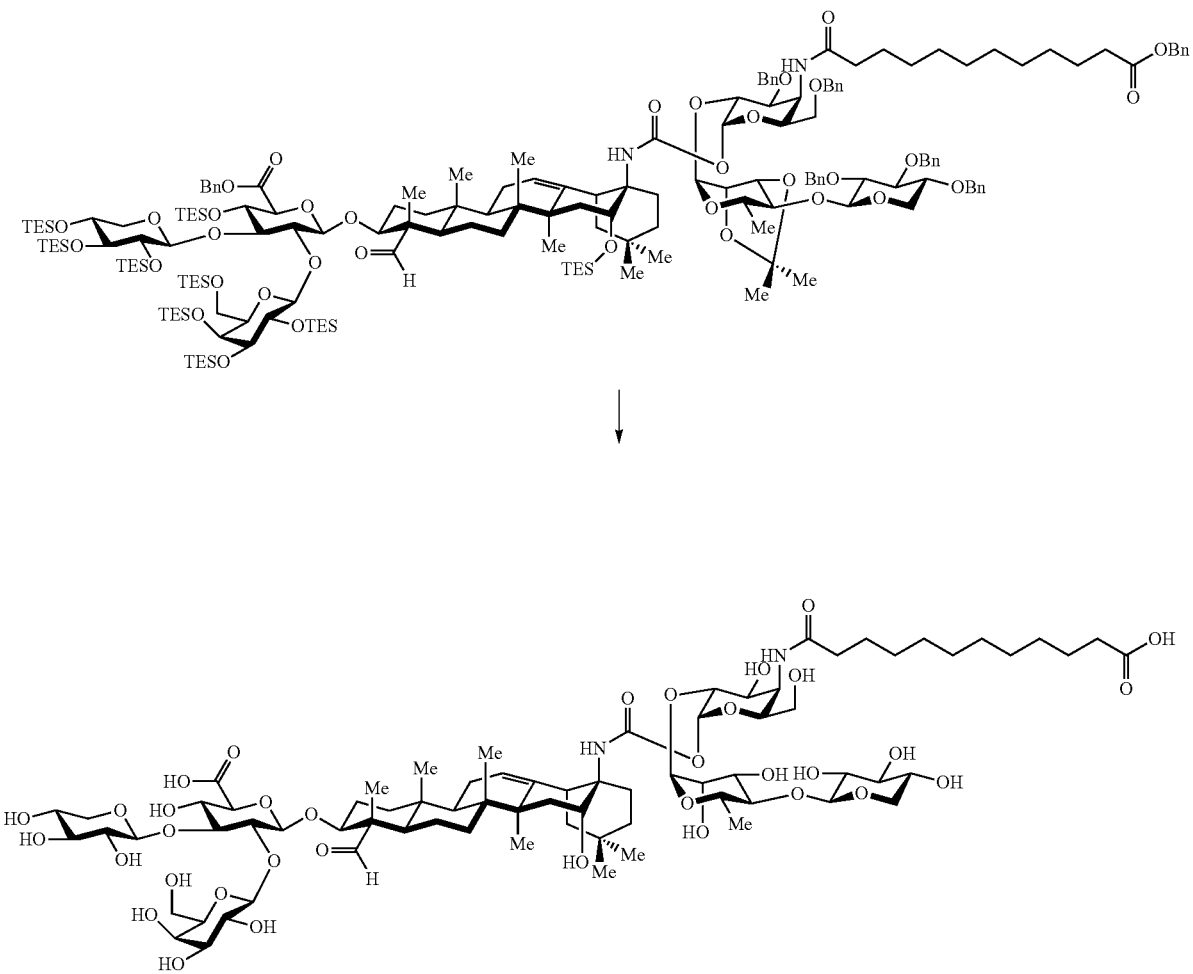

Production of α-Carbamate Variant α-4 (SQS-0-5-8-5)

A solution of fully protected β-carbamate analogue (α-S7) (5 mg, 0.0015 mmol, 1.0 equiv) in tetrahydrofuran (1 mL) and ethanol (1 mL) in a 25 mL round bottom flask was charged with 10% (dry basis) palladium on carbon, wet, Degussa type E101 NE/W (4 mg, 0.004 mmol, 4 equiv). Reaction mixture was stirred under hydrogen pressure (50 psi) overnight, then filtered through a 0.45 m polyvinylidene fluoride filter disk, washed with methanol (5 mL), and concentrated. To the hydrogenation product was added a pre-cooled (0° C.) solution of trifluoroacetic acid (1.0 mL, TFA/H2O 3:1). After vigorous stirring for 60 min, the solution was concentrated in vacuo at 0° C. to give white solid residue. This crude product was partially dissolved in a solution of aqueous acetonitrile (5:1 water:acetonitrile) and purified by RP-HPLC on an XBridge Prep BEH300 C18 column (5 μm, 10×250 mm) using a linear gradient of 15→51% acetonitrile (0.05% TFA) in over 18 min at a flow rate of 5 mL/min. The fraction containing the major peak (tR=17.2 min) was collected and lyophilized to dryness to afford SQS-0-5-8-5 (α-4) (2.0 mg, 82% yield) as a fluffy white solid.

1H-NMR (600 MHz, D2O/CD3CN) δ 9.90 (s, 1H), 6.45 (d, J=3.7 Hz, 1H), 6.11 (s, 1H), 5.89 (s, 1H), 5.31 (s, 1H), 5.19 (d, J=7.8 Hz, 1H), 5.07 (d, J=7.8 Hz, 1H), 4.97 (d, J=7.8 Hz, 1H), 4.93 (d, J=7.8 Hz, 1H), 4.86 (s, 1H), 4.47 (t, J=6.3 Hz, 1H), 4.46-4.36 (m, 3H), 4.35-4.20 (m, 5H), 4.18-4.11 (m, 2H), 4.11-3.95 (m, 5H), 3.93-3.82 (m, 4H), 3.77-3.66 (m, 3H), 2.98 (dd, J=13.5, 1.7 Hz, 1H), 2.77-2.72 (m, 1H), 2.46-2.35 (m, 3H), 2.31-2.14 (m, 4H), 2.01-1.98 (m, 1H), 1.82 (s, 3H), 1.72 (d, J=6.1 Hz, 3H), 1.63 (s, 2H), 1.60-1.53 (m, 1H), 1.48 (s, 3H), 1.37 (s, 3H), 1.36 (s, 3H); HRMS (ESI) m/z: Calcd for C76H122N2O35Na [M+Na]+ 1645.7726, found 1645.7754.

Example 5: Synthesis of β-Thioester Variant 5 (Sqs-0-13-5-5)

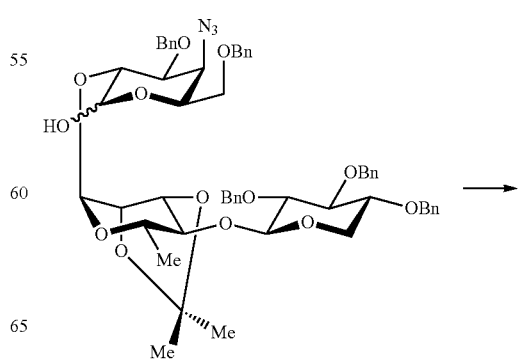

-continued

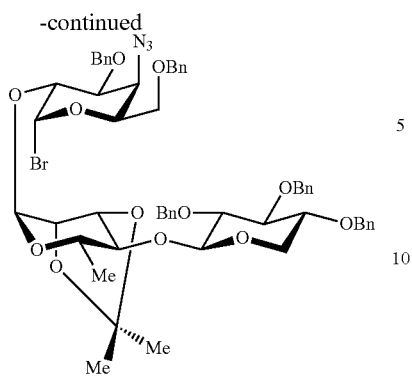

Production of Trisaccharide Glycosyl Bromide 20

Oxalyl bromide was added to an ice-cooled solution of hemiacetal 17 (125 mg, 0.128 mmol, 1.0 equiv), 2,4,6-tri-tertbutylpyridine (127 mg, 0.513 mmol, 4.0 equiv), and dimethylformamide (150 μL, 1.925 mmol, 15 equiv) in dichloromethane (2 mL) with immediate evolution of CO and $CO_2$. After five min, ice-bath was removed and warmed to ambient temperature. After three hours, solvent was removed with a stream of nitrogen and crude mixture was purified directly via silica gel chromatography (hexanes:ethyl acetate, 10:1 to 4:1) to give glycosyl bromide as a colorless, thin, and flaky film 20 (98 mg, 74% yield).

TLC $R_f$ 0.43 (hexanes:ethyl acetate, 4:1); FTIR (NaCl film) 3583, 3063, 3030, 2983, 2932, 2109, 1496, 1453, 1370, 1242, 1219, 1100, 1027, 992, 862, 792, 735, 697, 666 cm$^{-1}$; $^1$H-NMR (600 MHz, C6D6-d6) δ 7.49-7.06 (m, 25H), 6.62 (d, J=3.7 Hz, 1H), 5.34 (s, 1H), 5.16 (d, J=7.5 Hz, 1H), 5.02 (d, J=11.3 Hz, 1H), 4.93 (d, J=11.5 Hz, 1H), 4.86 (d, J=11.5 Hz, 1H), 4.77 (d, J=11.3 Hz, 1H), 4.48 (d, J=12.0 Hz, 1H), 4.40-4.32 (m, 3H), 4.33-4.25 (m, 3H), 4.24 (d, J=5.8 Hz, 1H), 4.20 (d, J=11.7 Hz, 1H), 4.12 (dq, J=9.9, 6.2 Hz, 1H), 4.07 (dd, J=9.6, 3.8 Hz, 1H), 3.97 (dd, J=9.9, 7.4 Hz, 1H), 3.92 (dd, J=9.7, 3.6 Hz, 1H), 3.86 (dd, J=3.6, 1.6 Hz, 1H), 3.82 (dd, J=11.5, 5.3 Hz, 1H), 3.65-3.46 (m, 5H), 3.18 (dd, J=11.6, 9.8 Hz, 1H), 1.45-1.40 (m, 6H), 1.20 (s, 3H); $^{13}$C-NMR (151 MHz, C6D6-d6) δ 139.63, 139.44, 139.01, 138.08, 137.99, 128.63, 128.44, 128.39, 128.34, 128.32, 128.23, 127.68, 127.67, 127.65, 127.55, 127.43, 109.18, 102.71, 100.72, 93.84, 84.15, 82.33, 78.60, 78.32, 78.10, 77.92, 76.85, 76.45, 75.43, 74.81, 73.55, 72.84, 72.76, 72.36, 67.98, 67.71, 66.32, 63.97, 60.24, 27.74, 26.18, 25.69, 17.73; HRMS (ESI) m/z: Calcd for $C_{55}H_{62}N_3O_{12}NaBr$ [M+Na] 1058.3415, found 1058.3418.

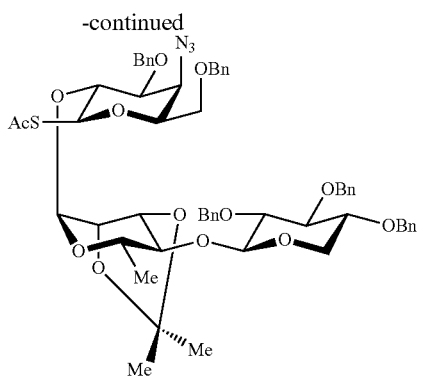

Production of Trisaccharide Glycosyl Thioacetate S8

Cesium carbonate (77 mg, 0.237 mmol, 5 equiv) was added to an ice-cooled solution of thioacetic acid (67 μL, 0.946 mmol, 20 equiv) and bromide 20 (49 mg, 0.047 mmol, 1 equiv) and in tetrahydrofuran/dimethylformamide (2 mL, 1:1). After one hour, reaction was diluted with ethyl acetate, washed with a saturated sodium bicarbonate and brine, dried over sodium sulfate, concentrated and purified with silica gel chromatography (hexanes/ethyl acetate, 10:1 to 2:1) to give thioacetate as a colorless oil S8 (42 mg, 87% yield).

TLC $R_f$ 0.55 (hexanes:ethyl acetate, 2:1); FTIR (NaCl film) 3088, 3063, 3030, 2983, 2904, 2872, 2162, 2109, 1706, 1704, 1700, 1496, 1453, 1419, 1381, 1363, 1310, 1274, 1241, 1221, 1091, 1021, 989, 952, 912, 864, 862, 814, 790, 736, 697, 668, 625 cm$^{-1}$; $^1$H-NMR (600 MHz, CDCl$_3$-d) δ 7.36-7.20 (m, 25H), 5.44 (s, 1H), 4.98 (d, J=10.1 Hz, 1H), 4.85 (d, J=7.6 Hz, 1H), 4.84-4.75 (m, 3H), 4.70 (d, J=11.2 Hz, 1H), 4.66 (d, J=11.7 Hz, 1H), 4.62 (d, J=11.0 Hz, 1H), 4.57 (d, J=11.7 Hz, 1H), 4.55-4.45 (m, 3H), 4.11 (d, J=2.8 Hz, 1H), 4.07 (dd, J=7.4, 5.7 Hz, 1H), 4.02 (d, J=5.7 Hz, 1H), 3.98 (t, J=9.5 Hz, 1H), 3.89 (dd, J=11.8, 4.1 Hz, 1H), 3.76-3.66 (m, 3H), 3.60-3.48 (m, 5H), 3.26 (t, J=8.1 Hz, 1H), 3.19-3.11 (m, 1H), 2.21 (s, 3H), 1.44 (s, 3H), 1.25 (s, 3H), 1.23 (d, J=6.2 Hz, 3H); $^{13}$C-NMR (151 MHz, CDCl$_3$) δ 192.87, 138.78, 138.59, 138.23, 137.47, 136.58, 128.62, 128.56, 128.53, 128.45, 128.39, 128.36, 128.31, 128.29, 128.26, 128.11, 128.08, 128.04, 127.96, 127.94, 127.81, 127.78, 127.62, 127.56, 109.04, 101.99, 98.83, 83.86, 83.16, 81.94, 81.47, 78.09, 77.94, 77.72, 76.17, 75.70, 75.58, 74.70, 73.70, 73.21, 73.05, 71.80, 67.89, 65.32, 63.81, 58.58, 30.77, 27.75, 26.42, 17.17; HRMS (ESI) m/z: Calcd for $C_{57}H_{65}N_3O_{13}SNa$ [M+Na]$^+$ 1054.4136, found 1054.4182.

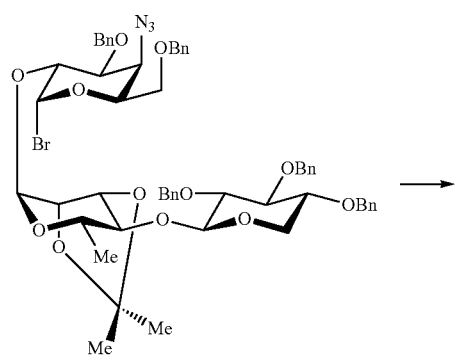

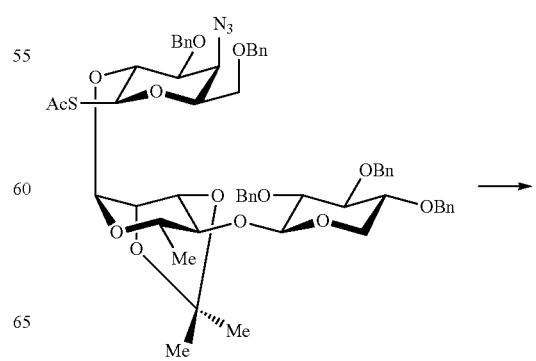

-continued

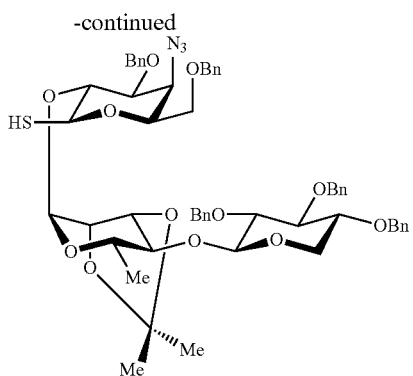

Production of Trisaccharide Thiohemiacetal 25

Hydrazine (6.1 μL, 0.194 mmol, 5.0 equiv) was added to a solution of thioacetate S8 (40 mg, 0.039 mmol, 1 equiv) and dithiothreitol (18 mg, 0.116 mmol, 3 equiv) in tetrahydrofuran/methanol (2 mL, 1:1). After 1 h, reaction contents was diluted with ethyl acetate, washed with water and brine, dried over sodium sulfated, concentrated, and purified with silica gel chromatography to give thiohemiacetal as a clear oil 25 (36 mg, 94%).

TLC $R_f$ 0.51 (hexanes:ethyl acetate, 2:1; FTIR (NaCl film) 3583, 3063, 3031, 2983, 2870, 2106, 1496, 1453, 1369, 1274, 1241, 1220, 1091, 1021, 990, 912, 862, 793, 736, 697, 665 cm$^{-1}$; $^1$H-NMR (500 MHz, CDCl$_3$) δ 7.40-7.26 (m, 25H), 5.52 (s, 1H), 4.93-4.80 (m, 4H), 4.71 (q, J=11.2, 10.7 Hz, 3H), 4.62 (d, J=11.7 Hz, 1H), 4.59-4.51 (m, 3H), 4.35 (t, J=8.9 Hz, 1H), 4.17 (dd, J=7.5, 5.7 Hz, 1H), 4.11 (d, J=3.4 Hz, 1H), 4.08 (d, J=5.7 Hz, 1H), 4.04 (dd, J=9.9, 6.6 Hz, 1H), 3.94 (dd, J=11.9, 4.1 Hz, 1H), 3.86 (t, J=9.2 Hz, 1H), 3.66-3.57 (m, 7H), 3.31 (dd, J=9.5, 8.7 Hz, 1H), 3.24-3.14 (m, 1H), 2.31 (d, J=8.4 Hz, 1H), 1.49 (s, 3H), 1.31 (s, 3H), 1.23 (d, J=6.2 Hz, 3H); $^{13}$C-NMR (151 MHz, CDCl$_3$) δ 138.75, 138.71, 138.20, 137.39, 136.55, 128.57, 128.51, 128.40, 128.32, 128.27, 128.25, 128.22, 128.06, 128.05, 128.04, 127.91, 127.76, 127.75, 127.50, 127.48, 108.97, 101.96, 98.80, 83.86, 82.88, 81.90, 79.70, 78.14, 77.92, 77.69, 77.60, 76.27, 75.71, 75.53, 74.71, 73.73, 73.17, 71.66, 68.25, 65.38, 63.76, 58.53, 27.74, 26.42, 17.24; HRMS (ESI) m/z: Calcd for C$_{55}$H$_{63}$N$_3$O$_{12}$SNa [M+Na]$^+$ 1012.4030, found 1012.4025.

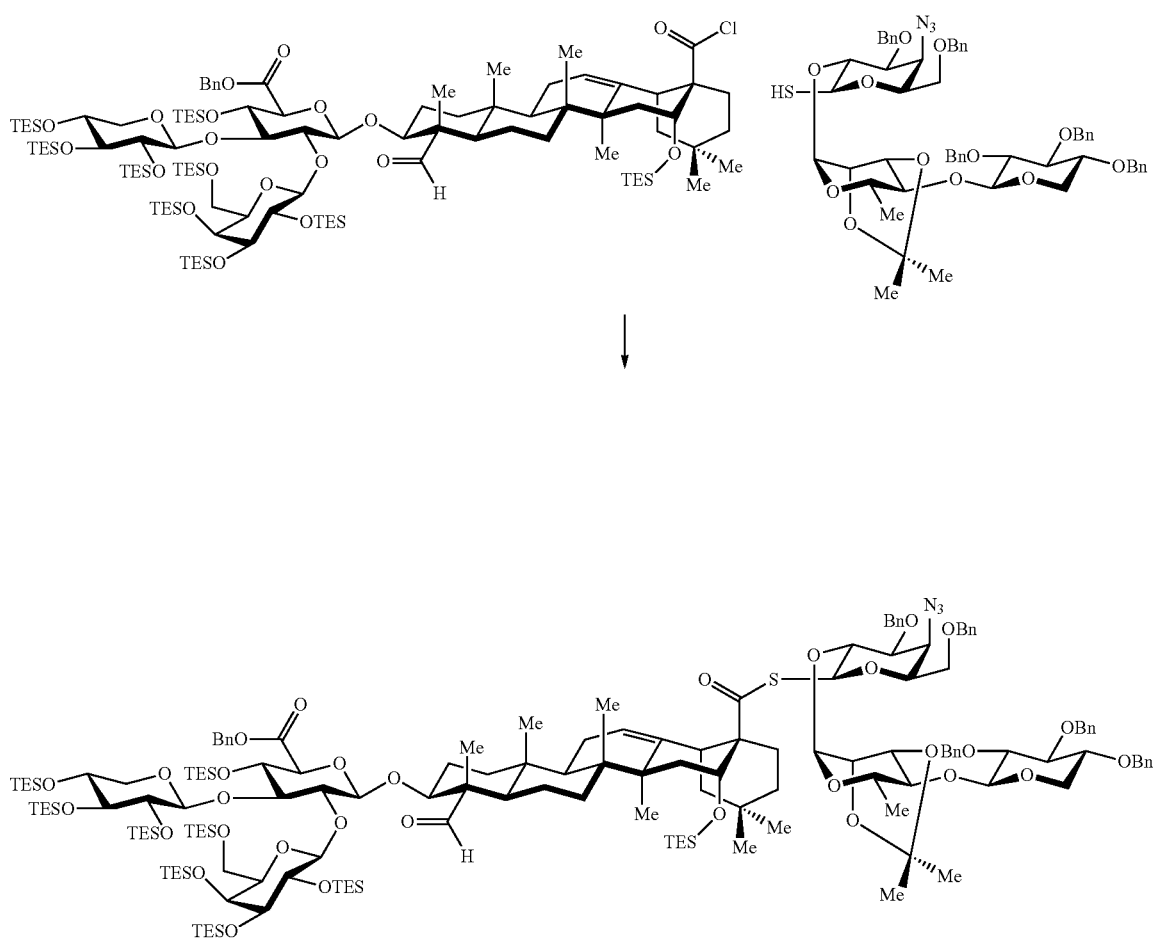

Production of Protected Prosapogenin β-Thioester Azide 26

Sodium hydride (60% dispersion in mineral oil, 4.7 mg, 0.115 mmol, 3 equiv) was added to an ice-cooled solution of thiohemiacetal 25 (38 mg, 0.038 mmol, 1.0 equiv) and acyl chloride 12 (88 mg, 0.042 mmol, 1.1 equiv) in tetrahydrofuran (5 mL). After two hours, saturated ammonium chloride (1 mL) was added and the mixture diluted with dichloromethane and washed with water and brine, then dried over sodium sulfate, concentrated, and purified with silica gel chromatography (hexanes/ethyl acetate, 20:1 to 4:1) to give glycosyl thioester 26 (102 mg, 87% yield) as a flaky white film. Characteristic chemical shift of newly formed thioester anomeric proton at 4.84 ppm, J=10.0 Hz and carbon at 81.6 ppm.

128.14, 128.12, 128.11, 128.03, 128.01, 128.00, 127.88, 127.85, 127.79, 127.75, 127.60, 127.59, 123.87, 108.91, 103.51, 102.28, 101.37, 100.82, 98.50, 86.26, 83.92, 83.61, 82.46, 81.62, 78.78, 78.70, 78.23, 78.01, 77.80, 76.43, 76.16, 75.94, 75.80, 75.76, 75.57, 75.53, 75.05, 75.03, 73.60, 73.20, 72.59, 72.50, 71.64, 71.60, 71.38, 71.05, 67.93, 66.84, 65.38, 65.32, 63.84, 60.25, 58.80, 56.19, 53.84, 53.43, 49.30, 46.67, 46.09, 41.81, 41.21, 39.84, 37.85, 36.04, 35.01, 33.94, 32.56, 32.20, 32.04, 30.32, 27.74, 26.46, 26.39, 25.31, 24.64, 23.40, 20.21, 17.57, 17.10, 15.75, 12.22, 7.55, 7.46, 7.25, 7.16, 7.13, 7.09, 6.98, 6.85, 6.78, 5.91, 5.63, 5.43, 5.36, 5.33, 5.31, 5.25, 5.22, 4.88, 4.40; HRMS (ESI) m/z: Calcd for $C_{163}H_{265}N_3O_{31}NaSi_9S$ [M+Na]+3067.6794, found 3067.6711.

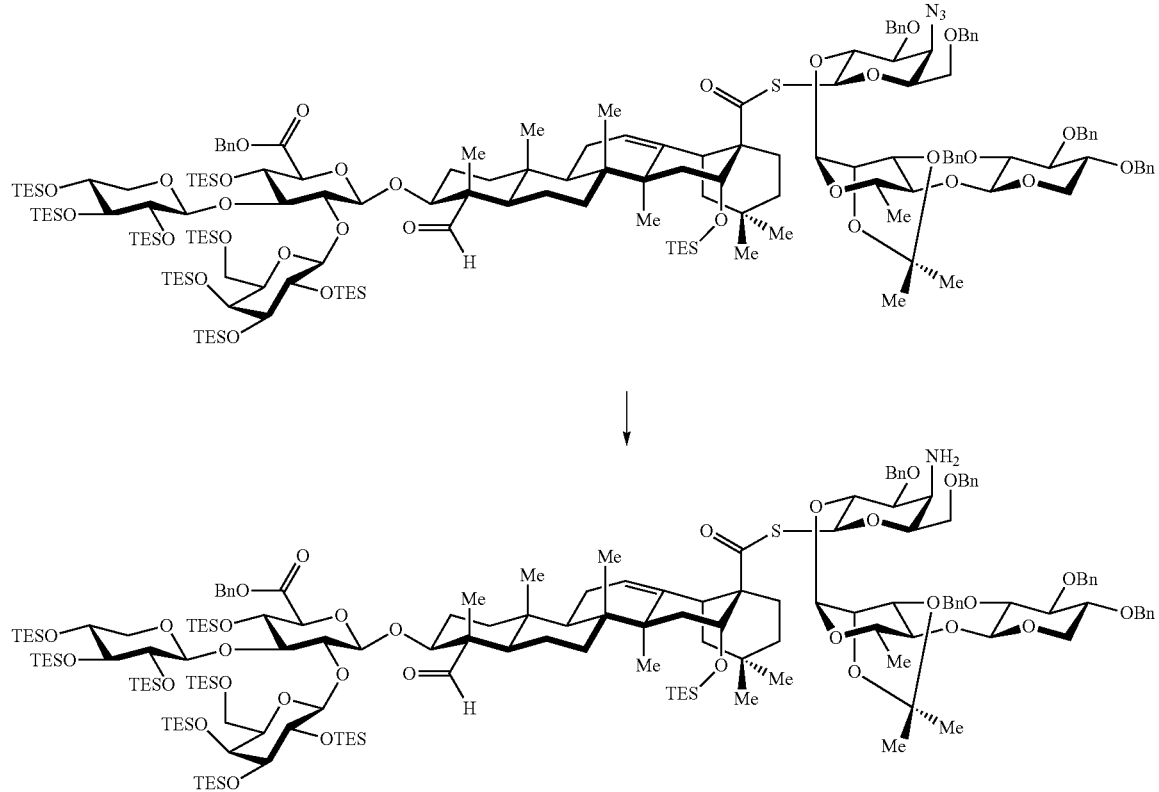

TLC $R_f$ 0.80 (hexanes:ethyl acetate, 2:1) FTIR (NaCl film) 2953, 2876, 2109, 1751, 1685, 1456, 1380, 1240, 1096, 1006, 900, 808, 733, 696, 665; $^1$H-NMR (500 MHz, $CDCl_3$-d) δ 9.68 (s, 1H), 7.39-7.27 (m, 30H), 5.55 (s, 1H), 5.32 (t, J=3.8 Hz, 1H), 5.29 (d, J=12.3 Hz, 1H), 5.09 (d, J=12.4 Hz, 1H), 4.91 (d, J=7.6 Hz, 1H), 4.86-4.80 (m, 3H), 4.76-4.70 (m, 2H), 4.63 (d, J=9.3 Hz, 1H), 4.61 (d, J=8.3 Hz, 1H), 4.58-4.51 (m, 4H), 4.49 (s, 1H), 4.42 (d, J=7.2 Hz, 1H), 4.19 (d, J=7.3 Hz, 1H), 4.15 (dd, J=3.4, 1.4 Hz, 1H), 4.13-4.04 (m, 3H), 3.99-3.66 (m, 13H), 3.65-3.53 (m, 7H), 3.51-3.32 (m, 7H), 3.30-3.23 (m, 2H), 3.19 (dd, J=11.5, 9.2 Hz, 1H), 3.13 (t, J=10.9 Hz, 1H), 2.84 (dd, J=13.3, 3.3 Hz, 1H), 2.22 (t, J=13.3 Hz, 1H), 1.95-1.75 (m, 4H), 1.74-1.57 (m, 5H), 1.53-1.46 (m, 5H), 1.45-1.23 (m, 17H), 1.19-1.05 (m, 2H), 1.03-0.85 (m, 114H), 0.84-0.52 (m, 77H); $^{13}$C-NMR (151 MHz, $CDCl_3$) δ 212.51, 204.16, 168.32, 142.00, 138.68, 138.48, 138.21, 137.60, 136.58, 135.23, 128.55, 128.46, 128.43, 128.42, 128.34, 128.32, 128.29, 128.24, 128.21, Production of Protected Prosapogenin β-Thioester Amine S9

An excess of hydrogen sulfide was bubbled via cannula through an ice-cooled solution of azide 26 (80 mg, 0.026 mmol, 1.0 equiv) in pyridine/triethylamine (3.5:1, 4.5 mL) for two min. Vent needle and cannula were removed, and septum sealed with Teflon tape and parafilm, then warmed to ambient temperature and stirred overnight. Hydrogen sulfide was removed with a stream of nitrogen, then resulting orange solution was concentrated and purified via silica gel chromatography (hexanes:[ethyl acetate+1% triethylamine], 5:1 to 2:1) furnishing amine S9 (71 mg, 90% yield).

TLC $R_f$ 0.50 (hexanes:ethyl acetate, 2:1+0.5% triethylamine); FTIR (NaCl film) 3583, 2951, 2876, 1751, 1724, 1685, 1496, 1457, 1380, 1240, 1097, 1006, 900, 807, 731 $cm^{-1}$; $^1$H-NMR (600 MHz, $CDCl_3$-d) δ 9.69 (s, 1H), 7.37-7.26 (m, 30H), 5.57 (s, 1H), 5.32 (t, J=3.8 Hz, 1H), 5.29 (d, J=12.3 Hz, 1H), 5.09 (d, J=12.4 Hz, 1H), 4.92 (d, J=7.6 Hz, 1H), 4.88-4.81 (m, 4H), 4.74-4.68 (m, 2H), 4.64 (d, J=8.3 Hz, 1H), 4.62 (d, J=7.4 Hz, 1H), 4.58 (d, J=11.8 Hz, 1H), 4.56 (d, J=7.5 Hz, 0.1H), 4.53-4.49 (m, 3H), 4.42 (d, J=7.3 Hz, 1H), 4.18 (d, J=7.4 Hz, 1H), 4.13 (dd, J=7.4, 5.6 Hz, 1H), 4.10 (d, J=5.7 Hz, 1H), 4.00 (dd, J=10.3, 8.5 Hz, 1H), 3.97-3.90 (m, 4H), 3.87 (d, J=9.2 Hz, 1H), 3.85-3.72 (m, 6H), 3.68-3.53 (m, 10H), 3.48 (ddd, J=10.5, 8.4, 5.1 Hz, 1H), 3.39 (dd, J=9.4, 2.5 Hz, 1H), 3.37-3.32 (m, 2H), 3.28 (dd, J=8.7, 7.5 Hz, 1H), 3.25 (t, J=8.0 Hz, 1H), 3.20 (dd, J=11.7, 9.3 Hz, 1H), 3.13 (t, J=11.0 Hz, 1H), 2.84 (dd, J=13.4, 4.6 Hz, 1H), 2.22 (t, J=13.2 Hz, 1H), 1.95-1.74 (m, 5H), 1.73-1.53 (m, 7H), 1.51 (s, 4H), 1.45-1.38 (m, 2H), 1.34 (s, 4H), 1.33-1.26 (m, 11H), 1.16-0.89 (m, 97H), 0.88 (s, 3H), 0.82 (s, 3H), 0.80-0.51 (m, 61H); $^{13}$C-NMR (151 MHz, CDCl$_3$) δ 212.59, 204.03, 168.36, 142.34, 138.70, 138.50, 138.24, 137.93, 136.88, 135.26, 128.55, 128.52, 128.49, 128.46, 128.44, 128.38, 128.35, 128.33, 128.31, 128.24, 128.18, 128.16, 128.15, 128.07, 128.05, 127.82, 127.78, 127.72, 127.65, 127.63, 123.70, 108.96, 103.55, 102.32, 101.39, 100.85, 98.36, 86.28, 83.95, 82.49, 81.76, 78.81, 78.73, 78.22, 78.03, 77.85, 76.45, 76.24, 75.97, 75.83, 75.79, 75.68, 75.09, 75.07, 73.59, 73.23, 72.62, 72.53, 71.41, 71.08, 70.80, 69.05, 66.86, 65.35, 63.87, 60:28, 56.29, 53.86, 49.36, 49.04, 46.84, 46.10, 41.68, 41.28, 39.86, 37.88, 36.08, 35.06, 33.95, 32.58, 32.19, 32.10, 30.35, 29.73, 27.81, 26.46, 26.44, 25.34, 24.66, 23.46, 20.24, 17.62, 17.21, 15.80, 12.24, 7.58, 7.49, 7.27, 7.19, 7.16, 7.12, 7.01, 6.88, 6.81, 5.94, 5.66, 5.46, 5.39, 5.36, 5.28, 5.25, 4.92, 4.43; HRMS (ESI) m/z: Calcd for $C_{163}H_{268}NO_{31}Si_9S$ [M+H]$^+$ 3019.7070, found 3019.7112.

mmol, 10 equiv) in tetrahydrofuran (3 mL) and stirred for 2 hours, then transferred via cannula to an ice-cooled solution of amine S9 (20 mg, 0.007 mmol, 1 equiv) in tetrahydrofuran (1 mL). After 2 h, suspension was diluted with saturated sodium bicarbonate and then extracted with ethyl acetate (3×25 ml). Combined organics were washed with brine, dried over sodium sulfate, concentrated, and purified with silica gel chromatography (hexanes:ethyl acetate+0.5% triethylamine, 10:1 to 1:1) to give fully protected thioester analogue S10 (19 mg, 87% yield) as a colorless film.

TLC R$_f$ 0.57 (hexanes:dichloromethane:ethyl acetate, 4:2:1) FTIR (NaCl film) 3583, 338.1, 2954, 2876, 1751, 1738, 1682, 1497, 1455, 1414, 1380, 1240, 1099, 1005, 901, 863, 806, 732, 696, 665 cm$^{-1}$; $^1$H-NMR (600 MHz, CDCl$_3$-d) δ 9.70 (s, 1H), 7.39-7.25 (m, 35H), 5.89 (s, 1H), 5.52 (s, 1H), 5.31 (d, J=3.7 Hz, 1H), 5.28 (d, J=12.4 Hz, 1H), 5.11 (s, 2H), 5.09 (d, J=12.4 Hz, 1H), 4.93-4.87 (m, 2H), 4.89-4.74 (m, 6H), 4.72 (d, J=11.7 Hz, 1H), 4.64 (d, J=3.4 Hz, 1H), 4.62 (d, J=4.4 Hz, 1H), 4.55 (d, J=7.4 Hz, 1H), 4.52 (d, J=11.8 Hz, 2H), 4.47-4.40 (m, 3H), 4.17 (d, J=7.4 Hz, 1H), 4.12 (dd, J=7.4, 5.6 Hz, 1H), 4.09 (d, J=5.6 Hz, 1H), 3.97-3.72 (m, 12H), 3.65-3.51 (m, 8H), 3.48 (ddd, J=10.4, 8.4, 5.1 Hz, 1H), 3.44-3.31 (m, 6H), 3.28 (dd, J=8.7, 7.4 Hz, 1H), 3.25 (t, J=8.0 Hz, 1H), 3.19 (dd, J=11.6, 9.1 Hz, 1H), 3.13 (t, J=11.0 Hz, 1H), 2.83 (dd, J=13.6, 4.5 Hz, 1H), 2.34 (t, J=7.6 Hz, 2H), 2.25-2.14 (m, 3H), 1.92-1.81 (m, 2H), 1.83-1.74 (m, 1H), 1.41 (ddd, J=13.5, 9.3, 3.8 Hz, 1H), 1.71-1.53 (m, 12H) 1.50 (s, 3H) 1.35 (s, 3H), 1.33-1.03 (m, 31H), 1.03-0.87 (m, 99H), 0.87 (s, 3H), 0.83 (s, 4H), 0.81-0.50 (m, 70H); $^{13}$C-NMR (151 MHz, CDCl$_3$) δ 212.56, 203.39,

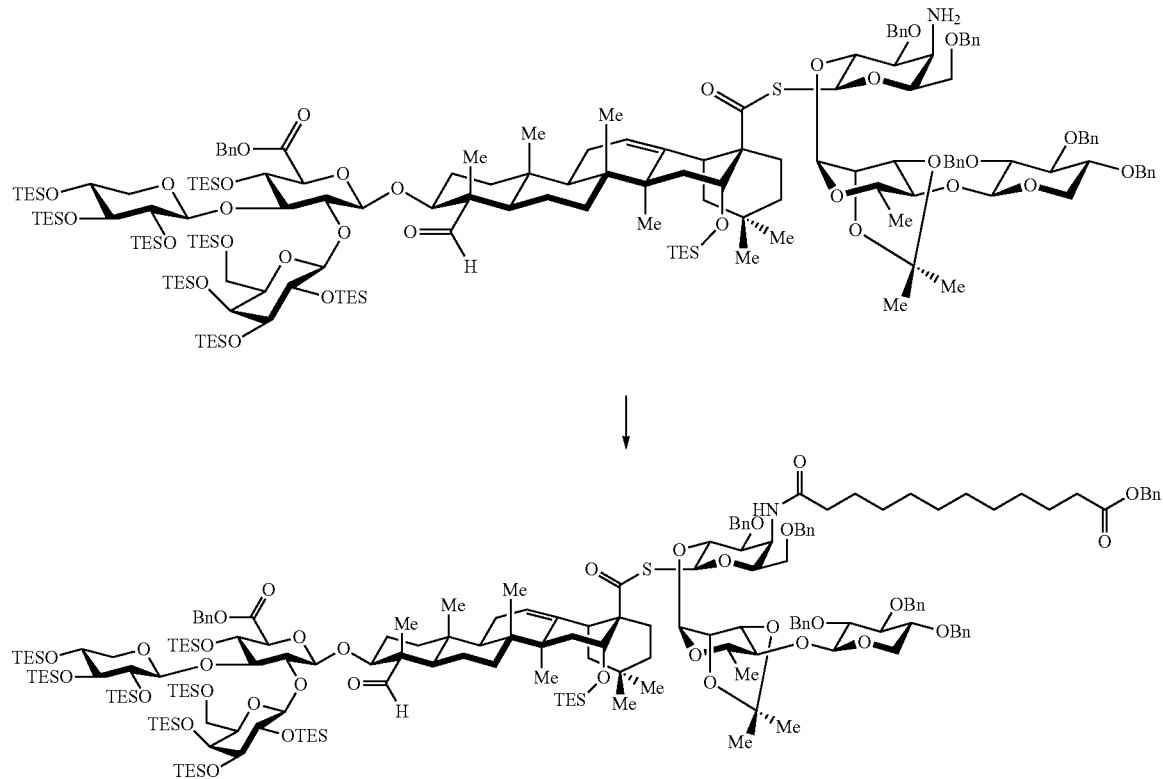

Production of Protected β-Thioester Variant S10

Isobutyl chloroformate (3.5 µL, 0.0264 mmol, 4 equiv) was added to an ice-cooled solution of carboxylic acid S2 (11 mg, 0.033 mmol, 5 equiv) and triethylamine (9 µL, 0.066

173.67, 173.31, 168.34, 142.85, 138.68, 138.49, 138.22, 137.85, 137.19, 136.12, 135.24, 128.72, 128.52, 128.44, 128.43, 128.39, 128.32, 128.31, 128.26, 128.25, 128.21, 128.15, 128.13, 128.08, 128.05, 128.02, 127.90, 127.79, 127.74, 127.63, 127.61, 127.59, 127.53, 122.89, 108.98, 103.57, 102.26, 101.37, 100.82, 98.39, 86.32, 83.91, 82.38, 81.95, 81.74, 78.79, 78.70, 78.06, 77.98, 77.92, 76.43, 76.12, 75.92, 75.84, 75.80, 75.74, 75.06, 74.99, 73.53, 73.20, 72.59, 72.50, 71.38, 71.07, 70.75, 68.76, 66.84, 66.03, 65.32, 65.26, 63.84, 60.25, 56.54, 53.80, 49.29, 46.86, 46.19, 45.99, 41.33, 41.28, 39.81, 37.83, 36.93, 36.03, 35.10, 34.33, 33.90, 32.53, 32.11, 32.08, 30.30, 29.70, 29.45, 29.40, 29.38, 29.24, 29.22, 29.14, 27.79, 26.42, 26.41, 25.87, 25.32, 24.97, 24.51, 23.40, 20.18, 17.67, 17.07, 15.79, 12.24, 7.55, 7.46, 7.24, 7.15, 7.13, 7.09, 6.98, 6.85, 6.78, 5.91, 5.63, 5.44, 5.36, 5.33, 5.25, 5.22, 4.90, 4.40; HRMS (ESI) m/z: Calcd for $C_{182}H_{293}NO_{34}NaSi_9S$ [M+Na]$^+$ 3343.8771, found 3343.8735.

1.0) Further hydrogenation results in diminished yields. To the hydrogenation product was added a pre-cooled (0° C.) solution of trifluoroacetic acid (2.0 mL, TFA/H$_2$O 3:1). After vigorous stirring for 60 min, the solution was concentrated in vacuo at 0° C. to give white solid residue. This crude product was partially dissolved in a solution of aqueous acetonitrile (4:1 water:acetonitrile) and purified by RP-HPLC on an XBridge Prep BEH300 C18 column (5 μm, 10×250 mm) using a linear gradient of 20→66%-acetonitrile (0.05% TFA) in over 16 min at a flow rate of 5 mL/min. The fraction containing the major peak (tR=13.2 min) was collected and lyophilized to dryness to afford β-Thioester variant 5 (SQS-0-13-5-5) (3.1 mg, 33% yield) as a fluffy white solid.

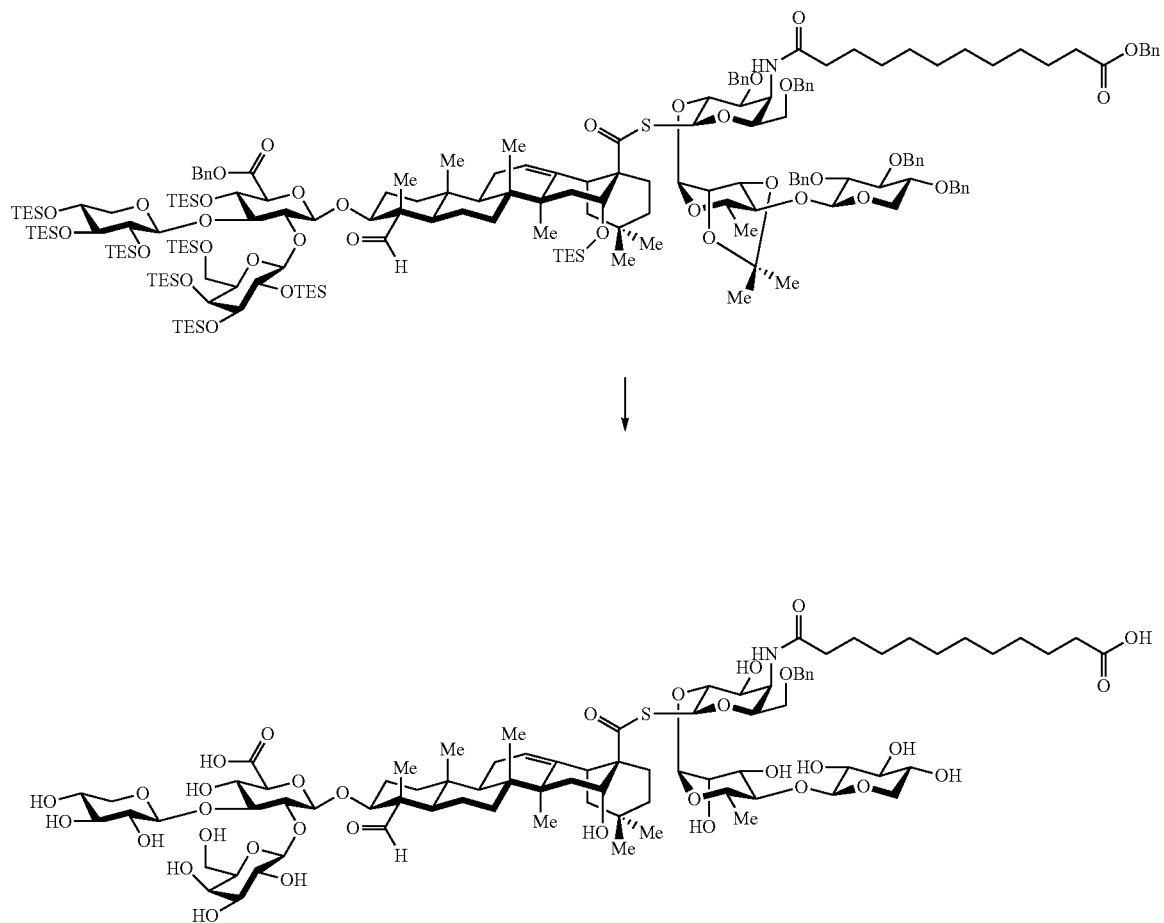

Production of β-Thioester Variant 5 (SQS-0-13-5-5)

A solution of fully protected β-thioester variant S10 (18 mg, mmol, 1.0 equiv) in tetrahydrofuran (4 mL) and ethanol (2 mL) in a 25 mL round bottom flask was charged with 10% (dry basis) palladium on carbon, wet, Degussa type E101 NE/W (β mg, 0.011 mmol, 4 equiv). Reaction mixture was stirred under hydrogen pressure (50 psi) for 11 h, then filtered through a 0.45 m polyvinylidene fluoride filter disk, washed with methanol (5 mL), and concentrated. Care must be taken to avoid quantitative reduction of the thioester to the corresponding aldehyde, which will occur if the reaction hydrogenation is allowed to proceed overnight. At the stated reaction time, a crude NMR in methanol-d4 showed 2.5 aromatic protons (relative to the C27 aldehyde, integrated to $^1$H NMR (600 MHz, D2O/CD3CN, 1:1) δ 9.91 (s, 1H), 5.87 (t, J=4.1 Hz, 1H), 5.55 (d, J=2.0 Hz, 1H), 5.38 (d, J=10.0 Hz, 1H), 5.22 (d, J=7.8 Hz, 1H), 5.10 (d, J=7.8 Hz, 1H), 5.00-4.95 (m, 2H), 4.92 (d, J=7.8 Hz, 1H), 4.46-4.36 (m, 5H), 4.35-4.25 (m, 4H), 4.24-4.12 (m, 6H), 4.09-3.95 (m, 6H), 3.93-3.84 (m, 4H), 3.82 (dd, J=11.5, 6.3 Hz, 1H), 3.78-3.70 (m, 3H), 3.67 (dd, J=9.3, 7.7 Hz, 1H), 3.45 (dd, J=13.6, 2.9 Hz, 1H), 2.81 (t, J=7.6 Hz, 3H), 2.79-2.67 (m, 3H), 2.47-2.32 (m, 5H), 2.32-2.14 (m, 6H), 2.07 (q, J=6.9 Hz, 6H), 1.97 (t, J=9.7 Hz, 2H), 1.89 (d, J=15.4 Hz, 2H), 1.85 (s, 3H), 1.76-1.69 (m, 2H), 1.64 (s, 3H), 1.63-1.58 (m, 2H), 1.48 (s, 3H), 1.44 (s, 4H), 1.40 (s, 3H), 1.38 (d, J=6.7 Hz, 2H), 1.19 (s, 3H); HRMS (ESI) m/z: Calcd for $C_{76}H_{121}NO_{34}NaS$ [M+Na]$^+$ 1646.7388, found 1646.7373.

Example 6: Synthesis of α-Glycosyl Ester Variant 6 (Sqs-0-0-8-5)

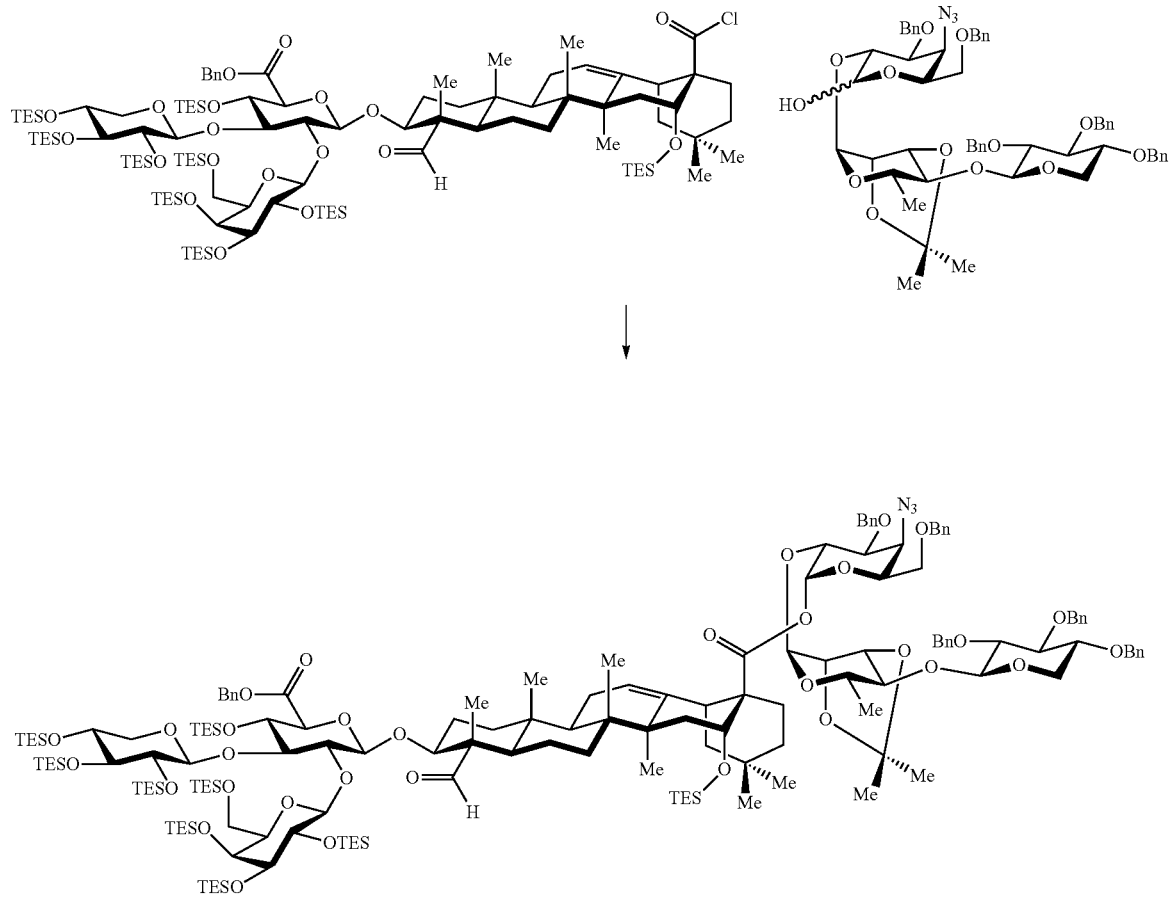

Production of Protected Prosapogenin α-Ester Azide 24

Sodium hydride was added to a solution of hemiacetal 17 (28 mg, 0.029 mmol, 1.5 equiv) in tetrahydrofuran/dimethylformamide (2.0 mL, 1:1) at −20° C. After 5 min, a solution acyl chloride 12 (40 mg, 0.019 mmol, 1.0 equiv) in tetrahydrofuran (1.5 mL) was added over 1 min. After 10 min, concentrated aqueous ammonium chloride (0.5 mL) was added. Suspension was diluted with water and extracted with benzene (3×25 mL). Combined organics were washed with brine, dried over sodium sulfate, concentrated, and purified with silica gel chromatography (hexanes/ethyl acetate, 20:1 to 4:1) furnishing separable esters (a ester 35 mg (α-24), (3 ester 6 mg (β-24), 70% total yield).

TLC $R_f$ 0.55 (benzene:ethyl acetate, 20:1); FTIR (NaCl film) 2953, 2876, 2106, 1752, 1736, 1455, 1380, 1240, 1098, 1005, 825, 732, 696 cm$^{-1}$; $^1$H-NMR (600 MHz, CDCl$_3$-d) δ 9.74 (s, 1H), 7.47-7.26 (m, 30H), 6.12 (d, J=3.7 Hz, 1H), 5.35-5.28 (m, 2H), 5.27 (t, J=3.8 Hz, 1H), 5.12 (d, J=12.4 Hz, 1H), 4.93 (d, J=11.1 Hz, 1H), 4.89 (d, J=7.4 Hz, 1H), 4.89-4.80 (m, 2H), 4.77 (d, J=11.7 Hz, 1H), 4.73 (d, J=11.7 Hz, 1H), 4.70 (d, J=11.1 Hz, 1H), 4.64 (dd, J=11.7, 4.1 Hz, 2H), 4.59 (d, J=7.5 Hz, 1H), 4.57-4.49 (m, 3H), 4.46 (d, J=7.2 Hz, 1H), 4.23 (dd, J=9.9, 3.8 Hz, 1H), 4.20 (d, J=7.4 Hz, 1H), 4.17 (dd, J=3.5, 1.6 Hz, 1H), 4.13 (dd, J=7.1, 5.6 Hz, 1H), 4.05 (d, J=5.6 Hz, 1H), 3.99-3.79 (m, 10OH), 3.78 (t, J=9.2 Hz, 1H), 3.68-3.54 (m, 9H), 3.55-3.45 (m, 2H), 3.42 (dd, J=9.4, 2.5 Hz, 1H), 3.41-3.33 (m, 2H), 3.35-3.29 (m, 1H), 3.28 (t, J=8.0 Hz, 1H), 3.26-3.19 (m, 1H), 3.16 (t, J=11.0 Hz, 1H), 2.94 (dd, J=14.4, 4.4 Hz, 1H), 2.15 (t, J=13.6 Hz, 1H), 1.86-1.75 (m, 4H), 1.77-1.55 (m, 7H), 1.52-1.47 (m, 2H), 1.38 (s, 4H), 1.33 (s, 6H), 1.24 (d, J=5.6 Hz, 3H), 1.14-0.86 (m, 101H), 0.87-0.56 (m, 78H); $^{13}$C-NMR (151 MHz, CDCl$_3$) δ 212.86, 174.19, 168.33, 142.70, 138.80, 138.41, 138.25, 137.45, 137.28, 135.26, 128.56, 128.52, 128.50, 128.48, 128.44, 128.40, 128.31, 128.28, 128.26, 128.23, 128.16, 128.13, 128.00, 127.96, 127.94, 127.90, 127.81, 127.78, 127.58, 127.50, 122.32, 109.19, 103.63, 102.83, 101.41, 100.85, 99.33, 91.33, 86.48, 83.78, 81.31, 78.83, 78.73, 78.32, 78.21, 77.98, 77.68, 76.65, 76.46, 76.09, 75.93, 75.82, 75.56, 75.08, 74.95, 74.51, 73.62, 73.15, 72.92, 72.62, 72.54, 72.41, 71.40, 71.09, 70.05, 68.30, 66.87, 65.35, 65.08, 63.70, 60.24, 59.95, 53.85, 49.60, 49.37, 46.37, 46.05, 41.50, 40.22, 39.53, 37.86, 36.09, 35.08, 34.69, 34.59, 34.55, 32.48, 32.40, 31.41, 30.36, 29.09, 27.83, 26.37, 26.32, 25.34, 25.30, 24.22, 23.21, 20.73, 20.27, 17.37, 17.13, 15.78, 12.27, 11.48, 7.59, 7.49, 7.27, 7.24, 7.22, 7.16, 7.01, 6.88, 6.81, 5.94, 5.66, 5.46, 5.39, 5.36, 5.33, 5.28, 5.25, 5.21, 5.04, 4.43; HRMS (ESI) m/z: Calcd for C$_{163}$H$_{265}$N$_3$O$_{32}$NaSi$_9$ 3051.7023 [M+Na], found 3051.7041.

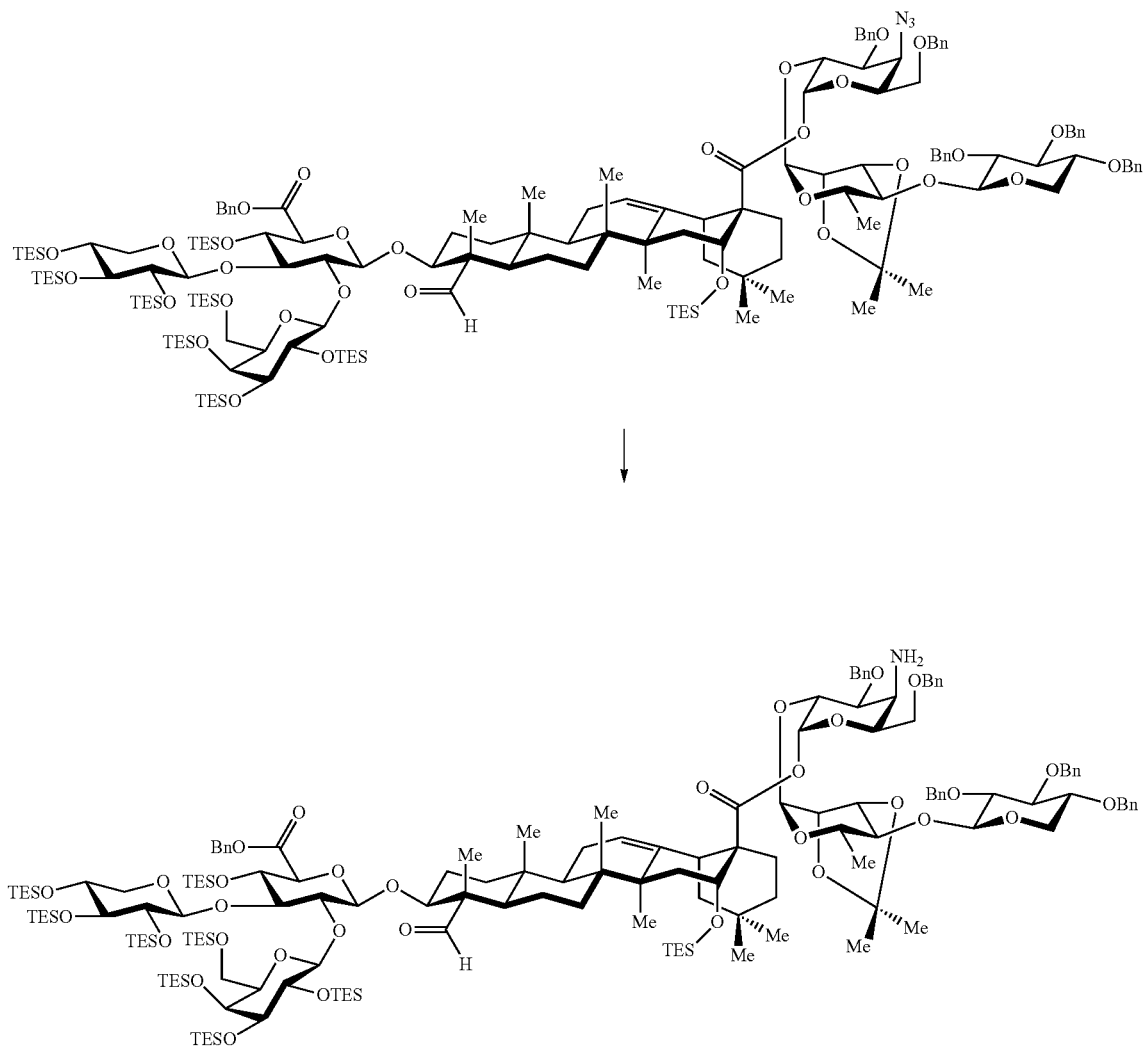

Production of Protected Prosapogenin α-Ester Amine S11

Hydrogen sulfide was bubbled via cannula through an ice-cooled solution of azide 24 (44 mg, 0.015 mmol, 1.0 equiv) in pyridine/triethylamine (3.5:1, 4.5 mL) for two min. Vent needle and cannula were removed, and septum sealed with Teflon tape and parafilm, then warmed to ambient temperature and stirred overnight. Hydrogen sulfide was removed with a stream of nitrogen, then resulting orange solution was concentrated and purified via silica gel chromatography (hexanes:[ethyl acetate+1% triethylamine], 5:1 to 2:1) furnishing amine S11 (36 mg, 83% yield) as a colorless oil.

TLC $R_f$ 0.33 (hexanes:ethyl acetate, 2:1+0.5% triethylamine; FTIR (NaCl film) 2951, 2876, 1753, 1726 cm$^{-1}$; $^1$H-NMR (600 MHz, CDCl$_3$-d) δ 9.70 (s, 1H), 7.42-7.25 (m, 33H), 6.15 (d, J=3.8 Hz, 1H), 5.30-5.26 (m, 2H), 5.24 (t, J=3:8 Hz, 1H), 5.09 (d, J=12.4 Hz, 1H), 4.91 (d, J=11.1 Hz, 1H), 4.87 (d, J=7.4 Hz, 1H), 4.85-4.77 (m, 2H), 4.72-4.65 (m, 3H), 4.61 (d, J=11.7 Hz, 1H), 4.58-4.52 (m, 4H), 4.47 (d, J=12.1 Hz, 1H), 4.42 (d, J=7.3 Hz, 1H), 4.19-4.13 (m, 2H), 4.11 (dd, J=7.6, 5.5 Hz, 1H), 4.06 (d, J=5.5 Hz, 1H), 3.98-3.89 (m, 4H), 3.88-3.71 (m, 6H), 3.67-3.51 (m, 10H), 3.51-3.45 (m, 2H), 3.41-3.28 (m, 5H), 3.25 (t, J=8.0 Hz, 1H), 3.20 (ddd, J=11.4, 7.6, 3.5 Hz, 1H), 3.13 (t, J=11.0 Hz, 1H), 2.92 (dd, J=14.4, 4.4 Hz, 1H), 2.12 (t, J=13.6 Hz, 1H), 1.87-1.73 (m, 4H), 1.73-1.53 (m, 6H), 1.52 (s, 3H), 1.50-1.43 (m, 4H), 1.36 (s, 3H), 1.35-1.24 (m, 1OH), 1.21 (d, J=6.1 Hz, 3H), 1.08-0.89 (m, 92H), 0.88 (s, 3H), 0.80 (s, 3H), 0.78 (d, J=7.8 Hz, 2H), 0.76 (s, 3H), 0.75-0.56 (m, 60H); $^{13}$C-NMR (151 MHz, CDCl$_3$) δ 212.88, 174.27, 168.33, 142.87, 138.82, 138.40, 138.26, 137.75, 137.70, 135.26, 128.48, 128.47, 128.43, 128.39, 128.38, 128.36, 128.31, 128.27, 128.25, 128.18, 128.15, 127.95, 127.93, 127.81, 127.78, 127.77, 127.72, 127.68, 127.64, 127.59, 127.56, 127.49, 122.20, 109.15, 103.63, 102.88, 101.40, 100.85, 99.05, 91.41, 86.48, 83.76, 81.20, 78.83, 78.73, 78.33, 78.29, 78.13, 77.99, 76.46, 76.19, 75.94, 75.82, 75.54, 75.08, 74.99, 74.47, 73.41, 73.14, 72.62, 72.53, 71.97, 71.58, 71.46, 71.39, 71.09, 68.86, 66.86, 65.34, 64.96, 63.68, 60.23, 53.85, 49.59, 49.58, 49.43, 46.43, 46.07, 42.86, 41.48, 40.17, 39.99, 39.54, 37.86, 36.09, 35.12, 34.56, 32.41, 31.46, 30.37, 29.73, 27.87, 26.40, 26.37, 26.34, 25.35, 24.25, 23.21, 21.48, 20.28, 17.78, 17.77, 17.39, 17.06, 15.77, 14.20, 13.13, 12.28, 12.17, 7.59, 7.49, 7.27, 7.25, 7.16, 7.14, 7.01, 6.88, 6.81, 5.94, 5.66, 5.46, 5.39, 5.32, 5.28, 5.25, 5.04, 4.43; HRMS (ESI) m/z: Calcd for $C_{182}H_{293}NO_{35}Si_9Na$ [M+Na]$^+$ 3327.8999, found 3327.9016.

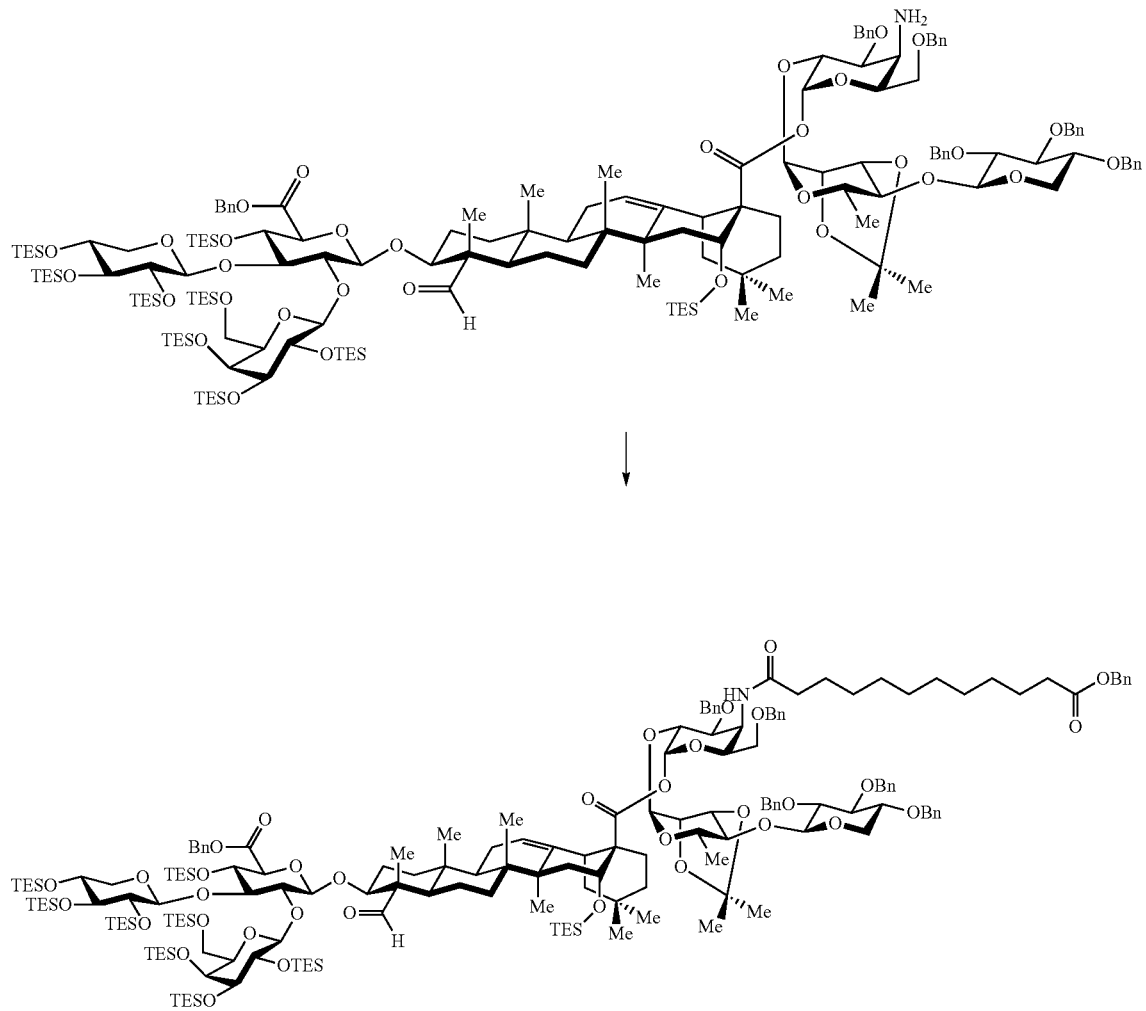

Production of Protected α-Ester Variant S12

Isobutyl chloroformate (6.3 μL, 0.048 mmol, 4 equiv) was added to an ice-cooled solution of carboxylic acid S2 (23 mg, 0.072 mmol, 6 equiv) and triethylamine (17 μL, 0.122 mmol, 10 equiv) in tetrahydrofuran (3 mL) and stirred for β hours, then transferred via cannula to an ice-cooled solution of amine S11 (36 mg, 0.012 mmol, 1 equiv) in tetrahydrofuran (1 mL). After 16 h, suspension was diluted with saturated sodium bicarbonate and then extracted with ethyl acetate (3×25 ml). Combined organics were washed with brine, dried over sodium sulfate, concentrated, and purified with silica gel chromatography (hexanes:ethyl acetate+0.5% triethylamine, 10:1 to 1:1) to give fully protected α-ester analogue S12 (30 mg, 76% yield) as a colorless film.

TLC $R_f$ 0.60 (hexanes:ethyl acetate, 2:1+0.5% triethylamine; $^1$H-NMR (600 MHz, CDCl$_3$-d) δ 9.69 (s, 1H), 7.40-7.21 (m, 35H), 6.15 (d, J=3.7 Hz, 1H), 5.50 (d, J=10.0 Hz, 1H), 5.30-5.26 (m, 2H), 5.19 (t, J=3.8 Hz, 1H), 5.11 (s, 2H), 5.09 (d, J=12.4 Hz, 1H), 4.91 (d, J=11.2 Hz, 1H), 4.89-4.85 (m, 2H), 4.84 (d, J=11.0 Hz, 1H), 4.79 (d, J=8.0 Hz, 1H), 4.77 (d, J=8.7 Hz, 1H), 4.70 (d, J=9.6 Hz, 1H), 4.68 (d, J=9.2 Hz, 1H), 4.61 (d, 1H), 4.55 (d, J=7.5 Hz, 1H), 4.53 (d, J=3.2 Hz, 1H), 4.49 (d, J=12.2 Hz, 1H), 4.44-4.39 (m, 3H), 4.16 (d, J=7.4 Hz, 1H), 4.10 (dd, J=7.6, 5.5 Hz, 1H), 4.08-4.04 (m, 2H), 3.94-3.89 (m, 3H), 3.87-3.76 (m, 6H), 3.74 (t, J=9.2 Hz, 1H), 3.67-3.62 (m, 1H), 3.62-3.51 (m, 6H), 3.50-3.43 (m, 2H), 3.43-3.28 (m, 5H), 3.25 (t, J=8.1 Hz, 1H), 3.22-3.17 (m, 1H), 3.13 (t, J=10.9 Hz, 1H), 2.89 (dd, J=14.4, 4.4 Hz, 1H), 2.35 (t, J=7.5 Hz, 2H), 2.18 (t, J=7.6 Hz, 2H), 2.11 (t, J=13.6 Hz, 1H), 1.81-1.71 (m, 4H), 1.71-1.53 (m, 10H), 1.51 (s, 4H), 1.49-1.41 (m, 2H), 1.38 (s, 3H), 1.34-1.16 (m, 25H), 1.03-0.88 (m, 86H), 0.87 (s, 3H), 0.79-0.78 (m, 3H), 0.75 (s, 3H), 0.74-0.55 (m, 55H); $^{13}$C-NMR (151 MHz, CDCl$_3$) δ 212.77, 174.17, 173.72, 173.57, 168.34, 142.80, 138.80, 138.34, 138.26, 137.68, 137.58, 136.13, 135.25, 128.55, 128.50, 128.48, 128.43, 128.38, 128.35, 128.30, 128.27, 128.25, 128.25, 128.21, 128.18, 128.17, 128.15, 128.02, 127.93, 127.77, 127.72, 127.70, 127.57, 127.50, 122.23, 109.16, 103.62, 102.88, 101.39, 100.84, 99.01, 90.84, 86.44, 83.75, 81.03, 78.81, 78.72, 78.23, 78.18, 77.97, 76.45, 76.04, 75.93, 75.85, 75.82, 75.55, 75.07, 74.92, 74.40, 73.35, 73.15, 72.62, 72.53, 72.12, 71.39, 71.27, 71.08, 70.92, 68.93, 66.86, 66.08, 65.34, 65.03, 63.69, 60.23, 53.83, 49.62, 49.40, 47.03, 46.38, 46.04, 41.47, 40.18, 39.52, 37.85, 36.99, 36.08, 35.09, 34.54, 34.35, 32.37, 32.32, 31.45, 30.33, 29.42, 29.38, 29.31, 29.27, 29.21, 29.18, 29.14, 27.85, 26.38, 26.33, 25.90, 25.33, 24.97, 24.21, 23.17, 20.24, 17.44, 17.00, 15.77, 12.27, 7.58, 7.48, 7.27, 7.22, 7.15, 7.14, 7.01, 6.87, 6.81, 5.94, 5.66, 5.46, 5.39, 5.32, 5.28, 5.24, 5.01, 4.43; HRMS (ESI) m/z: Calcd for $C_{182}H_{293}NO_{35}Si_9Na$ [M+Na]$^+$ 3327.8999, found 3327.9016.

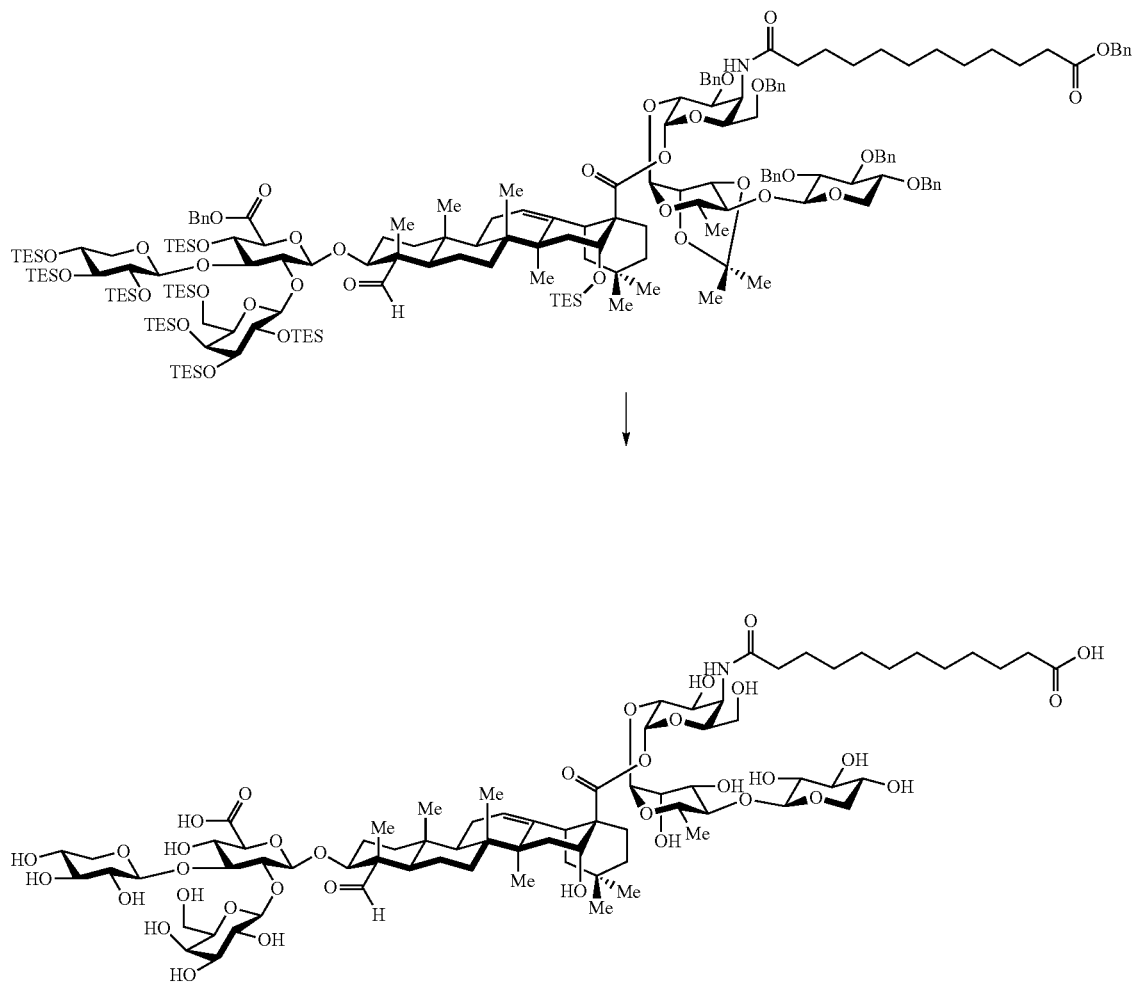

Production of α-Ester Variant 6 (SQS-0-0-8-5)

A solution of fully protected α-ester variant S12 (9 mg, 0.003 mmol, 1.0 equiv) in tetrahydrofuran (2 mL) and ethanol (2 mL) in a 25 mL round bottom flask was charged with 10% (dry basis) palladium on carbon, wet, Degussa type E101 NE/W (β mg, 0.011 mmol, 4 equiv). Reaction mixture was stirred under hydrogen pressure (50 psi) overnight, then filtered through a 0.45 μm polyvinylidene fluoride filter disk, washed with methanol (5 mL), and concentrated. To the hydrogenation product was added a pre-cooled (0° C.) solution of trifluoroacetic acid (2.0 mL, TFA/$H_2O$ 3:1). After vigorous stirring for 60 min, the solution was concentrated in vacuo at 0° C. to give white solid residue. This crude product was partially dissolved in a solution of aqueous acetonitrile (5:1 water:acetonitrile) and purified by RP-HPLC on an XBridge Prep BEH300 C18 column (5 m, 10×250 mm) using a linear gradient of 20→75%.acetonitrile (0.05% TFA) in over 19 min at a flow rate of 5 mL/min. The fraction containing the major peak (tR=10.10 min) was collected and lyophilized to dryness to afford α-ester variant 6 (SQS-0-0-8-5) (3.3 mg, 77% yield) as a fluffy white solid.

$^1$H-NMR (600 MHz, D20, CD3CN, 1:1) δ 9.29 (s, 1H), 5.97 (d, J=4.0 Hz, 1H), 5.26 (t, J=3.5 Hz, 1H), 4.72 (d, J=1.7 Hz, 1H), 4.60 (d, J=7.7 Hz, 1H), 4.48 (d, J=7.8 Hz, 1H), 4.39 (t, J=4.2 Hz, 1H), 4.36 (d, J=7.8 Hz, 1H), 4.34 (d, J=4.6 Hz, 1H), 4.32 (d, J=8.0 Hz, 1H), 3.97 (dd, J=10.5, 4.6 Hz, 1H), 3.88-3.78 (m, 5H), 3.78-3.59 (m, 8H), 3.59-3.51 (m, 2H), 3.50-3.33 (m, 9H), 3.33-3.21 (m, 6H), 3.20-3.04 (m, 5H), 2.77 (dd, J=14.1, 4.5 Hz, 1H), 2.20 (t, J=7.5 Hz, 3H), 2.18-2.00 (m, 4H), 1.88-1.76 (m, 4H), 1.71-1.57 (m, 5H), 1.55-1.41 (m, 8H), 1.41-1.30 (m, 4H), 1.23 (s, 3H), 1.12 (d, J=5.6 Hz, 3H), 1.01 (s, 3H), 0.86 (s, 3H), 0.82 (s, 3H), 0.80 (s, 3H), 0.78-0.73 (m, 1H), 0.62 (s, 3H); HRMS (ESI) m/z: Calcd for $C_{76}H_{121}NO_{35}Na$ [M+Na]$^+$ 1630.7617, found 1630.7596.

Example 7: Synthesis of α-Amide Variant 7 (SQS-0-6-8-5)

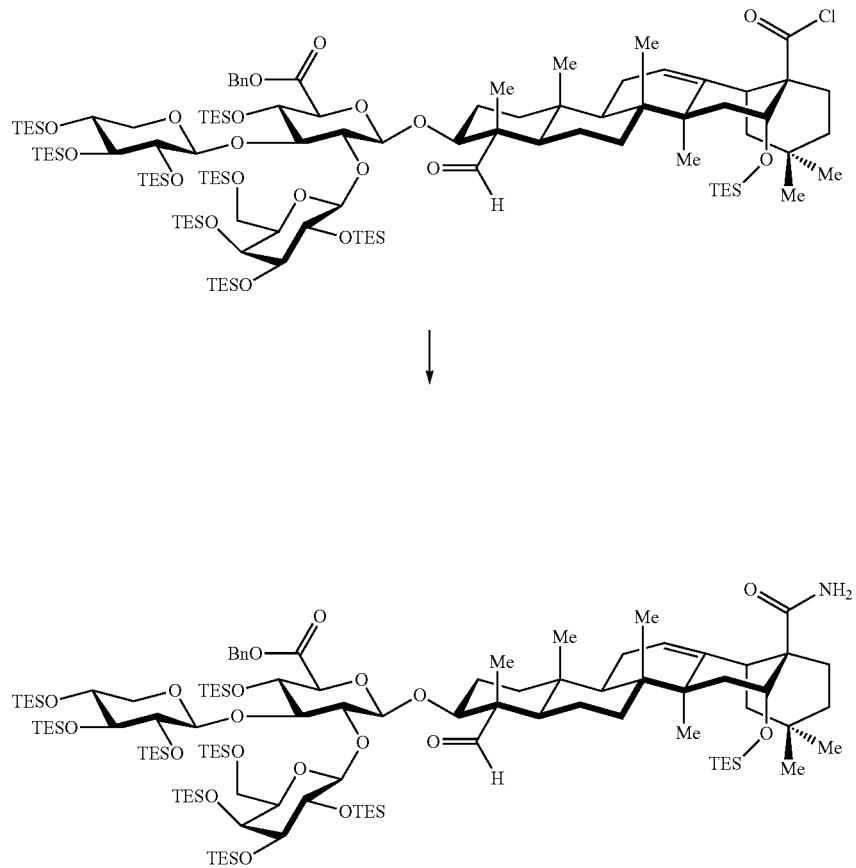

Production of Protected Prosapogenin Primary Amide 14

A large excess of freshly condensed ammonia (~1 ml, ~900 equiv) in dichloromethane (2 ml) was added to an ice-cooled solution of 12 (110 mg, 0.525 mmol, 1 equiv) in dichloromethane (5 ml). After 20 min, reaction mixture was warmed to room temperature allowing excess ammonia to evaporate. Mixture was diluted with water and layers separated. After extraction with with dichloromethane (2×10 mL), organic fractions combined and washed with brine, then dried over sodium sulfate, and concentrated and the purified by silica gel chromatography (hexanes:EtoAc+ 0.5% triethylamine 10:1 to 2:1) to afford 14 (100 mg, 92% yield) as a white foam.

TLC $R_f$ 0.26 (4:1 hexanes/ethyl acetate); FTIR (NaCl, film) 3454, 2953, 2911, 2877, 1753, 1725, 1674, 1602, 1456, 1414, 1377, 1239, 1104, 1005, 913, 864, 826, 740 cm$^{-1}$; $^1$H-NMR (600 MHz, CDCl$_3$) δ 9.72 (s, 1H), 7.39-7.29 (m, 5H), 6.06 (s, 1H), 5.46 (t, J=3.6 Hz, 1H), 5.36 (s, 1H), 5.28 (d, J=12.4 Hz, 1H), 5.10 (d, J=12.4 Hz, 1H), 4.56 (d, J=7.4 Hz, 1H), 4.49 (s, 1H), 4.43 (d, J=7.3 Hz, 1H), 4.18 (d, J=7.4 Hz, 1H), 3.95-3.90 (m, 2H), 3.88-3.82 (m, 2H), 3.82-3.77 (m, 2H), 3.75 (t, J=9.2 Hz, 1H), 3.62-3.53 (m, 3H), 3.48 (ddd, J=10.5, 8.4, 5.1 Hz, 1H), 3.39 (dd, J=9.4, 2.5 Hz, 1H), 3.35 (t, J=8.7 Hz, 2H), 3.25 (dd, J=8.7, 7.4 Hz, 1H), 3.13 (t, J=10.9 Hz, 1H), 2.57 (dd, J=13.7, 4.2 Hz, 1H), 2.36 (t, J=13.1 Hz, 1H), 2.03 (dt, J=14.6, 4.0 Hz, 1H), 1.92 (dd, J=8.9, 3.6 Hz, 2H), 1.90-1.42 (m, 12H), 1.32 (s, 3H), 1.30-1.25 (m, 2H), 1.19-0.84 (m, 96H), 0.79 (s, 3H), 0.78-0.55 (m, 53H); $^{13}$C-NMR (151 MHz, CDCl$_3$) δ 212.78, 180.71, 168.38, 145.17, 135.29, 128.47, 128.27, 128.14, 122.50, 103.71, 101.41, 100.85, 86.45, 78.81, 78.73, 76.46, 75.95, 75.91, 75.83, 75.09, 72.62, 72.53, 71.38, 71.11, 66.85, 65.34, 60.25, 53.81, 49.39, 49.19, 47.24, 45.99, 42.27, 41.95, 39.56, 37.95, 36.05, 35.39, 34.67, 34.54, 34.19, 32.57, 31.98, 31.61, 31.27, 30.54, 29.07, 26.32, 25.38, 25.29, 24.22, 23.40, 22.68, 20.71, 20.21, 16.90, 15.86, 14.14, 12.26, 11.45, 7.57, 7.47, 7.25, 7.16, 7.15, 7.14, 6.99, 6.85, 6.79, 5.93, 5.65, 5.45, 5.38, 5.34, 5.27, 5.23, 5.18, 5.01, 4.42; HRMS m/z (ESI): Calcd for C$_{108}$H$_{205}$NO$_{19}$Si$_9$Na [M+Na] 2095.2927, found 2095.3020.

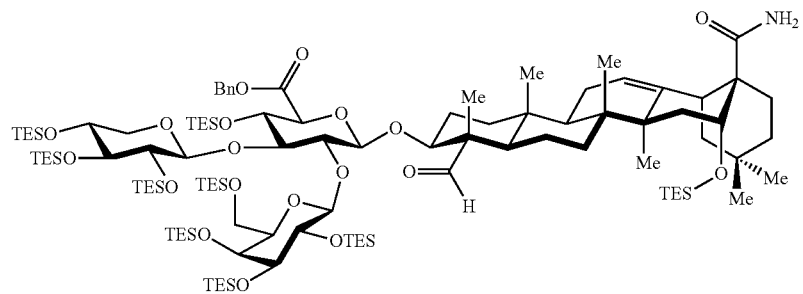
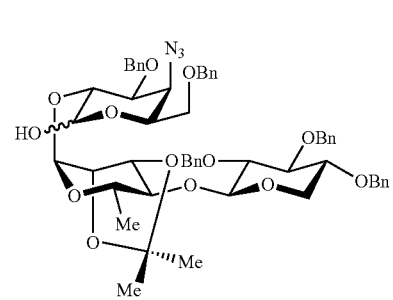
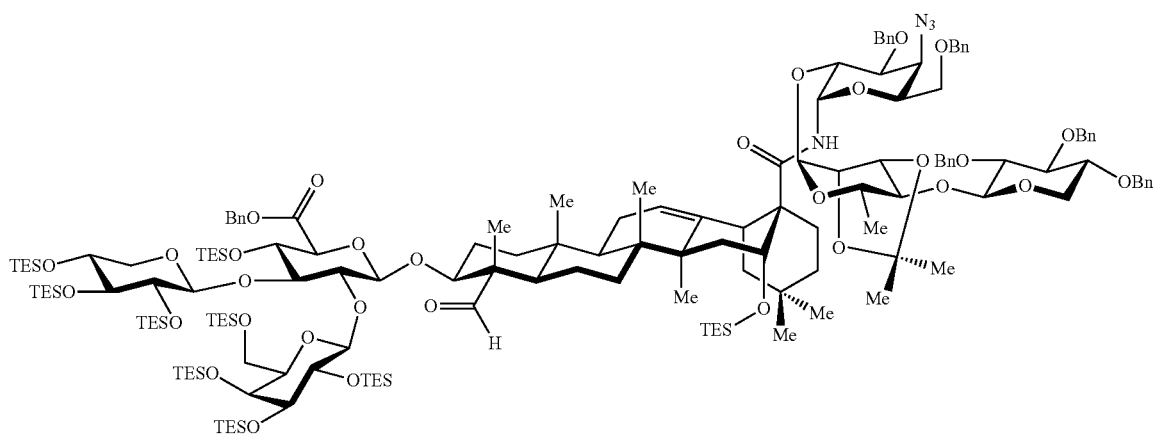

Production of Protected Prosapogenin α-Amide Azide 19

Trifluoromethanesulfonic anhydride (22 μL, 0.13 mmol, 3.0 equiv) was added to a solution of trisaccharide 17 (85 mg, 0.087 mmol, 2.00 equiv), phenyl sulfoxide (53 mg, 0.260 mmol, 6.0 equiv) and 2,4,6-tri-tertbutylpyridine (65 mg, 0.261 mmol, 6.0 equiv) in dichloromethane (5 mL) at −78° C. The reaction stirred in a cold bath at −78° C. for 8 min and then was transferred to a bath between −55 and −50° C. for 65 min. A solution of amide 14 (90 mg, 0.043 mmol, 1 equiv) was added in dichloromethane (2 mL) via syringe. Bath temperature was warmed to −45° C. for 45 min then 0° C. for 15 min. Triethylamine was added, concentrated and purified via silica gel chromatography (hexanes: [ethyl acetate+1% triethylamine], 10:1 to 2:1) furnishing readily separable dissacharides α-19 (80 mg) and β-19 (β mg) as a flaky white film (6.1:1, α:β, 71% total).

TLC $R_f$ 0.64 (2:1 hexanes/ethyl acetate); FTIR (NaCl, film) 3420, 2953, 2911, 2876, 2105, 1751, 1675, 1496, 1457, 1413, 1375, 1240, 1160, 1098, 1005, 898, 865, 825, 732, 697 cm$^{-1}$; $^1$H-NMR (600 MHz, CDCl$_3$) δ 9.71 (s, 1H), 7.98-7.92 (m, 1H), 7.59-7.54 (m, 1H), 7.53-7.48 (m, 1H), 7.42-7.26 (m, 27H), 6.64 (d, J=8.5 Hz, 1H), 5.43 (t, J=3.6 Hz, 1H), 5.29 (d, J=12.4 Hz, 1H), 5.19 (d, J=4.7 Hz, 1H), 5.10 (d, J=12.4 Hz, 1H), 4.92 (d, J=11.0 Hz, 1H), 4.89-4.81 (m, 4H), 4.73 (dd, J=11.5, 3.0 Hz, 2H), 4.68 (d, J=11.0 Hz, 1H), 4.63 (dd, J=11.5, 5.3 Hz, 2H), 4.56 (d, J=7.5 Hz, 1H), 4.52 (s, 2H), 4.48 (s, 1H), 4.43 (d, J=7.3 Hz, 1H), 4.21-4.15 (m, 2H), 4.09 (dd, J=7.1, 4.7 Hz, 1H), 4.00 (dd, J=3.0, 1.5 Hz, 1H), 3.96-3.90 (m; 3H), 3.88-3.70 (m, 8H), 3.67-3.51 (m, 8H), 3.51-3.45 (m, 2H), 3.39 (dd, J=9.4, 2.5 Hz, 1H), 3.38-3.29 (m, 3H), 3.25 (dd, J=8.6, 7.4 Hz, 1H), 3.22-3.16 (m, 1H), 3.13 (t, J=11.0 Hz, 1H), 2.62 (dd, J=13.4, 4.2 Hz, 1H), 2.33 (t, J=13.2 Hz, 1H), 1.98-1.63 (m, 7H), 1.62-1.45 (m, 5H), 1.44 (s, 3H), 1.43-1.30 (m, 10OH), 1.29 (s, 3H), 1.28-1.17 (m, 3H), 1.12-1.03 (m, 4H), 0.89 (s, 81H), 0.84 (s, 3H), 0.81-0.56 (m, 51H); $^{13}$C-NMR (151 MHz, CDCl$_3$) δ 212.68, 178.34, 168.32, 144.58, 141.57, 138.70, 138.57, 138.19, 137.70, 137.13, 135.25, 133.16, 129.26, 128.52, 128.49, 128.46, 128.44, 128.38, 128.35, 128.31, 128.29, 128.27, 128.22, 128.14, 128.08, 128.05, 128.04, 127.99, 127.97, 127.95, 127.94, 127.91, 127.88, 127.86, 127.85, 127.81, 127.76, 127.65, 127.57, 122.60, 110.03, 103.64, 102.61, 101.39, 100.82, 97.64, 86.47, 83.82, 82.01, 81.63, 79.21, 78.99, 78.79, 78.71, 78.32, 77.92, 76.76, 76.64, 76.44, 76.15, 75.90, 75.80, 75.65, 75.06, 74.75, 73.97, 73.53, 73.25, 72.76, 72.60, 72.50, 72.06, 71.38, 71.08, 69.00, 67.78, 66.83, 65.32, 63.77, 60.24, 59.21, 53.84, 49.36, 49.20, 47.17, 46.06, 41.87, 41.25, 39.70, 37.98, 36.02, 35.39, 34.66, 34.52, 34.09, 32.56, 32.21, 31.59, 31.46, 30.52, 29.06, 27.32, 26.25, 25.39, 25.31, 25.27, 24.16, 23.39, 22.66, 20.70, 20.26, 18.77, 17.91, 17.22, 15.95, 14.14, 12.27, 11.45, 7.56, 7.46, 7.25, 7.17, 7.14, 7.13, 6.98, 6.85, 6.79, 5.92, 5.63, 5.44, 5.37, 5.33, 5.25, 5.22, 4.95, 4.41; HRMS m/z (ESI): Calcd for $C_{163}H_{266}N_4O_{31}NaSi_9$ 3050.7182, found 3050.7034.

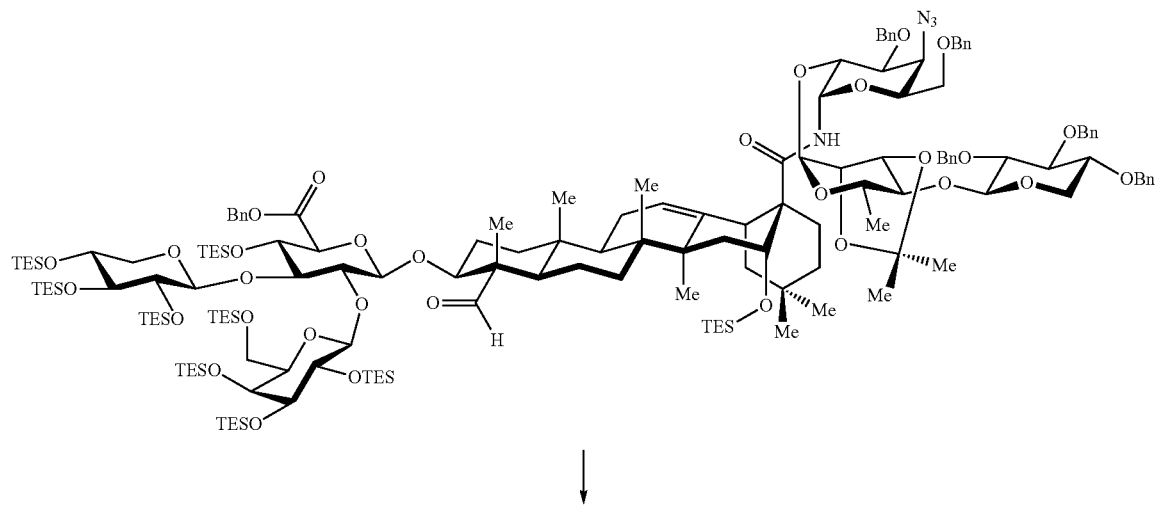

↓

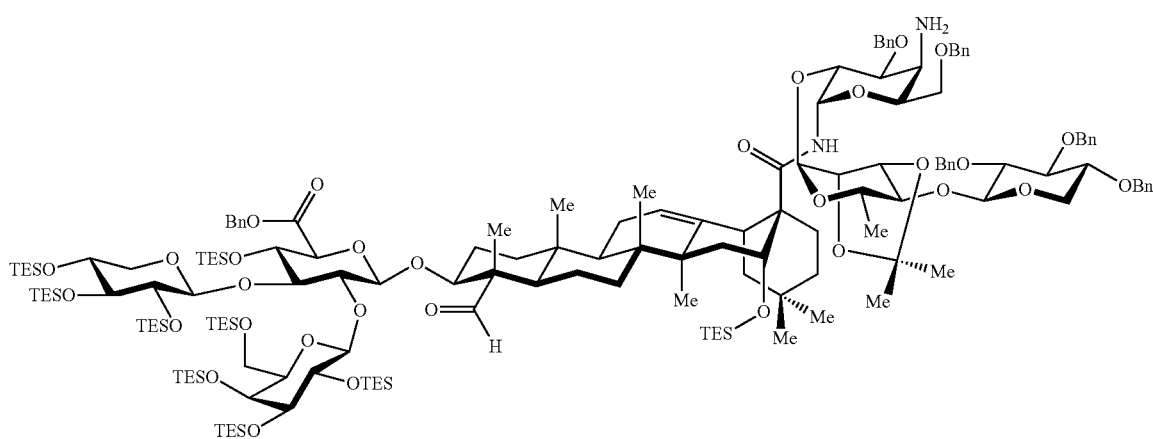

Production of Protected Prosapogenin α-Amide Amine S13

Hydrogen sulfide was bubbled via cannula through an ice-cooled solution of azide α-19 (45 mg, 0.0148 mmol, equiv) in pyridine/triethylamine (3.5:1, 4.5 mL) in a 50 mL conical vial. After two min, vent needle and cannula were removed, and septum sealed with Teflon tape and parafilm, then warmed to RT and stirred overnight. Hydrogen sulfide was removed with a stream of nitrogen, then resulting orange solution was concentrated and purified via silica gel chromatography (hexanes:[ethyl acetate+1% triethylamine], 5:1 to 2:1) furnishing amine S13 (36 mg, 81% yield).

TLC $R_f$ 0.35 (5:1 benzene:ethyl acetate); FTIR (NaCl film) 3393, 3031, 2953, 2911, 2876, 1752, 1724, 1676, 1497, 1457, 1414, 1380, 1240, 1169, 1097, 1006, 909, 864, 826, 737, 697, 666, 602 cm$^{-1}$; $^1$H-NMR (500 MHz, CDCl$_3$) δ 9.70 (s, 1H), 7.31 (s, 30H), 6.60 (d, J=8.5 Hz, 1H), 5.49-5.44 (m, OH), 5.44-5.39 (m, 1H), 5.33-5.25 (m, 2H), 5.10 (d, J=12.4 Hz, 1H), 4.94-4.79 (m, 4H), 4.75-4.59 (m, 5H), 4.60-4.51 (m, 4H), 4.48 (s, 1H), 4.42 (d, J=7.3 Hz, 1H), 4.18 (dt, J=7.6, 3.7 Hz, 2H), 4.10 (dd, J=6.7, 3.7 Hz, 1H), 3.96-3.70 (m, 10H), 3.71-3.51 (m, 11H), 3.48 (td, J=9.8, 9.3, 5.0 Hz, 1H), 3.44-3.27 (m, 5H), 3.25 (t, J=8.0 Hz, 1H), 3.19 (t, J=10.3 Hz, 1H), 3.13 (t, J=11.0 Hz, 1H), 2.62 (dd, J=14.5, 3.9 Hz, 1H), 2.32 (t, J=13.1 Hz, 1H), 1.99-1.92 (m, 1H), 1.92-1.85 (m, 1H), 1.83-1.74 (m, 2H), 1.73-1.47 (m, 7H), 1.40 (d, J=11.7 Hz, 1H), 1.37 (s, 6H), 1.35 (s, 2H), 1.30 (s, 6H), 1.29 (s, 6H), 1.28-1.15 (m, 2H), 1.13-1.02 (m, 3H), 1.03-0.85 (m, 98H), 0.84 (s, 3H), 0.83-0.52 (m, 61H); $^{13}$C-NMR (151 MHz, CDCl$_3$) δ 212.70, 178.33, 168.33, 144.82, 138.70, 138.55, 138.20, 138.08, 137.47, 135.24, 128.46, 128.43, 128.38, 128.31, 128.28, 128.13, 128.02, 127.96, 127.93, 127.80, 127.75, 127.70, 127.67, 127.58, 122.45, 109.77, 103.64, 102.58, 101.38, 100.82, 97.47, 86.42, 83.83, 82.56, 82.04, 79.38, 78.97, 78.79, 78.71, 78.15, 77.94, 76.59, 76.44, 76.21, 75.87, 75.80, 75.65, 75.07, 74.78, 74.46, 73.98, 73.39, 73.23, 72.60, 72.51, 71.38, 71.20, 71.08, 68.24, 68.10, 66.83, 65.32, 63.76, 60.25, 53.81, 49.31, 49.17, 48.77, 47.35, 45.93, 45.74, 41.88, 41.22, 39.73, 37.93, 36.00, 35.41, 33.97, 32.57, 32.06, 31.43, 30.50, 29.70, 27.46, 26.25, 25.57, 25.37, 24.34, 23.42, 20.22, 18.18, 17.16, 15.94, 12.27, 7.56, 7.46, 7.25, 7.17, 7.14, 7.13, 6.98, 6.85, 6.79, 5.92, 5.63, 5.44, 5.37, 5.33, 5.25, 5.22, 4.95, 4.41; HRMS (ESI) m/z: Calcd for $C_{163}H_{269}N_2O_{31}Si_9$ 3002.7458 [M+H], found 3002.7354.

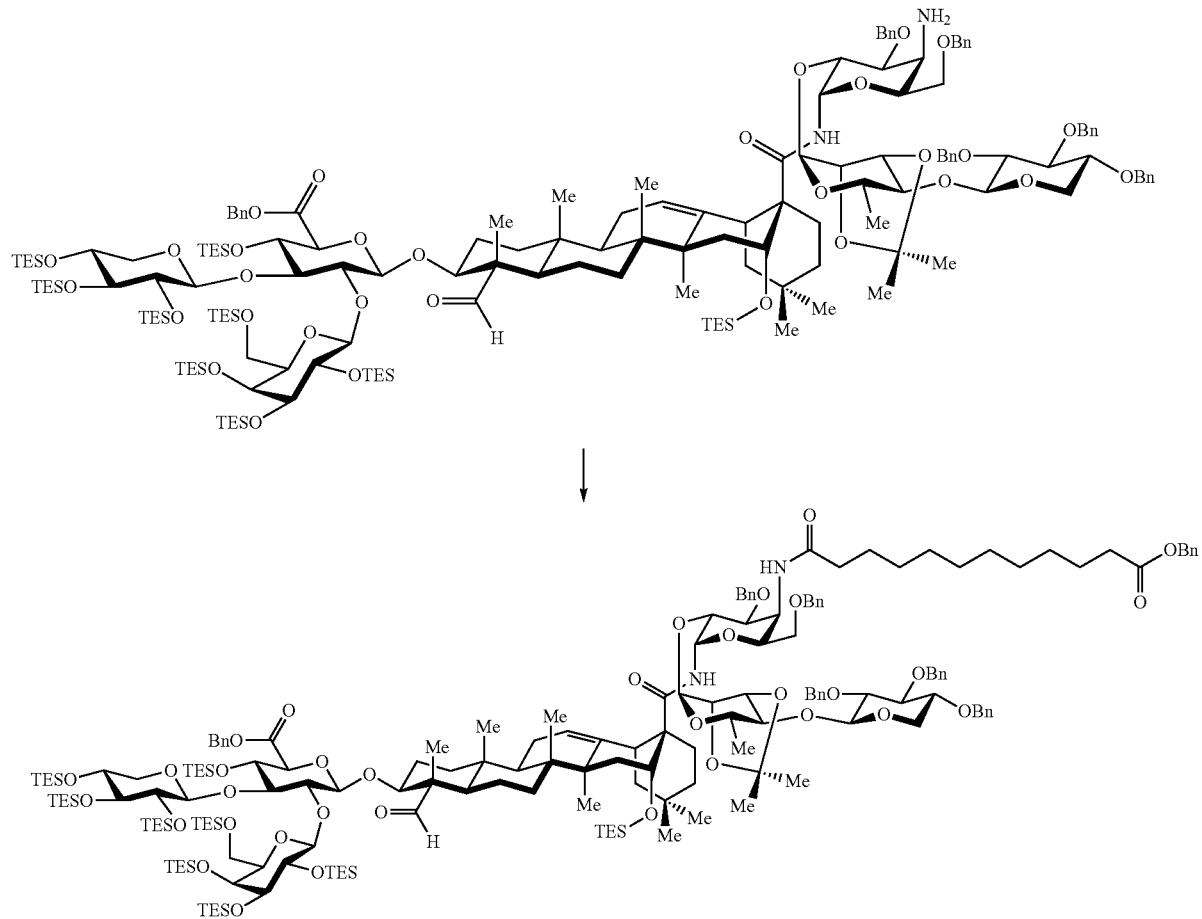

Production of Protected α-Amide Variant S14

Isobutyl chloroformate was added to an ice-cooled solution of carboxylic acid S2 (21 mg, 0.064 mmol, 6 equiv) and triethylamine (15 μL, 0.107 mmol, 10 equiv) in tetrahydrofuran (2 mL) and stirred for 4 hours, then transferred via cannula to an icecooled solution of amine S13 (32 mg, 0.011 mmol, 1.0 equiv) in tetrahydrofuran (1 mL). After 5 h, suspension was diluted with saturated sodium bicarbonate and then extracted with ethyl acetate (3×25 ml). Combined organics were washed with brine, dried over sodium sulfate, concentrated, and purified with silica gel chromatography (hexanes:ethyl acetate+0.5% triethylamine, 10:1 to 1:1) to give amide S14 (26 mg, 74% yield).

TLC $R_f$ 0.62 (2:1 hexanes:ethyl acetate); FTIR (NaCl film) 3610, 3584, 3032, 2954, 2878, 1745, 1725, 1680, 1549, 1499, 1457, 1415, 1381, 1242, 1168, 1099, 1009, 911, 865, 825, 733 cm$^{-1}$; $^1$H-NMR (600 MHz, CDCl$_3$-d) δ 9.71 (s, 1H), 7.43-7.20 (m, 35H), 6.54 (d, J=8.1 Hz, 1H), 5.45 (s, 1H), 5.32 (d, J=3.4 Hz, 1H), 5.28 (d, J=12.4 Hz, 1H), 5.12-5.06 (m, 3H), 4.90 (d, J=11.0 Hz, 1H), 4.88-4.80 (m, 6H), 4.72 (d, J=11.7 Hz, 1H), 4.67 (d, J=11.0 Hz, 1H), 4.62 (d, J=11.8 Hz, 1H), 4.56 (d, J=7.4 Hz, 1H), 4.52 (d, J=11.9 Hz, 1H), 4.46-4.39 (m, 4H), 4.20-4.13 (m, 2H), 4.08 (dd, J=6.5, 3.3 Hz, 1H), 3.95-3.88 (m, 4H), 3.87-3.69 (m, 8H), 3.65 (dd, J=9.1, 4.1 Hz, 1H), 3.63-3.52 (m, 7H), 3.51-3.45 (m, 3H), 3.43-3.31 (m, 5H), 3.31-3.27 (m, 1H), 3.25 (t, J=8.1 Hz, 1H), 3.22-3.16 (m, 1H), 3.13 (t, J=11.0 Hz, 1H), 2.66 (dd, J=13.6, 4.4 Hz, 1H), 2.36-2.26 (m, 3H), 2.14 (t, J=7.4 Hz, 2H), 1.98-1.85 (m, 3H), 1.85-1.75 (m, 3H), 1.74-1.50 (m, 14H), 1.49 (s, 4H), 1.42-1.33 (m, 6H), 1.12-1.04 (m; 4H), 1.04-0.81 (m, 110H), 0.81-0.54 (m, 69H); $^{13}$C-NMR (151 MHz, CDCl$_3$) δ 212.49, 178.25, 173.61, 172.87, 168.34, 145.03, 138.68, 138.57, 138.20, 137.81, 137.44, 136.11, 135.23, 128.65, 128.55, 128.51, 128.48, 128.44, 128.43, 128.40, 128.37, 128.35, 128.31, 128.28, 128.27, 128.23, 128.16, 128.15, 128.13, 128.09, 127.97, 127.94, 127.89, 127.85, 127.82, 127.80, 127.76, 127.73, 127.67, 127.65, 127.60, 127.58, 122.15, 109.74, 103.60, 102.51, 101.38, 100.83, 97.51, 86.38, 83.84, 82.08, 80.58, 78.79, 78.71, 78.02, 77.92, 76.68, 76.46, 76.43, 76.34, 75.87, 75.82, 75.79, 75.67, 75.06, 74.79, 74.74, 73.80, 73.48, 73.23, 72.59, 72.50, 71.38, 71.10, 71.05, 68.20, 67.65, 66.85, 66.05, 66.03, 65.33, 63.78, 60.25, 53.75, 49.23, 49.10, 47.39, 46.27, 45.87, 41.94, 41.05, 39.99, 39.81, 37.89, 37.01, 36.98, 36.62, 35.97, 35.39, 34.33, 34.31, 33.92, 33.17, 32.54, 31.98, 31.30, 30.47, 29.70, 29.54, 29.52, 29.48, 29.46, 29.43, 29.39, 29.38, 29.34, 29.28, 29.25, 29.22, 29.20, 29.16, 29.14, 29.11, 28.40, 27.53, 27.49, 26.26, 25.86, 25.80, 25.75, 25.66, 25.50, 25.31, 24.97, 24.94, 24.68, 24.38, 23.46, 23.35, 20.57, 20.20, 18.17, 17.19, 15.93, 14.41, 13.13, 12.16, 7.56, 7.46, 7.42, 7.26, 7.25, 7.22, 7.16, 7.14, 7.13, 7.10, 7.08, 7.06, 7.05, 6.98, 6.94, 6.90, 6.88, 6.85, 6.78, 5.92, 5.63, 5.43, 5.36, 5.32, 5.25, 5.23, 5.18, 5.17, 4.95, 4.92, 4.43, 4.41; HRMS (ESI) m/z: Calcd for $C_{182}H_{294}N_2O_{34}NaSi_9$ [M+Na]+3326.9159, found 3326.9211.

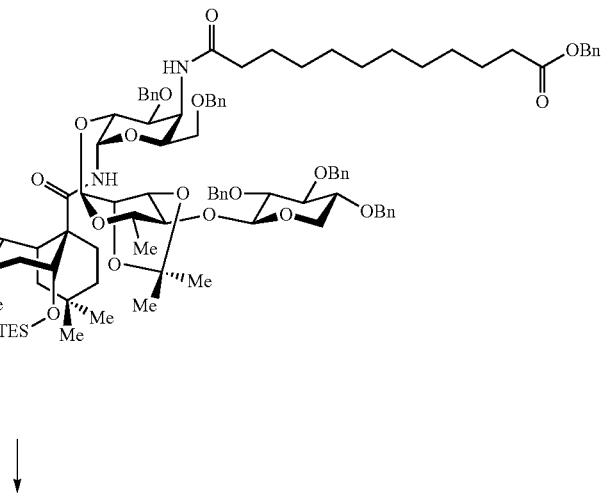
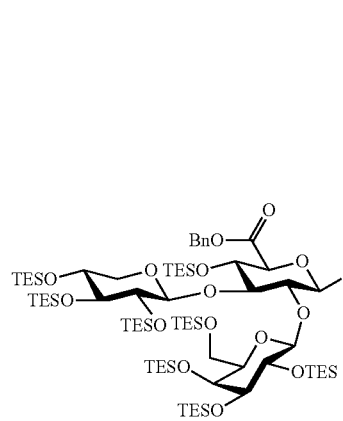
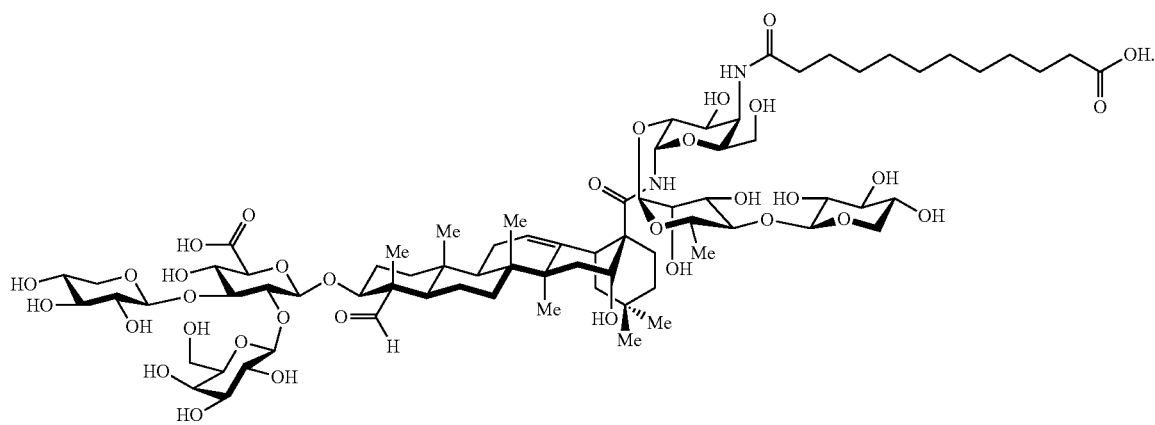

Production of α-Amide Variant 7 (SOS-0-6-8-5)

A solution of fully protected amide variant S14 (10.2 mg, 0.003 mmol, 1.0 equiv) in tetrahydrofuran (2 mL) and ethanol (2 mL) in a 25 mL round bottom flask was charged with 10% (dry basis) palladium on carbon, wet, Degussa type E101 NE/W (8 mg, 0.0042 mmol, 2.5 equiv). Reaction mixture was stirred under hydrogen pressure (50 psi) overnight, then filtered through a 0.45 m polyvinylidene fluoride filter disk, washed with methanol (5 mL), and concentrated. To the hydrogenation product was added a pre-cooled (0° C.) solution of trifluoroacetic acid (3.0 mL, TFA/H$_2$O 3:1). After vigorous stirring for 60 min, the solution was concentrated in vacuo at 0° C. to give white solid residue. This crude product was partially dissolved in a solution of aqueous acetonitrile (5:1 water:acetonitrile) and purified by RP-HPLC on an XBridge Prep BEH300 C18 column (5 μm, 10×250 mm) using a linear gradient of 15→46% acetonitrile (0.05% TFA) in water (0.05% TFA) to 14 min followed by another linear gradient from 46% to 90% acetonitrile (0.05% TFA) in water (0.05% TFA) to 16 min at a flow rate of 5 mL/min. The fraction containing the major peak (tR=14.72 min) was collected and lyophilized to dryness to afford α-amide variant 7 (SQS-0-6-8-5) (2.5 mg, 50% yield) as a white solid.

$^1$H-NMR (600 MHz, MeOD) δ 9.35 (s, 1H), 7.47 (d, J=8.3 Hz, 1H), 7.44 (d, J=8.9 Hz, 1H), 5.27 (s, 1H), 5.14 (s, 1H), 4.73-4.68 (m, 2H), 4.54-4.50 (m, 1H), 4.48 (d, J=7.7 Hz, 1H), 4.34 (t, J=8.2 Hz, 2H), 4.23-4.20 (dd, J=8.3, 3.8 Hz 1H), 4.19-4.15 (m, 1H), 3.85 (s, 1H), 3.83-3.60 (m, 11H), 3.60-3.53 (m, 2H), 3.51 (t, J=6.3 Hz, 1H), 3.45 (t, J=9.1 Hz, 1H), 3.43-3.35 (m, 5H), 3.33 (s, 3H), 3.27 (dd, J=12.2, 7.3 Hz, 1H), 3.10 (d, J=15.3 Hz, 7H), 2.92 (dd, J=14.2, 3.0 Hz, OH), 2.25-2.12 (m, 5H), 1.90-1.73 (m, 5H), 1.71-1.58 (m, 4H), 1.58-1.52 (m, 3H), 1.52-1.46 (m, 3H), 1.44-1.37 (m, 2H), 1.27 (s, 3H), 1.08 (s, 3H), 1.06-0.94 (m, 4H), 0.92 (s, 3H), 0.85 (s, 3H), 0.79 (s, 3H), 0.72 (s, 3H); HRMS (ESI) m/z: Calcd for C$_{76}$H$_{122}$N$_2$O$_{34}$Na (M+Na)$^+$ 1629.7777, found 1629.7731.

Example 8: Synthesis of β-Ether Variant 8
(Sqs-O-12-5-5)

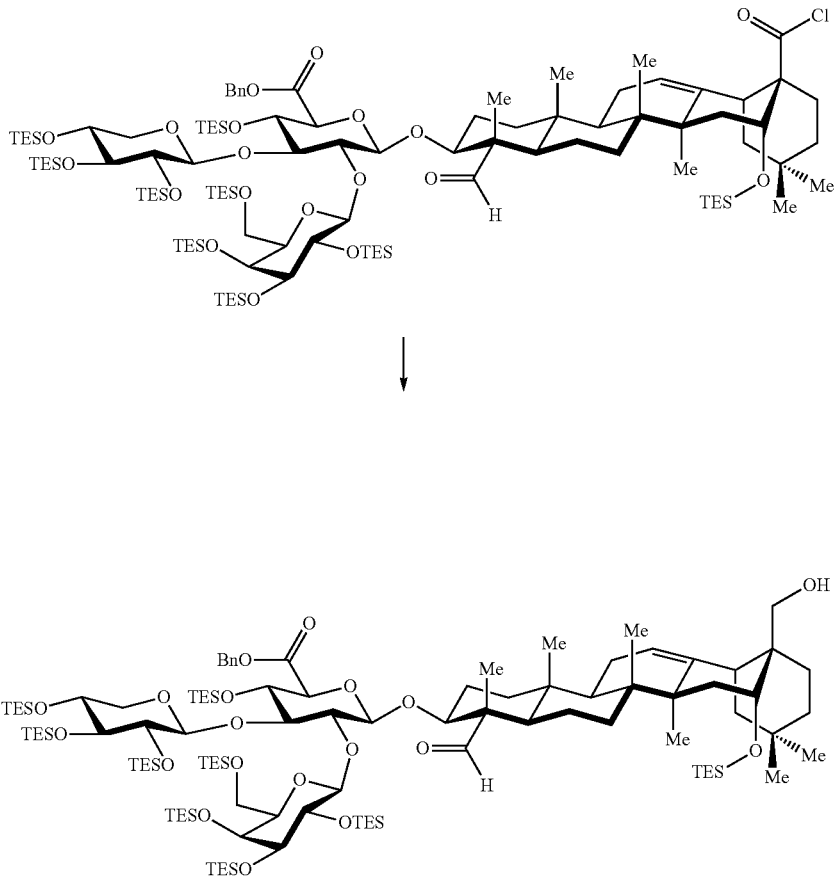

Production of Protected Prosapogenin Neopentyl Alcohol 15

Solid tetrabutylammonium borohydride (32 mg, 0.124 mmol, 2 equiv) was added to an ice-cooled solution of acyl chloride 12 (130 mg, 0.062 mmol, 1 equiv) in dichloromethane (4 mL) for 4 h then diluted with a saturated solution of sodium bicarbonate (50 mL). Aqueous mixture was extracted with dichloromethane (3×25 mL), organic fractions combined, washed with brine, dried over sodium sulfate, filtered, concentrated, and purified with silica gel chromatography (hexanes:ethyl acetate, 30:1 to 10:1) to give neopentyl alcohol 15 as a white foam (99 mg, 77%).

TLC $R_f$ 0.38 (4:1 hexanes/ethyl acetate); FTIR (NaCl film) 3538 (OH st), 2952, 2877, 1754, 1722, 1459, 1413, 1377, 1239, 1171, 1103, 1005, 908, 863, 825, 774, 728, 695 cm$^{-1}$; $^1$H-NMR (600 MHz, CDCl$_3$) δ 9.60 (s, 1H), 7.31-7.17 (m, 5H), 5.17 (d, J=12.4 Hz, 1H), 5.14 (t, J=3.7 Hz, 1H), 4.97 (d, J=12.4 Hz, 1H), 4.44 (d, J=7.4 Hz, 1H), 4.31 (d, J=7.2 Hz, 1H), 4.07 (d, J=7.4 Hz, 1H), 3.96 (t, J=3.3 Hz, 1H), 3.82 (s, 1H), 3.80 (d, J=8.9 Hz, 1H), 3.77-3.66 (m, 4H), 3.63 (t, J=9.2 Hz, 1H), 3.52-3.42 (m, 3H), 3.36 (ddd, J=10.5, 8.4, 5.1 Hz, 1H), 3.28 (dd, J=9.4, 2.5 Hz, 1H), 3.26-3.18 (m, 3H), 3.13 (t, J=8.0 Hz, 1H), 3.01 (dt, J=10.9, 5.4 Hz, 2H), 2.08 (t, J=13.2 Hz, 1H), 1.87 (dd, J=13.9, 4.3 Hz, 1H), 1.80-1.50 (m, 9H), 1.50-1.28 (m, 5H), 1.26 (s, 4H), 1.19 (s, 3H), 1.16-0.93 (m, 5H), 0.92-0.71 (m, 100H), 0.71-0.38 (m, 58H); $^{13}$C-NMR (151 MHz, CDCl$_3$) δ 212.67, 168.37, 143.98, 135.27, 128.47, 128.45, 128.28, 128.14, 121.89, 103.62, 101.40, 100.84, 86.32, 78.81, 78.73, 76.45, 75.96, 75.82, 75.08, 74.40, 72.62, 72.53, 71.39, 71.31, 71.09, 66.84, 65.34, 60.26, 53.89, 49.42, 47.44, 46.13, 42.10, 41.58, 40.33, 39.90, 38.02, 36.03, 35.96, 33.34, 32.85, 32.19, 30.78, 29.60, 26.76, 25.39, 24.37, 23.39, 20.27, 16.83, 15.95, 12.24, 7.57, 7.50, 7.48, 7.26, 7.21, 7.17, 7.15, 7.08, 7.02, 7.00, 6.96, 6.86, 6.80, 5.93, 5.66, 5.46, 5.42, 5.38, 5.35, 5.32, 5.30, 5.27, 5.24, 5.21, 5.07, 4.43; HRMS (ESI) m/z: Calcd for $C_{108}H_{206}O_{19}NaSi_9$ [M+Na]$^+$ 2082.2975, found 2082.2942.

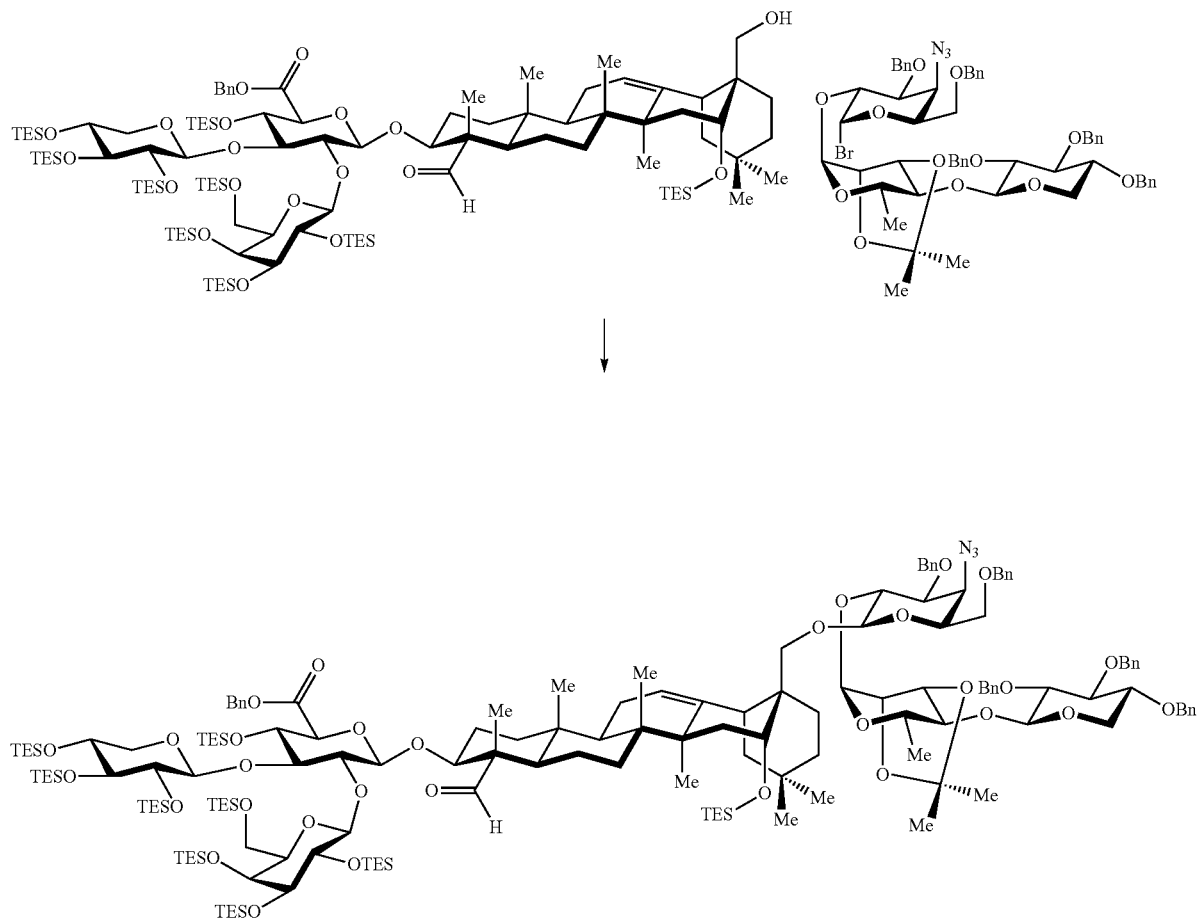

Production of Protected Prosapogenin β-Ether Azide 21

To a suspension of primary alcohol acceptor 15 (58 mg, 0.0280 mmol, 1.0 equiv), bromide donor 20 (29 mg, 0.0280 mmol, 1.0 equiv), 2,4,5-tritertbutylpyridine (20.8 mg, 0.084 mmol, 3.0 equiv), and ~25 mg 4 Å MS in 1 mL dichloromethane, cooled to −40° C., was added solid AgOTf (15 mg, 0.058 mmol, 2.1 equiv). After 45 min, reaction was warmed to 0° C., stirred for 15 min, then diluted with 5 mL dichloromethane. Crude suspension was sonicated for two min, filtered through a pad of celite, concentrated, and purified with silica gel chromatography (hexanes:ethyl acetate, 15:1 to 4:1) to give β-glycoside 21 (58 mg, 0.0192 mmol, 69% yield).

TLC $R_f$ 0.45 (hexanes:ethyl acetate, 5:1); FTIR (NaCl film) 2953, 2911, 2876, 2106, 1753, 1725, 1456, 1413, 1379, 1240, 1170, 1097, 1006, 910, 863, 825, 800, 735 cm$^{-1}$; $^1$H-NMR (600 MHz, CDCl$_3$-d) δ 9.69 (s, 1H), 7.42-7.16 (m, 30H), 5.37 (s, 1H), 5.28 (d, J=12.4 Hz, 1H), 5.15 (t, J=3.6 Hz, 1H), 5.09 (d, J=12.4 Hz, 1H), 4.89-4.80 (m, 4H), 4.72-4.66 (m, 2H), 4.64-4.60 (m, 2H), 4.57-4.51 (m, 4H), 4.42 (d, J=7.3 Hz, 1H), 4.19 (d, J=7.4 Hz, 1H), 4.14-4.11 (m, 2H), 4.09 (d, J=7.6 Hz, 1H), 4.00-3.97 (m, 2H), 3.97-3.89 (m, 4H), 3.87-3.72 (m, 8H), 3.64-3.53 (m, 1OH), 3.52-3.45 (m, 2H), 3.39 (dd, J=9.5, 2.5 Hz, 1H), 3.37-3.27 (m, 4H), 3.27-3.16 (m, 4H), 3.13 (t, J=10.9 Hz, 1H), 2.17 (t, J=13.2 Hz, 1H), 1.98 (dd, J=14.1, 4.5 Hz, 1H), 1.85-1.75 (m, 3H), 1.75-1.60 (m, 6H), 1.45 (s, 3H), 1.43-1.32 (m, 8H), 1.30 (s, 4H), 1.28 (s, 3H), 1.26-1.24 (m, 1H), 1.22 (d, J=6.1 Hz, 3H), 1.19-1.03 (m, 4H), 1.02-0.88 (m, 102H), 0.88-0.81 (m, 11H), 0.81-0.52 (m, 66H); $^{13}$C-NMR (151 MHz, CDCl$_3$) δ 212.35, 168.38, 144.17, 138.79, 138.60, 138.22, 137.52, 137.08, 135.24, 128.53, 128.52, 128.49, 128.45, 128.44, 128.41, 128.37, 128.32, 128.30, 128.27, 128.26, 128.24, 128.21, 128.14, 128.12, 128.08, 128.04, 128.01, 128.00, 127.99, 127.91, 127.90, 127.86, 127.82, 127.80, 127.76, 127.75, 127.72, 127.65, 127.51, 127.49, 121.68, 109.17, 103.48, 102.78, 102.07, 101.37, 100.83, 97.66, 86.06, 83.81, 82.06, 80.79, 78.78, 78.71, 78.25, 78.11, 78.01, 77.47, 76.42, 76.00, 75.81, 75.53, 75.49, 75.06, 74.69, 74.61, 74.36, 73.72, 73.18, 72.59, 72.51, 72.09, 71.38, 71.28, 71.06, 68.26, 66.83, 65.72, 65.33, 63.75, 60.25, 58.96, 53.90, 49.29, 47.41, 46.05, 41.98, 41.37, 39.90, 39:50, 37.96, 37.67, 35.99, 33.03, 32.85, 32.06, 31.59, 30.86, 30.79, 30.77, 30.31, 30.27, 29.70, 29.05, 27.78, 27.73, 26.63, 26.52, 26.41, 26.33, 26.27, 25.32, 25.27, 24.48, 23.36, 22.66, 20.21, 18.16, 18.13, 17.45, 16.85, 15.94, 14.14, 12.17, 11.45, 7.56, 7.48, 7.46, 7.25, 7.22, 7.20, 7.17, 7.13, 7.07, 7.00, 6.98, 6.95, 6.94, 6.91, 6.85, 6.79, 6.78, 5.91, 5.64, 5.44, 5.40, 5.36, 5.34, 5.30, 5.29, 5.27, 5.25, 5.23, 4.90, 4.41, 4.40; HRMS (ESI) m/z: Calcd for C$_{163}$H$_{267}$N$_3$O$_{31}$Si$_9$Na [M+Na] 3037.7230, found 3037.7188.

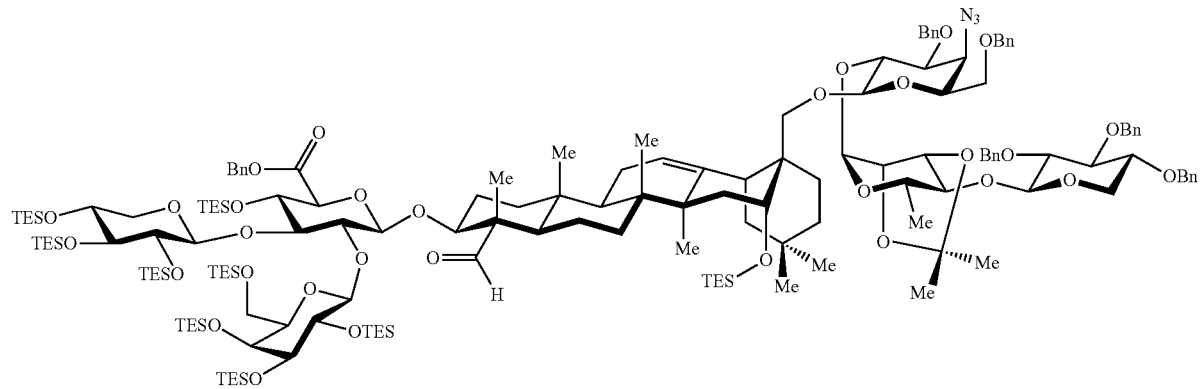

↓

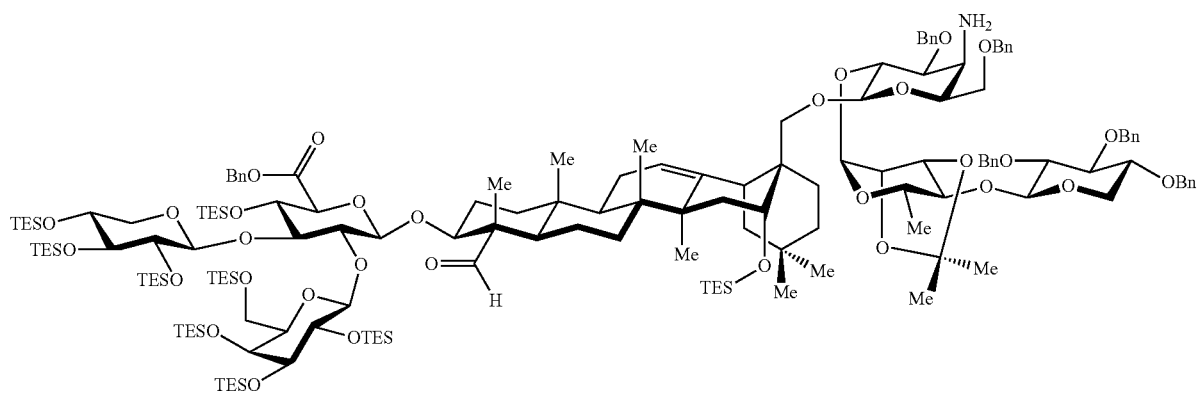

Production of Protected Prosapogenin β-Ether Amine S15

Hydrogen sulfide was bubbled via cannula through an ice-cooled solution of azide 21 (45 mg, 0.015 mmol, 1 equiv) in pyridine/triethylamine (3.5:1, 4.5 mL) for two min. Vent needle and cannula were removed, septum sealed with Teflon tape and parafilm, then warmed to RT and stirred overnight. Hydrogen sulfide was removed with a stream of nitrogen. The resulting orange solution was concentrated and purified via silica gel chromatography (hexanes:[ethyl acetate+1% triethylamine], 5:1 to 2:1) furnishing amine S15 (40 mg, 88% yield).

TLC $R_f$ 0.41 (hexanes:ethyl acetate, 2:1+0.5% triethylamine); FTIR (NaCl film) 3608, 3583, 3028, 2954, 2910, 2876, 1753, 1725, 1631, 1497, 1454, 1413, 1380, 1240, 1168, 1095, 1006, 900, 862, 825, 799, 730, 695, 665 cm$^{-1}$; $^1$H-NMR (600 MHz, CDCl$_3$-d) δ 9.70 (s, 1H), 7.38-7.22 (m, 31H), 5.40 (s, 1H), 5.29 (d, J=12.3 Hz, 1H), 5.17 (d, J=3.8 Hz, 1H), 5.10 (d, J=12.3 Hz, 1H), 4.91 (d, J=7.6 Hz, 1H), 4.89-4.81 (m, 3H), 4.71 (d, J=11.7 Hz, 1H), 4.65-4.62 (m, 2H), 4.61 (d, J=4.9 Hz, 1H), 4.58-4.55 (m, 3H), 4.49 (d, J=11.5 Hz, 1H), 4.43 (d, J=7.3 Hz, 1H), 4.20 (d, J=7.3 Hz, 1H), 4.19-4.13 (m, 3H), 4.03-3.98 (m, 1H), 3.98-3.90 (m, 3H), 3.91-3.69 (m, 7H), 3.68-3.53 (m, 9H), 3.48 (ddd, J=10.5, 8.5, 5.1 Hz, 1H), 3.42-3.19 (m, 10H), 3.14 (t, J=10.9 Hz, 1H), 2.19 (t, J=13.2 Hz, 1H), 2.02 (dd, J=14.0, 4.2 Hz, 1H), 1.86-1.50 (m, 13H), 1.47 (s, 3H), 1.35 (s, 6H), 1.31 (s, 3H), 1.29 (s, 3H), 1.23 (d, J=6.2 Hz, 3H), 1.20-1.12 (m, 3H), 1.11-1.05 (m, 2H), 1.04-0.90 (m, 89H), 0.89-0.82 (m, 10OH), 0.81-0.55 (m, 56H). $^{13}$C-NMR (151 MHz, CDCl$_3$) 212.40, 168.40, 144.16, 138.82, 138.60, 138.25, 138.00, 137.61, 135.27, 128.51, 128.49, 128.47, 128.44, 128.31, 128.29, 128.25, 128.15, 128.09, 127.92, 127.90, 127.81, 127.79, 127.77, 127.76, 127.55, 127.52, 121.77, 109.16, 103.50, 102.96, 102.10, 101.40, 100.86, 97.56, 86.07, 83.84, 82.12, 81.65, 78.82, 78.74, 78.27, 78.19, 78.04, 76.45, 76.04, 75.84, 75.67, 75.56, 75.09, 74.77, 74.53, 73.61, 73.28, 73.22, 72.62, 72.54, 71.42, 71.20, 71.09, 69.16, 66.86, 65.56, 65.36, 63.79, 60.29, 53.94, 49.35, 48.97, 47.44, 46.09, 42.01, 41.42, 39.96, 39.59, 38.01, 36.08, 36.02, 33.08, 32.89, 32.11, 30.82, 30.32, 27.80, 26.67, 26.36, 25.35, 24.53, 23.39, 20.24, 18.19, 16.96, 15.97, 12.19, 7.59, 7.49, 7.28, 7.26, 7.24, 7.20, 7.16, 7.03, 7.01, 6.88, 6.82, 5.94, 5.67, 5.47, 5.39, 5.37, 5.31, 5.28, 5.26, 4.95, 4.45; HRMS (ESI) m/z: Calcd for $C_{163}H_{270}NO_{31}Si_9$ [M+H]$^+$ 2989.7505, found 2989.7542.

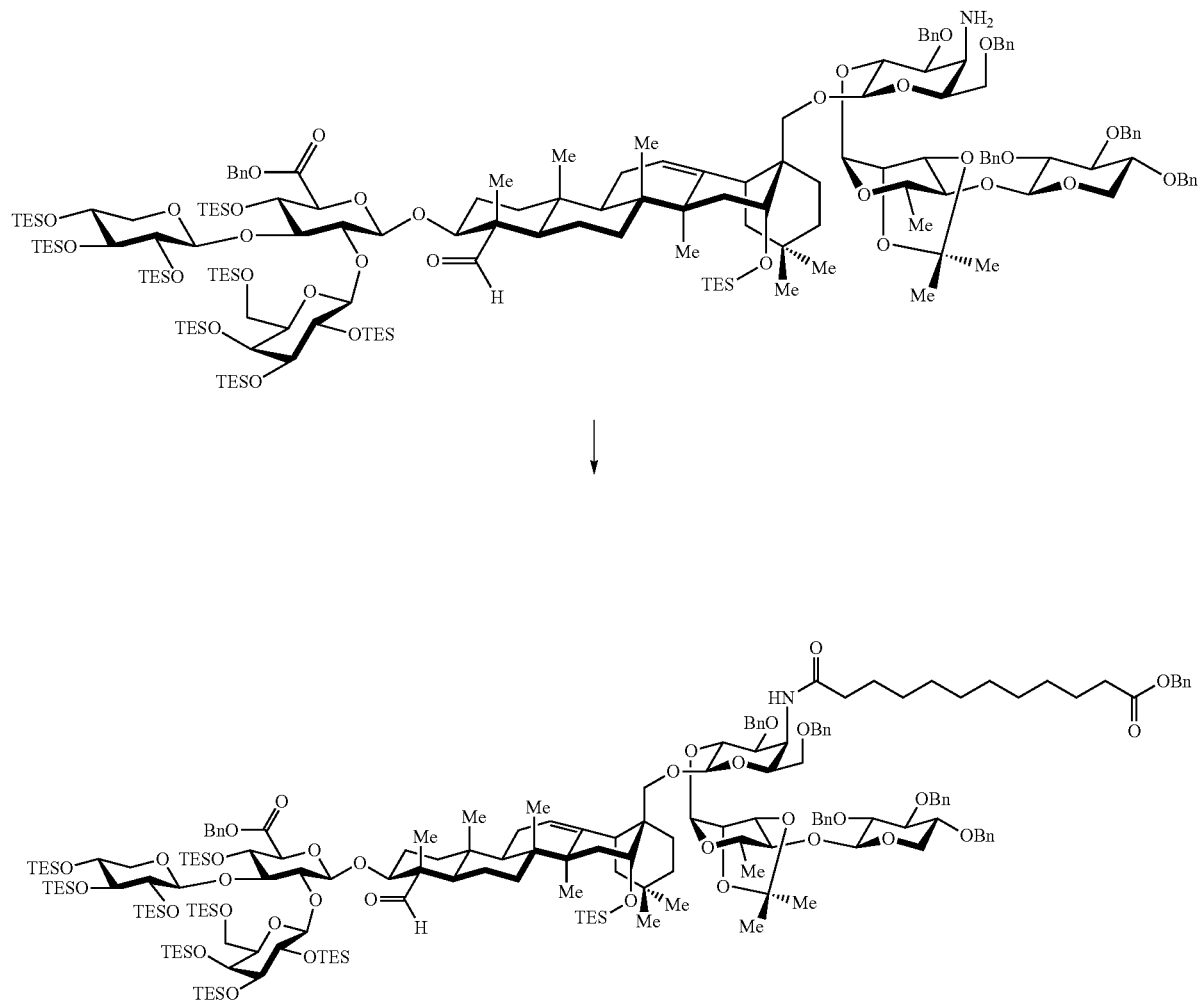

Production of Protected β-Ether Variant S16

Isobutyl chloroformate (7.0 μL, 0.053 mmol, 4 equiv) was added to an ice-cooled solution of carboxylic acid S2 (26 mg, 0.081 mmol, 6 equiv) and triethylamine (37 μL, 0.268 mmol, 20 equiv) in tetrahydrofuran (2 mL) and stirred for 2 hours, then transferred via cannula to an ice-cooled solution of amine S15 (40 mg, 0.0134 mmol, 1 equiv) in tetrahydrofuran (1.5 mL). After 4 h, suspension was diluted with saturated sodium bicarbonate and then extracted with ethyl acetate (3×25 ml). Combined organics were washed with brine, dried over sodium sulfate, concentrated, and purified with silica gel chromatography (hexanes:ethyl acetate+0.5% triethylamine, 10:1 to 1:1) to give fully protected glycosyl ether analogue S16 (25 mg, 57% yield) as a colorless film.

TLC $R_f$ 0.24 (hexanes:ethyl acetate, 4:1); $^1$H-NMR (600 MHz, CDCl$_3$) δ 9.70 (s, 1H), 7.40-7.16 (m, 35H), 5.52 (d, J=10.1 Hz, 1H), 5.38 (s, 1H), 5.28 (d, J=12.3 Hz, 1H), 5.15 (t, J=3.6 Hz, 1H), 5.13-5.07 (m, 3H), 4.92-4.78 (m, 5H), 4.76 (d, J=11.1 Hz, 1H), 4.71 (d, J=11.6 Hz, 1H), 4.63 (t, J=10.9 Hz, 2H), 4.56 (d, J=7.4 Hz, 1H), 4.55-4.47 (m, 2H), 4.43 (d, J=7.2 Hz, 1H), 4.39 (d, J=11.0 Hz, 1H), 4.21-4.14 (m, 3H), 4.12 (d, J=5.9 Hz, 1H), 3.99 (s, 1H), 3.97-3.90 (m, 3H), 3.89-3.71 (m, 6H), 3.65-3.42 (m, 13H), 3.40 (dd, J=9.4, 2.5 Hz, 1H), 3.38-3.17 (m, 7H), 3.13 (t, J=10.9 Hz, 1H), 2.35 (t, J=7.5 Hz, 2H), 2.24-2.14 (m, 3H), 2.02 (dd, J=14.0, 4.3 Hz, 1H), 1.86-1.75 (m, 3H), 1.75-1.49 (m, 15H), 1.44-1.05 (m, 33H), 1.04-0.82 (m, 104H), 0.82-0.50 (m, 60H); $^{13}$C-NMR (151 MHz, CDCl$_3$) δ 212.46, 173.70, 173.26, 168.40, 144.02, 138.82, 138.57, 138.24, 137.73, 137.59, 136.13, 135.27, 128.55, 128.47, 128.43, 128.35, 128.31, 128.29, 128.28, 128.21, 128.18, 128.17, 128.14, 128.09, 127.91, 127.86, 127.83, 127.79, 127.77, 127.74, 127.69, 127.61, 127.52, 121.90, 109.20, 103.53, 103.16, 102.13, 101.40, 100.86, 97.60, 86.15, 83.84, 82.15, 79.25, 78.82, 78.73, 78.30, 78.15, 78.13, 78.03, 76.45, 76.01, 75.85, 75.83, 75.76, 75.57, 75.12, 75.09, 74.82, 74.51, 73.72, 73.23, 72.70, 72.62, 72.54, 71.41, 71.09, 71.00, 68.86, 66.86, 66.08, 65.74, 65.36, 63.80, 60.28, 53.90, 49.32, 47.35, 46.18, 46.06, 41.92, 41.41, 39.94, 39.66, 38.00, 36.98, 36.08, 36.00, 34.35, 33:08, 32.86, 32.09, 30.81, 30.36, 29.73, 29.46, 29.41, 29.38, 29.28, 29.25, 29.16, 27.73, 26.66, 26.23, 25.90, 25.34, 24.98, 24.47, 23.39, 20.23, 18.07, 17.00, 15.96, 12.20, 7.59, 7.51, 7.49, 7.32, 7.28, 7.25, 7.23, 7.20, 7.16, 7.09, 7.05, 7.03, 7.01, 6.97, 6.92, 6.88, 6.82, 5.94, 5.67, 5.59, 5.56, 5.46, 5.43, 5.39, 5.37, 5.33, 5.30, 5.28, 5.26, 5.19, 5.17, 5.14, 5.08, 4.99, 4.95, 4.44; HRMS (ESI) m/z: Calcd for $C_{182}H_{295}N_3O_{34}Si_9Na$ [M+Na]+3133.9207, found 3133.9258.

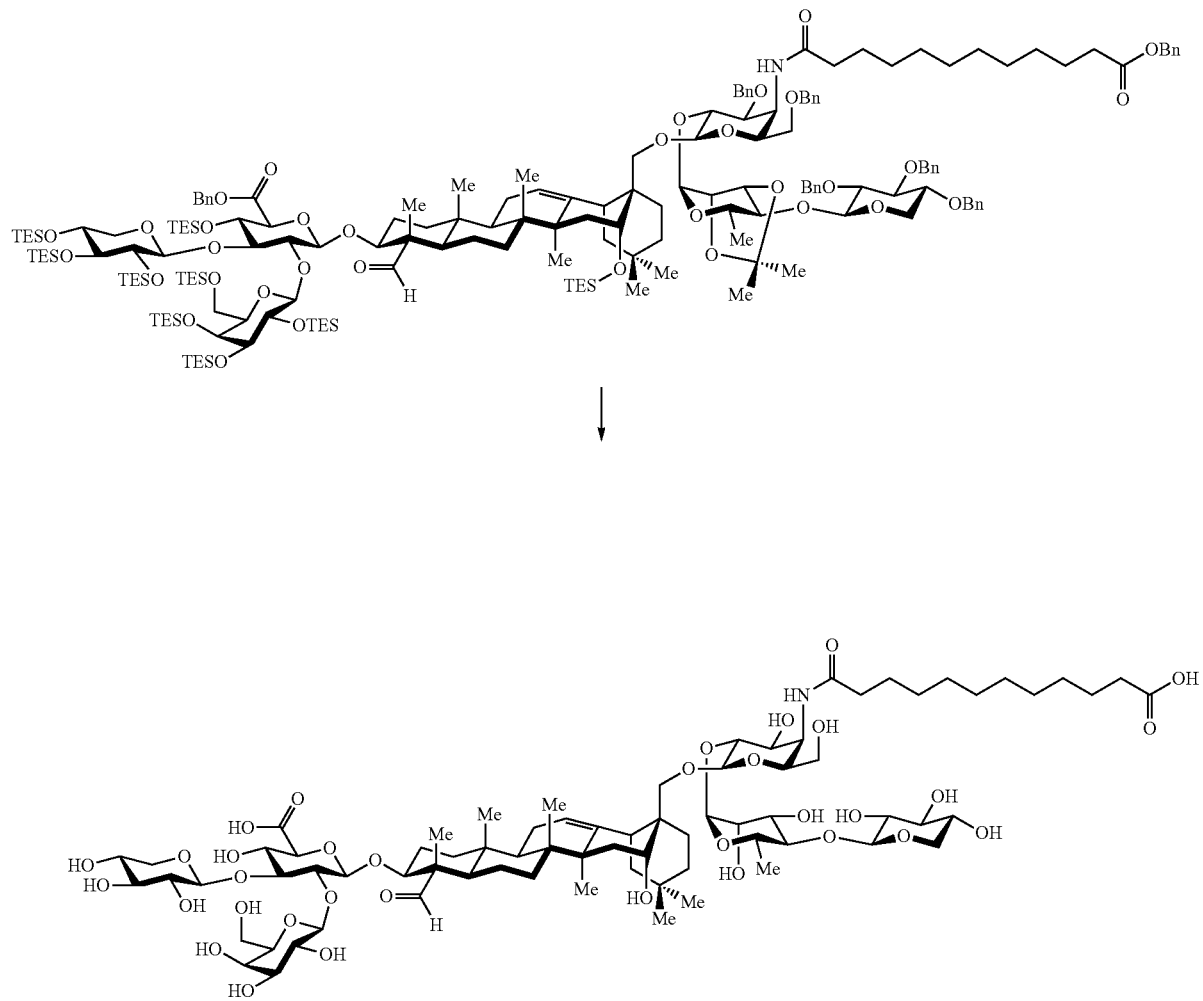

Production of β-ether variant 8 (SQS-0-12-5-5). A solution of fully protected ether variant S16 (25 mg, 0.008 mmol, 1.0 equiv) in tetrahydrofuran (2 mL) and ethanol (2 mL) in a 25 mL round bottom flask was charged with 10% (dry basis) palladium on carbon, wet, Degussa type E101 NE/W (25 mg, 0.023 mmol, 3 equiv). Reaction mixture was stirred under hydrogen pressure (50 psi) overnight, then filtered through a 0.45 m polyvinylidene fluoride filter disk, washed with methanol (5 mL), and concentrated. To the hydrogenation product was added a pre-cooled (0° C.) solution of trifluoroacetic acid (3.0 mL, TFA/H$_2$O 3:1). After vigorous stirring for 60 min, the solution was concentrated in vacuo at 0° C. to give white solid residue. This crude product was partially dissolved in a solution of aqueous acetonitrile (4:1 water:acetonitrile) and purified by RP-HPLC on an XBridge Prep BEH300 C18 column (5 μm, 10×250 mm) using a linear gradient of 20→66% acetonitrile (0.05% TFA) in water (0.05% TFA) over 16 min at a flow rate of 5 mL/min. The fraction containing the major peak (tR=12.55 min) was collected and lyophilized to dryness to afford β-ether variant 8 (SQS-0-12-5-5) (7.5 mg, 62% yield) as a white solid.

$^1$H-NMR (600 MHz, D2O/CD3CN, 1:1) δ 9.97 (s, 1H), 7.73 (d, J=9.7 Hz, 1H), 5.82 (t, J=3.6 Hz, 1H), 5.74 (d, J=1.9 Hz, 1H), 5.26 (d, J=7.8 Hz, 1H), 5.13 (d, J=7.8 Hz, 1H), 5.08 (d, J=7.8 Hz, 1H), 5.01 (d, J=7.8 Hz, 1H), 4.78 (s, 1H), 4.71 (d, J=7.6 Hz, 1H), 4.61 (d, J=4.0 Hz, 1H), 4.51-4.43 (m, 4H), 4.43-4.33 (m, 5H), 4.30 (t, J=8.9 Hz, 2H), 4.25-4.18 (m, 2H), 4.17-4.00 (m, 9H), 3.93 (p, J=8.9, 8.5 Hz, 6H), 3.86-3.77 (m, 4H), 3.78-3.72 (m, 1H), 2.90-2.77 (m, J=7.5 Hz, 5H), 2.75-2.65 (m, 2H), 2.48-2.41 (m, 3H), 2.41-2.01 (m, 17H), 1.90 (s, 3H), 1.83 (d, J=6.3 Hz, 5H), 1.74 (d, J=12.2 Hz, 1H), 1.69 (s, 3H), 1.64 (t, J=12.9 Hz, 1H), 1.55 (s, 3H), 1.47 (s, 3H), 1.46 (s, 3H), 2.83-2.77 (m, 1H), 1.43 (s, 3H); HRMS (ESI) m/z: Calcd for C$_{76}$H$_{23}$NO$_{34}$Na [M+Na]$^+$ 1616.7824, found 1616.7848.

Example 9: Synthesis of β-Thioether Variant 9 (Sqs-0-14-5-5)

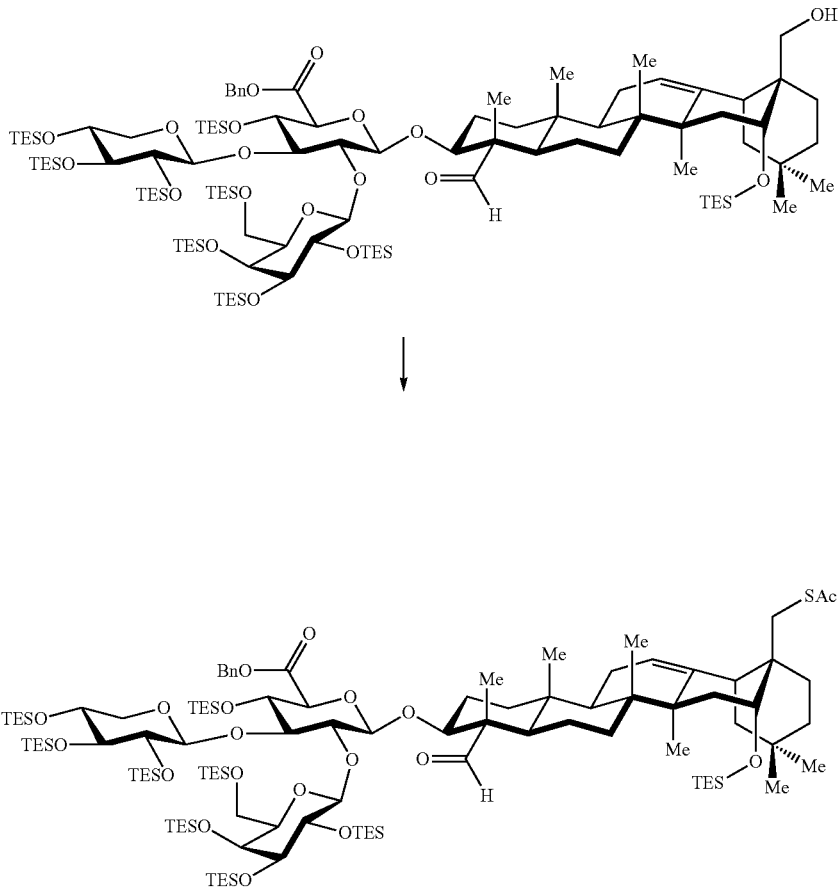

Production of Protected Prosapogenin Neopentyl Thioacetate S17

Triflic anhydride (12.6 μL, 0.075 mmol, 1.5 equiv) was added to an ice-cooled solution of neopentyl alcohol 15 (103 mg, 0.05 mmol, 1 equiv) and pyridine (80 μL, 1.0 mmol, 20 equiv) and dichloromethane (4 mL). After 15 min, dichloromethane was removed with a stream of argon. Residual volatiles were removed under reduced pressure. Resulting oil was taken up in tetrahydrofuran (2 mL), cooled to 0° C., then treated with 4 Å MS (~100 mg), and dimethylformamide (2 mL). Suspension was treated with potassium thioacetate (57 mg, 0.5 mmol, 10 equiv). After 2.5 h, suspension was decanted into a saturated solution of sodium bicarbonate and extracted with ethyl acetate (3×25 mL). Combined organics were washed with brine, dried over sodium sulfate, concentrated and purified with silica gel chromatography (hexanes:ethyl acetate, 50:1 to 25:1) to give thioacetate S17 (98 mg, 92%).

TLC $R_f$ 0.60 (10:1 hexanes/ethyl acetate); FTIR (NaCl film) 2953, 2911, 2876, 1754, 1723, 1700, 1696, 1653, 1635, 1576, 1560, 1539, 1457, 1414, 1375, 1239, 1171, 1103, 1005, 970, 898, 864, 826, 799, 736, 695, 668, 628 cm$^{-1}$; $^1$H-NMR (600 MHz, CDCl$_3$) δ 9.65 (s, 1H), 7.31-7.22 (m, 5H), 5.25-5.19 (m, 2H), 5.02 (d, J=12.4 Hz, 1H), 4.48 (d, J=7.4 Hz, 1H), 4.36 (d, J=7.3 Hz, 1H), 4.11 (d, J=7.4 Hz, 1H), 3.88-3.81 (m, 3H), 3.81-3.70 (m, 4H), 3.68 (t, J=9.2 Hz, 1H), 3.56-3.47 (m, 3H), 3.41 (ddd, J=10.5, 8.4, 5.1 Hz, 1H), 3.32 (dd, J=9.4, 2.5 Hz, 1H), 3.30-3.24 (m, 2H), 3.18 (dd, J=8.7, 7.4 Hz, 1H), 3.06 (t, J=11.0 Hz, 1H), 2.86 (d, J=13.4 Hz, 1H), 2.57 (d, J=13.5 Hz, 1H), 2.25 (s, 3H), 2.16 (dd, J=13.9, 12.4 Hz, 1H), 2.07 (dd, J=14.0, 4.0 Hz, 1H), 1.88-1.51 (m, 10OH), 1.49-1.44 (m, 2H), 1.43-1.30 (m, 3H), 1.29 (s, 3H), 1.24 (s, 3H), 1.16-1.10 (m, 2H), 1.07-0.99 (m, 2H), 0.97-0.81 (m, 93H), 0.79 (s, 3H), 0.75-0.47 (m, 56H); $^{13}$C-NMR (151 MHz, CDCl$_3$) δ 212.83, 195.72, 168.36, 143.29, 135.26, 128.48, 128.46, 128.30, 128.15, 128.11, 122.68, 103.65, 101.42, 100.84, 86.43, 78.82, 78.73, 76.45, 76.30, 75.95, 75.83, 75.81, 75.09, 72.62, 72.53, 71.38, 71.08, 66.85, 65.34, 60.22, 53.89, 49.43, 47.57, 46.13, 45.72, 41.44, 41.02, 39.89, 38.86, 38.02, 36.34, 36.03, 33.41, 32.80, 32.-13, 31.71, 30.83, 30.81, 26.82, 25.40, 24.29, 23.48, 20.24, 16.73, 15.94, 12.30, 7.58, 7.48, 7.27, 7.18, 7.17, 7.15, 7.00, 6.87, 6.81, 6.80, 5.93, 5.66, 5.46, 5.38, 5.36, 5.29, 5.27, 5.24, 5.01, 4.43; HRMS (ESI) m/z: Calcd for $C_{110}H_{208}O_{19}SSi_9Na$ [M+Na]$^+$ 2140.2883, found 2140.2852.

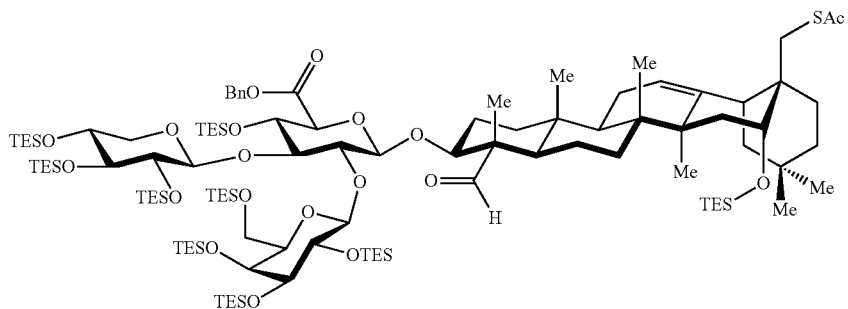

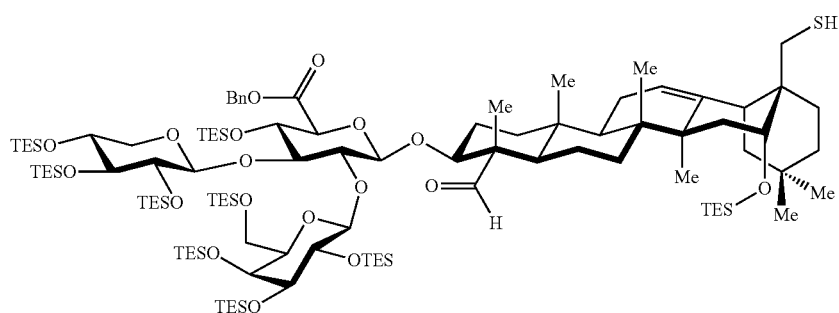

Production of Protected Prosapogenin Neopentyl Thiol 16

Hydrazine (10 μL, 0.323 mmol, 7 equiv) was added to a solution of thioacetate S17 (98 mg, 0.046 mmol, 1 equiv) and dithiothreitol (21 mg, 0.139 mmol, 3 equiv) in tetrahydrofuran/dimethylformamide (4 mL, 1:1) for 6 h, concentrated and purified with silica gel chromatography (hexanes: ethyl acetate) to give thiol 16 as a colorless film (86 mg, 90%).

TLC $R_f$ 0.71 (10:1 hexanes/ethyl acetate); FTIR (NaCl film) 2953, 2911, 2877, 1756, 1726, 1653, 1458, 1414, 1375, 1240, 1172, 1104, 1006, 971, 899, 865, 827, 801, 739, 695, 679, 668; $^1$H-NMR (600 MHz, CDCl$_3$) δ 9.72 (s, 1H), 7.34 (m, 5H), 5.29-5.25 (m, 2H), 5.09 (d, J=12.4 Hz, 1H), 4.56 (d, J=7.5 Hz, 1H), 4.43 (d, J=7.3 Hz, 1H), 4.18 (d, J=7.4 Hz, 1H), 4.14-4.09 (m, 1H), 3.94-3.89 (m, 2H), 3.88-3.77 (m, 4H), 3.75 (t, J=9.3 Hz, 1H), 3.63-3.54 (m, 3H), 3.51-3.45 (m, 1H), 3.39 (dd, J=9.3, 2.5 Hz, 1H), 3.37-3.32 (m, 2H), 3.25 (t, J=8.0 Hz, 1H), 3.13 (t, J=10.9 Hz, 1H), 2.38-2.31 (m, 1H), 2.31-2.22 (m, 2H), 2.15 (dd, J=14.0, 4.1 Hz, 1H), 1.87 (dt, J=11.1, 4.1 Hz, 2H), 1.82-1.73 (m, 2H), 1.72-1.38 (m, 10H), 1.37 (s, 3H), 1.31 (s, 2H), 1.25 (s, 1H), 1.23-1.15 (m, 2H), 1.16-1.05 (m, 3H), 1.04-0.89 (m, 92H), 0.87 (s, 3H), 0.87 (s, 3H), 0.81-0.55 (m, 57H); $^{13}$C-NMR (151 MHz, CDCl$_3$) δ 212.71, 168.34, 143.60, 135.25, 128.50, 128.46, 128.44, 128.27, 128.15, 128.13, 128.09, 122.34, 103.63, 101.40, 100.83, 78.80, 78.72, 76.44, 75.94, 75.81, 75.71, 75.08, 72.61, 72.51, 71.38, 71.08, 66.83, 65.33, 60.23, 41.39, 39.82, 38.41, 37.99, 36.71, 36.43, 36.42, 36.01, 33.12, 32.84, 32.09, 30.96, 30.84, 26.76, 25.38, 24.23, 23.43, 20.23, 16.71, 15.92, 12.25, 7.57, 7.49, 7.47, 7.25, 7.19, 7.15, 7.14, 7.01, 6.99, 6.85, 6.79, 6.78, 5.92, 5.65, 5.45, 5.41, 5.37, 5.35, 5.30, 5.28, 5.26, 5.23, 5.04, 4.42, 4.40; HRMS (ESI) m/z: Calcd for $C_{108}H_{206}O_{18}NaSi_9S$ [M+Na]$^+$ 2098.2746, found 2098.2778.

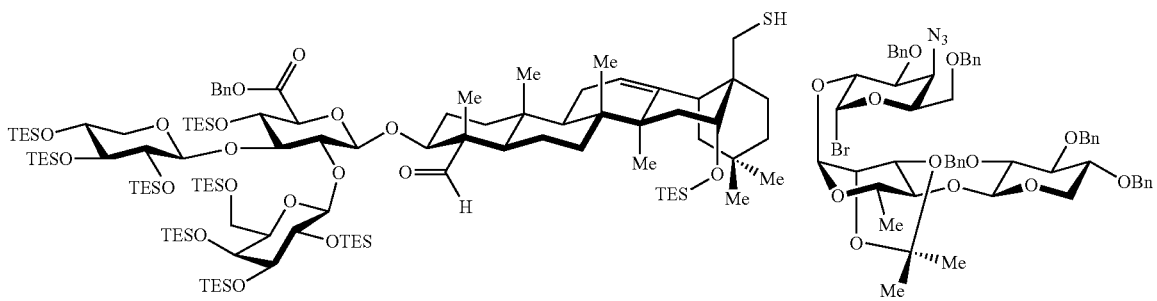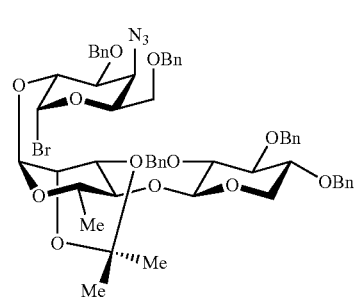

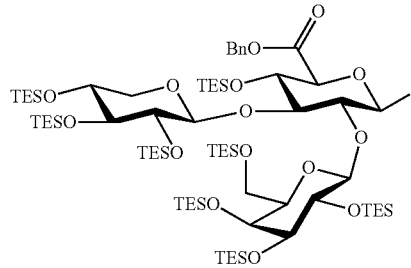
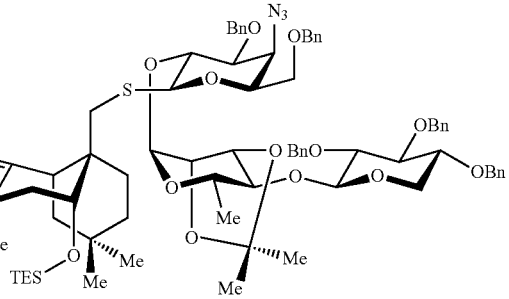

Production of Protected Prosapogenin β-Thioether Azide 22

A solution of bromide 20 (32 mg, 0.031 mmol, 1.5 equiv) in tetrahydrofuran (1.5 mL) was added dropwise to a suspension of thiol 16 (43 mg, 0.021 mmol, 1.0 equiv) and sodium hydride (60% dispersion in mineral oil, 2.5 mg, 0.062, 3.0 equiv) in tetrahydrofuran/dimethylformamide (2 mL, 1:1) over four min. After 20 min, a saturated solution of ammonium chloride was added, diluted with water, and extracted with (3×25 mL). Combined extracts were washed with brine, dried over sodium sulfate, and concentrated. Before loading onto silica column, silver triflate (2 mg) was added to crude solution in DCM to destroy excess glycosyl bromide. Mixture was purified with silica gel chromatography (benzene:ethyl acetate, 1:0 to 30:1) to give glycosyl thioether 22 as a colorless film (43 mg, 69% yield). Note: Extended reaction times gave lower yields, due to formation of the trisaccharide glycal, through base-promoted elimination of the thiolate.

TLC $R_f$ 0.52 (benzene:ethyl acetate, 20:1); FTIR (NaCl film) 3032, 2953, 2912, 2876, 2107, 1752, 1724, 1701, 1497, 1457, 1413, 1380, 1240, 1169, 1094, 1006, 899, 864, 826, 736, 697, 668, 610 cm$^{-1}$; $^1$H-NMR (600 MHz, CDCl$_3$-d) δ 9.69 (s, 1H), 7.40-7.24 (m, 30H), 5.53 (s, 1H), 5.28 (d, J=12.4 Hz, 1H), 5.19 (t, J=3.7 Hz, 1H), 5.09 (d, J=12.4 Hz, 1H), 4.91 (d, J=5.3 Hz, 1H), 4.89 (d, J=8.5 Hz, 1H), 4.87-4.79 (m, 2H), 4.72 (t, J=11.1 Hz, 2H), 4.64 (d, J=10.8 Hz, 1H), 4.61 (d, J=11.7 Hz, 1H), 4.57-4.52 (m, 4H), 4.42 (d, J=7.2 Hz, 1H), 4.20-4.16 (m, 2H), 4.14 (d, J=9.6 Hz, 1H), 4.10 (d, J=3.4 Hz, 1H), 4.08-4.01 (m, 2H), 4.00-3.97 (m, 1H), 3.96-3.73 (m, 9H), 3.64-3.52 (m, 9H), 3.48 (ddd, J=10.5, 8.4, 5.1 Hz, 1H), 3.39 (dd, J=9.4, 2.5 Hz, 1H), 3.37-3.32 (m, 2H), 3.30 (dd, J=8.9, 7.5 Hz, 1H), 3.25 (dd, J=8.7, 7.4 Hz, 1H), 3.22-3.16 (m, 1H), 3.13 (t, J=11.0 Hz, 1H), 2.49-2.37 (m, 2H), 2.21-2.05 (m, 2H), 1.84-1.73 (m, 3H), 1.55-1.46 (m, 7H), 1.39-1.22 (m, 16H), 1.11-0.83 (m, 99H), 0.83-0.50 (m, 63H); $^{13}$C-NMR (151 MHz, CDCl$_3$) δ 212.40, 168.35, 143.40, 138.78, 138.60, 138.23, 137.48, 137.46, 136.69, 135.23, 128.55, 128.51, 128.46, 128.44, 128.41, 128.32, 128.29, 128.27, 128.26, 128.24, 128.20, 128.18, 128.13, 128.12, 128.09, 128.02, 127.93, 127.91, 127.87, 127.76, 127.75, 127.54, 127.51, 127.49, 122.30, 108.91, 103.49, 102.27, 102.24, 101.37, 100.83, 98.65, 86.14, 84.66, 83.87, 83.20, 82.12, 78.78, 78.70, 78.25, 78.07, 77.99, 77.98, 76.42, 76.32, 76.10, 75.96, 75.80, 75.58, 75.43, 75.05, 74.81, 74.03, 73.75, 73.73, 73.19, 72.59, 72.51, 71.58, 71.38, 71.05, 68.23, 66.84, 65.44, 65.32, 63.80, 60.25, 58.59, 53.87, 49.24, 47.56, 46.05, 45.40, 45.35, 42.86, 41.53, 41.27, 41.20, 39.78, 39.54, 39.02, 39.01, 38.70, 37.94, 36.40, 36.38, 35.98, 35.95, 34.00, 33.03, 32.77, 32.04, 31.93, 31.65, 30.74, 30.73, 30.38, 29.73, 29.70, 28.91, 27.77, 26.76, 26.73, 26.61, 26.40, 25.31, 24.47, 24.35, 24.34, 23.76, 23.72, 23.35, 22.99, 22.97, 22.70, 20.22, 17.56, 17.54, 16.81, 16.09, 15.88, 14.14, 14.07, 14.06, 13.15, 12.19, 10.98, 10.96, 7.56, 7.46, 7.25, 7.19, 7.16, 7.13, 6.98, 6.85, 6.79, 6.78, 5.91, 5.64, 5.43, 5.36, 5.33, 5.27, 5.25, 5.22, 4.94, 4.41; HRMS (ESI) m/z: Calcd for C$_{163}$H$_{267}$N$_3$O$_{30}$NaSi$_9$S 3053.7001 [M+Na]$^+$, found 3053.7014.

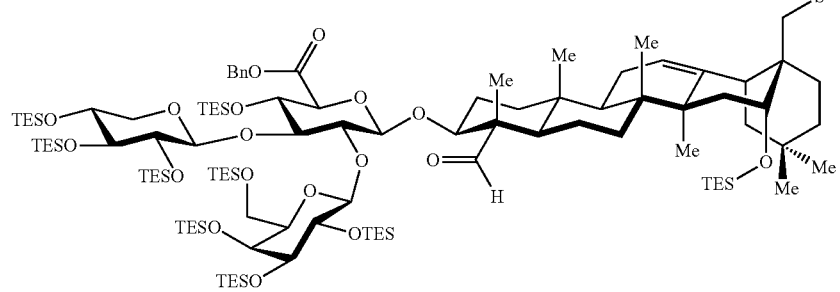
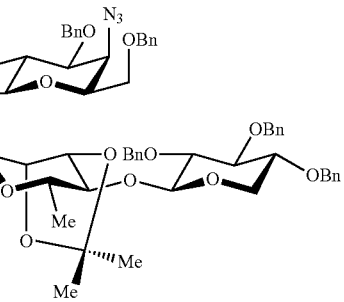

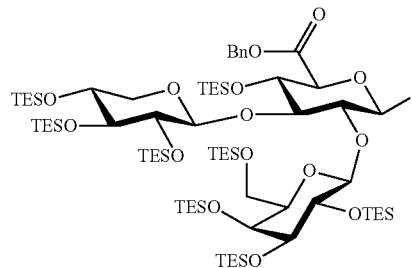
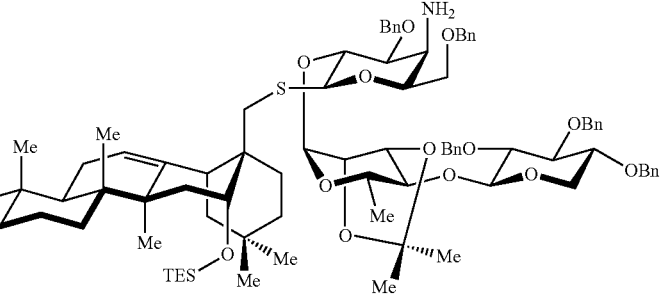

Production of Protected Prosapogenin β-Thioether Amine S18

Hydrogen sulfide was bubbled via cannula through an ice-cooled solution of azide 22 (41 mg, 0.014 mmol, 1.0 equiv) in pyridine/triethylamine (3.5:1, 4.5 mL) for two min. Vent needle and cannula were removed, and septum sealed with Teflon tape and parafilm, then warmed to RT and stirred overnight. Hydrogen sulfide was removed with a stream of nitrogen, then resulting orange solution was concentrated and purified via silica gel chromatography (hexanes:[ethyl acetate+1% triethylamine], 5:1 to 2:1) furnishing amine S18 (38 mg, 94% yield).

TLC $R_f$ 0.47 (hexanes:ethyl acetate, 2:1+0.5% triethylamine); FTIR (NaCl film) 3608, 2953, 2911, 2876, 1754, 1725, 1692, 1530, 1497, 1454, 1413, 1380, 1240, 1094, 1005, 825, 734, 696 cm$^{-1}$; $^1$H-NMR (500 MHz, CDCl$_3$) δ 9.68 (s, 1H), 7.42-7.27 (m, 32H), 5.55 (s, 1H), 5.28 (d, J=12.4 Hz, 1H), 5.23-5.17 (m, 1H), 5.10 (d, J=12.4 Hz, 1H), 4.94-4.89 (m, 2H), 4.88-4.79 (m, 2H), 4.71 (d, J=11.7 Hz, 1H), 4.68-4.52 (m, 7H), 4.49 (d, J=11.4 Hz, 1H), 4.42 (d, J=7.3 Hz, 1H), 4.23-4.16 (m, 3H), 4.12 (d, J=5.7 Hz, 1H), 4.11-4.04 (m, 1H), 4.02-3.98 (m, 1H), 3.98-3.91 (m, 3H), 3.90-3.73 (m, 6H), 3.73-3.66 (m, 1H), 3.67-3.54 (m, 9H), 3.53-3.44 (m, 2H), 3.42-3.29 (m, 5H), 3.26 (t, J=8.0 Hz, 1H), 3.22-3.18 (m, 1H), 3.13 (t, J=10.9 Hz, 1H), 2.52 (d, J=12.3 Hz, 1H), 2.43 (d, J=12.2 Hz, 1H), 2.23-2.07 (m, 2H), 1.84-1.76 (m, 3H), 1.76-1.65 (m, 3H), 1.63-1.53 (m, 4H), 1.39-1.24 (m, 17H), 1.17-1.07 (m, 2H), 1.08-0.88 (m, 100H), 0.87 (s, 4H), 0.81 (s, 4H), 0.80 (s, 3H), 0.77-0.52 (m, 61H); $^{13}$C-NMR (151 MHz, CDCl$_3$) δ 212.39, 168.36, 143.46, 138.81, 138.78, 138.57, 138.24, 137.97, 137.18, 135.23, 128.49, 128.46, 128.44, 128.42, 128.41, 128.37, 128.33, 128.28, 128.25, 128.13, 128.09, 128.00, 127.96, 127.93, 127.91, 127.87, 127.85, 127.83, 127.78, 127.75, 127.70, 127.66, 127.57, 127.52, 127.50, 122.28, 108.89, 103.50, 102.32, 102.29, 101.36, 100.83, 98.44, 86.11, 84.76, 83.97, 83.89, 82.18, 78.78, 78.71, 78.25, 78.10, 78.00, 77.98, 77.92, 76.54, 76.43, 76.40, 76.24, 75.97, 75.80, 75.60, 75.05, 74.86, 73.93, 73.65, 73.63, 73.20, 73.17, 72.59, 72.51, 71.39, 71.06, 70.64, 69.42, 66.84, 66.81, 65.34, 65.32, 63.81, 60.27, 53.87, 49.26, 49.02, 47.52, 46.03, 45.36, 42.86, 41.71, 41.31, 41.29, 41.22, 39.80, 39.56, 39.09, 39.03, 37.95, 36.61, 36.40, 36.37, 35.98, 35.96, 35.95, 33.07, 32.78, 32.01, 31.93, 31.71, 30.78, 30.75, 29.70, 29.66, 29.37, 28.40, 27.81, 27.78, 26.73, 26.71, 26.61, 26.42, 26.35, 25.31, 24.68, 24.40, 24.37, 23.34, 22.70, 22.39, 20.20, 17.56, 17.07, 16.92, 16.91, 16.09, 15.90, 15.88, 14.14, 13.13, 12.16, 7.56, 7.48, 7.46, 7.25, 7.21, 7.19, 7.17, 7.13, 7.00, 6.98, 6.95, 6.93, 6.88, 6.85, 6.79, 6.78, 5.91, 5.75, 5.64, 5.44, 5.40, 5.36, 5.33, 5.28, 5.27, 5.25, 5.23, 4.96, 4.94, 4.41, 4.40; HRMS (ESI) m/z: Calcd for C$_{163}$H$_{270}$NO$_{30}$Si$_9$S 3005.7277 [M+H]$^+$, found 3005.7317.

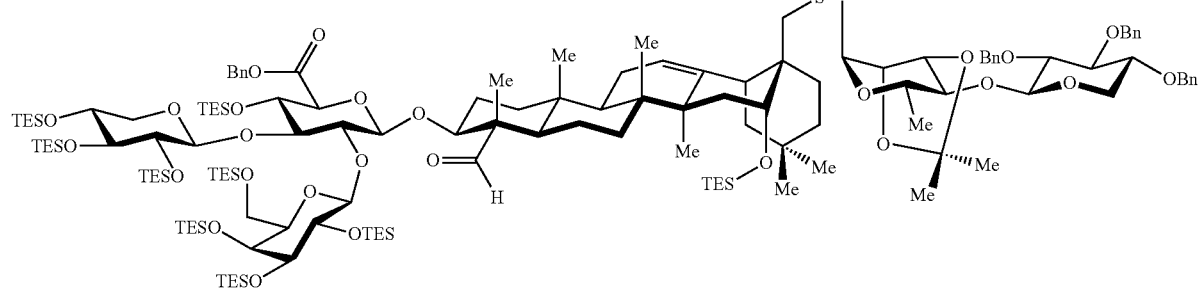

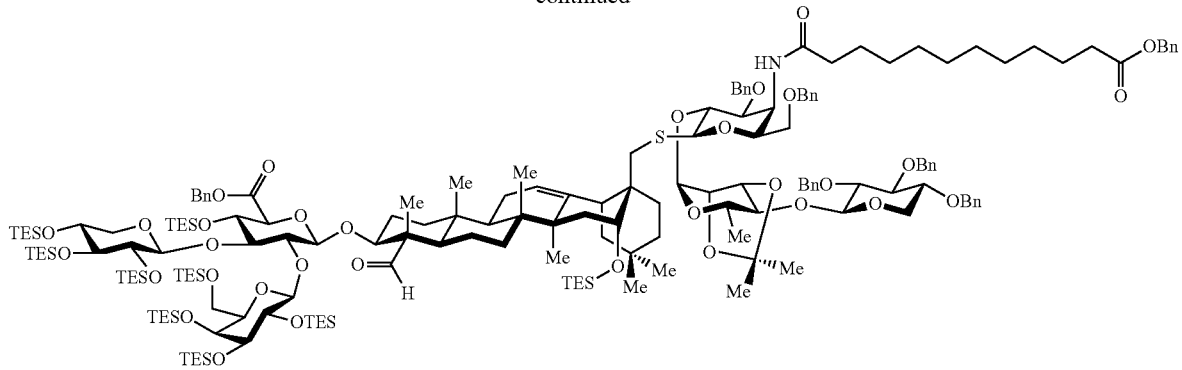

Production of protected β-thioether variant S19. Isobutyl chloroformate (6.4 μL, 0.049 mmol, 4 equiv) was added to an ice-cooled solution of carboxylic acid S2 (23.5 mg, 0.073 mmol, 6 equiv) and triethylamine (17 μL, 0.122 mmol, 10 equiv) in tetrahydrofuran (3 mL) and stirred for β hours, then transferred via cannula to an ice-cooled solution of amine S18 (37 mg, 0.012 mmol, 1 equiv) in tetrahydrofuran (1 mL). After 16 h, suspension was diluted with saturated sodium bicarbonate and then extracted with ethyl acetate (3×25 ml). Combined organics were washed with brine, dried over sodium sulfate, concentrated, and purified with silica gel chromatography (hexanes:ethyl acetate+0.5% triethylamine, 10:1 to 1:1) to give glycosyl thioether S19 27 mg, 67% yield) as a colorless film.

TLC $R_f$ (hexanes:ethyl acetate, 2:1+0.5% triethylamine); FTIR (NaCl film) 2952, 2876, 1752, 1741, 1732, 1886, 1681, 1497, 1455, 1380, 1240, 1100, 1006, 826, 734, 697 cm$^{-1}$; $^1$H-NMR (600 MHz, CDCl$_3$) δ 9.69 (s, 1H), 7.38-7.26 (m, 35H), 5.54 (s, 1H), 5.49 (d, J=10.2 Hz, 1H), 5.28 (d, J=12.4 Hz, 1H), 5.18 (s, 1H), 5.13-5.06 (m, 3H), 4.94-4.80 (m, 5H), 4.76 (d, J=11.0 Hz, 1H), 4.71 (d, J=11.7 Hz, 1H), 4.63 (dd, J=13.9, 11.2 Hz, 2H), 4.56 (d, J=7.4 Hz, 1H), 4.52-4.47 (m, 2H), 4.44-4.39 (m, 2H), 4.23 (d, J=8.6 Hz, 1H), 4.20-4.16 (m, 2H), 4.11 (d, J=5.7 Hz, 1H), 4.05 (dd, J=10.1, 6.1 Hz, 1H), 3.96-3.90 (m, 4H), 3.88-3.72 (m, 5H), 3.67-3.53 (m, 9H), 3.52-3.45 (m, 3H), 3.40 (dd, J=9.4, 2.5 Hz, 1H), 3.31 (dd, J=9.0, 7.5 Hz, 3H), 3.25 (dd, J=8.7, 7.4 Hz, 1H), 3.20 (dd, J=12.1, 10.2 Hz, 1H), 3.13 (t, J=10.9 Hz, 1H), 2.56 (d, J=12.2 Hz, 1H), 2.39 (d, J=12.2 Hz, 1H), 2.35 (t, J=7.6 Hz, 2H), 2.15 (dtt, J=18.0, 14.0, 8.5 Hz, 4H), 1.82-1.75 (m, 3H), 1.74-1.52 (m, 13H), 1.36 (s, 3H), 1.34-1.17 (m, 25H), 1.05-0.83 (m, 99H), 0.81-0.53 (m, 65H); $^{13}$C-NMR (151 MHz, CDCl$_3$) δ 212.41, 173.72, 173.38, 168.38, 143.46, 138.79, 138.58, 138.56, 138.26, 137.76, 137.19, 137.17, 136.14, 135.26, 128.74, 128.55, 128.53, 128.48, 128.46, 128.45, 128.43, 128.35, 128.32, 128.31, 128.29, 128.25, 128.18, 128.16, 128.15, 128.11, 127.96, 127.94, 127.83, 127.81, 127.79, 127.77, 127.74, 127.73, 127.70, 127.68, 127.63, 127.56, 127.53, 122.34, 108.90, 103.53, 102.44, 101.39, 100.86, 98.66, 86.14, 85.30, 83.91, 82.26, 81.10, 78.81, 78.73, 78.25, 78.18, 78.01, 77.46, 76.45, 76.30, 75.98, 75.84, 75.82, 75.63, 75.09, 74.91, 74.76, 73.73, 73.71, 73.22, 72.62, 72.54, 71.41, 71.09, 70.71, 69.10, 66.86, 66.84, 66.07, 65.46, 65.35, 63.85, 60.29, 53.86, 49.25, 47.40, 46.47, 46.03, 45.22, 42.86, 42.37, 41.30, 41.22, 39.81, 39.58, 39.10, 37.96, 36.92, 36.40, 36.37, 36.09, 35.95, 34.68, 34.55, 34.36, 33.14, 32.78, 31.96, 31.83, 31.62, 30.78, 29.73, 29.51, 29.46, 29.42, 29.40, 29.37, 29.29, 29.24, 29.21, 29.16, 29.08, 27.83, 26.76, 26.64, 26.49, 26.45, 25.90, 25.34, 25.30, 24.99, 24.39, 23.37, 22.69, 20.73, 20.20, 18.79, 17.51, 17.48, 16.86, 16.12, 15.91, 14.17, 13.15, 12.20, 11.48, 7.59, 7.51, 7.49, 7.30, 7.28, 7.22, 7.20, 7.19, 7.16, 7.03, 7.01, 6.88, 6.82, 6.81, 5.94, 5.66, 5.46, 5.42, 5.39, 5.36, 5.34, 5.31, 5.30, 5.28, 5.25, 4.96, 4.44, 4.42; HRMS (ESI) m/z: Calcd for $C_{182}H_{295}NO_{33}NaSi_9S$ 3329.8978 [M+Na]$^+$, found 3329.9033.

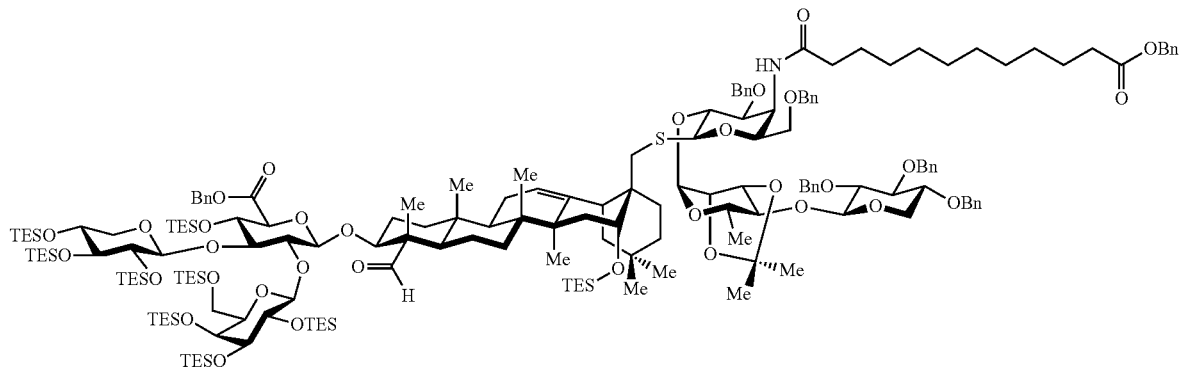

-continued

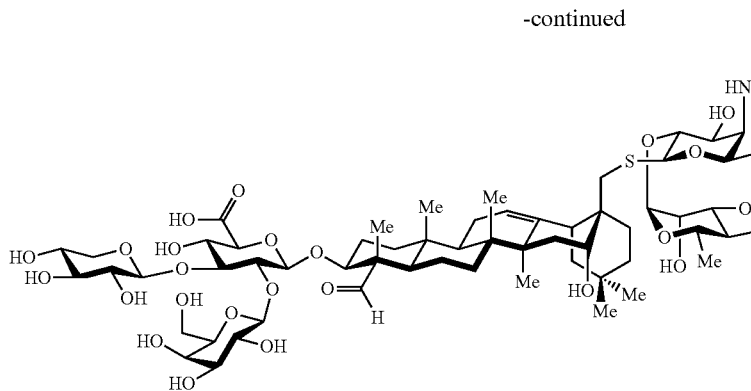

Production of β-Thioether Variant 9 (SOS-0-14-5-5)

A solution of fully protected thioether analogue (S19) (26 mg, 0.008 mmol, 1.0 equiv) in tetrahydrofuran (2 mL) and ethanol (2 mL) in a 25 mL round bottom flask was charged with 10% (dry basis) palladium on carbon, wet, Degussa type E101 NE/W (33 mg, 0.031 mmol, 4 equiv). Reaction mixture was stirred under hydrogen pressure (50 psi) overnight, then filtered through a 0.45 m polyvinylidene fluoride filter disk, washed with methanol (5 mL), and concentrated. To the hydrogenation product was added a pre-cooled (0° C.) solution of trifluoroacetic acid (4.0 mL, TFA/$H_2O$ 3:1). After vigorous stirring for 60 min, the solution was concentrated in vacuo at 0° C. to give white solid residue. This crude product was partially dissolved in a solution of aqueous acetonitrile (4:1 water:acetonitrile) and purified by RP-HPLC on an XBridge Prep BEH300 C18 column (5 μm, 10×250 mm) using a linear gradient of 20→75% acetonitrile (0.05% TFA) in water (0.05% TFA) over 19 min at a flow rate of 5 mL/min. The fraction containing the major peak (tR=12.60 min) was collected and lyophilized to dryness to afford β-thioether variant 9 (SQS-0-14-5-5) (5.8 mg, 46% yield) as a white solid.

$^1$H-NMR (600 MHz, D2O/CD3CN, 1:1) 9.99 (s, 1H), 7.64 (d, J=9.6 Hz, 1H), 5.89 (t, J=3.7 Hz, 1H), 5.60 (d, J=1.8 Hz, 1H), 5.28 (d, J=7.8 Hz, 1H), 5.15 (d, J=7.8 Hz, 1H), 5.08 (d, J=7.8 Hz, 1H), 5.02 (d, J=7.8 Hz, 1H), 4.80 (d, J=9.7 Hz, 1H), 4.72 (dq, J=9.7, 6.2 Hz, 1H), 4.58-4.54 (m, 1H), 4.52-4.50 (m, 1H), 4.50-4.45 (m, 1H), 4.42-4.29 (m, 7H), 4.25-4.21 (m, 2H), 4.16-4.05 (m, 8H), 4.05-4.00 (m, 1H), 3.98-3.88 (m, 4H), 3.85-3.79 (m, 3H), 3.79-3.74 (m, 1H), 3.20 (d, J=11.8 Hz, 1H), 3.13 (d, J=11.8 Hz, 1H), 2.88 (t, J=7.5 Hz, 2H), 2.86-2.80 (m, 2H), 2.80-2.75 (m, 2H), 2.71-2.68 (m, OH), 2.52-2.41 (m, 5H), 2.35-2.23 (m, 5H), 2.18-2.06 (m, 7H), 1.94 (s, 3H), 1.84 (d, J=6.1 Hz, 3H), 1.77-1.73 (m, 1H), 1.72 (s, 3H), 1.57 (s, 3H), 1.50 (s, 3H), 1.48 (s, 3H), 1.45 (s, 3H); HRMS (ESI) m/z: Calcd for C76H123NO33NaS 1632.7596 [M+Na]$^+$, found 1632.7648.

Example 10: Evaluation of Triterpene Saponin Variants

Figure 7:
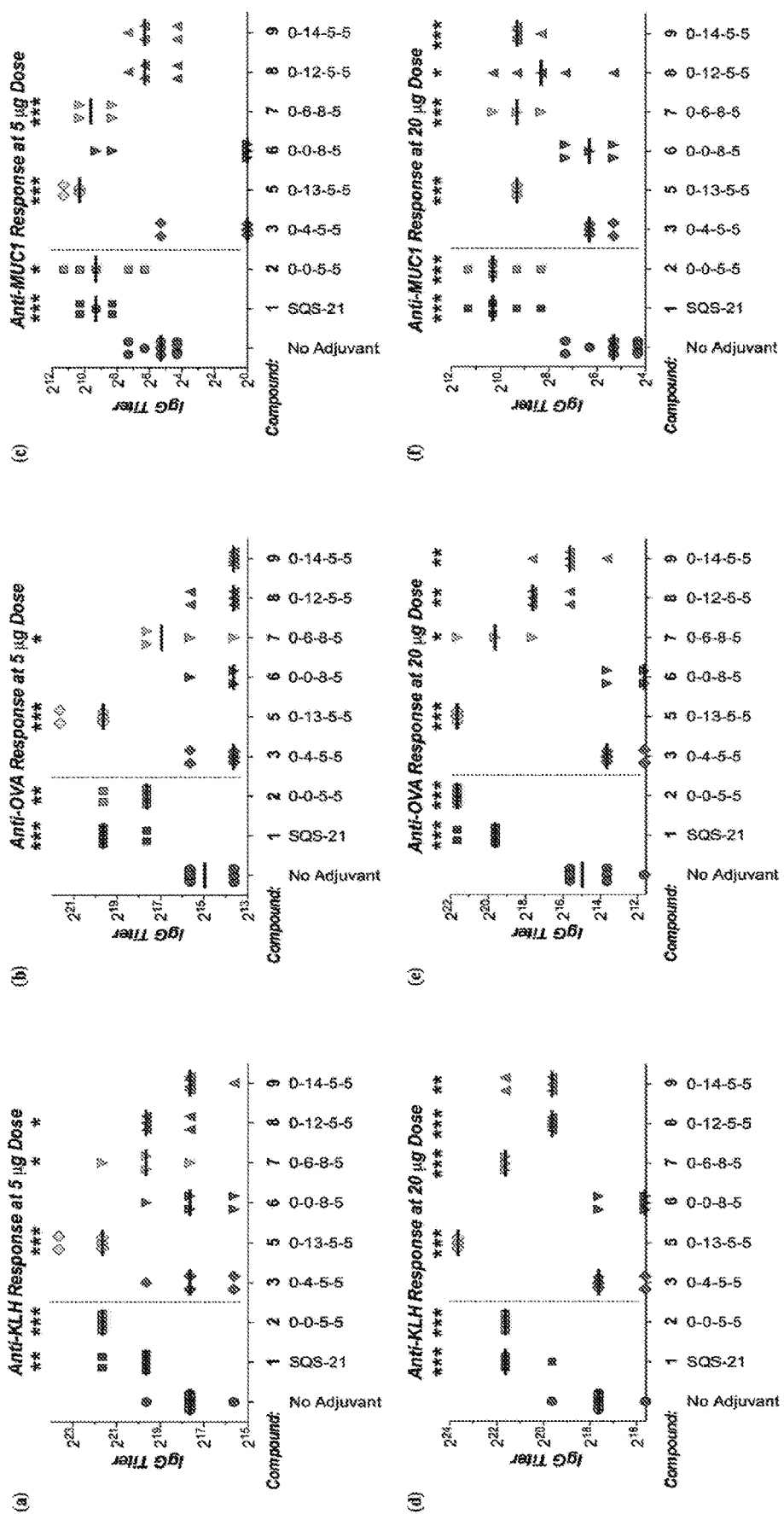
FIG. 7 shows adjuvant activity of QS saponin linkage variants in a preclinical mouse vaccination model. Panels a-c: anti-KLH (IgG) (Panel a), anti-OVA (IgG) (Panel b), and anti-MUC1 (IgG) (Panel c) antibody titers at 5 μg dose of each saponin variant. Panels d-f: anti-KLH (IgG) (Panel d), anti-OVA (IgG) (Panel e), and anti-MUC1 (IgG) (Panel f) antibody titers at 20 μg dose of each saponin variant. α/β-Glycosyl carbamates α/β-4 were inactive at both doses (not shown). Median titer values represented as horizontal bars. Statistical significance compared to the no-adjuvant negative control assessed using unpaired Student's t-test with CI=95%: *$p \leq 0.05$, $p < 0.01$, *$p < 0.001$.

FIG. 7 shows the adjuvant activity of these linkage variants in comparison to SQS-21 (synthetic QS-21, 2:1 mixture of 1a/1b) and the parent β-glycosyl ester lead compound 2 (SQS-0-0-5-5). There is currently no in vitro method to measure adjuvant activity, due in part to the unknown and likely multivariate mechanisms of saponin adjuvant action. Thus, we proceeded directly to testing these QS variants in vivo in a mouse vaccination model. Cohorts of mice were immunized with the saponin variant of interest (5 or 20 μg) and a four-antigen cocktail comprising: (1) the immunogenic peptide MUC1 (prostate and breast cancer antigen, non-glycosylated tandem repeat) conjugated to a highly immunogenic carrier protein KLH (keyhole limpet hemocyanin; MUC1-KLH), (2) the poorly immunogenic ganglioside GD3 (melanoma, neuroblastoma, sarcoma antigen) conjugated to KLH (GD3-KLH), and (3) the immunogenic protein antigen ovalbumin (OVA). The antibody titers elicited against all four antigens were evaluated by ELISA to compare the adjuvant activity of each QS analogue.

The above description is for the purpose of teaching the person of ordinary skill in the art how to practice the present disclosure, and it is not intended to detail all those obvious modifications and variations of it which will become apparent to the skilled worker upon reading the description. It is intended, however, that all such obvious modifications and variations be included within the scope of the present embodiment, which is defined by the following claims. The claims are intended to cover the claimed components and steps in any sequence which is effective to meet the objectives there intended, unless the context specifically indicates the contrary.

What is claimed is:

1. A compound of formula (I) or a pharmaceutically acceptable salt thereof,

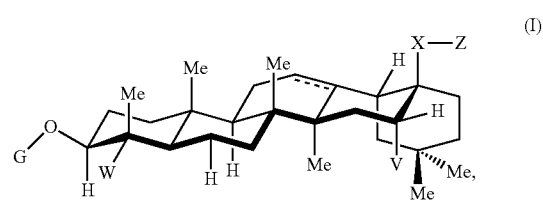

(I)

wherein G is hydrogen, a branched trisaccharide of formula V or a stereoisomer of formula V

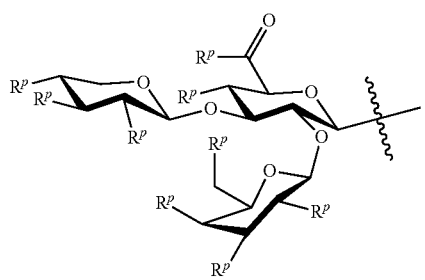

(V)

wherein W is Me, CHO, CH$_2$OR$^x$, C(O)R$^y$ or

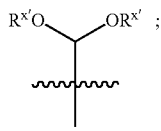

wherein each occurrence of R$^P$ is independently hydrogen or OR$^x$;

wherein each occurrence of R$^x$ is independently hydrogen or an optionally substituted group selected from 6-10-membered aryl, benzyl, C$_{1-6}$ aliphatic, or C$_{1-6}$ heteroaliphatic having 1-2 heteroatoms independently selected from the group consisting of nitrogen, oxygen, and sulfur; or two R$^x$ are taken together to form a 5-7-membered heterocyclic ring having 1-2 heteroatoms independently selected from the group consisting of nitrogen, oxygen, and sulfur;

wherein each occurrence of R$^{x'}$ is independently an optionally substituted group selected from 6-10-membered aryl, benzyl, C$_{1-6}$ aliphatic, or C$_{1-6}$ heteroaliphatic having 1-2 heteroatoms independently selected from the group consisting of nitrogen, oxygen, and sulfur; or two R$^{x'}$ are taken together to form a 5-7-membered heterocyclic ring having 1-2 heteroatoms independently selected from the group consisting of nitrogen, oxygen, and sulfur;

wherein each occurrence of R$^y$ is OH or OR$^x$;
wherein $=\!=$ is a single or double bond;
wherein V is hydrogen or OR$^x$;
wherein the —X—Z moiety is selected from the group consisting of

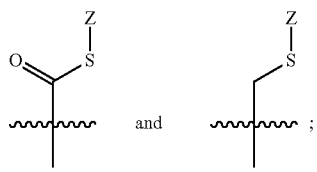

wherein Z comprises a carbohydrate domain having the structure:

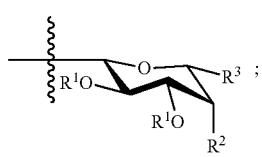

(IX)

wherein each occurrence of R$^1$ is R$^x$ or a carbohydrate domain having the structure

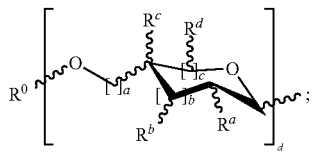

wherein each occurrence of a, b, and c is independently 0, 1, or 2;

wherein d is an integer from 1-5, wherein each d bracketed structure may be the same or different; with the proviso that the d bracketed structure represents a furanose or pyranose moiety, and the sum of b and c is 1 or 2;

wherein R$^0$ is hydrogen or an optionally substituted moiety selected from the group consisting of acyl, C$_{1-10}$ aliphatic, C$_{1-6}$ heteroaliphatic, 6-10-membered aryl, arylalkyl, 5-10-membered heteroaryl having 1-4 heteroatoms independently selected from nitrogen, oxygen, and sulfur, 4-7-membered heterocyclyl having 1-2 heteroatoms independently selected from the group consisting of nitrogen, oxygen, and sulfur;

wherein each occurrence of R$^a$, R$^b$, R$^c$, and R$^d$ is independently hydrogen, halogen, OH, OR, OR$^x$, NR$_2$, NHCOR, or an optionally substituted group selected from acyl, C$_{1-10}$ aliphatic, C$_{1-6}$ heteroaliphatic, 6-10-membered aryl, arylalkyl, 5-10-membered heteroaryl having 1-4 heteroatoms independently selected from nitrogen, oxygen, and sulfur; 4-7-membered heterocyclyl having 1-2 heteroatoms independently selected from the group consisting of nitrogen, oxygen, and sulfur, wherein each occurrence of R is independently hydrogen, an optionally substituted group selected from acyl, arylalkyl, 6-10-membered aryl, C1-12 aliphatic, or C1-12 heteroaliphatic having 1-2 heteroatoms independently selected from the group consisting of nitrogen, oxygen, and sulfur; or two R on the same nitrogen atom are taken with the nitrogen to form a 4-7-membered heterocyclic ring having 1-2 heteroatoms independently selected from the group consisting of nitrogen, oxygen, and sulfur;

wherein R$^2$ is NHC(O)R$^4$, OC(O)R$^4$, OC(O)OR$^4$, OC(O)NHR$^4$, OC(O)SR$^4$, NHC(O)OR$^4$, NHC(O)NHR$^4$, NHC(O)N(R$^4$)$_2$, NHR$^4$ or N(R$^4$)$_2$;

wherein R$^3$ is hydrogen, halogen, CH$_2$OR$^1$, or an optionally substituted group selected from the group consisting of acyl, C$_{1-10}$ aliphatic, C$_{1-6}$ heteroaliphatic, 6-10-membered aryl, arylalkyl, 5-10-membered heteroaryl having 1-4 heteroatoms independently selected from the group consisting of nitrogen, oxygen, and sulfur, and 4-7-membered heterocyclyl having 1-2 heteroatoms independently selected from the group consisting of nitrogen, oxygen, and sulfur;

wherein R$^4$ is T-R$^z$, herein T is a covalent bond or a bivalent C$_{1-12}$saturated or unsaturated, straight or branched, aliphatic or heteroaliphatic chain, and wherein R$^z$ is hydrogen, halogen, C(O)OR$^q$, NC(O)OR$^q$, OR$^q$, NHC(O)OR$^q$, OR$^1$, SR$^q$, NHC(S)R$^q$, OC(O)R$^q$, OC(O)OR$^q$, OC(O)NHR$^q$, OC(O)SR$^q$, NHC(O)OR$^q$, NHC(O)NHR$^q$, NHC(O)N(R$^q$)$_2$, NHR$^q$ or N(R$^q$)$_2$, or an optionally substituted group selected from acyl, arylalkyl, heteroarylalkyl, C$_{1-6}$ aliphatic, 6-10-membered aryl, 5-10-membered heteroaryl having 1-4 heteroatoms independently selected from nitrogen, oxygen, and sulfur, 4-7-membered heterocyclyl having 1-2 heteroatoms independently selected from the group consisting of nitrogen, oxygen and sulfur; or two $R^q$ on the same nitrogen atom are taken with the nitrogen to form a 4-7-membered heterocyclic ring having 1-2 heteroatoms independently selected from the group consisting of nitrogen, oxygen, and sulfur, and wherein $R^q$ is hydrogen, a detectable label, a protecting group, an optionally substituted group selected from acyl, arylalkyl, 6-10-membered aryl, $C_{1-12}$ aliphatic, and $C_{1-12}$ heteroaliphatic having 1-2 heteroatoms independently selected from the group consisting of nitrogen, oxygen, and sulfur, or an optionally substituted group selected from acyl, arylalkyl, 6-10-membered aryl, $C_{1-12}$ aliphatic, and $C_{1-12}$ heteroaliphatic having 1-2 heteroatoms independently selected from the group consisting of nitrogen, oxygen, and sulfur, wherein the optionally substituted group further comprises a detectable label.

2. The compound of claim 1, or a pharmaceutically acceptable salt thereof, wherein the —X—Z moiety is selected from the group consisting of

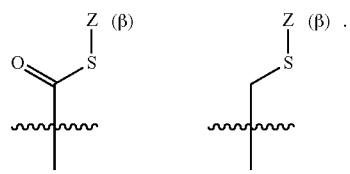

wherein β refers to the stereochemical configuration at the anomeric carbon in formula IX that is directly attached to the X moiety in formula I.

3. The compound of claim 1, or a pharmaceutically acceptable salt thereof, wherein the —X—Z moiety is

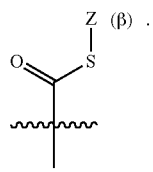

4. The compound of claim 1, or a pharmaceutically acceptable salt thereof, wherein G is hydrogen.

5. The compound of claim 1, or a pharmaceutically acceptable salt thereof, wherein G is

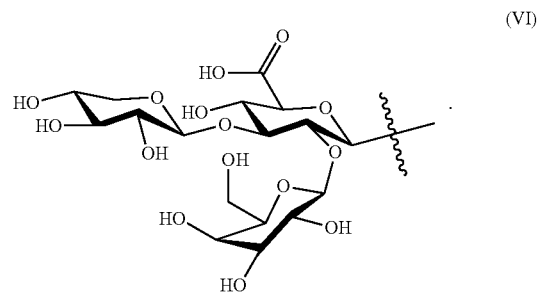

(VI)

6. The compound of claim 1, or a pharmaceutically acceptable salt thereof, wherein Z is (VII)

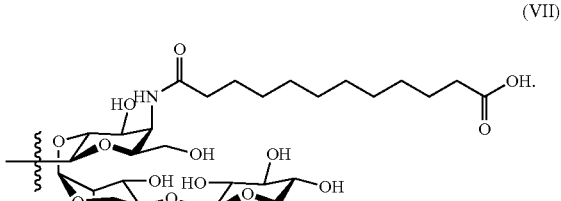

(VII)

7. The compound of claim 1, wherein the compound is selected from the group consisting of (5)

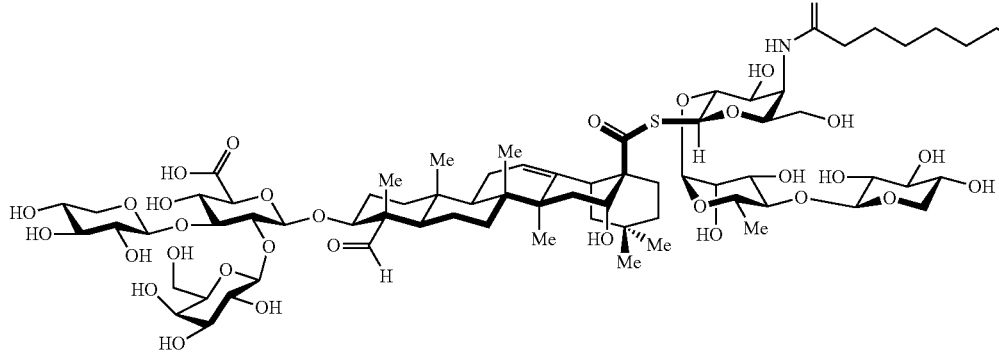

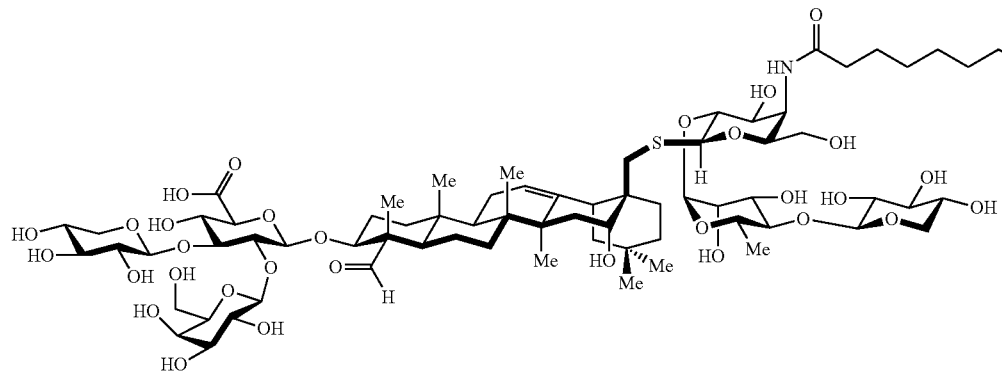
(9)
8. The compound of claim 1, wherein G is (VI)
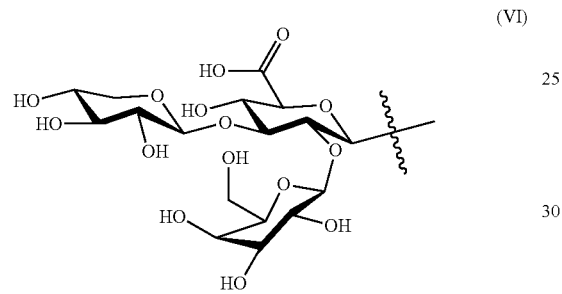
and wherein Z is selected from the group consisting of formula C1-C11 and mixtures thereof:
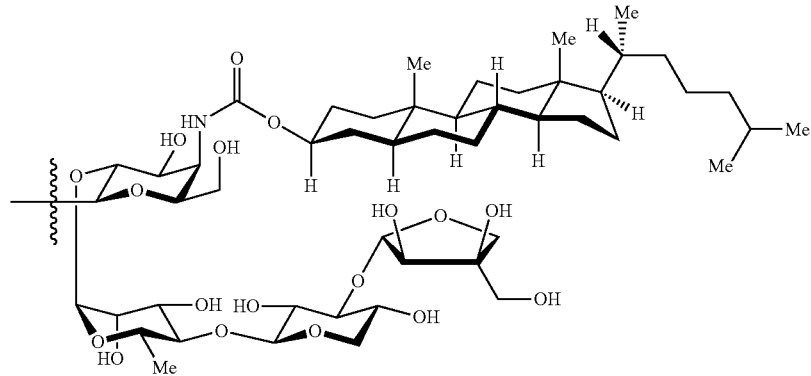
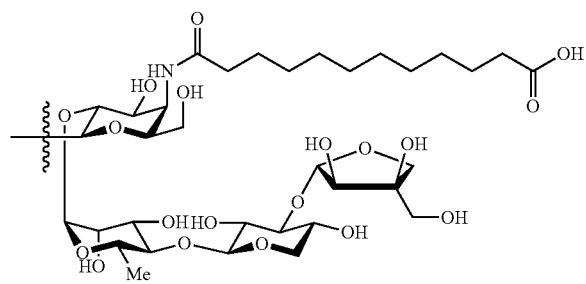
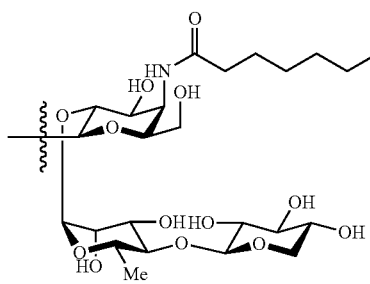

-continued
(C4)
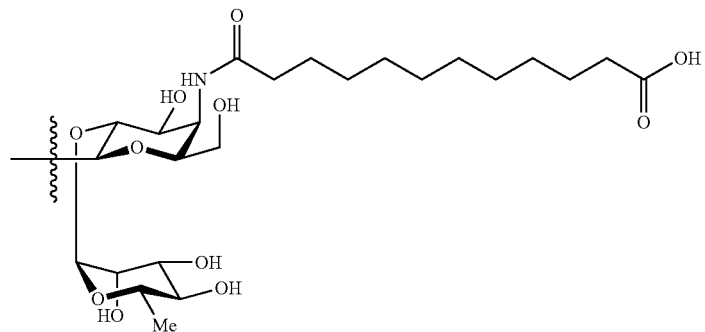
(C5)
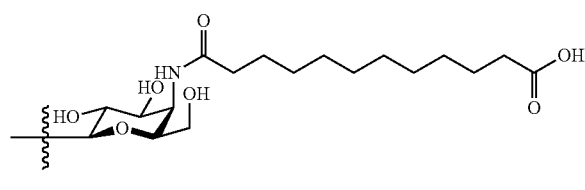
(C6)
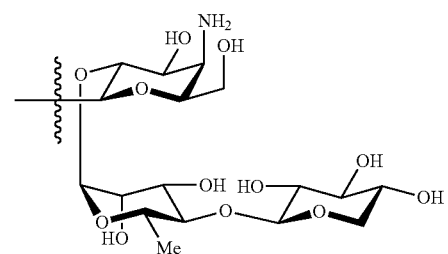
(C7)
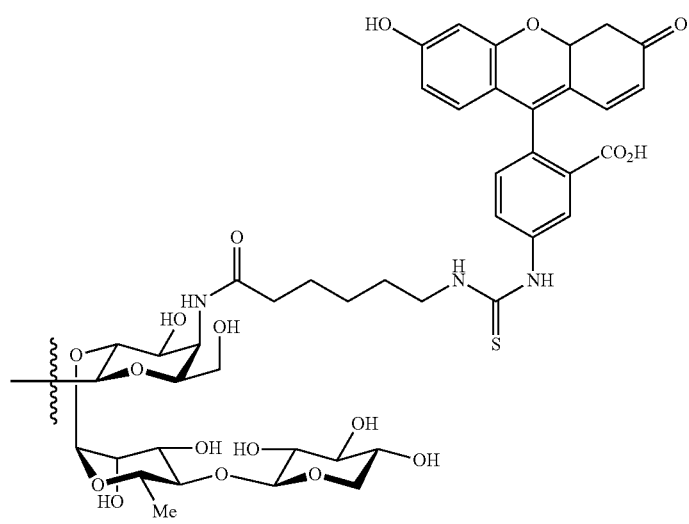
(C8)
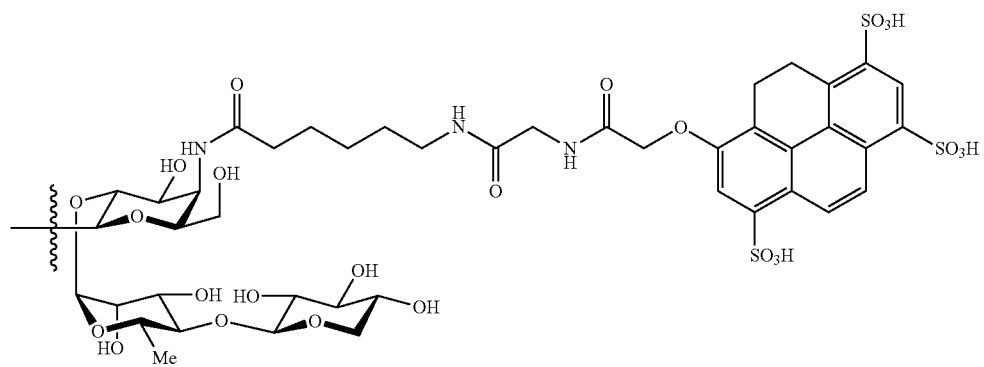

-continued
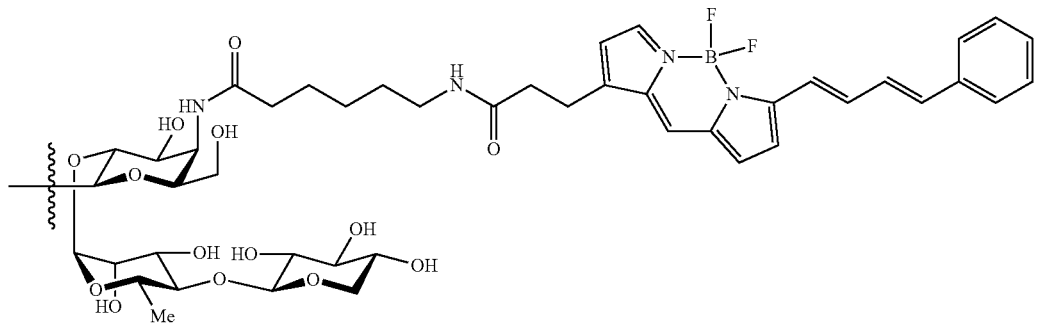
(C9)
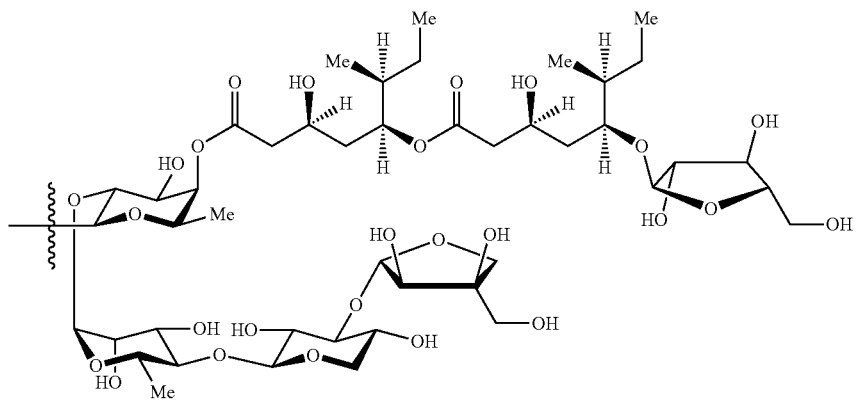
(C10)
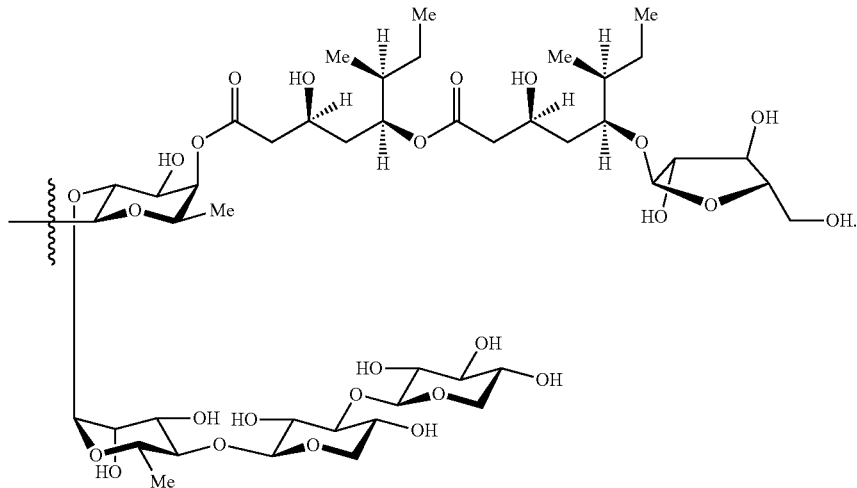
(C11)
9. The compound of claim 1, wherein G is hydrogen or (VI)
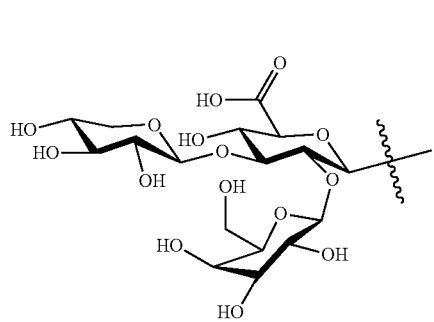
(VI)
wherein Z is
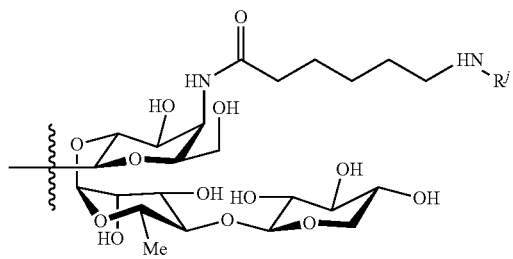
wherein $R^j$ is hydrogen,

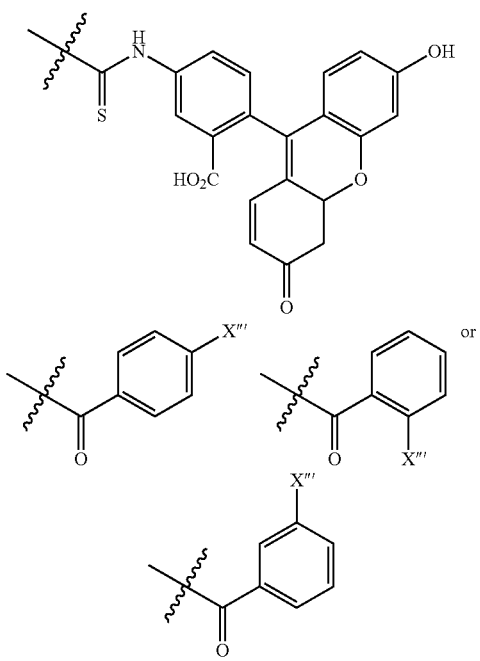

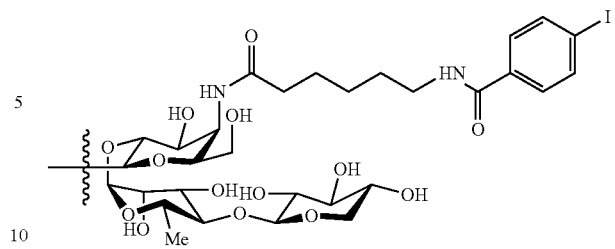

wherein X''' is I, $^{121}$I, $^{124}$I, $^{125}$I $^{131}$I, F, $^{18}$F, or SnMe$_3$.

10. The compound of claim 1, wherein G is hydrogen, wherein Z is and wherein W and V are selected from the group consisting of
(1) W is CH$_2$OH and V is OH,
(2) W is Me and V is OH,
(3) W is CHO and V is hydrogen,
(4) W is CH$_2$OH and V is hydrogen, and
(5) W is Me and V is hydrogen.

11. A pharmaceutical composition, comprising:
the compound of claim 1 or a pharmaceutically acceptable salt thereof;
an immunologically effective amount of an antigen; and
a pharmaceutically acceptable excipient.

12. A method for immunizing a subject, comprising:
administering to the subject an effective amount of the pharmaceutical composition of claim 11.

13. A method for treating a disorder in a subject, comprising:
administering to the subject an effective amount of the pharmaceutical composition of claim 12,
wherein the disorder is cancer, an infectious disease or a neurodegenerative disorder.

* * * * *